United States Patent
Szalay et al.

(10) Patent No.: US 10,238,700 B2
(45) Date of Patent: Mar. 26, 2019

(54) ONCOLYTIC VIRUS ADJUNCT THERAPY WITH AGENTS THAT INCREASE VIRUS INFECTIVITY

(71) Applicant: GENELUX CORPORATION, San Diego, CA (US)

(72) Inventors: Aladar A. Szalay, Highland, CA (US); Joseph Cappello, San Diego, CA (US); Nanhai G. Chen, San Diego, CA (US); Boris Minev, San Diego, CA (US)

(73) Assignee: Genelux Corporation, San Diego, CA (US)

( * ) Notice: Subject to any disclaimer, the term of this patent is extended or adjusted under 35 U.S.C. 154(b) by 251 days.

(21) Appl. No.: 15/109,214

(22) PCT Filed: Dec. 31, 2014

(86) PCT No.: PCT/US2014/073088
§ 371 (c)(1),
(2) Date: Jun. 30, 2016

(87) PCT Pub. No.: WO2015/103438
PCT Pub. Date: Jul. 9, 2015

(65) Prior Publication Data
US 2016/0339066 A1 Nov. 24, 2016

Related U.S. Application Data

(60) Provisional application No. 61/964,383, filed on Jan. 2, 2014.

(51) Int. Cl.
| | | |
|---|---|---|
| *C12N 7/00* | (2006.01) |
| *A61K 39/00* | (2006.01) |
| *A61K 47/44* | (2017.01) |
| *C07K 16/18* | (2006.01) |
| *A61K 35/768* | (2015.01) |
| *A61K 39/395* | (2006.01) |

(52) U.S. Cl.
CPC ........ *A61K 35/768* (2013.01); *A61K 39/3955* (2013.01); *A61K 47/44* (2013.01); *C07K 16/18* (2013.01); *C12N 7/00* (2013.01); *A61K 2039/505* (2013.01); *A61K 2039/545* (2013.01); *C12N 2710/24132* (2013.01)

(58) Field of Classification Search
CPC .. A61K 35/768; A61K 39/3955; A61K 47/44; A61K 2039/545; A61K 2039/505; A61K 2300/00; A61K 39/12; A61K 9/0019; A61K 2039/53; A61K 2039/572; A61K 2039/5254; A61K 39/395; A61K 38/1774; A61K 2039/51; A61K 2039/6018; A61K 2039/6056; A61K 2039/6075; A61K 47/6801; A61K 47/6803; A61K 47/6811; A61K 47/6929; C07K 16/18; C07K 14/005; C07K 2317/732; C07K 16/00; C07K 2319/33; C07K 2317/734; C12N 7/00; C12N 2710/24132; C12N 15/86; C12N 2710/24021; C12N 2710/24122; C12N 2710/24143; A61P 37/02; A61P 37/06

See application file for complete search history.

(56) References Cited

U.S. PATENT DOCUMENTS

| | | | |
|---|---|---|---|
| 3,539,794 A | 11/1970 | Rauhut et al. | 240/2.25 |
| 4,215,051 A | 7/1980 | Schroeder | 260/346.7 |
| 4,603,112 A | 7/1986 | Paoletti et al. | 435/235.1 |
| 4,722,848 A | 2/1988 | Paoletti et al. | 424/199.1 |
| 4,769,330 A | 9/1988 | Paoletti et al. | 435/436 |
| 4,946,778 A | 8/1990 | Ladner et al. | 435/69.6 |
| 5,033,252 A | 7/1991 | Carter | 53/425 |
| 5,052,558 A | 10/1991 | Carter | 206/439 |
| 5,110,587 A | 5/1992 | Paoletti et al. | 435/235.1 |
| 5,149,653 A | 9/1992 | Roser et al. | 435/260 |
| 5,171,081 A | 12/1992 | Pita et al. | 362/34 |
| 5,174,993 A | 12/1992 | Paoletti | 424/89 |
| 5,258,498 A | 11/1993 | Huston et al. | 530/350 |
| 5,323,907 A | 6/1994 | Kalvelage | 206/531 |
| 5,364,773 A | 11/1994 | Paoletti et al. | 435/69.1 |
| 5,624,837 A | 4/1997 | Fodor et al. | 435/240.2 |

(Continued)

FOREIGN PATENT DOCUMENTS

| | | |
|---|---|---|
| EP | 1 385 466 | 2/2004 |
| EP | 1 520 175 | 4/2005 |

(Continued)

OTHER PUBLICATIONS

Wakimoto H, Ikeda K, Abe T, Ichikawa T, Hochberg FH, Ezekowitz RA, Pasternack MS, Chiocca EA. The complement response against an oncolytic virus is species-specific in its activation pathways. Mol Ther. Mar. 2002;5(3):275-82.*

(Continued)

*Primary Examiner* — Rachel B Gill
(74) *Attorney, Agent, or Firm* — Dentons US LLP; Stephanie Seidman

(57) ABSTRACT

Provided are adjunct therapies for use in combinations and compositions with an oncolytic virus, such as a vaccinia virus. The adjunct therapies include co-administration and co-formulation of a complement inhibitor and/or a lipid emulsion composition with the oncolytic virus. Also provided herein are therapeutic methods using the adjunct therapies for treatment of disease and conditions employing an oncolytic therapeutic virus, such as for the treatment of hyperproliferative diseases or conditions including tumors or cancers.

25 Claims, No Drawings
Specification includes a Sequence Listing.

(56) References Cited

U.S. PATENT DOCUMENTS

| | | | |
|---|---|---|---|
| 5,627,264 A | 5/1997 | Fodor et al. | 530/350 |
| 5,658,727 A | 8/1997 | Barbas et al. | 435/5 |
| 5,667,988 A | 9/1997 | Barbas | 435/69.1 |
| 5,716,613 A | 2/1998 | Guber et al. | 424/93.2 |
| 5,716,826 A | 2/1998 | Gruber et al. | 435/320.1 |
| 5,719,054 A | 2/1998 | Boursnell et al. | 435/320.1 |
| 5,762,938 A | 6/1998 | Paoletti et al. | 424/199.1 |
| 5,840,300 A | 11/1998 | Williams et al. | 424/135.1 |
| 5,847,082 A | 12/1998 | Rother et al. | 530/350 |
| 5,851,529 A | 12/1998 | Guber et al. | 424/188.1 |
| 5,922,576 A | 7/1999 | He et al. | 435/91.41 |
| 5,976,796 A | 11/1999 | Szalay et al. | 435/6 |
| 6,093,700 A | 7/2000 | Mastrangelo et al. | 514/44 |
| 6,165,779 A | 12/2000 | Engler et al. | 435/320.1 |
| 6,255,289 B1 | 7/2001 | German et al. | 514/44 |
| 6,265,183 B1 | 7/2001 | Dorner et al. | 435/69.1 |
| 6,319,703 B1 | 11/2001 | Speck | 435/235.1 |
| 6,319,897 B1 | 11/2001 | Lambris et al. | 514/9 |
| 6,355,245 B1 | 3/2002 | Evans et al. | 536/23.53 |
| 6,428,968 B1 | 8/2002 | Molnar-Kimber et al. | 435/7.23 |
| 6,429,001 B1 | 8/2002 | Hardy | 435/235.1 |
| 6,573,090 B1 | 6/2003 | Breakefield et al. | 435/320.1 |
| 6,589,531 B1 | 7/2003 | Andino-Pavlovsky et al. | 424/199.1 |
| 6,632,670 B1 | 10/2003 | Wadsworth et al. | 435/455 |
| 6,635,472 B1 | 10/2003 | Lauermann | 435/320.1 |
| 6,653,103 B2 | 11/2003 | Peterson et al. | 435/69.1 |
| 6,664,099 B1 | 12/2003 | Worrall | 435/260 |
| 6,689,871 B1 | 2/2004 | Wolfe et al. | 530/412 |
| 6,723,316 B2 | 4/2004 | Laquerre | 424/93.2 |
| 6,800,288 B2 | 10/2004 | Ferko et al. | 424/199.1 |
| 6,872,357 B1 | 3/2005 | Bronshtein et al. | 422/41 |
| 6,897,045 B2 | 5/2005 | Engelhardt | 435/69.6 |
| 6,956,107 B2 | 10/2005 | Fung et al. | 530/387.1 |
| 6,998,468 B2 | 2/2006 | Fung et al. | 530/388.25 |
| 7,001,765 B2 | 2/2006 | Maass | 435/320.1 |
| 7,033,826 B2 | 4/2006 | Perricaudet et al. | 435/320.1 |
| 7,045,313 B1 | 5/2006 | Moss et al. | 435/69.1 |
| 7,091,030 B2 | 8/2006 | Setiawan | 435/235.1 |
| 7,153,510 B1 | 12/2006 | Rose | 424/199.1 |
| 7,172,893 B2 | 2/2007 | Rabinowitz et al. | 435/235.1 |
| 7,229,619 B1 | 6/2007 | Young et al. | 424/159.1 |
| 7,238,526 B2 | 7/2007 | Wilson | 435/382 |
| 7,241,447 B1 | 7/2007 | Engelhardt et al. | 424/193.1 |
| 7,537,924 B2 | 5/2009 | Coffin et al. | 435/235.1 |
| 7,550,147 B2 | 6/2009 | Howley et al. | 424/199.1 |
| 7,550,296 B2 | 6/2009 | Hermiston et al. | 435/473 |
| 7,588,767 B2 | 9/2009 | Szalay et al. | 424/199.1 |
| 7,588,771 B2 | 9/2009 | Szalay et al. | 424/232.1 |
| 7,662,398 B2 | 2/2010 | Szalay et al. | 424/232.1 |
| 7,662,627 B2 | 2/2010 | Johnson et al. | 435/367 |
| 7,731,952 B2 | 6/2010 | Mohr | 424/93.2 |
| 7,754,221 B2 | 7/2010 | Szalay et al. | 424/199.1 |
| 7,763,420 B2 | 7/2010 | Stritzker et al. | 435/4 |
| 7,731,974 B2 | 9/2010 | Bell et al. | 424/199.1 |
| 7,811,814 B2 | 10/2010 | Bohn et al. | 435/320.1 |
| 7,897,146 B2 | 3/2011 | Brown et al. | 424/93.1 |
| 7,906,111 B2 | 3/2011 | Wilson et al. | 424/93.2 |
| 7,927,585 B2 | 4/2011 | Snyder | 424/93.2 |
| 7,943,374 B2 | 5/2011 | Hildinger | 435/320.1 |
| 7,968,340 B2 | 6/2011 | Hallek et al. | 435/440 |
| 7,999,081 B2 | 8/2011 | Tedesco et al. | 530/388.25 |
| 8,007,780 B2 | 8/2011 | Arbetman | 424/93.2 |
| 8,052,968 B2 | 11/2011 | Chen et al. | 424/199.1 |
| 8,329,164 B2 | 12/2012 | Kim et al. | 424/93.3 |
| 8,507,456 B2 | 8/2013 | Purschke et al. | 514/44 |
| 9,492,534 B2 | 11/2016 | Szalay et al. | 424/199.1 |
| 9,944,903 B2 | 4/2018 | Szalay et al. | 424/93.3 |
| 2003/0059400 A1 | 3/2003 | Szalay | 424/93.2 |
| 2003/0153065 A1 | 8/2003 | Kovesdi et al. | 435/235.1 |
| 2003/0228261 A1 | 12/2003 | Szalay et al. | 424/9.34 |
| 2004/0009604 A1 | 1/2004 | Zhang | 435/456 |
| 2004/0038410 A1 | 2/2004 | Setiawan et al. | 436/8 |
| 2004/0175398 A1* | 9/2004 | Moyer | A61K 39/275 424/232.1 |
| 2004/0234455 A1 | 11/2004 | Szalay et al. | 424/9.6 |
| 2005/0031643 A1 | 2/2005 | Szalay et al. | 424/199.1 |
| 2005/0032044 A1 | 2/2005 | Setiwan | 435/5 |
| 2005/0220818 A1 | 10/2005 | Lorence | 424/214.4 |
| 2005/0260601 A1 | 11/2005 | Whitt et al. | 435/6 |
| 2006/0039894 A1 | 2/2006 | Mohr | 424/93.6 |
| 2006/0217530 A1 | 9/2006 | Taylor et al. | 530/317 |
| 2007/0098743 A1 | 5/2007 | Bell et al. | 424/224.1 |
| 2007/0110720 A1 | 5/2007 | Brown et al. | 424/93.2 |
| 2007/0202572 A1 | 8/2007 | Szalay et al. | 435/69.1 |
| 2007/0212727 A1 | 9/2007 | Szalay et al. | 435/6 |
| 2008/0193373 A1 | 8/2008 | Stritzker et al. | 424/1.17 |
| 2009/0010889 A1 | 1/2009 | Brown et al. | 424/93.2 |
| 2009/0053244 A1 | 2/2009 | Chen et al. | 424/174.1 |
| 2009/0081639 A1 | 3/2009 | Hill et al. | 435/5 |
| 2009/0098529 A1 | 4/2009 | Chen et al. | 435/5 |
| 2009/0117034 A1 | 5/2009 | Chen et al. | 424/1.17 |
| 2009/0136917 A1 | 5/2009 | Szalay et al. | 435/5 |
| 2009/0155287 A1 | 6/2009 | Chen et al. | 424/158.1 |
| 2009/0162288 A1 | 6/2009 | Chen et al. | 424/9.3 |
| 2009/0215147 A1 | 8/2009 | Zhang | 435/235.1 |
| 2009/0274728 A1 | 11/2009 | Brown et al. | 424/231.1 |
| 2009/0285860 A1 | 11/2009 | Martuza et al. | 424/277.1 |
| 2010/0062016 A1 | 3/2010 | Szalay et al. | 424/199.1 |
| 2010/0092515 A1 | 4/2010 | Conner | 424/231.1 |
| 2010/0113567 A1 | 5/2010 | Barber | 514/44 |
| 2010/0172877 A1 | 7/2010 | van den Pol | 424/93.6 |
| 2010/0178684 A1 | 7/2010 | Woo et al. | 435/235.1 |
| 2010/0196325 A1 | 8/2010 | Szalay et al. | 424/93.6 |
| 2010/0233078 A1 | 9/2010 | Szalay et al. | 424/1.17 |
| 2011/0064650 A1 | 3/2011 | Szalay | 424/1.11 |
| 2011/0158948 A1 | 6/2011 | Brown et al. | 424/93.2 |
| 2011/0177032 A1 | 7/2011 | Martuza et al. | 424/93.2 |
| 2011/0212530 A1 | 9/2011 | Baltimore et al. | 435/455 |
| 2011/0293527 A1 | 12/2011 | Chen et al. | 424/9.3 |
| 2012/0052003 A9 | 3/2012 | Szalay | 424/1.11 |
| 2012/0308484 A1 | 12/2012 | Szalay et al. | 424/9.3 |
| 2013/0273007 A1 | 10/2013 | Szalay et al. | 424/93.2 |
| 2013/0273052 A1 | 10/2013 | Gies et al. | 424/135.1 |
| 2014/0271549 A1 | 9/2014 | Szalay | 424/93.2 |
| 2017/0095552 A1 | 4/2017 | Szalay et al. | 424/186.1 |
| 2018/0195050 A1 | 7/2018 | Szalay et al. | 424/186.1 |

FOREIGN PATENT DOCUMENTS

| | | |
|---|---|---|
| EP | 1 606 411 | 12/2005 |
| WO | WO 1994/026786 | 11/1994 |
| WO | WO 1999/013899 | 3/1999 |
| WO | WO 99/18799 | 4/1999 |
| WO | WO 2004/014314 | 2/2004 |
| WO | WO 2004/026328 | 4/2004 |
| WO | WO 2005/047458 | 5/2005 |
| WO | WO 2008/100292 | 8/2008 |
| WO | WO 2008/150496 | 12/2008 |
| WO | WO 2009/139921 | 11/2009 |
| WO | WO 2012/174055 | 12/2012 |
| WO | WO 2013/104540 | 7/2013 |
| WO | WO 2015/103438 | 7/2015 |

OTHER PUBLICATIONS

Awasthi S, Lubinski JM, Friedman HM. Immunization with HSV-1 glycoprotein C prevents immune evasion from complement and enhances the efficacy of an HSV-1 glycoprotein D subunit vaccine. Vaccine. Nov. 16, 2009;27(49):6845-53. Epub Sep. 15, 2009.*

Rossi J, Leroux JC. "Chapter 4: Principles in the Development of Intravenous Lipid Emulsions." In: Role of Lipid Excipients in Modifying Oral and Parenteral Drug Delivery, Ed. Wasan KM. Copyright © 2007 John Wiley & Sons, Inc.*

Letter/Written Disclosure of the Information Disclosure Statement for the above-referenced application, filed herewith on Sep. 29, 2016, 2 pages.

AACR Press Release, "Virus shows promise for imaging and treating pancreatic cancer," Published on Sep. 15, 2011 [online]

(56) References Cited

OTHER PUBLICATIONS

Retrieved Jan. 28, 2013, Retrieved from: <URL:aacr.org/home/public--media/aacr-press-releases.aspx?d=2438, 2 pages.
Agranovski et al. "Rapid detection of airborne viruses by personal bioaerosol sampler combined with the PCR device," Atmospheric Environment 40:3924-3929 (2006).
Al'tshtein et al., "Isolation of a recombinant vaccinia virus based on the LIVP strain inducing the surface antigen of the hepatitis B virus," Dokl. Akad. Nauk. SSSR 285(3):696-699 (1985) [Article in Russian].
Ansel, H., Introduction to Pharmaceutical Dosage Forms, Fourth Edition, Philadelphia: Lea& Febiger, p. 126 (1985).
Arndt et al., "Helix-stabilized Fv (hsFv) antibody fragments: substituting the constant domains of a Fab fragment for a heterodimeric coiled-coil domain," J Mol Biol. 312(1): 221-228, 2001.
Ausubel et al., "Generation of recombinant vaccinia viruses," Unit 16.17 in Short Protocols in Molecular Biology $2^{nd}$ d edition: a compendium of Methods from Current Protocols in Molecular Biology, Green Publishing and John Wiley and Sons: New York, 15:16.71-16.82 (1992).
Baker et al., "Studies on the inhibition of C56-induced lysis (reactive lysis). VI. Modulation of C56-induced lysis polyanions and polycations," J. Immunol, 114:554-8 (1975).
Baroudy et al., "Incompletely base-paired flip-flop terminal loops link the two DNA strands of the vaccinia virus genome into one uninterrupted polynucleotide chain," Cell 28:315-324 (1982).
Bernards et al., "Effective tumor immunotherapy directed against an oncogene-encoded product using a vaccinia virus vector," Proc. Natl. Acad. Sci. U.S.A. 84:6854-6858 (1987).
Bird et al., "Single-chain antigen-binding proteins," Science 242(4877): 423-426 (1988).
Broder et al., "Recombinant vaccinia viruses," Mol. Biotechnol. 13:223-245 (1999).
Carrillo et al., "The multiple sequence alignment problem in biology," SIAM J. Applied Math 48:1073-1082 (1988).
Carroll and Georgiou, "Antibody-mediates inhibition of human C1s and the classical complement pathway," Immunobiology 218(8):1041-8 (2013).
Certified English translation of Al'tshtein [Altshteyn] et al., "Isolation of a recombinant vaccinia virus based on the LIVP strain inducing the surface antigen of the hepatitis B virus," Dokl. Akad. Nauk. SSSR. 285(3):696-699 (1985) [Article in Russian].
Chakrabarti et al., "Compact, synthetic, vaccinia virus early/late promoter for protein expression," BioTechniques 23(6):1094-1097 (1997).
Chamberlain et al., "Costimulation enhances the active immunotherapy effect of recombinant anticancer vaccines," Cancer Res. 56:2832-2836 (1996).
Chang et al., "Targeting vaccinia to solid tumors with local hyperthermia," Hum. Gene Ther. 16:435-444 (2005).
Chen et al., "A novel recombinant vaccinia virus expressing the human norepinephrine transporter retains oncolytic potential and facilitates deep tissue imaging," Mol. Med. 15(5-6):144-151 (2009).
Chen et al., "Oncolytic vaccinia virus: a theranostic agent for cancer," Future Virology, 5(6):763-784 (2010).
Chkheidze et al., "Identification of DNA binding proteins in vaccinia virus by DNA-protein crosslinking," FEBS 336(2):340-342 (1993).
Croyle et al., "Factors that influence stability of recombinant adenoviral preparations for human gene therapy," Pharm. Dev. Technol. 3(3):373-383 (1998).
Davison et al., "New vaccinia virus recombination plasmids incorporating a synthetic late promoter for high level expression of foreign proteins," Nucleic Acids Res. 18:4285-4286 (1990).
Davison et al., "Structure of vaccinia virus early promoters," J. Mol. Biol. 210:749-769 (1989).
Driscoll, "Lipid injectable emulsions: 2006," Nutr Clin Pract. 21(4):381-6 (2006).

Earl et al., "T-lymphocyte priming and protection against friend leukemia by vaccinia-retrovirus env gene recombinant," Science 234:728-731 (1986).
Englebienne, "Use of colloidal gold surface plasmon resonance peak shift to infer affinity constants from the interactions between protein antigens and antibodies specific for single or multiple epitopes," Analyst. 123:1599-1603 (1998).
Estin et al, "Recombinant vaccinia virus vaccine against the human melanoma antigen p97 for use in immunotherapy," Proc. Natl. Acad. Sci. U.S.A. 85:1052-1056 (1988).
Fitch et al., "Pharmacology and biological efficacy of a recombinant, humanized, single-chain antibody C5 complement inhibitor in patients undergoing coronary artery bypass graft surgery with cardiopulmonary bypass," Circulation. 100(25):2499-506 (1999).
Fredslund et al., "Structure of and influence of a tick complement inhibitor on human complement component 5," Nat Immunol. 9(7):753-60 (2008).
Frentzen et al., "Anti-VEGF single chain antibody GLAF-1 encoded by oncolytic vaccinia virus significantly enhances antitumor therapy," Proc. Natl. Acad. Sci. U.S.A. 106(31):12915-12920 (2009).
Frentzen et al., "Use of GLV-1h68 for Vaccinia Virotherapy and Monitoring," Gene Therapy of Solid Cancers, Methods in Molecular Biology 1317:225-237 (2015).
Fu et al., "Incorporation of the B18R gene of vaccinia virus into an oncolytic herpes simplex virus improves antitumor activity," Mol. Ther., 20:1871-1881 (2012).
Fung et al., "Pre-neutralization of C5a-mediated effects by the monoclonal antibody 137-26 reacting with the C5a moiety of native C5 without preventing C5 cleavage," Clin Exp Immunol. 133(2):160-9 (2003).
Galanis et al., "Phase II trial of intravenous administration of Reolysin(®) (Reovirus Serotype-3-dearing Strain) in patients with metastatic melanoma," Mol. Ther., 20:1998-2003 (2012).
Garcia-Aragoncillo et al., "Design of virotherapy for effective tumor treatment," Curr Opin Mol Ther 12:403-411 (2010).
Gentschev et al., "Preclinical evaluation of oncolytic vaccinia virus for therapy of canine soft tissue sarcoma," PLoS One 7:(5) 37239 (2012).
Gribskov et al., "Sigma factors from E. coli, B. subtilis, phage SP01, and phage T4 are homologous proteins," Nucl. Acids Res. 14:6745-6763 (1986).
Griffin, A.M., and Griffin, H.G., eds., Humana Press, New Jersey, 1994; Computer Analysis of Sequence Data, Part I, 13 pages.
Hagi et al., "Effects of the omega-6:omega-3 fatty acid ratio of fat emulsions on the fatty acid composition in cell membranes and the anti-inflammatory action," JPEN J Parenter Enteral Nutr. 34(3):263-70 (2010).
Hallden G. and G. Portella,"Oncolytic virotherapy with modified adenoviruses and novel therapeutic targets," Expert Opin Ther Targets 16:945-958 (2012).
He et al., "A simplified system for generating recombinant adenoviruses," Proc. Natl. Acad. Sci. 95(5):2509-2514 (1998).
Heo et al., "Sequential therapy with JX-594, a targeted oncolytic poxvirus, followed by sorafenib in hepatocellular carcinoma: preclinical and clinical demonstration of combination efficacy," Mol Ther. 19(6): 1170-1179 (2011).
Hillmen et al., "Effect of eculizumab on hemolysis and transfusion requirements in patients with paroxysmal nocturnal hemoglobinuria," N Engl J Med. 350(6): 552-9 (2004).
Hippalgaonkar et al., "Injectable lipid emulsions-advancements, opportunities and challenges," AAPS PharmSciTech. 11(4):1526-40 (2010).
Holmskov et al., "Collectins: collagenous C-type lectins of the innate immune defense system," Immunol Today, 15(2): 67-74 (1994).
Hong et al., "Inhibitory effect of K-76 monocarboxylic acid, an anticomplementary agent, on the C3b inactivator system," 127(1):104-8 (1981).
Hruby et al., "Vaccinia virus vectors: new strategies for producing recombinant vaccines," Clin. Micro. Rev. 3:153-170 (1990).
Huang, X. and W. Miller, "A time-efficient, linear-space local similarity algorithm," Adv. Appl. Math. 12:337-357 (1991).

(56) References Cited

OTHER PUBLICATIONS

Hultin et al., "Metabolism of emulsions containing medium- and long-chain triglycerides or interesterified triglycerides," J Lipid Res. 35(10):1850-60 (1994).
IUPAC-IUB commission on biochemical nomenclature a one-letter notation for amino acid sequences tentative rules, J. Biol. Chem. 243(13): 3557-3559 (1968).
IUPAC-IUB commission on bio-chemical nomenclature symbols for amino-acid derivatives and peptides. Recommendations (1971). Biochem. 11(9):1726-1732 (1972).
Kantor et al., "Antitumor activity and immune responses induced by a recombinant carcinoembryonic antigen-vaccinia virus vaccine," J. Natl. Cancer Inst. 84: 1084-1091 (1992).
Kaufman et al., "OPTIM trial: a Phase III trial of an oncolytic herpes virus encoding GM-CSF for unresectable stage III or IV melanoma," Future Oncol. 6:941-949 (2010).
Kelly et al., "Novel oncolytic agent GLV-1h68 is effective against malignant pleural mesothelioma," Hum. Gene Ther. 19(8):774-782 (2008).
Kim et al., "Overview analysis of adjuvant therapies for melanoma—a special reference to results from vaccinia melanoma oncolysate adjuvant therapy trials," Surg. Oncol. 10:53-59 (2001).
Kim et al., "Systemic armed oncolytic and immunologic therapy for cancer with JX-594, a targeted poxvirus expressing GM-CSF," Mol. Ther. 14(3):361-370 (2006).
Kipriyanov SM, "Generation of antibody molecules through antibody engineering," Methods Mol Biol 207: 3-25 (2003).
Kirn and Thorne, "Targeted and armed oncolytic poxviruses: novel multi-mechanistic therapeutic class for cancer," Nat. Rev. Cancer 9:64-71 (2009).
Klutchko et al., "2-Substituted aminopyrido[2,3-d]pyrimidin-7(8H)-ones. structure-activity relationships against selected tyrosine kinases and in vitro and in vivo anticancer activity," J Med Chem. 41(17):3276-92 (1998).
Kozak, "Structural features in eukaryotic mRNAs that modulate the initiation of translation," J. Biol. Chem. 266:19867-19870 (1991).
Kozlova et al., "Inactiviation and mineralization of aerosol deposited model pathogenic microorganisms over TiO2 and Pt/TiO2," Environ. Sci. Technol. 44:5121-5126 (2010).
Kuhn et al., "Directed evolution generates a novel oncolytic virus for the treatment of colon cancer," PLoS One 3(6):e2409 (2008).
Kutinova et al., "Hepatitis B virus proteins expressed by recombinant vaccinia viruses: influence of preS2 sequence on expression surface and nucleocapsid proteins in human diploid cells," Arch. Virol. 134:1-15 (1994).
Kutinova et al., "Search for optimal parent for recombinant vaccinia virus vaccines. Study of three vaccinia virus vaccinal strains and several virus lines derived from them," Vaccine 13(5): 487-493 (1995).
Lathe et al., "Tumour prevention and rejection with recombinant vaccinia," Nature 326:878-880 (1987).
Le Boeuf et al., "Synergistic interaction between oncolytic viruses augments tumor killing," Molecular Therapy: the Journal of the American Society of Gene Therapy 18:888-895 (2010).
Lin et al., "Oncolytic vaccinia virotherapy of anaplastic thyroid cancer in vivo," J. Clin. Endocrinol. Metab. 93:4403-4407 (2008).
Lin et al., "Treatment of anaplastic thyroid carcinoma in vitro with a mutant vaccinia virus," Surgery 142(6):976-83 (2007). Presented at the 28th Annual Meeting of the American Association of Endocrine Surgeons, Tuscon, Arizona, Apr. 29 to May 1, 2007.
Liu et al., "The Targeted oncolytic poxvirus JX-594 demonstrates antitumoral, antivascular, and anti-HBV activities in patients with hepatocellular carcinoma," Mol. Ther. 16(9): 1637-1642 (2008).
Loo et al., "Inhibition of cellular cytotoxicity of leukocytes for herpes simplex virus-infected cells in vitro and in vivo by intralipid," J Infect Dis. 146(1):64-70 (1982).
Mackett et al., "General method for production and selection of infectious vaccinia virus recombinants expressing foreign genes," J. Virol., 49(3): 857-864 (1984).

Magge et al., "Inhibitors of C5 complement enhance vaccinia virus oncolysis," Cancer Gene Therapy 20(6):342-350 (2013).
Malhotra et al., "Collectins, collectin receptors and the lectin pathway of complement activation," Clin Exp Immunol. 97(2):4-9 (1994).
Malmqvist, "BIACORE: an affinity biosensor system for characterization of biomolecular interactions," Biochem. Soc. Trans. 27:335-340 (1999).
Mastrangelo et al., "Intratumoral recombinant GM-CSF-encoding virus as gene therapy in patients with cutaneous melanoma," Cancer Gene Ther. 6(5):409-422 (1998).
Mayer et al., "Short-time infusion of fish oil-based lipid emulsions, approved for parenteral nutrition, reduces monocyte proinflammatory cytokine generation and adhesive interaction with endothelium in humans," J Immunol. 171(9):4837-43 (2003).
Mayford et al., "CaMKII regulates the frequency-response function of hippocampal synapses for the production of both LTD and LTP," Cell 81: 891-904 (1995).
McAneny et al., "Results of a Phase I trial of a recombinant vaccinia virus that expresses carcinoembryonic antigen in patients with advanced colorectal cancer," Ann. Surg. Oncol. 3(5): 495-500 (1996).
McCart et al., "Complex interaction between the replicating oncolytic effect and the enzyme/prodrug effect of vaccinia-mediated tumor regression," Gene Ther. 7: 1217-1223 (2000).
McCart et al., "Systemic cancer therapy with a tumor-selective vaccinia virus mutant lacking thymidine kinase and vaccinia growth factor genes," Cancer Res. 61: 8751-8757 (2001).
McLoughlin et al., "TNFerade, an adenovector carrying the transgene for human tumor necrosis factor alpha, for patients with advanced solid tumors: surgical experience and long-term follow-up," Ann. Surg. Oncol., 12:825-830 (2005).
Mikryukov et al., "Structural-functional organization of segment of vaccinia virus genome," Soviet Biotechnology (Biotekhnologiya) 4: 19-25 (1988) [English edition, corresponds to pp. 442-449 in the Russian language edition].
Mollnes et al., "Identification of a human C5 beta-chain epitope exposed in the native complement component but concealed in the SC5b-9 complex," Scand J Immunol. 28(3):307-12 (1988).
Morgan and Harris, "Complement therapeutics; history and current progress," Mol Immunol. 40(2-4): 159-70 (2003).
Morton et al., "Initial testing of the replication competent Seneca Valley virus (NTX-010) by the pediatric preclinical testing program," Pediatr Blood Cancer, 55:295-303 (2010).
Moss, "Poxvirus vectors: cytoplasmic expression of transferred genes," Curr. Opin. Genet. Dev. 3:86-90 (1993).
Msaouel et al., "Clinical testing of engineered oncolytic measles virus strains in the treatment of cancer: an overview," Curr. Opin. Mol. Ther., 11:43-53 (2009).
Needleman et al., "A general method applicable to the search for similarities in the amino acid sequences of two proteins," J. Mol. Biol. 48:443-453 (1970).
Newman et al., "Stability of undiluted and diluted vaccinia-virus vaccine, dryvax," J. Inf. Dis. 187:1319-1322 (2003).
Nunn et al., "Complement inhibitor of C5 activation from the soft tick Ornithodoros moubata," J Immunol. 174(4):2084-91 (2005).
Oertli et al., "Non-replicating recombinant vaccinia virus encoding murine B-7 molecules effective costimulation of naive CD4+ splenocytes in vitro," J. Gen. Virol. 77: 3121-3125 (1996).
Pack et al., "Improved bivalent miniantibodies, with identical avidity as whole antibodies, produced by high cell density fermentation of *Escherichia coli*," Biotechnology 11(11):1271-1276 (1993).
Parato et al., "The oncolytic poxvirus JX-594 selectively replicates in and destroys cancer cells driven by genetic pathways commonly activated in cancers," Mol. Ther., 20:749-758 (2012).
Park et al., "Use of a targeted oncolytic poxvirus, JX-594, in patients with refractory primary or metastatic liver cancer: a phase I trial," Lancet Oncol. 9(6): 533-542 (2008).
Patel et al., "A poxvirus-derived vector that directs high levels of expression of cloned genes in mammalian cells," Proc. Natl. Acad. Sci. U.S.A. 85: 9431-9435 (1988).
Paul, ed., Fundamental Immunology, 2nd ed., Raven Press, New York, pp. 332-336 (1989).

(56) References Cited

OTHER PUBLICATIONS

Pinkert et al., "An albumin enhancer located 10 kb upstream functions along with its promoter to direct efficient, liver-specific expression in transgenic mice," Genes Dev. 1: 268-276 (1987).
Plotkin, S. and W. Orenstein, editors. "Recombinant vaccinia virus vaccines," in Vaccines. 3rd edition. Philadelphia: Saunders, 4 pages (1999).
Proctor et al., "Transdermal pharmacology of small molecule cyclic C5a antagonists," Adv Exp Med Biol. 586:329-45 (2006).
Qin et al., "Cancer gene therapy using tumor cells infected with recombinant vaccinia virus expressing GM-CSF," Hum. Gene Ther. 7: 1853-1860 (1996).
Qu et al., "Recent developments in low molecular weight complement inhibitors," Mol Immunol. 47(2-3):185-95 (2009).
Racaniello et al., "Cloned poliovirus complementary DNA is infectious in mammalian cells," Science 214:916-919 (1981).
Rao et al., "Il-12 is an effective adjuvant to recombinant vaccinia virus-based tumor vaccines," J. Immunol. 156: 3357-3365 (1996).
Rich, R.L. and D.G., Myszka, "Advances in surface plasmon resonance biosensor analysis," Curr. Opin. Biotechnol 11:54 (2000), 54-61, 8 pages.
Ricklin and Lambris, "Complement-targeted therapeutics," Nat Biotechnol., 25(11):1265-75 (2007).
Ricklin and Lambris, "Compstatin: a complement inhibitor on its way to clinical application," Adv Exp Med Biol. 632:273-92 (2008).
Roth et al., "p53 as a target for cancer vaccines: recombinant canarypox virus vectors expressing p53 protect mice against lethal tumor cell challenge," Proc. Natl. Acad. Sci. U.S.A. 93: 4781-4786 (1996).
Rothschild et al., "Intravenous lipid emulsion in clinical toxicology," Scand J Trauma Resusc Emerg Med. 5;18:51 (2010), 8 pages.
Roussev et al., "Natural killer cell functional activity suppression by intravenous immunoglobulin, intralipid and soluble human leukocyte antigen-G," Am. J. Reprod. Immunol., 57(4):262-9 (2007).
Sahu et al., "Interaction of vaccinia virus complement control protein with human complement proteins: factor I-mediated degradation of C3b to iC3b1 inactivates the alternative complement pathway," J Immunol. Jun. 1; 160(11):5596-604 (1998).
Sahu et al., "Inhibition of human complement by a C3-binding peptide isolated from a phage-displayed random peptide library," J Immunol. 157(2):884-91 (1996).
Sambrook, et al., Molecular Cloning: A Laboratory Manual, 2nd Ed., Cold Spring Harbor Press (1989), 3 pages.
Scheiflinger et al., "Construction of chimeric vaccinia viruses by molecular cloning and packaging," Proc. Natl. Acad. Sci. 89:9977-9981 (1992).
Schwartz, R. and M. Dayhoff, eds., "Matrices for detecting distant relationships," in Atlas of protein sequence and structure, Chapter 23, National Biomedical Research Foundation, pp. 353-358 (1978).
Shchelkunov et al., "The gene encoding the late nonstructural 36K protein of vaccinia virus is essential for virus reproduction," Virus Res. 28: 273-283 (1993).
Shen et al., "Fighting cancer with vaccinia virus: teaching new tricks to an old dog," Mol. Ther. 11(2):180-195 (2005).
Shine, J. and L. Dalgarno, "Determinant of cistron specificity in bacterial ribosomes," Nature 254(5495):34-38 (1975).
Smith et al., "Infectious poxvirus vectors have capacity for at least 25000 base pairs of foreign DNA," Gene 25: 21-28 (1983).
Smith et al., "Oncolytic viruses as novel anticancer agents: turning one scourge against another," Exp. Opin. Invest. Drugs 9(2):311-327 (2000).
Smith et al., "Comparison of biosequences," Adv. Appl. Math. 2:482-489 (1981).
Sroller et al., "Effect of 3-beta-hydroxysteroid dehydrogenase gene deletion on virulence and immunogenicity of different vaccinia viruses and their recombinants," Arch. Virol. 143:1311-1320 (1998).
Strunk et al., "Inhibition of in vitro synthesis of the second (C2) and fourth (C4) components of complement in guinea pig peritoneal macrophages by a soybean oil emulsion," Pediatr Res. 13(3):188-93 (1978), 3 pages.
Strunk et al., "Intralipid alters macrophage membrane fatty acid composition and inhibits complement (C2) synthesis," Lipids. 18(7): 493-500 (1983).
Timiryasova et al., "Construction of recombinant vaccinia viruses using PUV-inactivated virus as a helper," BioTechniques 31:534-540 (2001).
Traktman, P., "Poxvirus DNA replication, in DNA Replication in Eukaryotic Cells (Depamphilis, D., ed.)," Cold Spring Harbor Laboratory, Cold Spring, NY, pp. 775-798 (1996).
Vidal et al., "Tissue-specific control elements of the Thy-1 gene," EMBO J. 9(3): 833-840 (1990).
Waitzberg et al., "New parenteral lipid emulsions for clinical use," JPEN J Parenter Enteral Nutr. 30(4):351-67 (2006).
Wang et al., "Oncolytic vaccinia virus GLV-1h68 strain shows enhanced replication in human breast cancer stem-like cells in comparison to breast cancer cells," J. Transl. Med. 10(1):167 (2012).
Watson et al., Molecular Biology of the Gene, 4th Edition, 1987, The Benjamin/Cummings Pub. co., p. 224, 25 pages.
Whitlow and Filpula, "Single-chain Fv proteins and their fusion proteins," Methods: A companion to methods in enzymology, 2(2): 97-105 (1991).
Yu et al. "Visualization of tumors and metastases in live animals with bacteria and vaccinia virus encoding light-emitting proteins," Nat. Biotech. 22(3): 313-320 (2004).
Yu et al., "Oncolytic vaccinia therapy of squamous cell carcinoma," Mol. Cancer 8:45 (2009), 9 pages.
Yu et al., "A Renilla luciferase-Aequorea GFP (ruc-gfp) fusion gene construct permits real-time detection of promoter activation by exogenously administered mifepristone in vivo," Mol. Genet. Genomics. 268(2):169-178 (2002).
Yu et al., "Regression of human pancreatic tumor xenografts in mice after a single systemic injection of recombinant vaccinia virus GLV-1h68," Mol. Cancer Ther. 8:141-151 (2009).
Zhang et al., "Eradication of solid human breast tumors in nude mice with an intravenously injected light emitting oncolytic vaccinia virus," Cancer Res. 67(20):10038-10046 (2007).
Zhang et al., "The highly attenuated oncolytic recombinant vaccinia virus GLV-1h68: comparative genomic features and the contribution of F14.5L inactivation," Mol. Genet. Genomics 282(4):417-435 (2009).
Zimmermann et al., "Independent regulatory elements in the nestin gene direct transgene expression to neural stem cells," Neuron 12: 11-24 (1994).
Zinoviev et al., "Identification of the gene encoding vaccinia virus immunodominant protein p35," Gene 147: 209-214 (1994).
International Search Report and Written Opinion, dated Sep. 4, 2015, in connection with International Patent Application No. PCT/US2014/073088, 19 pages.
Response, dated Dec. 3, 2015, in connection with International Patent Application No. PCT/US2014/073088, 35 pages.
Written Opinion, dated Dec. 18, 2015, in connection with International Patent Application No. PCT/US2014/073088, 9 pages.
International Preliminary Report on Patentability, dated May 4, 2016, in connection with International Patent Application No. PCT/US2014/073088, 11 pages.
Letter/Written Disclosure of the Supplemental Information Disclosure Statement for the above-referenced application, filed herewith on Oct. 15, 2018, 2 pages.
Genelux Press Release, "Genelux Initiates Two Clinical Trials of GL-ONC1 in Ovarian Cancer and Solid Organ Cancers with Leading Oncology Institutions," Published Jul. 28, 2016 [online]; Retrieved Jul. 23, 2018, from: <URL:genelux.com/wp-content/uploads/2012/04/2016.07.28-Genelux-Florida-Hospital-UCSD-Phase-1-Trials-Initiation-Release-FINAL.pdf, 3 pages.
Genelux Press Release, "Genelux Initiates Phase 2 Clinical Trial of GL-ONC1 in Recurrent Ovarian Cancer," Published Sep. 27, 2017 [online]; Retrieved Jul. 23, 2018, from: <URL:genelux.com/wp-content/uploads/2012/04/2017.09.27-Genelux-Initiates-Phase-2-Clinical-Trial-of-GL-ONC1-in-Recurrent-Ovarian-Cancer.pdf, 2 pages.
Genelux Press Release, "Genelux Announces Gynecologic Oncology Associates/Women's Cancer Research Foundation as New Site for the Ongoing Phase 2 VIRO-15 Study," Published Jan. 4, 2018

(56) References Cited

OTHER PUBLICATIONS

[online]; Retrieved Jul. 23, 2018, from: <URL:genelux.com/wp-content/uploads/2012/04/2018.01.04-Genelux-Announces-GOA-as-New-Site.pdf, 2 pages.
U.S. Appl. No. 14/638,604, filed Mar. 4, 2015, 2015/0175976, Jun. 25, 2015.
U.S. Appl. No. 13/506,369, filed Apr. 13, 2012, 2012/0308484, Dec. 6, 2012.
U.S. Appl. No. 15/331,742, filed Oct. 21, 2016, 2017/0095552, Apr. 6, 2017.
U.S. Appl. No. 15/910,525, filed Mar. 2, 2018, 2018/0195050, Jul. 12, 2018.
U.S. Appl. No. 16/020,850, filed Jun. 27, 2018.

* cited by examiner

ONCOLYTIC VIRUS ADJUNCT THERAPY WITH AGENTS THAT INCREASE VIRUS INFECTIVITY

RELATED APPLICATIONS

This application is the U.S. National Stage of International Application. No. PCT/US2014/073088, filed Dec. 31, 2014, which claims benefit of priority to U.S. provisional application Ser. No. 61/964,383, filed Jan. 02, 2014, to Aladar A. Szalay, Joseph Cappello, Nanhai G. Chen and Boris Minev, entitled "ONCOLYTIC VIRUS ADJUNCT THERAPY WITH AGENTS THAT INCREASE VIRUS INFECTIVITY." Where permitted, the subject matter of U.S. provisional application Ser. No. 61/964,383 is incorporated by reference in its entirety.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Dec. 30, 2014, is 4,434 kilobytes in size, and titled 4847SEQPC1.txt. A substitute Sequence Listing is filed electronically herewith, the contents of which are incorporated by reference in their entirety. The electronic file was created on Oct. 15, 2018, is 4,434 kilobytes in size, and is titled 4847SEQPC2.txt.

FIELD OF THE INVENTION

Provided are adjunct therapies for use in combinations or compositions with an oncolytic virus, such as a vaccinia virus, to increase infectivity of the virus. The adjunct therapies include co-administration or co-formulation of a complement inhibitor and/or a lipid emulsion composition. Also provided herein are therapeutic methods using the adjunct therapies for treatment of disease and conditions with employing the combinations, compositions and methods, such as for the treatment of hyperproliferative diseases and conditions including tumors and cancers.

BACKGROUND

Oncolytic viral therapy is effected by administering a virus that accumulates in tumor cells and replicates in the tumor cells. For example, vaccinia is an oncolytic virus that accumulates in wounds and tumors. By virtue of replication in the cells, and optional delivery of therapeutic agents, tumor cells are lysed, and the tumor shrinks and can be eliminated. Vaccinia viruses are typically administered systemically or locally. There still exists a need for improved or alternative methods of administering vaccinia viruses for various therapeutic and diagnostic applications. Accordingly, it is among the objects herein, to provide virus compositions that can be employed for diagnostic and/or therapeutic methods.

SUMMARY

Provided are methods, uses, compositions, combinations for increasing the infectivity of oncolytic viruses, such as vaccinia viruses. Infectivity is increased by treating a subject with an anti-complement molecule, particularly an antibody, such as an anti-C5 antibody and/or other complement inhibitors known to those of skill in the art. Treatment can be effected simultaneously with administration of the virus, before, after and intermittently with administration of the viruses. Uses of the antibodies for such treatment, including treatment of tumors are provided. Infectivity can be increased by pretreatment, such as incubation, of the oncolytic viruses with a biocompatible lipid as described herein. The antibodies, biocompatible lipid compositions, and viruses include any and all described herein. Both modes of increasing infectivity can be employed together. These methods also can be used and combined with other methods for increasing infectivity as well as for use with viruses that are modified to have increased infectivity, such as, but not limited to, vaccinia viruses, such as vaccinia viruses with modified to increase the production of extracellular enveloped virus (EEV) forms. These include vaccinia virus in which the A34R polypeptide is modified, such as with the mutation K151E (see, U.S. Pat. No. 8,329,164, which describes vaccinia viruses with increased infectivity by virtue of modification of the virus).

Provided are uses of anti-complement molecules, such as antibodies, for increasing infectivity of oncolytic viruses. Anti-C5 antibodies, are used to increase the infectivity of oncolytic viruses, such as vaccinia viruses. Composition and combinations and kits containing the antibodies and viruses also are provided.

In particular, provided are methods and uses of an anti-complement component 5 (C5) antibody for increasing infectivity of an oncolytic virus. Anti-C5 antibodies, include, for example, eculizumab, pexelizumab, TSA12/22 or MB12/122, and variants thereof that bind to C5. The antibodies for all methods and uses provided herein can be full-length antibodies or binding fragments thereof, such as Fabs and single chain antibodies. The antibodies and oncolytic virus can be provided in separate compositions or in a single composition. The antibodies increase the effectiveness of the oncolytic virus, such as by increasing the infectivity of the virus. Infectivity can be assessed by any suitable method, including measuring titer of the virus in a body fluid, such as blood or serum. The antibody and virus can be administered separately, in the same composition, sequentially or intermittently or in any suitable regimen. The antibody can be administered before the virus is administered or intermittently therewith or after the virus is administered. The oncolytic virus can be pretreated with a lipid emulsion containing a biocompatible lipid that is comprised of fatty acids and/or fatty acid derivatives. The lipid emulsion is as described herein and comprises a biocompatible lipid that is comprised of fatty acids and/or fatty acid derivatives, wherein the composition is an emulsion. Also provided are the compositions containing an oncolytic virus; and an anti-complement component 5 (C5) antibody, such as, but not limited to, eculizumab, pexelizumab, TSA12/22 or MB12/122, and variants thereof that bind to C5 and antigen binding fragments thereof. The composition containing the antibody and the virus can also include the biocompatible lipid component that is comprised of fatty acids and/or fatty acid derivatives.

In general, any therapeutic virus can be used in the methods, uses, compositions and combinations provided herein. These include oncolytic viruses, and their use for treatment of tumors, as well as diagnosis and monitoring treatment. The viruses include any described herein, including, but not limited to, the LIVP strains of vaccinia virus described herein and known to those of skill in the art such as other strains of vaccinia virus, herpes simplex viruses, oncolytic adenoviruses, measles virus, reoviruses and others.

Provided are compositions that contain therapeutic viruses, particularly therapeutic oncolytic viruses, and methods of treatment by administering or using the compositions. The compositions, which contain a biocompatible lipid and/or lipid-treated virus, typically are emulsions. The compositions and/or methods provide the viruses whereby the infectivity of the virus is increased. It is increased such by virtue of increased half-life and/or changes to the virus that protect it from the immune system or enhance interaction and/or uptake by target cells, such as cells that are the target of therapy with therapeutic oncolytic viruses. Target cells include, but are not limited to, tumor cells, circulating tumor cells, metastasizing tumor cells, cells in wounded or inflamed tissue. Target cells include cells in subjects to whom the composition is administered and also include, in vitro cell lines, and ex vivo cells, including cells for cell therapy, stem cells and other such cells.

Therapeutic oncolytic viruses include, but are not limited to, vaccinia viruses, measles viruses, oncolytic adenoviruses, vesicular stomatitis virus, herpes simplex viruses and other oncolytic viruses. Exemplary of such viruses are LIVP, Wyeth and Copenhagen strain vaccinia virus, such as JX594 and derivatives thereof and the GLV-ONC1 (GLV-1h68) and derivatives thereof, and clonal strains of LIVP and Copenhagen. Other exemplary viruses include the Onyx strains of adenovirus. By increasing infectivity, the amount of virus that infects target cells is effectively increased, and it is increased without increasing dosage.

Provided are compositions that contain a therapeutic oncolytic virus, or mixture thereof, and a biocompatible lipid component. Such compositions generally are emulsions. Also provided are lipid-treated therapeutic oncolytic viruses. The lipid-treated viruses include viruses that have been contacted with a composition containing a biocompatible lipid, and, are formulated for systemic administration or local administration, such as by parenteral administration, including intravenous administration, and by peritoneal administration.

Lipids include any known to those of skill in the art that can be administered systemically. These include vegetable oils, such as soybean oil, which contain a mixture of various lipids. The lipid component includes, but is not limited to, fatty acids and fatty acid derivatives, such as triglycerides, diglycerides, monoglycerides, phospholipids, and mixtures thereof. The triglycerides and the triglycerides are long-chain triglycerides (LCTs), medium-chain triglycerides (MCTs) and mixtures thereof. Exemplary long-chain triglycerides are linoleate, oleate, palmitate, linolenate, stearate and mixtures thereof. Medium-chain triglycerides include caprylic acid and capric acid.

The lipids can be provided as oils, including plant oil, vegetable oil, animal oil, fish oil, mineral oil, chemically synthesized oil and mixtures thereof. Plant and vegetable oils include soybean oil, cottonseed oil, safflower oil, corn oil, coconut oil, sesame oil, peanut oil, olive oil, castor oil and mixtures thereof.

Exemplary compositions are emulsions that contain: a biocompatible lipid component in an amount between 0.001% and 50%, inclusive, such at least 0.0002%, 0.2%, 2% and 40%-50%, inclusive, by weight, of the lipid emulsion; and optionally an emulsifier in an amount between 0.2% and 5%, inclusive, by weight, of the lipid emulsion; and the remainder an aqueous phase in an amount between 50% and 98%, inclusive, by weight, of the lipid emulsion.

Emulsifiers are biocompatible and can be naturally-occurring emulsifier or synthetic emulsifiers, such as phospholipid derived from an egg or soy source, including, but not limited to, egg yolk phospholipids, hydrogenated egg yolk phospholipids, soybean phospholipids, hydrogenated soybean phospholipids and mixtures thereof. Exemplary of emulsifiers is lecithin. The concentration of the emulsifier as a wt % of the composition is between 0.0002% and 5%, 0.0002% and 2%, 0.0002% and 1%, 0.0002% and 0.2%, 0.0002% and 0.02%, 0.0002% and 0.002%, 0.002% and 2%, 0.002% and 1%, 0.002% and 0.2%, 0.002% and 0.02%, 0.02% and 2%, 0.02% and 1%, 0.02% and 0.2%, 0.2% and 5%, 0.2% and 2%, or 2% and 5%, each inclusive. Generally the concentration of the emulsifier is less than 2% wt % of the composition.

The aqueous phase typically is water or isotonic aqueous medium and contains the virus, particularly in a multiple dosage or single dosage concentration or amounts.

Other components in the compositions, including tonicity modifiers, pH adjusters and other such components. For example, the compositions can contain a tonicity modifier, such as glycerin, in an amount between 0.00002%, 00001%, 0001%, 0.2% and 5%, inclusive, by weight of the emulsion, generally less than 2%. Exemplary tonicity modifiers include glycerin, sodium chloride, potassium chloride, mannitol, sucrose, lactose, fructose, maltose, dextrose, dextrose anhydrous, xylitol, sorbitol, propylene glycol, polyoxyethylated hydrocarbons, and $C_6$-$C_{20}$ saturated and unsaturated aliphatic acids.

Tonicity modifiers include, but are not limited to, glycerin, sodium chloride, potassium chloride, mannitol, sucrose, lactose, fructose, maltose, dextrose, dextrose anhydrous, xylitol, sorbitol, propylene glycol, polyoxyethylated hydrocarbons, and $C_6$-$C_{20}$ saturated or unsaturated aliphatic acids. Concentrations of the tonicity modifier as a wt % of the composition is between 0.0002% and 5%, 0.0002% and 2%, 0.0002% and 1%, 0.0002% and 0.2%, 0.0002% and 0.02%, 0.0002% and 0.002%, 0.002% and 2%, 0.002% and 1%, 0.002% and 0.2%, 0.002% and 0.02%, 0.02% and 2%, 0.02% and 1%, 0.02% and 0.2%, 0.2% and 5%, 0.2% and 2%, or 2% and 5%, each inclusive.

The compositions contain an aqueous medium such as isotonic solutions selected from among Ringer's solution, Ringer's lactate solution, phosphate-buffered saline (PBS), TRIS-buffered saline (TBS), Hank's balanced salt solution (HBSS), Earle's balanced salt solution (EBSS), standard saline citrate (SSC), HEPES-buffered saline (HBS), Grey's balanced salt solution (GBSS), and normal saline (NaCl). The concentration of the aqueous phase can be between 40% and 99.9%, 50 and 99%, 60% and 99%, 70% and 99%, 80% and 99%, 90% and 99%, 70% and 95% or 80% and 90%, each inclusive.

Other exemplary compositions include lipid emulsions that contain: a biocompatible lipid component in a concentration between 10% and 30%, inclusive, by weight, of the lipid emulsion, wherein the biocompatible lipid component is selected from among soybean oil, safflower oil, olive oil, and mixtures thereof; an egg yolk phospholipid(s) in a concentration that is at or about 1.2% by weight, of the lipid emulsion; glycerin in a concentration between 2.25% and 2.5%, inclusive, by weight, of the lipid emulsion; and water in a concentration that is between 60% and 90%, inclusive, by weight, of the lipid emulsion. For example, the liquid emulsion comprises: 10%, 20% or 30% by weight soybean oil; 1.2% by weight egg yolk phospholipid; and 2.5% by weight glycerin.

To prepare the lipid-treated virus, the virus is contacted with the lipid, such as by incubation. Incubation is effected for a time sufficient to increase infectivity of the virus, such as for example, at least 5 minutes, 10 minutes, 15 minutes, 30 minutes, such as 30 minutes to 12 hours, 30 minutes to 6 hours, 30 minutes to 4 hours, 30 minutes to 2 hours, 30 minutes to 1 hours, 1 hour to 12 hours, 1 hour to 6 hours, 1 hour to 4 hours, 1 hour to 2 hours, 2 hours to 12 hours, 2 hours to 6 hours, 2 hours to 4 hours, 4 hours to 12 hours, 4 hours to 6 hours, or 6 hours to 12 hours. Incubation can be effected at any temperature at which the virus remains infective, such as, but are limited to, 0° to 42° C., inclusive, including for example, 32° C. to 40-45° C., at or about 35° C. to 42° C., typically at least 37° C.

The concentration of the biocompatible lipid component can be at a weight percentage (wt %) of the composition between 0.001% and 40%, inclusive, such as for example, 0.001% and 20%, 0.001% and 10%, 0.001% and 5%, 0.001% and 2%, 0.001% and 1%, 0.001% and 0.01%, 0.01% and 20%, 0.01% and 10%, 0.01% and 5%, 0.01% and 2%, 0.01% and 1%, 0.01% and 0.1%, 0.1% and 20%, 0.1% and 10%, 0.1% and 5%, 0.1% and 2%, 0.1% and 1%, 0.5% and 20%, 0.5% and 10%, 0.5% and 5%, 0.5% and 2%, 0.5% and 1%, 2% and 20%, 2% and 10%, 5% and 20%, 5% and 10%, or 10% and 20%, each inclusive.

Oncolytic viruses, as discussed above, include any therapeutic oncolytic virus, such, but not limited to, a Newcastle Disease virus, parvovirus, vaccinia virus, measles virus, reovirus, vesicular stomatitis virus (VSV), oncolytic adenoviruses, adeno-associated virus, poliovirus, herpes viruses, sindbis virus and seneca valley virus, and derivatives that that are modified to contain heterologous nucleic acid, including heterologous nucleic acid encoding a heterologous gene product.

Vaccinia viruses and related viruses include strains selected from among Lister, Western Reserve (WR), Copenhagen (Cop), Bern, Paris, Tashkent, Tian Tan, Wyeth (DRYVAX), IHD-J, IHD-W, Brighton, Ankara, CVA382, Modified Vaccinia Ankara (MVA), Dairen I, LC16m8, LC16M0, LIVP, ACAM2000, WR 65-16, Connaught, New York City Board of Health (NYCBH), EM-63 and NYVAC strain. Included are clonal strains of each as well as those containing heterologous nucleic acid.

Exemplary viruses are Copenhagen and Lister strains, such as LIVP, including clonal strains thereof. Heterologous nucleic acid includes that encoding a therapeutic gene product and/or a reporter gene and/or promoter or regulatory region. Heterologous gene product is selected from among an anticancer agent, an antimetastatic agent, an antiangiogenic agent, an immunomodulatory molecule, an antigen, a cell matrix degradative gene, genes for tissue regeneration and reprogramming human somatic cells to pluripotency, enzymes that modify a substrate to produce a detectable product or signal or are detectable by antibodies, proteins that can bind a contrasting agent, genes for optical imaging or detection, genes for PET imaging and genes for MRI imaging. For example, the heterologous gene product is a therapeutic agent selected from among a hormone, a growth factor, a cytokine, a chemokine, a costimulatory molecule, a ribozyme, a transporter protein, a single chain antibody, such an anti-VEGF or anti-VEGFR, or anti-EGFR antibody, an antisense or ds RNA or other RNA product, a prodrug converting enzyme, an siRNA, a microRNA, a toxin, an antitumor oligopeptide, a mitosis inhibitor protein, an antimitotic oligopeptide, an anti-cancer polypeptide antibiotic, an angiogenesis inhibitor, a tumor suppressor, a cytotoxic protein, a cytostatic protein and a tissue factor.

The oncolytic viruses are present in the composition in multidose and single dosage amounts, including, but not limited to between or between about $1\times10^5$ and $1\times10^{12}$ pfu, $1\times10^6$ to $1\times10^{10}$ pfu, or $1\times10^7$ to $1\times10^{10}$ pfu, each inclusive, such as at least or about at least or $1\times10^6$, $1\times10^7$, $1\times10^8$, $1\times10^9$, $2\times10^9$, $3\times10^9$, $4\times10^9$, $5\times10^9$ pfu, or $1\times10^{10}$ pfu.

Another exemplary compositions contains an oncolytic virus in an amount that is between or between about $1\times10^6$ to $1\times10^{10}$ pfu, inclusive; a biocompatible lipid component as a wt % of the composition of less than 10%; an emulsifier as a wt % of the composition of less than 2%; a tonicity modifier as a wt % of the composition of less than 2%; and an aqueous phase as a wt % of the composition that is greater than 85%. The virus typically is provided as part of the aqueous phase.

The volume of the composition can be any volume, and can be for single or multiple dosage administration, including, but not limited to, from or from about 0.01 mL to 100 mL, 0.1 mL to 100 mL, 1 mL to 100 mL, 10 mL to 100 mL, 0.01 mL to 10 mL, 0.1 mL to 10 mL, 1 mL to 10 mL, 0.02 mL to 20 mL, 0.05 mL to 5 mL, 0.5 mL to 50 mL, or 0.5 mL to 5 mL, each inclusive.

The infectivity of the virus can be manifested, such as by increased titer or half-life of the oncolytic virus when exposed to a bodily fluid, such as blood or serum. Infectivity can be increased by any amount, including, but not limited to, at least 1.1-fold, 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold, 6-fold, 7-fold, 8-fold, 9-fold, or 10-fold.

The compositions can be formulated for direct administration. They can be formulated for local or systemic injection, such as intravenous administration.

Also provided are combinations that include two compositions: a first composition comprising an oncolytic virus; and a second composition comprising a lipid. Typically the second composition is an emulsion. It can be provided as a lipid alone or a lipid with an emulsifier. In such cases the lipid component is up to 100% of the composition, and with the optional emulsifier in an amount sufficient to aid in emulsifying the lipid with the virus composition, which typically is an aqueous compositions.

The compositions can be formulated separately, or they can be combined. They can be administered separately or combined or administered sequentially. The oncolytic virus is any oncolytic virus, as described above. The lipid, which generally is provided as an emulsion composition contains a biocompatible lipid component and optionally an emulsifier. The lipid component is present in any suitable concentration, typically from at least about or at 1% to 50%, such as, but not limited to, between 2% and 40%, 5% and 40%, or 10% and 30%, each inclusive. wherein the lipid component is comprised of fatty acids and/or fatty acid derivatives.

The lipid component can be any lipid or oil, such as soybean oil, which contains a mixture of various lipid components. As described above, the lipid component can be any lipid or mixture or source thereof known to those of skill in the art that can be administered systemically. These include vegetable oils, such as soybean oil, which contain a mixture of various lipids. The lipid component includes, but is not limited to, fatty acids and fatty acid derivatives, such as triglycerides, diglycerides, monoglycerides, phospholipids, and mixtures thereof. The triglycerides and the triglycerides are long-chain triglycerides (LCTs), medium-chain triglycerides (MCTs) and mixtures thereof. Exemplary long-chain triglycerides are linoleate, oleate, palmitate, linolenate, stearate and mixtures thereof. Medium-chain triglycerides include caprylic acid and capric acid.

The lipids can be provided as oils, including plant oil, vegetable oil, animal oil, fish oil, mineral oil, chemically synthesized oil and mixtures thereof. Plant and vegetable oils include soybean oil, cottonseed oil, safflower oil, corn oil, coconut oil, sesame oil, peanut oil, olive oil, castor oil and mixtures thereof.

Other exemplary compositions include lipid emulsions that contain: a biocompatible lipid component in a concentration between 1-50%, such as 10% and 30%, inclusive, by weight, of the lipid emulsion, wherein the biocompatible lipid component is selected from among soybean oil, safflower oil, olive oil, and mixtures thereof; an egg yolk phospholipid(s) in a concentration that is at or about 1.2% by weight, of the lipid emulsion; glycerin in a concentration between 2.25% and 2.5%, inclusive, by weight, of the lipid emulsion; and water in a concentration that is between 60% and 90%, inclusive, by weight, of the lipid emulsion. For example, the liquid emulsion comprises: 10%, 20% or 30% by weight soybean oil; 1.2% by weight egg yolk phospholipid; and 2.5% by weight glycerin.

Exemplary compositions are emulsions that contain: a biocompatible lipid component in an amount between 0.001% and 50%, inclusive, such at least 0.0002%, 0.2%, 2% and 40%-50%, inclusive, by weight, of the lipid emulsion; and optionally an emulsifier in an amount between 0.2% and 5%, inclusive, by weight, of the lipid emulsion; and the remainder an aqueous phase in an amount between 50% and 98%, inclusive, by weight, of the lipid emulsion. Emulsifiers are biocompatible and can be naturally-occurring emulsifier or synthetic emulsifiers, such as phospholipid derived from an egg or soy source, including, but not limited to, egg yolk phospholipids, hydrogenated egg yolk phospholipids, soybean phospholipids, hydrogenated soybean phospholipids and mixtures thereof. Exemplary of emulsifiers is lecithin. The concentration of the emulsifier as a wt % of the composition is between 0.0002% and 5%, 0.0002% and 2%, 0.0002% and 1%, 0.0002% and 0.2%, 0.0002% and 0.02%, 0.0002% and 0.002%, 0.002% and 2%, 0.002% and 1%, 0.002% and 0.2%, 0.002% and 0.02%, 0.02% and 2%, 0.02% and 1%, 0.02% and 0.2%, 0.2% and 5%, 0.2% and 2%, or 2% and 5%, each inclusive. Generally the concentration of the emulsifier is less than 2% wt % of the composition.

Other components in the compositions, include tonicity modifiers, pH adjusters and other such components. For example, the compositions can contain a tonicity modifier, such as glycerin, in an amount between 0.00002%, 00001%, 0001%, 0.2% and 5%, inclusive, by weight of the emulsion, generally less than 2%. Exemplary tonicity modifiers include glycerin, sodium chloride, potassium chloride, mannitol, sucrose, lactose, fructose, maltose, dextrose, dextrose anhydrous, xylitol, sorbitol, propylene glycol, polyoxyethylated hydrocarbons, and $C_6$-$C_{20}$ saturated and unsaturated aliphatic acids.

Tonicity modifiers include, but are not limited to, glycerin, sodium chloride, potassium chloride, mannitol, sucrose, lactose, fructose, maltose, dextrose, dextrose anhydrous, xylitol, sorbitol, propylene glycol, polyoxyethylated hydrocarbons, and $C_6$-$C_{20}$ saturated or unsaturated aliphatic acids. Concentrations of the tonicity modifier as a wt % of the composition is between 0.0002% and 5%, 0.0002% and 2%, 0.0002% and 1%, 0.0002% and 0.2%, 0.0002% and 0.02%, 0.0002% and 0.002%, 0.002% and 2%, 0.002% and 1%, 0.002% and 0.2%, 0.002% and 0.02%, 0.02% and 2%, 0.02% and 1%, 0.02% and 0.2%, 0.2% and 5%, 0.2% and 2%, or 2% and 5%, each inclusive.

The compositions contain an aqueous medium such as isotonic solutions selected from among Ringer's solution, Ringer's lactate solution, phosphate-buffered saline (PBS), TRIS-buffered saline (TBS), Hank's balanced salt solution (HBSS), Earle's balanced salt solution (EBSS), standard saline citrate (SSC), HEPES-buffered saline (HBS), Grey's balanced salt solution (GBSS), and normal saline (NaCl). The concentration of the aqueous phase can be between 40% and 99.9%, 50 and 99%, 60% and 99%, 70% and 99%, 80% and 99%, 90% and 99%, 70% and 95% or 80% and 90%, each inclusive.

The lipid compositions optionally include an emulsifier, such as a lecithin or other phospholipid. Emulsifiers are biocompatible and can be naturally-occurring emulsifiers or synthetic emulsifiers, such as phospholipid derived from an egg or soy source, including, but not limited to, egg yolk phospholipids, hydrogenated egg yolk phospholipids, soybean phospholipids, hydrogenated soybean phospholipids and mixtures thereof. Exemplary of emulsifiers is lecithin. The concentration of the emulsifier as a wt % of the composition is between 0.0002% and 5%, 0.0002% and 2%, 0.0002% and 1%, 0.0002% and 0.2%, 0.0002% and 0.02%, 0.0002% and 0.002%, 0.002% and 2%, 0.002% and 1%, 0.002% and 0.2%, 0.002% and 0.02%, 0.02% and 2%, 0.02% and 1%, 0.02% and 0.2%, 0.2% and 5%, 0.2% and 2%, or 2% and 5%, each inclusive. Generally the concentration of the emulsifier is less than 2% wt % of the composition.

The lipid composition in the combination typically is provided as an emulsion with an aqueous phase that is water or an isotonic composition. The concentration of the aqueous phase can be any amount, depending upon how much lipid the composition provides. Generally in the aqueous phase, when present, constitutes at least 1%, 2%, 5%, 10%, 20%, 30%, 40%, 50% or more of the emulsions, such as between 50% and 98%, 60% and 90%, or 65% and 80%, each inclusive. The emulsion compositions can include tonicity modifiers as discussed above in any suitable amount for adjusting osmolality of the resulting composition, such as, as a weight percentage of the lipid emulsion, between 0.1 to 0.2% and 5%, 0.5% and 4%, or 1% and 3%, each inclusive.

Tonicity modifiers for all embodiments herein can be selected from among glycerin, sodium chloride, potassium chloride, mannitol, sucrose, lactose, fructose, maltose, dextrose, dextrose anhydrous, xylitol, sorbitol, propylene glycol, polyoxyethylated hydrocarbons, and $C_6$-$C_{20}$ saturated or unsaturated aliphatic acids. The lipid emulsions herein for the combination and other embodiments can be formulated for any suitable route of administration, including local, such as peritoneal administration, and systemic administration, such as intravenous, such as an intravenous liquid emulsion (ILE).

Exemplary of the lipid compositions are those that are a lipid component alone or a lipid component with the emulsifier, or an emulsion. Exemplary of lipid emulsions are those that contain: a biocompatible lipid component in a concentration between 10% and 30%, inclusive, by weight, of the lipid emulsion, wherein the biocompatible lipid component is selected from among soybean oil, safflower oil, olive oil, and mixtures thereof; an egg yolk phospholipid(s) in a concentration that is at or about 1.2% by weight, of the lipid emulsion; glycerin in a concentration between 2.25% and 2.5%, inclusive, by weight, of the lipid emulsion; and water (or an aqueous isotonic solution) in a concentration that is between 60% and 90%, inclusive, by weight, of the lipid emulsion. For example, the liquid emulsion contains: up to 10%, 20% or 30% by weight soybean oil; 1-2%, such as 1.2% by weight egg yolk phospholipid; and 1%-5%, such as 2.5% by weight glycerin.

The combinations include compositions of any virus, particularly oncolytic viruses. As discussed above, oncolytic include any oncolytic virus, such, but not limited to, a Newcastle Disease virus, parvovirus, vaccinia virus, measles virus, reovirus, vesicular stomatitis virus (VSV), oncolytic adenoviruses, adeno-associated virus, poliovirus, herpes viruses, sindbis virus and seneca valley virus, and derivatives that that are modified to contain heterologous nucleic acid, including heterologous nucleic acid encoding a heterologous gene product.

Vaccinia viruses and related viruses include strains selected from among Lister, Western Reserve (WR), Copenhagen (Cop), Bern, Paris, Tashkent, Tian Tan, Wyeth (DRY-VAX), IHD-J, IHD-W, Brighton, Ankara, CVA382, Modified Vaccinia Ankara (MVA), Dairen I, LC16m8, LC16M0, LIVP, ACAM2000, WR 65-16, Connaught, New York City Board of Health (NYCBH), EM-63 and NYVAC strain. Included are clonal strains of each as well as those containing heterologous nucleic acid.

Exemplary viruses are Copenhagen and Lister strains, such as LIVP, including clonal strains thereof. Heterologous nucleic acid includes that encoding a therapeutic gene product and/or a reporter gene and/or promoter or regulatory region. Heterologous gene product is selected from among an anticancer agent, an antimetastatic agent, an antiangiogenic agent, an immunomodulatory molecule, an antigen, a cell matrix degradative gene, genes for tissue regeneration and reprogramming human somatic cells to pluripotency, enzymes that modify a substrate to produce a detectable product or signal or are detectable by antibodies, proteins that can bind a contrasting agent, genes for optical imaging or detection, genes for PET imaging and genes for MRI imaging. For example, the heterologous gene product is a therapeutic agent selected from among a hormone, a growth factor, a cytokine, a chemokine, a costimulatory molecule, a ribozyme, a transporter protein, a single chain antibody, such an anti-VEGF or anti-VEGFR, or anti-EGFR antibody, an antisense or ds RNA or other RNA product, a prodrug converting enzyme, an siRNA, a microRNA, a toxin, an antitumor oligopeptide, a mitosis inhibitor protein, an antimitotic oligopeptide, an anti-cancer polypeptide antibiotic, an angiogenesis inhibitor, a tumor suppressor, a cytotoxic protein, a cytostatic protein and a tissue factor.

The composition containing virus contains any concentration of virus, since dosage can be selected by volume administered or diluted. Concentrations are as discussed above with respect to the compositions above.

The oncolytic viruses are present in the composition in multidose and single dosage amounts, including, but not limited to between or between about $1\times10^5$ and $1\times10^{12}$ pfu, $1\times10^6$ to $1\times10^{10}$ pfu, or $1\times10^7$ to $1\times10^{10}$ pfu, each inclusive, such as at least or about at least or $1\times10^6$, $1\times10^7$, $1\times10^8$, $1\times10^9$, $2\times10^9$, $3\times10^9$, $4\times10^9$, $5\times10^9$ pfu, or $1\times10^{10}$ pfu.

Another exemplary compositions contains an oncolytic virus in an amount that is between or between about $1\times10^6$ to $1\times10^{10}$ pfu, inclusive; a biocompatible lipid component as a wt % of the composition of less than 10%; an emulsifier as a wt % of the composition of less than 2%; a tonicity modifier as a wt % of the composition of less than 2%; and an aqueous phase as a wt % of the composition that is greater than 85%. The virus typically is provided as part of the aqueous phase.

The volume of the composition can be any volume, and can be for single or multiple dosage administration, including, but not limited to, from or from about 0.01 mL to 100 mL, 0.1 mL to 100 mL, 1 mL to 100 mL, 10 mL to 100 mL, 0.01 mL to 10 mL, 0.1 mL to 10 mL, 1 mL to 10 mL, 0.02 mL to 20 mL, 0.05 mL to 5 mL, 0.5 mL to 50 mL, or 0.5 mL to 5 mL, each inclusive.

The combinations can also include additional compositions, and are additional agents in one or both of the compositions, such as another active agent, such as an anti-cancer compound or therapeutic agent or another different oncolytic virus, and/or a diagnostic agent. Exemplary of such agents are additional active agents selected from among a therapeutic compound, an agent that increases virus infectivity, a therapeutic or diagnostic virus, an antiviral or chemotherapeutic agent, or an agent or compound for modulation of gene expression of endogenous or heterologous genes encoded by the virus. Therapeutic compounds include those selected from among a cytokine, growth factor, photosensitizing agent, radionuclide, toxin, siRNA molecule, enzyme/prodrug pair, anti-metabolite, signaling modulator, anti-cancer antibiotic, anti-cancer antibody, angiogenesis inhibitor, chemotherapeutic compound, antimetastatic compound or a combination of any thereof.

Also provided are combinations of the compositions that contain the virus and lipid as one compositions, and a second compositions containing an additional active agent such as, but not limited to a therapeutic compound, an agent that increases virus infectivity, a therapeutic or diagnostic virus, an antiviral or chemotherapeutic agent, or an agent or compound for modulation of gene expression of endogenous or heterologous genes encoded by the virus. Additional active agents include anti-cancer agents, and also agents that modulate or alter or improve properties of the virus. Therapeutic compounds include, for example, any selected from among a cytokine, growth factor, photosensitizing agent, radionuclide, toxin, siRNA molecule, enzyme/prodrug pair, anti-metabolite, signaling modulator, anti-cancer antibiotic, anti-cancer antibody, angiogenesis inhibitor, chemotherapeutic compound, antimetastatic compound and a combination of any thereof.

In particular the additional agent for inclusion in the combination and also in any composition provided herein or as part of any combination provided herein, an agent that modulates or alters or improves a property of the virus, such as an agent that increases infectivity of the virus. These include agents that alter the immune response to the virus so that less is cleared upon administration. Additional agents include complement inhibitors, such as any agent that inhibits complement activation or the activity of any protein in a complement pathway, such as, inhibition of the activity of any of complement proteins C1, C2, C3, C4, C5, C5a, C5aR, C3aR, Factor B, Factor P, C1q and MBP. For example C5, refers to component 5 (C5) of complement, Such agents are known to those of skill in the art, and include, for example, antibodies specific for one or more of these proteins. Exemplary inhibitors include, for example, cobra venom factor (CVF), heparin, TA 106, TNX-234, anti-properdin, C1-INH, a compstatin or derivative or analog thereof, soluble CR1, K76COOH, eculizumab, pexelizumab, TSA12/22, MSA12/22, ARC 1005, TNX-558, NOX-D19, PMX-53, PMX-201, PMX-205, neutrazumab, and variants, analogs or derivatives thereof that inhibit a complement activity.

For example, inhibitors include complement C5 inhibitions, such as anti-C5 antibodies. These include any known to those of skill in the art, such as eculizumab, pexelizumab, TSA12/22 or MB12/122, or a variant thereof.

Provided are combinations containing a virus, particularly an oncolytic virus; and an complement inhibitor, such as an anti-C5 antibody. The virus can be provided as a composition, including as a lipid emulsion as described above. The virus is typically an oncolytic virus, such as any described herein, including, but not limited to, a Newcastle Disease virus, parvovirus, vaccinia virus, measles virus, reovirus, vesicular stomatitis virus (VSV), oncolytic adenoviruses, adeno-associated virus, poliovirus, herpes viruses, sindbis virus and seneca valley virus, derivatives of any of these virus modified to contain nucleic acid encoding a heterologous nucleic acid, such as encoding a gene product.

Oncolytic viruses, as discussed above, include any oncolytic virus, such, but not limited to, a Newcastle Disease virus, parvovirus, vaccinia virus, measles virus, reovirus, vesicular stomatitis virus (VSV), oncolytic adenoviruses, adeno-associated virus, poliovirus, herpes viruses, sindbis virus and seneca valley virus, and derivatives that are modified to contain heterologous nucleic acid, including heterologous nucleic acid encoding a heterologous gene product.

Vaccinia viruses and related viruses include strains selected from among Lister, Western Reserve (WR), Copenhagen (Cop), Bern, Paris, Tashkent, Tian Tan, Wyeth (DRY-VAX), IHD-J, IHD-W, Brighton, Ankara, CVA382, Modified Vaccinia Ankara (MVA), Dairen I, LC16m8, LC16M0, LIVP, ACAM2000, WR 65-16, Connaught, New York City Board of Health (NYCBH), EM-63 and NYVAC strain. Included are clonal strains of each as well as those containing heterologous nucleic acid.

Exemplary viruses are Copenhagen and Lister strains, such as LIVP, including clonal strains thereof. Heterologous nucleic acid includes that encoding a therapeutic gene product and/or a reporter gene and/or promoter or regulatory region. Heterologous gene product is selected from among an anticancer agent, an antimetastatic agent, an antiangiogenic agent, an immunomodulatory molecule, an antigen, a cell matrix degradative gene, genes for tissue regeneration and reprogramming human somatic cells to pluripotency, enzymes that modify a substrate to produce a detectable product or signal or are detectable by antibodies, proteins that can bind a contrasting agent, genes for optical imaging or detection, genes for PET imaging and genes for MRI imaging. For example, the heterologous gene product is a therapeutic agent selected from among a hormone, a growth factor, a cytokine, a chemokine, a costimulatory molecule, a ribozyme, a transporter protein, a single chain antibody, such an anti-VEGF or anti-VEGFR, or anti-EGFR antibody, an antisense or ds RNA or other RNA product, a prodrug converting enzyme, an siRNA, a microRNA, a toxin, an antitumor oligopeptide, a mitosis inhibitor protein, an antimitotic oligopeptide, an anti-cancer polypeptide antibiotic, an angiogenesis inhibitor, a tumor suppressor, a cytotoxic protein, a cytostatic protein and a tissue factor.

The oncolytic viruses are present in the composition in multidose and single dosage amounts, including, but not limited to between or between about $1 \times 10^5$ and $1 \times 10^{12}$ pfu, $1 \times 10^6$ to $1 \times 10^{10}$ pfu, or $1 \times 10^7$ to $1 \times 10^{10}$ pfu, each inclusive, such as at least or about at least or $1 \times 10^6$, $1 \times 10^7$, $1 \times 10^8$, $1 \times 10^9$, $2 \times 10^9$, $3 \times 10^9$, $4 \times 10^9$, $5 \times 10^9$ pfu, or $1 \times 10^{10}$ pfu.

Another exemplary compositions contains an oncolytic virus in an amount that is between or between about $1 \times 10^6$ to $1 \times 10^{10}$ pfu, inclusive; a biocompatible lipid component as a wt % of the composition of less than 10%; an emulsifier as a wt % of the composition of less than 2%; a tonicity modifier as a wt % of the composition of less than 2%; and an aqueous phase as a wt % of the composition that is greater than 85%. The virus typically is provided as part of the aqueous phase.

The volume of the composition can be any volume, and can be for single or multiple dosage administration, including, but not limited to, from or from about 0.01 mL to 100 mL, 0.1 mL to 100 mL, 1 mL to 100 mL, 10 mL to 100 mL, 0.01 mL to 10 mL, 0.1 mL to 10 mL, 1 mL to 10 mL, 0.02 mL to 20 mL, 0.05 mL to 5 mL, 0.5 mL to 50 mL, or 0.5 mL to 5 mL, each inclusive.

The infectivity of the virus can be manifested, such as by increased titer or half-life of the oncolytic virus when exposed to a bodily fluid, such as blood or serum. Infectivity can be increased by any amount, including, but not limited to, at least 1.1-fold, 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold, 6-fold, 7-fold, 8-fold, 9-fold, or 10-fold.

The compositions can be formulated for direct administration. They can be formulated for local or systemic injection, such as intravenous administration.

The concentration of anti-C5 antibody is one that selectively or specifically binds to C5, such as eculizumab. It can have an affinity sufficient to inhibit activity of a C5 protein, such affinities generally range from at least $10^{-6}$M, such as having a dissociation constant of less than $10^{-6}$, $10^{-7}$, $10^{-8}$, $10^{-9}$, $10^{-10}$, $10^{-11}$, or $10^{-12}$M. The antibody can be one that specifically or selectively binds the alpha chain of C5. Also included are anti-C5 antibodies that specifically or selectively bind to the beta chain of C5. Anti-C5 antibodies, include any known to those of skill in the art and include, but are not limited to, eculizumab, pexelizumab, TSA12/22 or MB12/122 and variants of any of these antibodies that retain the ability to specifically or selectively bind to C5.

The amount of the anti-C5 antibody in the compositions and combinations herein is one that increases the infectivity of the virus for pre-treatment or is suitable to administer to a subject to increase infectivity of the virus by any mechanism. Concentrations include, but are not limited to, 1 mg to 5000 mg, 10 mg to 5000 mg, 100 mg to 5000 mg, 100 mg to 2500 mg, 100 mg to 1000 mg, 100 mg to 500 mg, 500 mg to 5000 mg, 500 mg to 2500 mg, 500 mg to 1000 mg, 1000 mg to 2500 mg, 2000 mg to 5000 mg or 1500 mg to 2500 mg, each inclusive, such as at least or about at least or about 100 mg, 200 mg, 300 mg, 400 mg, 500 mg, 600 mg, 700 mg, 800 mg, 900 mg or 1000 mg. The volume of the composition is any suitable or convenient volume.

The compositions containing the virus can be any suitable volume, and include, but are not limited to, from about 0.01 mL to 100 mL, 0.1 mL to 100 mL, 1 mL to 100 mL, 10 mL to 100 mL, 0.01 mL to 10 mL, 0.1 mL to 10 mL, 1 mL to 10 mL, 0.02 mL to 20 mL, 0.05 mL to 5 mL, 0.5 mL to 50 mL, or 0.5 mL to 5 mL, each inclusive.

As discussed above, the compositions and combinations, and methods below, increase infectivity of the viruses, and in particular increase infectivity for a target cell compared to in the absence of the anti-C5 antibody. Target cells and tissues include those in vivo in a subject and also in vitro cell lines or is a cell, such as cell therapy compositions, infected ex vivo. Target cells include cells in solid tumors, cells in blood and lymph disorders, circulating tumor cells and metastasizing tumor cells. Infectivity can be manifested by observing increased titer, particularly as a function of time, or half-life of the oncolytic virus when exposed to a body fluid, such as blood and serum. As noted above an increase in infectivity refers to any increase include an increase of at least 1.1-fold, 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold, 6-fold, 7-fold, 8-fold, 9-fold, or 10-fold.

It can be manifested by virtue of decreased immune response to the virus and/or a change in properties of the virus, such as, for example, increased binding to a target cell or to blood cells compared to in the absence of the anti-C5 antibody. Increased binding refers to any increase, including at least 1.1-fold, 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold, 6-fold, 7-fold, 8-fold, 9-fold, or 10-fold.

Kits, which comprise the combinations and/or compositions provided herein are provided. The kits optionally include packaging, devices and components for administration of the viruses and lipids compositions and combinations and instructions for use.

Provided are methods for increasing the infectivity any virus, particularly the oncolytic viruses described herein, are provided. The methods include methods in which a virus, such as an oncolytic virus, is contacted in vitro with a biocompatible lipid component for a sufficient time to produce a lipid-treated virus that exhibits increased infectivity for a target cell compared to the oncolytic virus in the absence of contacting with the biocompatible lipid component.

Methods of treating diseases in which immunoprivileged cells and tissues, are involved are provided. The immunoprivileged cells and tissues are the cells and tissues, such as tumor cells, circulating tumor cells, and metastasizing cancerous cells, that are the targets of oncolytic therapy. The target cells can be treated in vivo, ex vivo and/or in vitro as described herein.

Hence, provided are methods for treating a disease or condition in a subject treatable by an oncolytic virus. The compositions, and combinations herein provide for methods in which the infectivity of viruses, particularly oncolytic viruses is enhanced by adjunct therapy. Hence the combination and compositions can be administered to a subject and/or the viruses can be contacted with the lipid containing compositions to produce lipid-treated viruses with enhanced infectivity; such viruses can then be administered to a subject.

In particular in some embodiments, provided are methods for increasing the infectivity of the viruses that include, for example: a) contacting an oncolytic virus in vitro with a biocompatible lipid component for a sufficient time to produce a lipid-treated virus composition, wherein the lipid-treated virus exhibits increased infectivity for a target cell compared to the oncolytic virus in the absence of contacting with the biocompatible lipid component; and b) administering the lipid-treated virus composition to the subject. Treatment is manifested, for example, by increased titer or half-life of the oncolytic virus when exposed to a bodily fluid, such as blood or serum. Any increase is contemplated, such as, but not limited to at least 1.1-fold, 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold, 6-fold, 7-fold, 8-fold, 9-fold, or 10-fold. The virus, such as the oncolytic virus, is contacted with a biocompatible lipid component for 5 minutes, 10 minutes, 15 minutes, 20 minutes, 30 minutes, 1 hour, such as at least 30 minutes to 12 hours, 15 hours, 20 hours, 24 hours, 30 minutes to 6 hours, 30 minutes to 4 hours, 30 minutes to 2 hours, 1 hour to 12 hours, 1 hour to 6 hours, 1 hour to 4 hours, 1 hour to 2 hours, 2 hours to 12 hours, 2 hours to 6 hours, 2 hours to 4 hours, 4 hours to 12 hours, 4 hours to 6 hours, or 6 hours to 12 hours. As described for the composition above, contacting can be effected at any temperature at which the virus remains viable, including but not limited to at or between 0° to 42° C., inclusive, such as at or about 20° C. to 40° C., 10° C. to 30° C., 35° C. to 42° C., inclusive. Typically contacting is effected at or about or at least 37° C.

Lipids for contacting the virus include any known to those of skill in the art that can be administered systemically. These include vegetable oils, such as soybean oil, which contain a mixture of various lipids. The lipid component includes, but is not limited to, fatty acids and fatty acid derivatives, such as triglycerides, diglycerides, monoglycerides, phospholipids, and mixtures thereof. The triglycerides and the triglycerides are long-chain triglycerides (LCTs), medium-chain triglycerides (MCTs) and mixtures thereof. Exemplary long-chain triglycerides are linoleate, oleate, palmitate, linolenate, stearate and mixtures thereof. Medium-chain triglycerides include caprylic acid and capric acid.

The lipids can be provided as oils, including plant oil, vegetable oil, animal oil, fish oil, mineral oil, chemically synthesized oil and mixtures thereof. Plant and vegetable oils include soybean oil, cottonseed oil, safflower oil, corn oil, coconut oil, sesame oil, peanut oil, olive oil, castor oil and mixtures thereof.

Generally the lipid is provided as an emulsion that contains the lipid in an aqueous phase, such as water or an isotonic aqueous solution. Exemplary compositions are emulsions that contain: a biocompatible lipid component in an amount between 0.001% and 50%, inclusive, such at least 0.0002%, 0.2%, 2% and 40%-50%, inclusive, by weight, of the lipid emulsion; and optionally an emulsifier in an amount between 0.2% and 5%, inclusive, by weight, of the lipid emulsion; and the remainder an aqueous phase in an amount between 50% and 98%, inclusive, by weight, of the lipid emulsion.

The lipid emulsions herein for the combination and other embodiments can be formulated for any suitable route of administration, including local, such as peritoneal administration, and systemic administration, such as intravenous, such as an intravenous liquid emulsion (ILE).

Emulsifiers are biocompatible and can be naturally-occurring emulsifier or synthetic emulsifiers, such as phospholipid derived from an egg or soy source, including, but not limited to, egg yolk phospholipids, hydrogenated egg yolk phospholipids, soybean phospholipids, hydrogenated soybean phospholipids and mixtures thereof. Exemplary of emulsifiers is lecithin. The concentration of the emulsifier as a wt % of the composition is between 0.0002% and 5%, 0.0002% and 2%, 0.0002% and 1%, 0.0002% and 0.2%, 0.0002% and 0.02%, 0.0002% and 0.002%, 0.002% and 2%, 0.002% and 1%, 0.002% and 0.2%, 0.002% and 0.02%, 0.02% and 2%, 0.02% and 1%, 0.02% and 0.2%, 0.2% and 5%, 0.2% and 2%, or 2% and 5%, each inclusive. Generally the concentration of the emulsifier is less than 2% wt % of the composition.

The aqueous phase typically is water or isotonic aqueous medium and contains the virus, particularly in a multiple dosage or single dosage concentration or amounts.

Other components in the compositions, including tonicity modifiers, pH adjusters and other such components. For example, the compositions can contain a tonicity modifier, such as glycerin, in an amount between 0.00002%, 00001%, 0001%, 0.2% and 5%, inclusive, by weight of the emulsion, generally less than 2%. Exemplary tonicity modifiers include glycerin, sodium chloride, potassium chloride, mannitol, sucrose, lactose, fructose, maltose, dextrose, dextrose anhydrous, xylitol, sorbitol, propylene glycol, polyoxyethylated hydrocarbons, and $C_6$-$C_{20}$ saturated and unsaturated aliphatic acids.

Tonicity modifiers include, but are not limited to, glycerin, sodium chloride, potassium chloride, mannitol, sucrose, lactose, fructose, maltose, dextrose, dextrose anhydrous, xylitol, sorbitol, propylene glycol, polyoxyethylated hydrocarbons, and $C_6$-$C_{20}$ saturated or unsaturated aliphatic acids. Concentrations of the tonicity modifier as a wt % of the composition is between 0.0002% and 5%, 0.0002% and 2%, 0.0002% and 1%, 0.0002% and 0.2%, 0.0002% and 0.02%, 0.0002% and 0.002%, 0.002% and 2%, 0.002% and 1%, 0.002% and 0.2%, 0.002% and 0.02%, 0.02% and 2%, 0.02% and 1%, 0.02% and 0.2%, 0.2% and 5%, 0.2% and 2%, or 2% and 5%, each inclusive.

The compositions contain an aqueous medium such as isotonic solutions selected from among Ringer's solution, Ringer's lactate solution, phosphate-buffered saline (PBS), TRIS-buffered saline (TBS), Hank's balanced salt solution (HBSS), Earle's balanced salt solution (EBSS), standard saline citrate (SSC), HEPES-buffered saline (HBS), Grey's balanced salt solution (GBSS), and normal saline (NaCl). The concentration of the aqueous phase can be between 40% and 99.9%, 50 and 99%, 60% and 99%, 70% and 99%, 80% and 99%, 90% and 99%, 70% and 95% or 80% and 90%, each inclusive.

Exemplary of a lipid emulsion is one that contains: a biocompatible lipid component in an amount between 2% and 50%, inclusive, by weight, of the lipid emulsion; an emulsifier in an amount between 0.1% or 0.2% and 5%, inclusive, by weight, of the lipid emulsion; and an aqueous phase in an amount between 50% and 98%, inclusive, by weight, of the lipid emulsion. In one embodiment the lipid emulsion for treatment of the virus contains: the biocompatible lipid component in a concentration between 10% and 30%, inclusive, by weight, of the lipid emulsion, where the biocompatible lipid component is selected from among soybean oil, safflower oil, olive oil, and mixtures thereof; an egg yolk phospholipid(s), such as lecithin, in a concentration that is at or about 1.2% by weight, of the lipid emulsion; glycerin in a concentration between 2.25% and 2.5%, inclusive, by weight, of the lipid emulsion; and water, or an isotonic aqueous medium, in a concentration that is between 60% and 90%, inclusive, by weight, of the lipid emulsion. In particular embodiments, the lipid emulsion contains: at least or at 10%, 20% or 30% by weight soybean oil; 1-2%, such as 1.2% by weight egg yolk phospholipid; and at 2-5% such as 2.5% by weight glycerin.

In the methods, the viruses include any oncolytic virus, such, but not limited to, a Newcastle Disease virus, parvovirus, vaccinia virus, measles virus, reovirus, vesicular stomatitis virus (VSV), oncolytic adenoviruses, adeno-associated virus, poliovirus, herpes viruses, sindbis virus and seneca valley virus, and derivatives that that are modified to contain heterologous nucleic acid, including heterologous nucleic acid encoding a heterologous gene product.

Vaccinia viruses and related viruses include strains selected from among Lister, Western Reserve (WR), Copenhagen (Cop), Bern, Paris, Tashkent, Tian Tan, Wyeth (DRYVAX), IHD-J, IHD-W, Brighton, Ankara, CVA382, Modified Vaccinia Ankara (MVA), Dairen I, LC16m8, LC16M0, LIVP, ACAM2000, WR 65-16, Connaught, New York City Board of Health (NYCBH), EM-63 and NYVAC strain. Included are clonal strains of each as well as those containing heterologous nucleic acid, such as nucleic acid encoding a gene product.

In particular, the viruses include vaccinia viruses, such as LIVP viruses, Copenhagen, Wyeth and others, such as, for example, viruses designated GLV-ONC1 and derivatives thereof and JX-594 and derivatives thereof, and clonal isolates of any vaccinia strain.

Any of the viruses used in the methods and compositions and combinations herein can be modified, including by insertion of heterologous nucleic acid, as well as deletion of nucleic acid. Inserted nucleic acid includes, for example, nucleic acid encoding a heterologous gene product, such as a therapeutic product or reporter gene product. Exemplary are any selected from among an anticancer agent, an antimetastatic agent, an antiangiogenic agent, an immunomodulatory molecule, an antigen, a cell matrix degradative gene, genes for tissue regeneration and reprogramming human somatic cells to pluripotency, enzymes that modify a substrate to produce a detectable product or signal or are detectable by antibodies, proteins that can bind a contrasting agent, genes for optical imaging or detection, genes for PET imaging and genes for MRI imaging. Other examples include, but are not limited to, a heterologous gene product that is a therapeutic agent selected from among a hormone, a growth factor, a cytokine, a chemokine, a costimulatory molecule, a ribozyme, a transporter protein, a single chain antibody, an antisense RNA, a prodrug converting enzyme, an siRNA, a microRNA, a toxin, an antitumor oligopeptide, a mitosis inhibitor protein, an antimitotic oligopeptide, an anti-cancer polypeptide antibiotic, an angiogenesis inhibitor, a tumor suppressor, a cytotoxic protein, a cytostatic protein and a tissue factor.

Provided herein are methods of treatment of a disease or condition in a subject treatable by an therapeutic oncolytic virus. Disease and conditions include cancers and proliferative disorders. The disease or condition is a cancer, tumor or metastasis, such as solid tumor. Cancers include, carcinomas, sarcomas, lymphomas and leukemias and other blood disorders, such as cancer of the tongue, mouth, throat, stomach, cecum, colon, rectum, breast, ovary, uterus, thyroid, adrenal cortex, lung, kidney, prostate or pancreas. The subjects include humans and non-human animals, particularly domesticated and farm animals and experimental animals, such as, chimpanzees, gorillas, horse, cat, dog, cow, pig, sheep, goat, mouse, rabbit, chicken, rat, and guinea pig.

In some embodiments, the methods include administering a composition that contains a lipid-treated therapeutic oncolytic virus. In such compositions, the concentration of virus is any that is suitable for treatment, such, but not limited to, concentrations in which the oncolytic viruses are present in the composition in multidose and single dosage amounts, including, but not limited to between or between about $1\times10^5$ and $1\times10^{12}$ pfu, $1\times10^6$ to $1\times10^{10}$ pfu, or $1\times10^7$ to $1\times10^{10}$ pfu, each inclusive, such as at least or about at least or $1\times10^6$, $1\times10^7$, $1\times10^8$, $1\times10^9$, $2\times10^9$, $3\times10^9$, $4\times10^9$, $5\times10^9$ pfu, or $1\times10^{10}$ pfu.

Another exemplary compositions contains an oncolytic virus in an amount that is between or between about $1\times10^6$ to $1\times10^{10}$ pfu, inclusive; a biocompatible lipid component as a wt % of the composition of less than 10%; an emulsifier as a wt % of the composition of less than 2%; a tonicity modifier as a wt % of the composition of less than 2%; and an aqueous phase as a wt % of the composition that is greater than 85%. The virus typically is provided as part of the aqueous phase.

The volume of the composition can be any volume, and can be for single or multiple dosage administration, including, but not limited to, from or from about 0.01 mL to 100 mL, 0.1 mL to 100 mL, 1 mL to 100 mL, 10 mL to 100 mL, 0.01 mL to 10 mL, 0.1 mL to 10 mL, 1 mL to 10 mL, 0.02 mL to 20 mL, 0.05 mL to 5 mL, 0.5 mL to 50 mL, or 0.5 mL to 5 mL, each inclusive.

Also provided are methods of treating a disease or condition in a subject treatable by an oncolytic virus, comprising administering any of combinations of virus and lipid compositions provided herein, particularly the lipid emulsion compositions. The composition containing the lipid emulsion is administered prior to, simultaneously with, intermittently with or subsequently to administration of the composition comprising the oncolytic virus. In one embodiment the composition comprising the lipid emulsion is administered prior to administration of the composition comprising the oncolytic virus. Exemplary of such methods are methods in which the lipid emulsion is administered at least 5 minutes, 10 minutes, 20 minutes, 30 minutes, 45 minutes before, such as 5 minutes to 6 hours, 5 minutes to 4 hours, 5 minutes to 2 hours, 5 minutes to 1 hour, 5 minute to 30 minutes, 30 minutes to 6 hours, 30 minutes to 4 hours, 30 minutes to 2 hours, 30 minutes to 1 hour, 1 hour to 6 hours, 1 hour to 4 hours, 1 hour to 2 hours, 2 hours to 6 hours, 2 hours to 4 hours, or 4 hours to 6 hours prior to administration of the composition comprising the oncolytic virus.

The amount of lipid emulsion is an amount that increases infectivity of the therapeutic oncolytic virus, such as but not limited to, an amount that delivers at least 1 gram (g), 5 g, 10 g, 20 g, 25 g, such as 1 g to 50 g, 1 g to 40 g, 1 g to 30 g, 1 g to 20 g, 1 g to 10 g, 1 g to 5 g, 5 g to 50 g, 5 g to 40 g, 5 g to 30 g, 5 g to 20 g, 5 g to 1 g, 10 g to 50 g, 10 g to 40 g, 10 g to 30 g, 10 g to 20 g, 20 g to 50 g, 20 g to 40 g, or 20 g to 30 g of the biocompatible lipid component. The amount of lipid emulsion composition is sufficient to deliver the desired amount. Such volumes include, at least 1 mL, 2 mL, 3 mL, 5 mL, 10 mL, 50 mL, 100 mL, 150 mL, 200 mL, 300 mL, 400 mL, such as where 1 mL to 500 mL, 1 mL to 200 mL, 1 mL to 100 mL, 1 mL to 50 mL, 50 mL to 500 mL, 50 mL to 200 mL, 50 mL to 100 mL, 100 mL to 500 mL, 100 mL to 200 mL, or 200 mL to 500 mL of lipid emulsion composition is administered. Typically at least 50 mL or 100 mL of lipid emulsion composition is administered.

In these methods in which viruses and lipid emulsions are administered and in the methods in which the lipid-treated virus is administered, they can be administered with a complement inhibitor. The complement inhibitor can be administered separately or in the same composition as the virus or lipid. Any inhibitor of a complement pathway component is contemplated These include any agent that inhibits complement activation or the activity of any protein in a complement pathway, such as, inhibition of the activity of any of C1, C2, C3, C4, C5, C5a, C5aR, C3aR, Factor B, Factor P, C1q and MBP. Such agents are known to those of skill in the art, and include, for example, include antibodies specific for one or more of these proteins. Exemplary inhibitors include, for example, cobra venom factor (CVF), heparin, TA 106, TNX-234, anti-properdin, C1-INH, a compstatin or derivative or analog thereof, soluble CR1, K76COOH, eculizumab, pexelizumab, TSA12/22, MSA12/22, ARC 1005, TNX-558, NOX-D19, PMX-53, PMX-201, PMX-205, neutrazumab, and variants, analogs or derivatives thereof that inhibit a complement activity. For example, inhibitors include C5 inhibitors, such as anti-C5 antibodies. These include any known to those of skill in the art, such as eculizumab, pexelizumab, TSA12/22 or MB12/122, or a variant thereof. In some embodiments, the complement inhibitor is an anti-C5 antibody, such as, but a not limited to, eculizumab, pexelizumab, TSA12/22 or MB12/122, or a C5-inhibiting variant thereof. In some embodiments, the complement inhibitor is an anti-C5 antibody.

Also provided are methods in which the combination containing any therapeutic oncolytic virus, including a lipid-treated virus, and a composition containing a complement inhibitor are administered. Treatment is effected by administering the virus and the complement inhibitor, which includes any noted above and herein. Exemplary of complement inhibitors are anti-C5 antibodies, such as, but not limited to eculizumab. In the methods, the composition comprising the complement inhibitor, such as anti-C5 antibody, is administered prior to, simultaneously with, intermittently with or subsequently to administration of the composition comprising the oncolytic virus.

The composition comprising the complement inhibitor, such as the anti-C5 antibody, is administered prior to administration of the composition containing the oncolytic virus. It can be administered at least 5 minutes, 10 minutes, 20 minutes, 30 minutes, 45 minutes before, such as 5 minutes to 6 hours, 5 minutes to 4 hours, 5 minutes to 2 hours, 5 minutes to 1 hour, 5 minute to 30 minutes, 30 minutes to 6 hours, 30 minutes to 4 hours, 30 minutes to 2hours, 30 minutes to 1 hour, 1 hour to 6 hours, 1 hour to 4 hours, 1 hour to 2 hours, 2 hours to 6 hours, 2 hours to 4 hours, or 4 hours to 6 hours prior, such as at least 30 minutes prior to administration of the composition comprising the oncolytic virus.

The complement inhibitor, such as an antibody, depends upon the particular inhibitor and the disease treated and the treatment regimen Typical amounts include, but are not limited to, administering an amount to deliver 100 mg to 5000 mg, 200 mg to 2000 mg, 500 mg to 1000 mg, 200 mg to 5000 mg, 200 mg to 1000 mg, 500 mg to 5000 mg, 1000 mg to 2000 mg, 1000 mg to 5000 mg or 2000 mg to 5000 mg, such as at least 800 mg, 900 mg, 1000 mg, 1200 mg or 1500 mg.

The composition containing the virus is administered in an amount that delivers sufficient virus to treat the disease or condition. Such amount depends upon the virus, disease or condition and treatment regimen. Exemplary are administering the composition containing the therapeutic oncolytic virus is administered to deliver at least $1 \times 10^5$ pfu virus, $1 \times 10^6$ pfu virus, $1 \times 10^7$ pfu virus, $1 \times 10^8$ pfu virus, $1 \times 10^9$ pfu virus, $1 \times 10^{10}$ pfu virus, $1 \times 10^{11}$ pfu virus, or $1 \times 10^{12}$ pfu virus, such as between $1 \times 10^5$ and $1 \times 10^{12}$ pfu, $1 \times 10^6$ to $1 \times 10^{10}$ pfu, or $1 \times 10^7$ to $1 \times 10^{10}$ pfu, each inclusive, such as at least or about at least or $1 \times 10^6$, $1 \times 10^7$, $1 \times 10^8$, $1 \times 10^9$, $2 \times 10^9$, $3 \times 10^9$, $4 \times 10^9$, $5 \times 10^9$ pfu, or $1 \times 10^{10}$ pfu. In one embodiment the composition comprising the oncolytic virus is administered between $1 \times 10^8$ pfu virus and $1 \times 10^{10}$ pfu virus, inclusive.

In the methods, the compositions can be administered locally or systemically; for the combinations, the compositions can be administered by different routes. In particular embodiments, the composition(s) is(are) administered intravenously or intraperitoneally.

The compositions and combinations provided here are for use in treating a disease or condition that is one that is treatable by an oncolytic virus. Also provided are uses of the compositions and combinations for treating a disease or condition that is treated by an oncolytic virus. The combinations and uses can be those, wherein, when administered to a subject, the anti-C5 antibody is administered prior to the oncolytic virus.

Diseases and conditions include proliferative disorders, including cancers and inflammatory diseases. The disease or condition can be a tumor or a metastasis. The disease or condition is a cancer, tumor or metastasis, such as a solid tumor. Cancers include, carcinomas, sarcomas, lymphomas and leukemias and other blood disorders, such as cancer of the tongue, mouth, throat, stomach, cecum, colon, rectum, breast, ovary, uterus, thyroid, adrenal cortex, lung, kidney, prostate or pancreas. The subjects include humans and non-human animals, particularly domesticated and farm animals and experimental animals, such as, chimpanzees, gorillas, horse, cat, dog, cow, pig, sheep, goat, mouse, rabbit, chicken, rat, and guinea pig.

Diseases and conditions include proliferative disorders, including cancers as noted above and herein. Cancers include, but are not limited to, a carcinoma, sarcoma, lymphoma and leukemia, such as cancer of the tongue, mouth, throat, stomach, cecum, colon, rectum, breast, ovary, uterus, thyroid, adrenal cortex, lung, kidney, prostate or pancreas.

DETAILED DESCRIPTION

Outline
  A. Definition
  B. Oncolytic Virus Therapy
    1. Oncolytic Viruses
    2. Virus Therapies to Increase Infectivity
  C. Oncolytic Viruses
    1. Vaccinia Viruses
      Lister and LIVP Strains
    2. Heterologous Nucleic Acid and Modified Viruses
      a. Exemplary Modifications
      b. Control of Heterologous Gene Expression
      c. Exemplary Modified or Recombinant Viruses
      d. Methods of Generating Modified Viruses
    3. Methods of Producing Viruses
      a. Host cells for Propagation
      b. Concentration Determination
      c. Storage Methods
  D. Adjunct Therapy with Complement Inhibitors
    1. The Complement System and Virus Neutralization
      a. Complement Pathways
        i. Classical Pathway
        ii. Alternative Pathway
        iii. Lectin Pathway
      b. Complement Effector Mechanisms
        i. Opsonization
        ii. Virolysis by the Membrane Attack Complex (MAC)
        iii. Proinflammatory Mediator Anaphylatoxin
    2. Exemplary Complement Inhibitors
      Anti-C5 Antibody
  E. Adjunct Therapy with Lipids and Lipid Emulsions
    1. Components of Lipid Emulsions
      a. Lipid Component
      b. Emulsifiers
      c. Aqueous Phase
      d. Additional Ingredients
    2. Exemplary Injectable Lipid Emulsions (ILE)
      a. Long-chain triglyceride (LCT) emulsions
      b. Medium-chain triglyceride (MCT) emulsions
      c. Fish Oil emulsions
      d. Mixtures of LCTs, MCTs and fish oils
      e. Synthetic lipid emulsions
  F. Pharmaceutical Compositions, Formulations and Articles of Manufacture
    1. Formulation and Dosage Forms
      a. Oncolytic Virus
      b. Lipid Emulsion (e.g. Lipid-treated Virus)
      c. Complement Inhibitor Compositions
    2. Combinations
    3. Packaging and Articles of Manufacture
  G. Methods of Assessing Infectivity and Virus Activity
    1. Viral Infectivity and Anti-Tumorigenecity
    2. Toxicity/Safety
  H. Therapeutic Methods of Adjunct Therapy
    1. Hyperproliferative Disease or Disorder
    2. Dosage and Administration
    3. Combination Therapy
      a. Oncolytic or Therapeutic Virus
      b. Therapeutic Compounds
  I. Examples A. Definitions Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, "adjunct therapy" or "adjunctive therapy" refers to a treatment in which another treatment is used with a primary treatment to assist or enhance the primary treatment. Thus, it is a treatment that is given in addition to the primary, main or initial treatment. The adjunct therapy increases the effectiveness of the primary treatment in treating a condition. For purposes herein, treatment with an oncolytic virus is the primary or main treatment, and one or more different treatments are employed to increase the effectiveness of the oncolytic virus therapy, such as by increasing infectivity. For purposes herein, adjunct therapy includes therapy with lipid components (e.g. lipid emulsions) and/or a complement inhibitor (e.g. an anti-C5 antibody), which increases the virus infectivity, and hence therapeutic efficacy, of treatments with an oncolytic virus.

As used herein, "combination therapy" refers to a treatment in which a subject is given two or more therapeutic agents, such as at least two or at least three therapeutic agents, for treating a single disease. For purposes herein, a combination therapy can include a treatment regime that includes administration of an oncolytic virus and another anti-cancer agent, each for treating the same hyperproliferative disease or conditions, such as the same tumor or cancer.

As used herein, infectivity with reference to an oncolytic virus refers to the ability of the virus to infect a cell. Virus infectivity is affected by virus titer, half-life, tropism and interaction with a target cell. In particular, the infectivity of a virus is affected by processes that affect virus receptor binding to a target cell, target cell uptake, aggregation, phagocytosis or clearance, or lysis. For example, the infectivity of a virus can be affected by processes that alter a virus from binding to its receptors or being taken up by target cells, by antibody-mediated aggregation of virus particles, by phagocytic clearance mechanisms, or by complement-mediated lysis that disrupts virus cell membranes.

As used herein, increased virus infectivity refers to processes that result in an increase in the ability of a virus to infect a cell. The increased infectivity can occur due to processes that result in increased binding to target cell receptors or uptake by target cells, decreased virus aggregation, decreased virus clearance, or decreased virus lysis in the presence of the adjunct therapy compared to the absence of the adjunct therapy. Infectivity of a virus can be increased in the presence of an adjunct therapy that effects one or more of the above properties. For purposes herein, infectivity of a virus is increased in the presence of an adjunct therapy, such as a complement inhibitor (e.g. anti-C5 antibody) or lipid emulsion (e.g. 20% soybean oil intravenous fat emulsion, which is marketed under the trademark Intralipid® lipid emulsion), that reduces virus inactivation, such as by reducing virus clearance of lysis. Increased infectivity can be assessed directly or indirectly. For example, infectivity can be assessed by monitoring viral titer (e.g. as assessed by the number of plaques produced in a plaque assay), changes in viral gene expression or host gene expression or cytotoxicity for tumor cells or other target cells. The pharmacokinetic properties of a virus, such as half-life, also can be assessed as a parameter indicative of increased infectivity. Generally, the infectivity of oncolytic virus in the presence of an adjunct therapy provided herein (i.e. lipid emulsion and/or complement inhibitor) is increased at least 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold, 6-fold, 7-fold, 8-fold, 9-fold, 10-fold or more compared to the absence of the adjunct therapy.

As used herein, Intralipid® lipid emulsion, refers to the lipid emulsion (10%, 20% or 30% fat emulsion) containing 10%-30% soybean oil, respectively, and also contains 1.2% egg yolk phospholipids, 2.25% glycerin and water for injection, and adjusted to a pH of 6 to 8.9 using sodium hydroxide.

As used herein, "virus titer" or "viral titer" refers to the concentration of a virus and is a given number of infectious virus units per volume, such as plaque forming units (pfu)/mL. Virus titer can be determined by serial dilution of a sample for infection of target cells in order to quantify the number of infectious or active virus in a sample. For example, virus titer can be determined using a plaque assay.

As used herein, "virus load" refers to the virus titer in a bodily fluid. For example, the particular viral titer can be dependent on the amount of virus administered, the presence of active virus, and the rate of clearance and/or the half-life of virus in the blood. Hence, the relative degree of virus titer can correlate to the infectivity of the virus. The higher the virus load or titer, generally the greater the infectivity of the virus.

As used herein, "half-life" with reference to a virus refers to the time taken for half of infectious circulating virus to be cleared from the body.

As used herein "binding to blood cells" with reference to a virus refers to the association of virus with blood cells. Association can be determined by contacting blood cells with virus for a sufficient time and under conditions to achieve binding, followed by centrifugation and washing of cells to remove loosely bound or unbound virus. For example, binding can be for at least 20 minutes to 6 hours or more, such as generally at least 30 minutes, 1 hour or 2 hours, and at physiologic temperatures (e.g. at or about 37° C.).

As used herein, "blood cells" refer to cells isolated from whole blood, such as normal human blood, by centrifugation. Such cells include red cells, white cells (i.e. leukocytes and cells of the immune system) and platelets.

As used herein, a "virus" or virus vector refers to any of a large group of infectious entities that cannot grow or replicate without a host cell. Viruses typically contain a protein coat surrounding an RNA or DNA core of genetic material, but no semipermeable membrane, and are capable of growth and multiplication only in living cells. Viruses include, but are not limited to, poxviruses, herpesviruses, adenoviruses, adeno-associated viruses, lentiviruses, retroviruses, rhabdoviruses, papillomaviruses, vesicular stomatitis virus, measles virus, Newcastle disease virus, picornavirus, Sindbis virus, papillomavirus, parvovirus, reovirus, coxsackievirus, influenza virus, mumps virus, poliovirus, and semliki forest virus.

As used herein, oncolytic viruses refer to viruses that replicate selectively in tumor cells in tumorous subjects. Some oncolytic viruses can kill a tumor cell following infection of the tumor cell. For example, an oncolytic virus can cause death of the tumor cell by lysing the tumor cell or inducing cell death of the tumor cell.

As used herein, a therapeutic virus, such as a therapeutic oncolytic virus, is a virus that is used to treat disease or condition. Typically they are not pathogenic or have been rendered non-pathogenic.

As used herein the term "vaccinia virus" or "VACV" or "VV" denotes a large, complex, enveloped virus belonging to the poxvirus family. It has a linear, double-stranded DNA genome approximately 190 kbp in length, and which encodes approximately 200 proteins. Vaccinia virus strains include, but are not limited to, strains of, derived from, or modified forms of Western Reserve (WR), Copenhagen, Tashkent, Tian Tan, Lister, Wyeth, IHD-J, and IHD-W, Brighton, Ankara, MVA, Dairen I, LIPV, LC16M8, LC16MO, LIVP, WR 65-16, Connaught, New York City Board of Health vaccinia virus strains.

As used herein, Lister Strain of the Institute of Viral Preparations (LIVP) or LIVP virus strain refers to a virus strain that is the attenuated Lister strain (ATCC Catalog No. VR-1549) that was produced by adaption to calf skin at the Institute of Viral Preparations, Moscow, Russia (Al'tshtein et al. (1985) *Dokl. Akad. Nauk USSR* 285:696-699). The LIVP strain can be obtained, for example, from the Institute of Viral Preparations, Moscow, Russia (see. e.g., Kutinova et al. (1995) Vaccine 13:487-493); the Microorganism Collection of FSRI SRC VB Vector (Kozlova et al. (2010) Environ. Sci. Technol. 44:5121-5126); or can be obtained from the Moscow Ivanovsky Institute of Virology (C0355 K0602; Agranovski et al. (2006) Atmospheric Environment 40:3924-3929). It also is well known to those of skill in the art; it was the vaccine strain used for vaccination in the USSR and throughout Asia and India. The strain now is used by researchers and is well known (see e.g., Altshteyn et al. (1985) *Dokl. Akad. Nauk USSR* 285:696-699; Kutinova et al. (1994) *Arch. Virol.* 134:1-9; Kutinova et al. (1995) *Vaccine* 13:487-493; Shchelkunov et al. (1993) *Virus Research* 28:273-283; Sroller et al. (1998) *Archives Virology* 143: 1311-1320; Zinoviev et al., (1994) *Gene* 147:209-214; and Chkheidze et al. (1993) *FEBS* 336:340-342). Among the LIVP strains is one that contains a genome having a sequence of nucleotides set forth in SEQ ID NO: 1 or 2, or a sequence that is at least or at least about 97%, 98% or 99% identical to the sequence of nucleotides set forth in SEQ ID NO: 1 or 2. An LIVP virus strain encompasses any virus strain or virus preparation that is obtained by propagation of LIVP through repeat passage in cell lines.

As used herein, an LIVP clonal strain or LIVP clonal isolate refers to a virus that is derived from the LIVP virus strain by plaque isolation, or other method in which a single clone is propagated, and that has a genome that is homogenous in sequence. Hence, an LIVP clonal strain includes a virus whose genome is present in a virus preparation propagated from LIVP. An LIVP clonal strain does not include a recombinant LIVP virus that is genetically engineered by recombinant means using recombinant DNA methods to introduce heterologous nucleic acid. In particular, an LIVP clonal strain has a genome that does not contain heterologous nucleic acid that contains an open reading frame encoding a heterologous protein. For example, an LIVP clonal strain has a genome that does not contain non-viral heterologous nucleic acid that contains an open reading frame encoding a non-viral heterologous protein. As described herein, however, it is understood that any of the LIVP clonal strains provided herein can be modified in its genome by recombinant means to generate a recombinant virus. For example, an LIVP clonal strain can be modified to generate a recombinant LIVP virus that contains insertion of nucleotides that contain an open reading frame encoding a heterologous protein.

As used herein, LIVP 1.1.1 is an LIVP clonal strain that has a genome having a sequence of nucleotides set forth in SEQ ID NO: 5, or a genome having a sequence of nucleotides that has at least 97%, 98%, or 99% sequence identity to the sequence of nucleotides set forth in SEQ ID NO: 5.

As used herein, LIVP 2.1.1 is an LIVP clonal strain that has a genome having a sequence of nucleotides set forth in SEQ ID NO: 6, or a genome having a sequence of nucleotides that has at least 97%, 98%, or 99% sequence identity to the sequence of nucleotides set forth in SEQ ID NO: 6.

As used herein, LIVP 4.1.1 is an LIVP clonal strain that has a genome having a sequence of nucleotides set forth in SEQ ID NO: 7, or a genome having a sequence of nucleotides that has at least 97%, 98% or 99% sequence identity to the sequence of nucleotides set forth in SEQ ID NO: 7.

As used herein, LIVP 5.1.1 is an LIVP clonal strain that has a genome having a sequence of nucleotides set forth in SEQ ID NO: 8, or a genome having a sequence of nucleotides that has at least 97%, 98% or 99% sequence identity to the sequence of nucleotides set forth in SEQ ID NO: 8.

As used herein, LIVP 6.1.1 is an LIVP clonal strain that has a genome having a sequence of nucleotides set forth in SEQ ID NO: 9, or a genome having a sequence of nucleotides that has at least 97%, 98% or 99% sequence identity to the sequence of nucleotides set forth in SEQ ID NO: 9.

As used herein, LIVP 7.1.1 is an LIVP clonal strain that has a genome having a sequence of nucleotides set forth in SEQ ID NO: 10, or a genome having a sequence of nucleotides that has at least 97%, 98% or 99% sequence identity to the sequence of nucleotides set forth in SEQ ID NO: 10.

As used herein, LIVP 8.1.1 is an LIVP clonal strain that has a genome having a sequence of nucleotides set forth in SEQ ID NO: 11, or a genome having a sequence of nucleotides that has at least 97%, 98% or 99% sequence identity to the sequence of nucleotides set forth in SEQ ID NO: 11.

As used herein, LIVP GLV-1h68 (also designated GLV-ONC1) is an LIVP virus that contains ruc-gfp (a luciferase and green fluorescent protein fusion gene (see e.g. U.S. Pat. No. 5,976,796), beta-galactosidase (LacZ) and beta-glucuronidase (gusA) reporter genes inserted into the F14.5L, J2R (thymidine kinase) and A56R (hemagglutinin) loci, respectively. The genome of GLV-1h68 has a sequence of nucleotides set forth in SEQ ID NO: 3 or a sequence of nucleotides that has at least 97%, 98% or 99% sequence identity to the sequence of nucleotides set forth in SEQ ID NO: 3.

As used herein, the term "modified virus" or "recombinant virus" refers to a virus that is altered compared to a parental strain of the virus. Typically modified viruses have one or more truncations, mutations, insertions or deletions in the genome of virus. A modified virus can have one or more endogenous viral genes modified and/or one or more intergenic regions modified. Exemplary modified viruses can have one or more heterologous nucleic acid sequences inserted into the genome of the virus. Modified viruses can contain one or more heterologous nucleic acid sequences in the form of a gene expression cassette for the expression of a heterologous gene.

As used herein, a modified LIVP virus strain refers to an LIVP virus that has a genome that is not contained in LIVP, but is a virus that is produced by modification of a genome of a strain derived from LIVP. Typically, the genome of the virus is modified by substitution (replacement), insertion (addition) or deletion (truncation) of nucleotides. Modifications can be made using any method known to one of skill in the art such as genetic engineering and recombinant DNA methods. Hence, a modified virus is a virus that is altered in its genome compared to the genome of a parental virus. Exemplary modified viruses have one or more heterologous nucleic acid sequences inserted into the genome of the virus. Typically, the heterologous nucleic acid contains an open reading frame encoding a heterologous protein. For example, modified viruses herein can contain one or more heterologous nucleic acid sequences in the form of a gene expression cassette for the expression of a heterologous gene.

As used herein, "production by recombinant methods" or "methods using recombinant DNA methods" or variations thereof refers to the use of the well-known methods of molecular biology for expressing proteins encoded by cloned DNA. As used herein a "gene expression cassette" or "expression cassette" is a nucleic acid construct, containing nucleic acid elements that are capable of effecting expression of a gene in hosts that are compatible with such sequences. Expression cassettes include at least promoters and optionally, transcription termination signals. Typically, the expression cassette includes a nucleic acid to be transcribed operably linked to a promoter. Expression cassettes can contain genes that encode, for example, a therapeutic gene product, or a detectable protein or a selectable marker gene.

As used herein, a heterologous nucleic acid (also referred to as exogenous nucleic acid or foreign nucleic acid) refers to a nucleic acid that is not normally produced in vivo by an organism or virus from which it is expressed or that is produced by an organism or a virus but is at a different locus, or that mediates or encodes mediators that alter expression of endogenous nucleic acid, such as DNA, by affecting transcription, translation, or other regulatable biochemical processes. Hence, heterologous nucleic acid is often not normally endogenous to a virus into which it is introduced. Heterologous nucleic acid can refer to a nucleic acid molecule from another virus in the same organism or another organism, including the same species or another species. Heterologous nucleic acid, however, can be endogenous, but is nucleic acid that is expressed from a different locus or altered in its expression or sequence (e.g., a plasmid). Thus, heterologous nucleic acid includes a nucleic acid molecule not present in the exact orientation or position as the counterpart nucleic acid molecule, such as DNA, is found in a genome. Generally, although not necessarily, such nucleic acid encodes RNA and proteins that are not normally produced by the virus or in the same way in the virus in which it is expressed. Any nucleic acid, such as DNA, that one of skill in the art recognizes or considers as heterologous, exogenous or foreign to the virus in which the nucleic acid is expressed is herein encompassed by heterologous nucleic acid. Examples of heterologous nucleic acid include, but are not limited to, nucleic acid that encodes exogenous peptides/proteins, including diagnostic and/or therapeutic agents. Proteins that are encoded by heterologous nucleic acid can be expressed within the virus, secreted, or expressed on the surface of the virus in which the heterologous nucleic acid has been introduced.

As used herein, a heterologous protein or heterologous polypeptide (also referred to as exogenous protein, exogenous polypeptide, foreign protein or foreign polypeptide) refers to a protein that is not normally produced by a virus.

As used herein, the term, "therapeutic gene product" or "therapeutic polypeptide" or "therapeutic agent" refers to any heterologous protein expressed by the therapeutic virus that ameliorates the symptoms of a disease or disorder or ameliorates the disease or disorder. Therapeutic agents include, but are not limited to, moieties that inhibit cell growth or promote cell death, that can be activated to inhibit cell growth or promote cell death, or that activate another agent to inhibit cell growth or promote cell death. Optionally, the therapeutic agent can exhibit or manifest additional properties, such as, properties that permit its use as an imaging agent, as described elsewhere herein. Exemplary therapeutic agents include, for example, cytokines, growth factors, photosensitizing agents, radionuclides, toxins, antimetabolites, signaling modulators, anti-cancer antibiotics, anti-cancer antibodies, angiogenesis inhibitors, chemotherapeutic compounds or a combination thereof.

As used herein, a "reporter gene" is a gene that encodes a reporter molecule that can be detected when expressed by a virus provided herein or encodes a molecule that modulates expression of a detectable molecule, such as a nucleic acid molecule or a protein, or modulates an activity or event that is detectable. Hence reporter molecules include nucleic acid molecules, such as expressed RNA molecules, and proteins.

As used herein, a detectable label or detectable moiety or diagnostic moiety (also imaging label, imaging agent, or imaging moiety) refers to an atom, molecule or composition, wherein the presence of the atom, molecule or composition can be directly or indirectly measured. Detectable labels can be used to image one or more of any of the viruses provided herein. Detectable labels include, for example, chemiluminescent moieties, bioluminescent moieties, fluorescent moieties, radionuclides, and metals. Methods for detecting labels are well known in the art. Such a label can be detected, for example, by visual inspection, by fluorescence spectroscopy, by reflectance measurement, by flow cytometry, by X-rays, by a variety of magnetic resonance methods such as magnetic resonance imaging (MRI) and magnetic resonance spectroscopy (MRS). Methods of detection also include any of a variety of tomographic methods including computed tomography (CT), computed axial tomography (CAT), electron beam computed tomography (EBCT), high resolution computed tomography (HRCT), hypocycloidal tomography, positron emission tomography (PET), single-photon emission computed tomography (SPECT), spiral computed tomography, and ultrasonic tomography. Direct detection of a detectable label refers to, for example, measurement of a physical phenomenon of the detectable label itself, such as energy or particle emission or absorption of the label itself, such as by X-ray or MRI. Indirect detection refers to measurement of a physical phenomenon of an atom, molecule or composition that binds directly or indirectly to the detectable label, such as energy or particle emission or absorption, of an atom, molecule or composition that binds directly or indirectly to the detectable label. In a non-limiting example of indirect detection, a detectable label can be biotin, which can be detected by binding to avidin. Non-labeled avidin can be administered systemically to block nonspecific binding, followed by systemic administration of labeled avidin. Thus, included within the scope of a detectable label or detectable moiety is a bindable label or bindable moiety, which refers to an atom, molecule or composition, wherein the presence of the atom, molecule or composition can be detected as a result of the label or moiety binding to another atom, molecule or composition. Exemplary detectable labels include, for example, metals such as colloidal gold, iron, gadolinium, and gallium-67, fluorescent moieties, and radionuclides. Exemplary fluorescent moieties and radionuclides are provided elsewhere herein.

As used herein, operative linkage of heterologous nucleic acids to regulatory and effector sequences of nucleotides, such as promoters, enhancers, transcriptional and translational stop sites, and other signal sequences refers to the relationship between such nucleic acid, such as DNA, and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA. Thus, operatively linked or operationally associated refers to the functional relationship of a nucleic acid, such as DNA, with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or transcription, it can be necessary to remove, add or alter 5' untranslated portions of the clones to eliminate extra, potentially inappropriate, alternative translation initiation (i.e., start) codons or other sequences that can interfere with or reduce expression, either at the level of transcription or translation. In addition, consensus ribosome binding sites can be inserted immediately 5' of the start codon and can enhance expression (see, e.g., Kozak *J. Biol. Chem.* 266: 19867-19870 (1991) and Shine and Delgarno, *Nature* 254 (5495):34-38 (1975)). The desirability of (or need for) such modification can be empirically determined.

As used herein, the phrases "operatively positioned," "operatively linked," "under control," and "under transcriptional control" mean that a promoter is in a correct functional location and orientation in relation to a nucleic acid sequence to control transcriptional initiation and expression of that sequence.

As used herein, an "internal ribosome entry site" (IRES) refers to a nucleotide sequence that allows for translation initiation in the middle of a messenger RNA (mRNA) sequence as part of protein synthesis.

As used herein, a heterologous promoter refers to a promoter that is not normally found in the wild-type organism or virus or that is at a different locus as compared to a wild-type organism or virus. A heterologous promoter is often not endogenous to a virus into which it is introduced, but has been obtained from another virus or prepared synthetically. A heterologous promoter can refer to a promoter from another virus in the same organism or another organism, including the same species or another species. A heterologous promoter, however, can be endogenous, but is a promoter that is altered in its sequence or occurs at a different locus (e.g., at a different location in the genome or on a plasmid). Thus, a heterologous promoter includes a promoter not present in the exact orientation or position as the counterpart promoter is found in a genome.

A synthetic promoter is a heterologous promoter that has a nucleotide sequence that is not found in nature. A synthetic promoter can be a nucleic acid molecule that has a synthetic sequence or a sequence derived from a native promoter or portion thereof. A synthetic promoter also can be a hybrid promoter composed of different elements derived from different native promoters.

As used herein, a virus preparation or virus composition, for example an LIVP virus preparation, refers to a virus composition obtained by propagation of a virus strain, for example an LIVP virus strain, an LIVP clonal strain or a modified or recombinant virus strain, in vivo or in vitro in a culture system. For example, an LIVP virus preparation refers to a viral composition obtained by propagation of a virus strain in host cells, typically upon purification from the culture system using standard methods known in the art. A virus preparation generally is made up of a number of virus particles or virions. If desired, the number of virus particles in the sample or preparation can be determined using a plaque assay to calculate the number of plaque forming units per sample unit volume (pfu/mL), assuming that each plaque formed is representative of one infective virus particle. Each virus particle or virion in a preparation can have the same genomic sequence compared to other virus particles (i.e. the preparation is homogeneous in sequence) or can have different genomic sequences (i.e. the preparation is heterogeneous in sequence). It is understood to those of skill in the art that, in the absence of clonal isolation, heterogeneity or diversity in the genome of a virus can occur as the virus reproduces, such as by homologous recombination events that occur in the natural selection processes of virus strains (Plotkin & Orenstein (eds) "Recombinant Vaccinia Virus Vaccines" in Vaccines, $3^{rd}$ edition (1999)).

As used herein, plaque forming unit (pfu) or infectious unit (IU) refers to the number of infectious or live viruses. It thus reflects the amount of active virus in the preparation. The pfu can be determined using a plaque formation assay or an end-point dilution assay, which are standard assays known to one of skill in the art.

As used herein, a lipid refers to any of a class of organic compounds that are fatty acids or their derivatives and are insoluble in water but soluble in organic solvents. Lipids include fats, fatty acids, and derivatives of fatty acids, including triglycerides, diglycerides, monoglycerides, and phospholipids. They include many natural oils, waxes, and steroids.

As used herein, "fatty acid" refers to straight-chain hydrocarbon molecules with a carboxyl (—COOH) group at one end of the chain.

As used herein, a lipid component refers to a composition or material containing a lipid or lipids. Typically, the lipid component is an oil, such as a plant, vegetable, animal, fish, mineral, or chemically synthesized oil. For example, the lipid component is a triglyceride-containing oil, for example, a soybean oil or safflower oil or mixtures thereof.

As used herein, a biocompatible lipid or a biocompatible lipid component refers to a lipid or lipid composition that is not harmful to living tissues. Generally, biocompatibility is achieved when the body of a subject accepts the lipid or composition as a normal constituent and the material undergoes normal metabolic degradation. A biocompatible lipid can be a synthetic lipid or a natural or naturally occurring lipid. For example, a biocompatible lipid can include natural oils, such as soybean oil, cotton-seed oil, safflower oil and others described herein or known in the art. Biocompatibility of compositions generally also is achieved by formulation as an isotonic solution having a physiologic pH.

As used herein, soybean oil refers to a vegetable oil extracted from the seeds of the soybean (Glycine max). Per 100 g, soybean oil has 16 g of saturated fat, 23 g of mono-unsaturated fat, and 58 g of poly-unsaturated fat. The major unsaturated fatty acids in soybean oil triglycerides are the poly-unsaturates, alpha-linolenic acid (C-18:3), 7-10%, and linoleic acid (C-18:2), 51%; and the mono-unsaturate, oleic acid (C-18:1), 23%. It also contains the saturated fatty acids, stearic acid, (C-18:0), 4%, and palmitic acid, (c-16:0), 10%.

As used herein, an emulsion refers to a colloidal dispersion of two immiscible liquids, for example, an oil and an aqueous liquid, for example, water, one of which is part of a continuous phase and the other of which is part of a dispersed phase. In an oil-in-water emulsion, the dispersed phase is an oil phase and the continuous phase is an aqueous (e.g., water) phase. Emulsions typically are stabilized by one or more emulsifiers (or surfactants). Emulsifiers form an interfacial film between the oil and water phase of the emulsion, providing stability.

As used herein, "lipid emulsion" or "fat emulsion" refer to an emulsion of a lipid component with an aqueous liquid. The lipid emulsions can contain one or more additional ingredients. Typically, the lipid emulsions provided herein are oil-in-water emulsions that contain a lipid component, an emulsifier, an aqueous phase, and optionally a tonicity modifier.

As used herein, an "intravenous lipid emulsion" or "injection lipid emulsion," i.e. ILE, (also termed intravenous fat emulsions or IVFE) refer to emulsions of fats or lipids that contain one or more triglyceride-containing oils, a phospholipid emulsifier, and typically a tonicity modifier (e.g. glycerin) to maintain isotonicity in blood. ILEs typically are used in parenteral feeding, but also are used as a delivery vehicle for drugs that are poorly soluble in water. Commercially available ILEs include any described herein or known in the art. For example, commercially available ILEs include, but are not limited to any made from soybean oil (e.g. Intralipid® lipid emulsion 10%, 20% or 30%; or Liposyn® III lipid emulsion 20%) or combined safflower/soybean oil (e.g. Liposyn® II 10%, containing 5% safflower oil and 5% soybean oil).

As used herein, "emulsifier" refers to a surface-active agent that stabilizes an emulsion. An emulsifier can include synthetic and naturally occurring amphiphilic molecules that have hydrophobic portion(s) and hydrophilic portion(s). Due to their amphiphilic (amphipathic) nature, emulsifiers typically can reduce the surface tension between two immiscible liquids, for example, the oil and water phases in an emulsion, stabilizing the emulsion. An emulsifier contains phospholipids, and can include surfactants and other natural or synthetic emulsifiers. For example, natural emulsifiers include those made from ingredients derived from nature, such as egg yolks that contain lecithin.

As used herein, the term "tonicity modifier" is used to mean a compound or compounds that can be used to adjust the tonicity of the lipid emulsion. Suitable tonicity modifiers include glycerin (i.e., glycerol or glycerin), sodium chloride, potassium chloride, mannitol, sucrose, lactose, fructose, maltose, dextrose, dextrose anhydrous, xylitol, sorbitol, propylene glycol, polyoxyethylated hydrocarbons, $C_6$-$C_{20}$ saturated or unsaturated aliphatic acids, and other tonicity modifiers known to those of skill in the art.

As used herein, "natural" or "naturally occurring" is used to refer to a composition, emulsion and/or ingredients in the composition or emulsion that can be found in nature and are not solely man-made. For example, egg yolk phospholipids are naturally occurring emulsifiers. Typically, the lipid emulsions provided herein contain one or more natural ingredients.

As used herein, "w/w," "by weight," "% by weight," "wt %" and "weight percent" are used synonymously to express the ratio of the mass of one component of a composition compared to the mass of the entire composition. For example, when the amount of a particular ingredient represents 1%, by weight (w/w) of a concentrate, the mass of that ingredient is 1% of the mass of the entire concentrate. Similarly, when the amount of an ingredient is 50% (w/w) of the concentrate, the mass of that ingredient is 50% of the entire mass of the concentrate. Similarly, when a composition and/or a compound contains 10%, by weight of an ingredient, the mass of the ingredient is 10% of the total mass of the composition or compound. When a composition contains 10 wt % of an ingredient, the mass of that ingredient is 10% of the mass of the entire composition. When only a concentration, amount, or percentage (without units) is listed, it is to be understood that the concentration or percentage is a concentration or percentage by weight.

As used herein, a lipid-treated virus refers to a virus that has been exposed or contacted with a lipid or lipid component sufficient to increase infectivity of the virus. For example, a lipid-treated virus includes a virus composition that is mixed with an emulsion containing a biocompatible lipid component (e.g. soybean oil) or formed as an emulsion with a biocompatible lipid component (e.g. soybean oil). The contacting or exposure can include a pretreatment of a virus composition with a lipid component, such as a biocompatible lipid component, under conditions sufficient to allow lipid portions to interact with the virus. For example, contacting can be at a temperature of 0° to 42° C., such as generally greater than 21° C., for 5 minutes to 12 hours, such as generally 30 minutes to 6 hours, for example, at least or about at least 1 hour, 2 hours, 3 hours, 4 hours or more. Contacting typically is at a physiologic temperature (e.g. at or about 37° C.).

As used herein, a complement inhibitor refers to any molecule that reduces or eliminates complement activity in a complement pathway by preventing or reducing activation and/or propagation of the complement cascade that results in the formation of the membrane attack complex (MAC) and/or effector molecules. A complement inhibitor can operate on one or more of the complement pathways, i.e., classical, alternative or lectin pathway. The inhibitor can be a molecule that prevents or reduces the activity of one or more of the complement components C1, C2, C3, C4, C5, C6, C7, C8, C9, Factor B, Factor D, properdin, C1r, C1s, C2a, C3a, C3b, C4a, C4b, C5a, C5b, Bb, C3 convertase, C5 convertase, MAC, complement receptor 1 (CR1), CR2, CR3 or CR4. The reduction in complement activity can be incremental (e.g., a 10%, 20%, 30%, 40%, 50%, 60%, 70%, 80%, or 90% reduction in activity) or complete. For example, in some embodiments, a complement inhibitor can inhibit complement activity by at least 10 (e.g., at least 15, 20, 25, 30, 35, 40, 45, 50, 55, 60, 65, 70, 75, 80, 85, 90, or 95 or greater) % in a standard in vitro red blood cell hemolysis assay or an in vitro CH50eq assay. See, e.g., Kabat and Mayer (eds), "Experimental Immunochemistry, 2$^{nd}$ Edition," 135-240, Springfield, Ill., C C Thomas (1961), pages 135-139, or a conventional variation of that assay such as the chicken erythrocyte hemolysis method as described in, e.g., Hillmen et al. (2004) *N Engl J Med* 350(6):552.

The complement inhibitor can be a soluble protein, a binding molecule such as an antibody or active fragment hereof, or a small organic molecule. For example, a complement inhibitor can be a soluble or membrane-bound protein such as, for example, membrane cofactor protein (MCP), decay accelerating factor (DAF/CD55), CD59, mouse complement receptor 1-related gene/protein y (Crry), human complement receptor 1 (CR1) or factor H; an antibody specific for a component of a complement pathway such as, for example, eculizumab (an anti-C5 antibody marketed under the name Soliris®), pexelizumab (the antigen-binding fragment of eculizumab), an anti-factor B antibody (such as the monoclonal antibody 1379 produced by ATCC Deposit No. PTA-6230), an anti-properdin antibody, an anti-factor D antibody, and others described herein or known in the art; or a small molecule or a linear or cyclic peptide such as, for example, compstatin or N-acetylaspartylglutamic acid (NAAGA). Other complement inhibitors are known to a skilled artisan, including any of the exemplary described complement inhibitors herein.

As used herein, a "C3 inhibitor" is a molecule or substance that prevents or reduces the cleavage of C3 into C3a and C3b.

As used herein, a "C5 inhibitor" is a molecule or substance that prevents or reduces the cleavage of C5 into C5a or C5b, thereby preventing the formation of the membrane attack complex (MAC, i.e. C5b-9) or generation of the C5a anaphylatoxin.

As used herein, a "C5a inhibitor" is a molecule or substance that prevents or reduces the activity of C5a.

As used herein, a "C5aR inhibitor" is a molecule or substance that prevents or reduces the binding of C5a to the C5a receptor.

As used herein, a "C3aR inhibitor" is a molecule or substance that prevents or reduces binding of C3a to the C3a receptor.

As used herein, a "factor D inhibitor" is a molecule or substance that prevents or reduces the activity of Factor D.

As used herein, a "factor B inhibitor" is a molecule or substance that prevents or reduces the activity of factor B.

As used herein, a "C4 inhibitor" is a molecule or substance that prevents or reduces the cleavage of C4 into C4b and C4a.

As used herein, a "C1q inhibitor" is a molecule or substance that prevents or reduces C1q binding to antibody-antigen complexes, virions, infected cells, or other molecules to which C1q binds to initiate complement activation.

As used herein, "binding molecule" refers to any molecule that specifically exhibits binding activity to specifically bind a binding partner, such as a protein or portion thereof. With reference to a binding molecule that is a complement inhibitor, the binding partner is a complement component, and binding inhibits interaction of the complement component with a sequentially interacting molecule in a complement pathway cascade. A binding molecule can be a peptide or polypeptide, such as an antibody.

As used herein, binding activity refer to characteristics of a molecule, e.g. a polypeptide, relating to whether or not, and how, it binds one or more binding partners. Binding activities include the ability to bind the binding partner(s), the affinity with which it binds to the binding partner (e.g. high affinity), the avidity with which it binds to the binding partner, the strength of the bond with the binding partner and specificity for binding with the binding partner.

As used herein, "bind," "bound" and grammatical variations thereof refer to the participation of a molecule in any attractive interaction with another molecule, resulting in a stable association in which the two molecules are in close proximity to one another. Binding includes, but is not limited to, non-covalent bonds, covalent bonds (such as reversible and irreversible covalent bonds), and includes interactions between molecules such as, but not limited to, proteins, nucleic acids, carbohydrates, lipids, and small molecules, such as chemical compounds including drugs. Exemplary of bonds are antibody-antigen interactions and receptor-ligand interactions. When an antibody "binds" a particular antigen, bind refers to the specific recognition of the antigen by the antibody, through cognate antibody-antigen interaction, at antibody combining sites. Binding also can include association of multiple chains of a polypeptide, such as antibody chains which interact through disulfide bonds.

As used herein, "specifically bind" or "immunospecifically bind" with respect to an antibody or antigen-binding fragment thereof are used interchangeably herein and refer to the ability of the antibody or antigen-binding fragment to form one or more noncovalent bonds with a cognate antigen, by noncovalent interactions between the antibody combining site(s) of the antibody and the antigen. Typically, an antibody that immunospecifically binds (or that specifically binds) to an antigen is one that binds to the antigen with an affinity constant $K_a$ of about or $1\times10^7$ $M^{-1}$ or $1\times10^8$ $M^{-1}$ or greater (or a dissociation constant ($K_d$) of $1\times10^{-7}$M or $1\times10^{-8}$M or less). Affinity constants can be determined by standard kinetic methodology for antibody reactions, for example, immunoassays, surface plasmon resonance (SPR) (Rich and Myszka (2000) *Curr. Opin. Biotechnol* 11:54; Englebienne (1998) *Analyst.* 123:1599), isothermal titration calorimetry (ITC) or other kinetic interaction assays known in the art (see, e.g., Paul, ed., Fundamental Immunology, 2nd ed., Raven Press, New York, pages 332-336 (1989); see also U.S. Pat. No. 7,229,619 for a description of exemplary SPR and ITC methods). Instrumentation and methods for real time detection and monitoring of binding rates are known and are commercially available (e.g., BiaCore 2000, Biacore AB, Uppsala, Sweden and GE Healthcare Life Sciences; Malmqvist (2000) *Biochem. Soc. Trans.* 27:335).

As used herein, "antibody" refers to immunoglobulins and immunoglobulin fragments, whether natural or partially or wholly synthetically, such as recombinantly, produced, including any fragment thereof containing at least a portion of the variable heavy chain and light region of the immunoglobulin molecule that is sufficient to form an antigen binding site and, when assembled, to specifically bind antigen. Hence, an antibody includes any protein having a binding domain that is homologous or substantially homologous to an immunoglobulin antigen-binding domain (antibody combining site). For example, an antibody refers to an antibody that contains two heavy chains (which can be denoted H and H') and two light chains (which can be denoted L and L'), where each heavy chain can be a full-length immunoglobulin heavy chain or a portion thereof sufficient to form an antigen binding site (e.g. heavy chains include, but are not limited to, VH chains, VH-CH1 chains and VH-CH1-CH2-CH3 chains), and each light chain can be a full-length light chain or a portion thereof sufficient to form an antigen binding site (e.g. light chains include, but are not limited to, VL chains and VL-CL chains). Each heavy chain (H and H') pairs with one light chain (L and L', respectively). Typically, antibodies minimally include all or at least a portion of the variable heavy (VH) chain and/or the variable light (VL) chain. The antibody also can include all or a portion of the constant region.

For purposes herein, the term antibody includes full-length antibodies and portions thereof including antibody fragments. Antibody fragments, include, but not limited to, Fab fragments, Fab' fragments, F(ab')$_2$ fragments, Fv fragments, disulfide-linked Fvs (dsFv), Fd fragments, Fd' fragments, single-chain Fvs (scFv), single-chain Fabs (scFab), diabodies, anti-idiotypic (anti-Id) antibodies, or antigen-binding fragments of any of the above. Antibody also includes synthetic antibodies, recombinantly produced antibodies, multispecific antibodies (e.g., bispecific antibodies), human antibodies, non-human antibodies, humanized antibodies, chimeric antibodies, and intrabodies. Antibodies provided herein include members of any immunoglobulin type (e.g., IgG, IgM, IgD, IgE, IgA and IgY), any class (e.g. IgG1, IgG2, IgG3, IgG4, IgA1 and IgA2) or subclass (e.g., IgG2a and IgG2b).

As used herein, a full-length antibody is an antibody having two full-length heavy chains (e.g. VH-CH1-CH2-CH3 or VH-CH1-CH2-CH3-CH4) and two full-length light chains (VL-CL) and hinge regions, such as human antibodies produced by antibody secreting B cells and antibodies with the same domains that are produced synthetically.

As used herein, antibody fragment or antibody portion refers to any portion of a full-length antibody that is less than full length but contains at least a portion of the variable region of the antibody sufficient to form an antigen binding site (e.g. one or more CDRs) and thus retains the binding specificity and/or an activity of the full-length antibody; antibody fragments include antibody derivatives produced by enzymatic treatment of full-length antibodies, as well as synthetically, e.g. recombinantly produced derivatives. Examples of antibody fragments include, but are not limited to, Fab, Fab', F(ab)$_2$, single-chain Fvs (scFv), Fv, dsFv, diabody, Fd and Fd fragments (see, for example, *Methods in Molecular Biology*, Vol 207: *Recombinant Antibodies for Cancer Therapy Methods and Protocols* (2003); Chapter 1; p 3-25, Kipriyanov). The fragment can include multiple chains linked together, such as by disulfide bridges and/or by peptide linkers. An antibody fragment generally contains at least about 50 amino acids and typically at least 200 amino acids.

As used herein, an Fv antibody fragment is composed of one variable heavy domain ($V_H$) and one variable light ($V_L$) domain linked by noncovalent interactions.

As used herein, a dsFv refers to an Fv with an engineered intermolecular disulfide bond, which stabilizes the $V_H$-$V_L$ pair.

As used herein, an Fd fragment is a fragment of an antibody containing a variable domain ($V_H$) and one constant region domain ($C_H1$) of an antibody heavy chain.

As used herein, a Fab fragment is an antibody fragment that results from digestion of a full-length immunoglobulin with papain, or a fragment having the same structure that is produced synthetically, e.g. by recombinant methods. A Fab fragment contains a light chain (containing a $V_L$ and $C_L$) and another chain containing a variable domain of a heavy chain ($V_H$) and one constant region domain of the heavy chain ($C_H1$).

As used herein, a F(ab')$_2$ fragment is an antibody fragment that results from digestion of an immunoglobulin with pepsin at pH 4.0-4.5, or a fragment having the same structure that is produced synthetically, e.g. by recombinant methods. The F(ab')$_2$ fragment essentially contains two Fab fragments where each heavy chain portion contains an additional few amino acids, including cysteine residues that form disulfide linkages joining the two fragments.

As used herein, a Fab' fragment is a fragment containing one half (one heavy chain and one light chain) of the F(ab')$_2$ fragment.

As used herein, an Fd' fragment is a fragment of an antibody containing one heavy chain portion of a F(ab')$_2$ fragment.

As used herein, an Fv' fragment is a fragment containing only the V$_H$ and V$_L$ domains of an antibody molecule.

As used herein, hsFv refers to antibody fragments in which the constant domains normally present in a Fab fragment have been substituted with a heterodimeric coiled-coil domain (see, e.g., Arndt et al. (2001) *J Mol Biol.* 7:312:221-228).

As used herein, an scFv fragment refers to an antibody fragment that contains a variable light chain (V$_L$) and variable heavy chain (V$_H$), covalently connected by a polypeptide linker in any order. The linker is of a length such that the two variable domains are bridged without substantial interference. Exemplary linkers are (Gly-Ser)$_n$ residues with some Glu or Lys residues dispersed throughout to increase solubility.

As used herein, diabodies are dimeric scFv; diabodies typically have shorter peptide linkers than scFvs, and preferentially dimerize.

As used herein, a minibody is an engineered antibody construct containing the variable heavy (VH) and variable light (VL) chain domains of a native antibody fused to the hinge region and to the CH3 domain of the imunoglobulin molecule. Minibodies are thus small versions of whole antibodies encoded in a single protein chain which retain the antigen binding region, the CH3 domain to permit assembly into a bivalent molecule and the antibody hinge to accommodate dimerization by disulfide linkages.

As used herein, anti-C5 antibody refers to an antibody or antigen-binding fragment thereof that specifically binds to the complement component C5. Anti-C5 antibodies or antigen-binding fragments thereof include those that bind to the C5 alpha chain or C5 beta chain. Exemplary anti-C5 antibodies include antibodies that bind to a C5 epitope set forth in SEQ ID NO:48 or SEQ ID NO:49.

As used herein, eculizumab refers to an anti-C5 antibody that is humanized IgG2/4 kappa antibody, made up of two 448 amino acid heavy chains and two 214 amino acid light chains. The heavy chains are composed of human IgG2 sequences in constant region 1, the hinge and the adjacent portion of constant region 2, and human IgG4 sequences in the remaining part of constant region 2 and 3. The light chain is composed of human kappa sequences. The sequence of amino acids of the heavy chain of eculizumab is set forth in SEQ ID NO:44 and the sequence of amino acids of the light chain is set forth in SEQ ID NO:45. Eculizumab specifically binds to an epitope in C5 set forth in SEQ ID NO:48.

As used herein, an antigen-binding fragment of eculizumab refers to an antibody derived from eculizumab but that is less than the full length of eculizumab but contains at least a portion of the variable region of the antibody sufficient to form an antigen binding site (e.g. one or more CDRs) and thus retains the binding specificity and/or activity of eculizumab. For example, an antigen-binding fragment of eculizumab contains one or more of the CDRs set forth in any of SEQ ID NOS:36-41. Typically, an antigen-binding fragment of eculizumab recognizes the same epitope on C5 as eculizumab, such as the epitope set forth in SEQ ID NO:48. Exemplary of antigen-binding fragments of eculizumab include antibodies that contain the sequence of amino acids set forth in SEQ ID NO:42 (variable heavy chain) and the sequence of amino acids set forth in SEQ ID NO:43 (variable light chain), or a portion of SEQ ID NO:42 and SEQ ID NO:43 sufficient to bind to C5. For example, exemplary of an antigen-binding fragment of eculizumab is an scFv antigen-binding fragment designated pexelizumab or a variant thereof, such as set forth in SEQ ID NO: 4 or SEQ ID NO:47.

As used herein, a variant or mutant with reference to a complement inhibitor refers to a modified form of the inhibitor that contains one or more amino acid modifications compared to a reference complement inhibitor. Typically, a variant or mutant retains an activity of the reference inhibitor, but the activity can be increased or decreased. Typically, a variant or mutant exhibits 50% to 500% of the activity of the reference inhibitor, such as generally at least 80%, 90%, 100%, 110%, 120%, 130%, 140%, 150%, 200% or more of the activity of the reference inhibitor.

As used herein, modification is in reference to modification of a sequence of amino acids of a polypeptide or a sequence of nucleotides in a nucleic acid molecule and includes deletions, insertions, and replacements (e.g. substitutions) of amino acids and nucleotides, respectively. Exemplary of modifications are amino acid substitutions. An amino-acid substituted polypeptide can exhibit 65%, 70%, 80%, 85%, 90%, 91%, 92%, 93%, 94%, 95%, 96%, 97%, 98% or more sequence identity to a polypeptide not containing the amino acid substitutions. Amino acid substitutions can be conservative or non-conservative. Generally, any modification to a polypeptide retains an activity of the polypeptide. Methods of modifying a polypeptide are routine to those of skill in the art, such as by using recombinant DNA methodologies.

As used herein, a variant of eculizumab refers to an antibody derived from eculizumab or an antigen-binding fragment thereof that exhibits one or more modifications in eculizumab and that specifically binds C5, such as specifically bind to the epitope set forth in SEQ ID NO:48. Exemplary variants of eculizumab include those that have a sequence of amino acids for a variable heavy chain that exhibit at least 75%, 80%, 85%, 90%, 91%, 92%, 93%, 94%, 95%, 96%, 97%, 98%, 99% or more sequence identity to the sequence of amino acids set forth in SEQ ID NO:44 and/or a sequence of amino acids for a variable light chain that exhibits at least 75%, 80%, 85%, 90%, 91%, 92%, 93%, 94%, 95%, 96%, 97%, 98%, 99% or more sequence identity to the sequence of amino acids set forth in SEQ ID NO:45, and that specifically bind to C5. Variants also include variants that have a sequence of amino acids for a variable heavy chain that exhibit at least 75%, 80%, 85%, 90%, 91%, 92%, 93%, 94%, 95%, 96%, 97%, 98%, 99% or more sequence identity to the sequence of amino acids set forth in SEQ ID NO:46 or 47.

As used herein, a derivative with reference to a complement inhibitor refers to a form of the inhibitor that has undergone change or modification from a reference drug or agent, but still retains activity (e.g. exhibits increased or decreased activity) compared to the reference drug or agent. Typically a derivative form of a compound means that a side chain of the compound has been modified or changed.

As used herein, an analogue or analog with reference to a complement inhibitor is a form of the inhibitor that is related to a reference drug, but whose chemical and biological activities can be different. Typically, analogues exhibit similar activities to a reference drug or agent, but the activity can be increased or decreased or otherwise improved. Typically, an analogue form of a compound or drug means that the backbone core of the structure is modified or changed compared to a reference drug. An analog can be a variant or mutant of a complement inhibitor.

As used herein, nucleic acids include DNA, RNA and analogs thereof, including peptide nucleic acids (PNA) and mixtures thereof. Nucleic acids can be single or double-stranded. Nucleic acids can encode gene products, such as, for example, polypeptides, regulatory RNAs, microRNAs, siRNAs and functional RNAs.

As used herein, a peptide refers to a polypeptide that is greater than or equal to 2 amino acids in length, and less than or equal to 40 amino acids in length.

As used herein, the amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

As used herein, "amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. NH$_2$ refers to the free amino group present at the amino terminus of a polypeptide. COOH refers to the free carboxy group present at the carboxyl terminus of a polypeptide. In keeping with standard polypeptide nomenclature described in J. Biol. Chem. 243:3557-3559 (1968), and adopted 37 C.F.R. §§1.821-1.822, abbreviations for amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

All amino acid residue sequences represented herein by formulae have a left to right orientation in the conventional direction of amino-terminus to carboxyl-terminus. In addition, the phrase "amino acid residue" is defined to include the amino acids listed in the Table of Correspondence (Table 1) and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues, to an amino-terminal group such as NH$_2$ or to a carboxyl-terminal group such as COOH.

As used herein, the "naturally occurring α-amino acids" are the residues of those 20 α-amino acids found in nature which are incorporated into protein by the specific recognition of the charged tRNA molecule with its cognate mRNA codon in humans. Non-naturally occurring amino acids thus include, for example, amino acids or analogs of amino acids other than the 20 naturally-occurring amino acids and include, but are not limited to, the D-stereoisomer of amino acids. Exemplary non-natural amino acids are described herein and are known to those of skill in the art.

As used herein, suitable conservative substitutions of amino acids are known to those of skill in the art and can be made generally without altering the biological activity of the resulting molecule. Those of skill in the art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p.224). Such substitutions can be made in accordance with those set forth in TABLE 2 as follows:

TABLE 2

| Original residue | Exemplary conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are contemplated, and they can be determined empirically or in accord with known conservative substitutions.

As used herein, a DNA construct is a single- or double-stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule may not be paired. Such unpaired ends will, in general, not exceed 20 nucleotides in length.

As used herein, recitation that nucleotides or amino acids "correspond to" nucleotides or amino acids in a disclosed sequence, such as set forth in the Sequence listing, refers to nucleotides or amino acids identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carrillo et al. (1988) *SIAM J Applied Math* 48:1073).

As used herein, "sequence identity" refers to the number of identical or similar amino acids or nucleotide bases in a comparison between a test and a reference polypeptide or polynucleotide. Sequence identity can be determined by sequence alignment of nucleic acid or protein sequences to identify regions of similarity or identity. For purposes herein, sequence identity is generally determined by alignment to identify identical residues. The alignment can be local or global. Matches, mismatches and gaps can be identified between compared sequences. Gaps are null amino acids or nucleotides inserted between the residues of aligned sequences so that identical or similar characters are aligned. Generally, there can be internal and terminal gaps. Sequence identity can be determined by taking into account gaps as the number of identical residues/length of the shortest sequence×100. When using gap penalties, sequence identity can be determined with no penalty for end gaps (e.g. terminal gaps are not penalized). Alternatively, sequence identity can be determined without taking into account gaps as the number of identical positions/length of the total aligned sequence×100. Typically, with reference to sequence identity of virus strains, sequence identity of nucleotide sequences containing nucleotides corresponding to the inverted terminal repetitions (ITRs) is determined using global alignment, whereby terminal gaps are not penalized.

As used herein, a "global alignment" is an alignment that aligns two sequences from beginning to end, aligning each letter in each sequence only once. An alignment is produced, regardless of whether or not there is similarity or identity between the sequences. For example, 50% sequence identity based on "global alignment" means that in an alignment of the full sequence of two compared sequences each of 100 nucleotides in length, 50% of the residues are the same. It is understood that global alignment also can be used in determining sequence identity even when the length of the aligned sequences is not the same. The differences in the terminal ends of the sequences will be taken into account in determining sequence identity, unless the "no penalty for end gaps" is selected. Generally, a global alignment is used on sequences that share significant similarity over most of their length. Exemplary algorithms for performing global alignment include the Needleman-Wunsch algorithm (Needleman et al. *J. Mol. Biol.* 48: 443 (1970). Exemplary programs for performing global alignment are publicly available and include the Global Sequence Alignment Tool available at the National Center for Biotechnology Information (NCBI) website (ncbi.nlm.nih.gov/), and the program available at deepc2.psi.iastate.edu/aat/align/align.html.

As used herein, a "local alignment" is an alignment that aligns two sequences, but only aligns those portions of the sequences that share similarity or identity. Hence, a local alignment determines if sub-segments of one sequence are present in another sequence. If there is no similarity, no alignment will be returned. Local alignment algorithms include BLAST or Smith-Waterman algorithm (*Adv. Appl. Math.* 2: 482 (1981)). For example, 50% sequence identity based on "local alignment" means that in an alignment of the full sequence of two compared sequences of any length, a region of similarity or identity of 100 nucleotides in length has 50% of the residues that are the same in the region of similarity or identity.

For purposes herein, sequence identity can be determined by standard alignment algorithm programs used with default gap penalties established by each supplier. Default parameters for the GAP program can include: (1) a unary comparison matrix (containing a value of 1 for identities and 0 for non identities) and the weighted comparison matrix of Gribskov et al. *Nucl. Acids Res.* 14: 6745 (1986), as described by Schwartz and Dayhoff, eds., *Atlas of Protein Sequence and Structure*, National Biomedical Research Foundation, pp. 353-358 (1979); (2) a penalty of 3.0 for each gap and an additional 0.10 penalty for each symbol in each gap; and (3) no penalty for end gaps. Whether any two nucleic acid molecules have nucleotide sequences (or any two polypeptides have amino acid sequences) that are at least 80%, 85%, 90%, 95%, 96%, 97%, 98% or 99% "identical," or other similar variations reciting a percent identity, can be determined using known computer algorithms based on local or global alignment (see e.g. wikipedia.org/wiki/Sequence_alignment_software, providing links to dozens of known and publicly available alignment databases and programs). Generally, for purposes herein sequence identity is determined using computer algorithms based on global alignment, such as the Needleman-Wunsch Global Sequence Alignment tool available from NCBI/BLAST (blast.ncbi.nlm.nih.gov/Blast.cgi?CMD=Web&Page_TYPE=BlastHome); LAlign (William Pearson implementing the Huang and Miller algorithm (*Adv. Appl. Math.* (1991) 12:337-357)); and program from Xiaoqui Huang available at deepc2.psi.iastate.edu/aat/align/ align.html. Generally, when comparing nucleotide sequences herein, an alignment with no penalty for end gaps (e.g. terminal gaps are not penalized) is used.

Therefore, as used herein, the term "identity" represents a comparison or alignment between a test and a reference polypeptide or polynucleotide. In one non-limiting example, "at least 90% identical to" refers to percent identities from 90 to 100% relative to the reference polypeptide or polynucleotide. Identity at a level of 90% or more is indicative of the fact that, assuming for exemplification purposes a test and reference polypeptide or polynucleotide length of 100 amino acids or nucleotides are compared, no more than 10% (i.e., 10 out of 100) of amino acids or nucleotides in the test polypeptide or polynucleotide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences are defined as nucleic acid or amino acid substitutions, insertions or deletions. Depending on the length of the compared sequences, at the level of homologies or identities above about 85-90%, the result can be independent of the program and gap parameters set; such high levels of identity can be assessed readily, often without relying on software.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound.

As used herein, the term assessing, determining or measuring, used interchangeably herein, is intended to include quantitative and qualitative determination in the sense of obtaining an absolute value for the activity, expression or presence of a product, and also of obtaining an index, ratio, percentage, visual or other value indicative of the level of the activity, expression or presence. Assessment can be direct or indirect.

As used herein, activity refers to the in vitro or in vivo activities of a compound or virus provided herein. For example, in vivo activities refer to physiological responses that result following in vivo administration thereof (or of a composition or other mixture). Activity, thus, encompasses resulting therapeutic effects and pharmaceutical activity of such compounds, compositions and mixtures. Activities can be observed in in vitro and/or in vivo systems designed to test or use such activities.

As used herein, "anti-tumor activity" or "anti-tumorigenic" refers to virus strains that prevent or inhibit the formation or growth of tumors in vitro or in vivo in a subject. Anti-tumor activity can be determined by assessing a parameter or parameters indicative of anti-tumor activity. These include, but are not limited to, infectivity of tumor cells, accumulation of virus in tumor tissues, viral nucleic acid replication in tumor cells, virus production in tumor cells, viral gene expression in tumor cells, cytotoxicity of tumor cells, tumor cell selectivity, tumor cell type selectivity, decreased tumor size, increased tumor volume, decreased tumor weight, and initiation of specific and nonspecific anti-tumor immune responses. Assays that assess any of the above parameters or other anti-tumorigenic properties are known to one of skill in the art. Exemplary assays are described herein. Hence, a virus that exhibits any one or more of the above activities or properties exhibits anti-tumor activity.

As used herein, "toxicity" (also referred to as virulence or pathogenicity herein) with reference to a virus refers to the deleterious or toxic effects to a host upon administration of the virus. For an oncolytic virus, such as LIVP, the toxicity of a virus is associated with its accumulation in non-tumorous organs or tissues, which can impact the survival of the host or result in deleterious or toxic effects. Toxicity can be measured by assessing one or more parameters indicative of toxicity, which include, but are not limited to, decreased survival of the subject, decreased body weight, fever, rash, allergy, fatigue, abdominal pain, induction of an immune response in the subject and pock formation. Assays or measures that assess any of the above parameters or other toxic properties known to one of skill in the art are described herein or are known to one of skill in the art. Hence, a virus that mediates any one or more of the above activities or properties in a host exhibits some degree of toxicity.

As used herein, a tumor cell or cancer cell refers to a cell that divides and reproduces abnormally because growth and division is not regulated or controlled, i.e. cells that are susceptible to uncontrolled growth. A tumor cell can be a benign or malignant cell. Typically, the tumor cell is a malignant cell that can spread to other parts of the body, a process known as metastasis.

As used herein, the terms immunoprivileged cells and immunoprivileged tissues refer to cells and tissues, such as solid tumors, which are sequestered from the immune system. Generally, administration of a virus to a subject elicits an immune response that clears the virus from the subject. Immunoprivileged sites, however, are shielded or sequestered from the immune response, permitting the virus to survive and generally to replicate Immunoprivileged tissues include proliferating tissues, such as tumor tissues and other tissues and cells involved in other proliferative disorders, wounds and other tissues involved in inflammatory responses.

As used herein, a disease or disorder refers to a pathological condition in an organism resulting from, for example, infection or genetic defect, and characterized by identifiable symptoms. An exemplary disease as described herein is a neoplastic disease, such as cancer.

As used herein, proliferative disorder or condition or hyperproliferative disorder or condition includes any disorders involving abnormal proliferation of cells. Such disorders include, but are not limited to, neoplastic diseases, inflammatory responses and disorders, e.g. including wounds or lesions involving wound healing processes, psoriasis, restenosis, macular degeneration, diabetic retinopathies, endometriosis, benign prostatic hypertrophy, hypertrophic scarring, cirrhosis, proliferative vitreoretinopathy, retinopathy of prematurity, and immunoproliferative diseases or disorders, e.g. inflammatory bowel disease, rheumatoid arthritis, systemic lupus erythematosus (SLE) and vascular hyperproliferation secondary to retinal hypoxia or vasculitis.

As used herein, a wound or lesion refers to any damage to any tissue in a living organism. The tissue can be an internal tissue, such as the stomach lining or a bone, or an external tissue, such as the skin. As such, a wound or lesion can include, but is not limited to, a gastrointestinal tract ulcer, a broken bone, a neoplasia, and cut or abraded skin. A wound or lesion can be in a soft tissue, such as the spleen, or in a hard tissue, such as bone. The wound or lesion can have been caused by any agent, including traumatic injury, infection or surgical intervention.

As used herein, a tumor, also known as a neoplasm, is an abnormal mass of tissue that results when cells proliferate at an abnormally high rate. Tumors can show partial or total lack of structural organization and functional coordination with normal tissue. Tumors can be benign (not cancerous), or malignant (cancerous). As used herein, a tumor is intended to encompass hematopoietic tumors as well as solid tumors.

Malignant tumors can be broadly classified into three major types. Carcinomas are malignant tumors arising from epithelial structures (e.g. breast, prostate, lung, colon, pancreas). Sarcomas are malignant tumors that originate from connective tissues, or mesenchymal cells, such as muscle, cartilage, fat or bone. Leukemias and lymphomas are malignant tumors affecting hematopoietic structures (structures pertaining to the formation of blood cells) including components of the immune system. Other malignant tumors include, but are not limited to, tumors of the nervous system (e.g. neurofibromatomas), germ cell tumors, and blastic tumors.

As used herein, neoplastic disease refers to any disorder involving cancer, including tumor development, growth, metastasis and progression.

As used herein, cancer is a term for diseases caused by or characterized by any type of malignant tumor, including metastatic cancers, lymphatic tumors, and blood cancers. Exemplary cancers include, but are not limited to, acute lymphoblastic leukemia, acute lymphoblastic leukemia, acute myeloid leukemia, acute promyelocytic leukemia, adenocarcinoma, adenoma, adrenal cancer, adrenocortical carcinoma, AIDS-related cancer, AIDS-related lymphoma, anal cancer, appendix cancer, astrocytoma, basal cell carcinoma, bile duct cancer, bladder cancer, bone cancer, osteosarcoma/malignant fibrous histiocytoma, brainstem glioma, brain cancer, carcinoma, cerebellar astrocytoma, cerebral astrocytoma/malignant glioma, ependymoma, medulloblastoma, supratentorial primitive neuroectodermal tumor, visual pathway or hypothalamic glioma, breast cancer, bronchial adenoma/carcinoid, Burkitt lymphoma, carcinoid tumor, carcinoma, central nervous system lymphoma, cervical cancer, chronic lymphocytic leukemia, chronic myelogenous leukemia, chronic myeloproliferative disorder, colon cancer, cutaneous T-cell lymphoma, desmoplastic small round cell tumor, endometrial cancer, ependymoma, epidermoid carcinoma, esophageal cancer, Ewing's sarcoma, extracranial germ cell tumor, extragonadal germ cell tumor, extrahepatic bile duct cancer, eye cancer/intraocular melanoma, eye cancer/retinoblastoma, gallbladder cancer, gallstone tumor, gastric/stomach cancer, gastrointestinal carcinoid tumor, gastrointestinal stromal tumor, giant cell tumor, glioblastoma multiforme, glioma, hairy-cell tumor, head and neck cancer, heart cancer, hepatocellular/liver cancer, Hodgkin lymphoma, hyperplasia, hyperplastic corneal nerve tumor, in situ carcinoma, hypopharyngeal cancer, intestinal ganglioneuroma, islet cell tumor, Kaposi's sarcoma, kidney/renal cell cancer, laryngeal cancer, leiomyoma tumor, lip and oral cavity cancer, liposarcoma, liver cancer, non-small cell lung cancer, small cell lung cancer, lymphomas, macroglobulinemia, malignant carcinoid, malignant fibrous histiocytoma of bone, malignant hypercalcemia, malignant melanomas, marfanoid habitus tumor, medullary carcinoma, melanoma, merkel cell carcinoma, mesothelioma, metastatic skin carcinoma, metastatic squamous neck cancer, mouth cancer, mucosal neuromas, multiple myeloma, mycosis fungoides, myelodysplastic syndrome, myeloma, myeloproliferative disorder, nasal cavity and paranasal sinus cancer, nasopharyngeal carcinoma, neck cancer, neural tissue cancer, neuroblastoma, oral cancer, oropharyngeal cancer, osteosarcoma, ovarian cancer, ovarian epithelial tumor, ovarian germ cell tumor, pancreatic cancer, parathyroid cancer, penile cancer, pharyngeal cancer, pheochromocytoma, pineal astrocytoma, pineal germinoma, pineoblastoma, pituitary adenoma, pleuropulmonary blastoma, polycythemia vera, primary brain tumor, prostate cancer, rectal cancer, renal cell tumor, reticulum cell sarcoma, retinoblastoma, rhabdomyosarcoma, salivary gland cancer, seminoma, Sezary syndrome, skin cancer, small intestine cancer, soft tissue sarcoma, squamous cell carcinoma, squamous neck carcinoma, stomach cancer, supratentorial primitive neuroectodermal tumor, testicular cancer, throat cancer, thymoma, thyroid cancer, topical skin lesion, trophoblastic tumor, urethral cancer, uterine/endometrial cancer, uterine sarcoma, vaginal cancer, vulvar cancer, Waldenstrom's macroglobulinemia or Wilm's tumor. Exemplary cancers commonly diagnosed in humans include, but are not limited to, cancers of the bladder, brain, breast, bone marrow, cervix, colon/rectum, kidney, liver, lung/bronchus, ovary, pancreas, prostate, skin, stomach, thyroid, or uterus. Exemplary cancers commonly diagnosed in dogs, cats, and other pets include, but are not limited to, lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilm's tumor, Burkitt's lymphoma, microglioma, neuroblastoma, osteoclastoma, oral neoplasia, fibrosarcoma, osteosarcoma and rhabdomyosarcoma, genital squamous cell carcinoma, transmissible venereal tumor, testicular tumor, seminoma, Sertoli cell tumor, hemangiopericytoma, histiocytoma, chloroma (e.g., granulocytic sarcoma), corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma and cystadenoma, follicular lymphoma, intestinal lymphosarcoma, fibrosarcoma and pulmonary squamous cell carcinoma. Exemplary cancers diagnosed in rodents, such as a ferret, include, but are not limited to, insulinoma, lymphoma, sarcoma, neuroma, pancreatic islet cell tumor, gastric MALT lymphoma and gastric adenocarcinoma. Exemplary neoplasias affecting agricultural livestock include, but are not limited to, leukemia, hemangiopericytoma and bovine ocular neoplasia (in cattle); preputial fibrosarcoma, ulcerative squamous cell carcinoma, preputial carcinoma, connective tissue neoplasia and mastocytoma (in horses); hepatocellular carcinoma (in swine); lymphoma and pulmonary adenomatosis (in sheep); pulmonary sarcoma, lymphoma, Rous sarcoma, reticuloendotheliosis, fibrosarcoma, nephroblastoma, B-cell lymphoma and lymphoid leukosis (in avian species); retinoblastoma, hepatic neoplasia, lymphosarcoma (lymphoblastic lymphoma), plasmacytoid leukemia and swimbladder sarcoma (in fish), caseous lymphadenitis (CLA): chronic, infectious, contagious disease of sheep and goats caused by the bacterium Corynebacterium pseudotuberculosis, and contagious lung tumor of sheep caused by jaagsiekte.

As used herein, a "metastasis" refers to the spread of cancer from one part of the body to another. For example, in the metastatic process, malignant cells can spread from the site of the primary tumor in which the malignant cells arose and move into lymphatic and blood vessels, which transport the cells to normal tissues elsewhere in an organism where the cells continue to proliferate. A tumor formed by cells that have spread by metastasis is called a "metastatic tumor," a "secondary tumor" or a "metastasis."

As used herein, an anticancer agent or compound (used interchangeably with "antitumor or antineoplastic agent") refers to any agents, or compounds, used in anticancer treatment. These include any agents, when used alone or in combination with other compounds or treatments, that can alleviate, reduce, ameliorate, prevent, or place or maintain in a state of remission of clinical symptoms or diagnostic markers associated with neoplastic disease, tumors and cancer, and can be used in methods, combinations and compositions provided herein. Anticancer agents include antimetastatic agents. Exemplary anticancer agents include, but are not limited to, chemotherapeutic compounds (e.g., toxins, alkylating agents, nitrosoureas, anticancer antibiotics, antimetabolites, antimitotics, topoisomerase inhibitors), cytokines, growth factors, hormones, photosensitizing agents, radionuclides, signaling modulators, anticancer antibodies, anticancer oligopeptides, anticancer oligonucleotides (e.g., antisense RNA and siRNA), angiogenesis inhibitors, radiation therapy, or a combination thereof. Exemplary chemotherapeutic compounds include, but are not limited to, Ara-C, cisplatin, carboplatin, paclitaxel, doxorubicin, gemcitabine, camptothecin, irinotecan, cyclophosphamide, 6-mercaptopurine, vincristine, 5-fluorouracil, and methotrexate. As used herein, reference to an anticancer or chemotherapeutic agent includes combinations or a plurality of anticancer or chemotherapeutic agents unless otherwise indicated.

As used herein, a "chemosensitizing agent" is an agent which modulates, attenuates, reverses, or affects a cell's or organism's resistance to a given chemotherapeutic drug or compound. The terms "modulator", "modulating agent", "attenuator", "attenuating agent", or "chemosensitizer" can be used interchangeably to mean "chemosensitizing agent." In some examples, a chemosensitizing agent can also be a chemotherapeutic agent. Examples of chemosensitizing agents include, but are not limited to, radiation, calcium channel blockers (e.g., verapamil), calmodulin inhibitors (e.g., trifluoperazine), indole alkaloids (e.g., reserpine), quinolines (e.g., quinine), lysosomotropic agents (e.g., chloroquine), steroids (e.g., progesterone), triparanol analogs (e.g., tamoxifen), detergents (e.g., Cremophor EL), texaphyrins, and cyclic antibiotics (e.g., cyclosporine).

As used herein, a subject includes any organism, including an animal for whom diagnosis, screening, monitoring or treatment is contemplated. Animals include mammals such as primates and domesticated animals. An exemplary primate is human.

As used herein, an "individual" can be a subject.

As used herein, a patient refers to a human subject exhibiting symptoms of a disease or disorder. Hence, a patient refers to a subject, such as a mammal, primate, human, or livestock subject, afflicted with a disease condition or for which a disease condition is to be determined or risk of a disease condition is to be determined.

As used herein, treatment of a subject that has a condition, disorder or disease means any manner of treatment in which the symptoms of the condition, disorder or disease are ameliorated or otherwise beneficially altered. Treatment encompasses any pharmaceutical use of the viruses described and provided herein.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, treatment of a subject that has a hyperproliferative disease or disorder, such as a neoplastic disease, including a tumor or metastasis, means any manner of treatment in which the symptoms of having the disease are ameliorated or otherwise beneficially altered. For example, typically, treatment of a tumor or metastasis in a subject encompasses any manner of treatment that results in slowing of tumor growth, lysis of tumor cells, reduction in the size of the tumor, prevention of new tumor growth, or prevention of metastasis of a primary tumor, including inhibition of vascularization of the tumor, tumor cell division, tumor cell migration or degradation of the basement membrane or extracellular matrix.

As used herein, therapeutic effect means an effect resulting from treatment of a subject that alters, typically improves or ameliorates the symptoms of a disease or condition or that cures a disease or condition. A therapeutically effective amount refers to the amount of a composition, molecule or compound which results in a therapeutic effect following administration to a subject.

As used herein, effective treatment or efficacy of treatment with a virus is one that can increase survival compared to the absence of treatment therewith. For example, a virus is an effective treatment if it stabilizes disease, causes tumor regression, decreases severity of disease or slows down or reduces metastasizing of the tumor.

As used herein, dosing regime refers to the amount of agent, for example, oncolytic virus administered, and the frequency of administration. The dosing regime is a function of the disease or condition to be treated, and thus can vary.

As used herein, frequency of administration refers to the time between successive administrations of treatment. For example, frequency can be days, weeks or months. For example, frequency can be more than once weekly, for example, twice a week, three times a week, four times a week, five times a week, six times a week or daily. Frequency also can be one, two, three or four weeks. The particular frequency is function of the particular disease or condition treated.

As used herein, a "cycle of administration" refers to the repeated schedule of the dosing regime of administration of an oncolytic virus therapy that is repeated over successive administrations. For example, an exemplary cycle of administration is a 28 day cycle that can be repeated.

As used herein, when referencing dosage based on mg/kg of the subject, an average human subject is considered to have a mass of about 70 kg-75 kg, such as 70 kg.

As used herein, a composition refers to any mixture. It can be a solution, suspension, liquid, gel, powder, paste, aqueous, non-aqueous or any combination thereof.

As used herein, a formulation refers to a composition containing at least one active pharmaceutical or therapeutic agent and one or more excipients.

As used herein, a co-formulation refers to a composition containing two or more active or pharmaceutical or therapeutic agents and one or more excipients.

As used herein, a combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, direct administration refers to administration of a composition without dilution.

As used herein, a single dosage formulation refers to a formulation for use only once. Typically, a single dosage formulation is for direct administration.

As used herein, a multiple dosage formulation refers to a formulation for use in repeat administrations.

As used herein, "intravenous administration" refers to delivery of a therapeutic directly into a vein.

As used herein, a kit is a packaged combination, optionally, including instructions for use of the combination and/or other reactions and components for such use.

As used herein, an "article of manufacture" is a product that is made and sold. As used throughout this application, the term is intended to encompass articles containing a vaccinia virus alone or in combination with a second therapy or a therapeutic energy source contained in the same or separate articles of packaging.

As used herein, a device refers to a thing made or adapted for a particular task. Exemplary of devices herein are devices that cover or coat or are capable of contacting the epidermis or surface of the skin. Examples of such devices include, but are not limited to, a wrap, bandage, bind, dress, suture, patch, gauze or dressing.

As used herein, the singular forms "a," "an" and "the" include plural referents unless the context clearly dictates otherwise.

As used herein, ranges and amounts can be expressed as "about" or "approximately" a particular value or range. "About" or "approximately" also includes the exact amount. Hence, "about 5 milliliters" means "about 5 milliliters" and also "5 milliliters." Generally "about" includes an amount that would be expected to be within experimental error.

As used herein, "about" or "about the same" means within an amount that one of skill in the art would consider to be the same or to be within an acceptable range of error. For example, typically, for pharmaceutical compositions, within at least 1%, 2%, 3%, 4%, 5% or 10% is considered about the same. Such amount can vary depending upon the tolerance for variation in the particular composition by subjects.

As used herein, "optional" or "optionally" means that the subsequently described event or circumstance does or does not occur, and that the description includes instances where said event or circumstance occurs and instances where it does not.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

For clarity of disclosure, and not by way of limitation, the detailed description is divided into the subsections that follow.

B. Oncolytic Virus Therapy

Provided herein are combinations therapies of an oncolytic virus, such as a vaccinia virus, and a modulator(s) of the innate immune system for use in maintaining the infectivity and/or bioactivity of the oncolytic virus in bodily fluids. In particular, the adjunct therapies provided herein maintain the infectivity of the oncolytic virus (e.g. vaccinia virus) for treating proliferative diseases and conditions, such as tumors. For example, the innate immune system is the first line of host defense and functions in advance of the adaptive immune system to recognize and inactivate or clear foreign pathogens. Consistent with innate immune involvement, oncolytic viruses, such as vaccinia virus, exhibit a loss of infectivity and rapid elimination of the virus from the blood, which can undermine the utility of the virus to infect target cells, such as cancer cells, throughout the body. Thus, therapies that reduce virus clearance and/or inactivation by the innate immune system, and thereby increase virus infectivity, are desired.

In particular, the complement system is a primary pathway involved in the innate immune-mediated inactivation of foreign substances, such as bacteria and viruses. Thus, provided herein are combinations and compositions of an oncolytic virus and an inhibitor of the complement system (e.g. anti-C5 antibody) for use in methods of co-administration for maintaining the infectivity and/or bioactivity of the oncolytic virus for treating a proliferative disorder, such as a tumor.

In addition, it is also found herein that lipid emulsions (e.g. 20% soybean oil intravenous fat emulsion) either co-formulated or co-administered with a virus reduce virus inactivation and/or clearance, and hence increase virus infectivity. Thus, also provided herein are lipid-emulsion oncolytic virus compositions or combinations containing a virus and a lipid emulsion for use in methods for maintaining the infectivity of the oncolytic virus for treating a proliferative disorder, such as a tumor. A lipid-emulsion oncolytic virus also can be used in methods and uses of adjunct therapy with a complement inhibitor (e.g. anti-C5 antibody) or other immune modulator agent or therapeutic agent.

1. Oncolytic Viruses

Oncolytic viruses are viruses that accumulate in tumor cells and replicate in tumor cells. By virtue of replication in the cells, and optional delivery of therapeutic agents encoded by the virus, tumor cells are lysed, and the tumor shrinks and can be eliminated. Also, many oncolytic viruses such as vaccinia viruses have a broad host and cell type range. For example, vaccinia viruses can accumulate in immunoprivileged cells or immunoprivileged tissues, including tumors and/or metastases, and also including wounded tissues and cells. Among oncolytic viruses being studied include, for example, adenovirus, Herpes Simplex Virus, Vesticular Stomatic virus, Reovirus, Coxsackie virus and Vaccinia virus. Vaccinia virus strains have been shown to specifically colonize solid tumors, while not infecting other organs (see, e.g., Zhang et al. (2007) *Cancer Res* 67:10038-10046; Yu et al., (2004) *Nat Biotech* 22:313-320; Heo et al., (2011) *Mol Ther* 19:1170-1179; Liu et al. (2008) *Mol Ther* 16:1637-1642; Park et al., (2008) *Lancet Oncol,* 9:533-542).

Various oncolytic viruses, including vaccinia viruses, have been demonstrated to exhibit antitumor activities. In one study, for example, nude mice bearing nonmetastatic colon adenocarcinoma cells were systemically injected with a WR strain of vaccinia virus modified by having a vaccinia growth factor deletion and an enhanced green fluorescence protein inserted into the thymidine kinase locus. The virus was observed to have antitumor effect, including one complete response, despite a lack of exogenous therapeutic genes in the modified virus (McCart et al. (2001) *Cancer Res* 1:8751-8757). In another study, vaccinia melanoma oncolysate (VMO) was injected into sites near melanoma positive lymph nodes in a Phase III clinical trial of melanoma patients. As a control, New York City Board of Health strain vaccinia virus (VV) was administered to melanoma patients.

The melanoma patients treated with VMO had a survival rate better than that for untreated patients, but similar to patients treated with the VV control (Kim et al. (2001) *Surgical Oncol* 10:53-59).

LIVP strains of vaccinia virus also have been used for the diagnosis and therapy of tumors, and for the treatment of wounded and inflamed tissues and cells (see e.g. Lin et al. (2007) Surgery, 142:976-983; Lin et al. (2008) J. Clin. Endocrinol., Metab., 93:4403-7; Kelly et al. (2008) Hum gene There., 19:774-782; Yu et al. (2009) Mol Cancer Ther., 8:141-151; Yu et al. (2009) Mol Cancer, 8:45; U.S. Pat. Nos. 7,588,767; 8,052,968; and U.S. Patent Publication No. US20040234455). For example, when intravenously administered, LIVP strains have been demonstrated to accumulate in internal tumors at various loci in vivo, and have been demonstrated to effectively treat human tumors of various tissue origin, including, but not limited to, breast tumors, thyroid tumors, pancreatic tumors, metastatic tumors of pleural mesothelioma, squamous cell carcinoma, lung carcinoma and ovarian tumors. LIVP strains of vaccinia, including attenuated forms thereof, exhibit less toxicity than WR strains of vaccinia virus, and results in increased and longer survival of treated tumor-bearing animal models (see e.g. U.S. Patent Publication No. US20110293527).

In addition, oncolytic viruses possess a large carrying capacity for foreign genes that can be inserted into the vaccinia genome. Hence, oncolytic viruses can be optimized to encode therapeutic genes, including anti-cancer genes, that can increase the therapeutic or anti-tumor activity of the virus. In particular, vaccinia virus can carry up to 25 kb of exogenous DNA fragments (approximately 12% of the vaccinia genome size). The ability to modify viruses, such as vaccinia viruses, is facilitated due to the high sequence homology among different strains for designing and generating modified viruses in other strains. Techniques for production of modified viruses, including vaccinia strains, by genetic engineering are well established (Moss (1993) *Curr. Opin. Genet. Dev.* 3: 86-90; Broder and Earl (1999) *Mol. Biotechnol.* 13: 223-245; Timiryasova et al. (2001) *Biotechniques* 31: 534-540).

Vaccinia viruses also exhibit low toxicity. While most oncolytic viruses are natural pathogens, vaccinia virus has a unique history in its widespread application as a smallpox vaccine that has resulted in an established track record of safety in humans. Toxicities related to vaccinia administration occur in less than 0.1% of cases, and can be effectively addressed with immunoglobulin administration.

Although oncolytic viruses, such as vaccinia viruses, can accumulate in immunoprivileged cells and tissues, the systemic administration of viruses exposes them to the immune system. An active immune response against the virus can develop quickly, resulting in clearance and inactivation of the virus in the serum. For example, pharmacokinetic (PK) analysis of virus administered intravenously typically reveals that there is little detectable live virus or only a low titer live virus soon after administration. The result is that effectiveness of the virus to accumulate in desired tissues is reduced and/or a larger concentration of virus must be administered to obtained a desired efficacy. Therefore, therapies and methods that prolong the titer, PK or half-life of the virus in the circulation are desired.

2. Virus Therapies to Increase Infectivity

As indicated above, therapeutic uses of oncolytic viruses (e.g. vaccinia viruses) are hampered by the rapid and efficient inactivation and loss of infectivity of the virus after administration into the body. The oncolytic virus (e.g. vaccinia virus) can rapidly lose its infectivity after exposure to blood. Components of the innate and acquired immune systems are likely responsible for the inactivity of the viruses.

Among the immune system mechanisms involved in virus inactivation is the complement system. Complement is activated upon exposure to foreign substances, including bacteria and viruses. As described in more detail in Section D below, the activation is the result of a cascade of enzymatic and biochemical changes in the proteins of the complement system, ultimately leading to the binding of complement to the surface of the foreign substance. The infectivity of the virus is reduced by this binding either directly as a function of the binding itself or through subsequent interactions that the bound complement components can direct. The immediate effect is rapid and efficient loss of infectivity of the exposed virus. Secondary effects can include more rapid phagocytosis and destruction of the complement-bound virus by macrophages and other blood cells and cells of the reticuloendothelial system, and elimination of the virus from the blood stream. Loss of infectivity and rapid elimination of the virus from the blood undermines the utility of the virus if its intended use is to infect target cells, such as cancer cells, throughout the body.

Provided herein are combinations, composition and methods that reduce or eliminate complement-mediated inactivation of the virus, and that thereby enhance the intended oncolytic use of the virus. In particular, it is found herein that co-administration of an oncolytic virus to a subject in the presence of a complement inhibitor, separately or formulated together, results in decreased serum inactivation of the virus and an increase in virus titer and recovery of the virus from the serum. The complement inhibitor can be any inhibitor that targets a complement pathway, but generally is an inhibitor that targets a component in the common pathway of complement activation, and thereby inhibits the terminal portion of the complement pathway. Exemplary of such inhibitors are inhibitors that target the C3 or C5 complement components. Adjunct therapies with a complement inhibitor can be used in methods of administration of the virus to any body fluid or compartment in the body in which complement is present, and in particular by systemic administration methods to the blood.

Among complement inhibitors, it is found herein that anti-complement antibody inhibitors (e.g. anti-C5 antibody, for example eculizumab) offer protective benefits to the virus that do not exist with other complement inhibitors, including by generalized complement inhibition achieved by heat inactivation. For example, as shown in the Examples herein, exposure of virus to blood cells in the presence of serum containing an anti-C5 antibody (e.g. eculizumab) results in a substantial increase in virus that is bound to blood cells compared to conditions in which the anti-C5 antibody (e.g. eculizumab) is not present. Based on the total increase in recovery of virus, along with an increase propensity to bind to blood cells, the results demonstrate that cell binding of the virus preserves infectivity and provides a protective advantage to the virus. In some cases, the anti-complement antibody (e.g. anti-C5 antibody, such as eculizumab) can increase the infectivity of the virus that is bound to blood cells in serum in excess of that obtained in the absence of serum. These results are not achieved when the complement in the serum is instead inhibited by heat inactivation. Thus, the mechanism for this protective effect could be that the anti-complement antibody itself binds to a complement component (e.g. C5) already coated on the virus, and the bound antibody then interacts with its Fc receptors on the surface of blood cells.

The adjunct therapies provided herein employing separate administration of a complement inhibitor (e.g. anti-complement antibody), such as by co-administration or co-formulation with an oncolytic virus, offers advantages compared to prior art methods. Strategies employed in the art rely on engineering the oncolytic virus to encode heterologous immunomodulatory polypeptides that can attenuate the immune response (see e.g. U.S. Patent Publication No. US2010/0178684). Such strategies, however, are not ideal because in order to express the immunomodulatory protein, the virus must first infect and enter the host cell and/or replicate in the host cells. By this time, virus can already be exposed to immune modulators in the serum that inactivate or clear the virus so that it never reaches the host cell. Further, after infection, a virus produces its own complement-control proteins that can circumvent complement-mediated clearance. For example, vaccinia virus encodes a complement control protein designated VCP that inhibits complement activation (Sahu et al. (1998) *J. Immunol,* 160:5596-5604). Thus, delivering a virus that only encodes a complement protein after infection of host cells fails to address the problem of virus neutralization and inactivation that occurs by immune modulators prior to infection of cells.

In contrast, in the methods provided herein, the complement inhibitor (e.g. anti-complement antibody) can be administered prior to, simultaneously with, intermittently with, or subsequently to administration of the oncolytic virus. Typically, the complement inhibitor (e.g. anti-complement antibody, such as anti-C5 antibody) is administered prior to delivery of the oncolytic virus in order to pretreat the serum or other bodily fluid so that complement is inhibited upon delivery of the virus to the bodily fluid. Thus, when the virus is delivered to the bodily fluid, the virus is not susceptible to virus neutralization, clearance or inactivation that would otherwise occur in the absence of the complement inhibitor (e.g. anti-complement antibody, such as anti-C5 antibody).

It is also found herein that adjunct therapies employing lipid emulsions also offer protective effects to the virus, and thereby increases virus infectivity. Lipid emulsions are fat emulsions that contain various phospholipids and fatty acids. Lipid emulsions typically are administered for parenteral nutrition, but also have been shown to exhibit immunomodulatory properties. For example, lipid emulsions have been reported to suppress NK cell cytotoxicity (Roussev et al. (2007) *Am. J Reprod. Immunol.,* 57:262-9); inhibit the synthesis of complement proteins, such as C2 and C4, by macrophages (Strunk et al. (1979) *Pediatric Research,* 13:188-193; Strunk et al. (1983) *Lipids,* 18:493-500); and inhibit antibody-dependent cellular cytotoxicity (ADCC) (Loo et al. (1982) *Journal of Infectious Diseases,* 146:64-70). In adjunct therapies provided herein, a lipid emulsion can be co-administered to a bodily fluid prior to, simultaneously with, intermittently with or subsequently to administration or delivery of an oncolytic virus, and typically prior to administration of an oncolytic virus. In such examples, the virus infectivity of the oncolytic virus is increased compared to therapies that do not include co-administration (e.g. preadministration) with a lipid emulsion.

It is also found herein, however, that lipid emulsions can also increase virus infectivity when the virus is pretreated with lipid in an emulsion (i.e. lipid-emulsion oncolytic virus), even at concentrations that are substantially lower than would be required in preadministration methods. For example, it is found herein that pretreatment of an equal volume of an oncolytic virus stock with a standard 20% soybean intravenous fat emulsion (e.g. Intralipid® lipid emulsion) for at least 1 hour at 37° C., and typically up to or between 1 to 4 hours, followed by further dilution of the pretreated virus stock to an appropriate concentration for use or administration, results in an increased titer and recovery of the virus in serum, and hence increased virus infectivity. It is likely that pretreatment with lipids and other components in the lipid emulsion alters the virus coat, and thereby changes (e.g. reduces) the interaction of the virus with components of the innate immune system, such as complement. Thus, while lipid emulsions have been shown to suppress natural killer (NK) cells and other immune processes, it is believed that the effect of the lipid emulsions on virus infectivity of a lipid-pretreated virus is because the lipid component alters the properties of the virus as opposed to direct effects of the lipid component or emulsion on immune cells. For example, administration of a lipid emulsion to serum prior to addition of virus, and at concentrations similar to the concentrations of lipid present when the same dosage of virus is administered as a lipid-treated virus, do not reduce the amount of serum inactivation of the virus in the same manner as the lipid-treated virus.

The following sections describe exemplary oncolytic viruses, including vaccinia viruses, exemplary complement inhibitors and lipid emulsions that can be used in combination with an oncolytic virus as descried herein. Exemplary dosage regimes and methods for treatment of proliferative disorders using the oncolytic virus therapies also are described.

C. Oncolytic Virus

Provided herein are methods to increase the infectivity of an oncolytic virus by administration of the virus in combination or formulation with an agent(s), such as a complement inhibitors or lipid component, that increases virus titer or half-life compared to the absence of the agent(s). Oncolytic viruses are characterized by their largely tumor cell specific replication, resulting in tumor cell lysis and efficient tumor regression. Oncolytic viruses effect treatment by colonizing or accumulating in tumor cells, including metastatic tumor cells such as circulating tumor cells, and replicating. They provide an effective weapon in the tumor treatment arsenal. Oncolytic viruses include Newcastle Disease virus, parvovirus, vaccinia virus, reovirus, measles virus, vesticular stomatitis virus (VSV), oncolytic adenoviruses and herpes viruses. In many cases, tumor selectivity is an inherent property of the virus, such as vaccinia viruses and other oncolytic viruses. Generally oncolytic viruses effect treatment by replicating in tumors or tumor cells resulting in lysis.

Oncolytic viruses for use in the combinations, compositions, use or methods provided here are well known to one of skill in the art and include, for example, vesicular stomatitis virus, see, e.g., U.S. Pat. Nos. 7,731,974, 7,153,510, 6,653,103 and U.S. Pat. Pub. Nos. 2010/0178684, 2010/0172877, 2010/0113567, 2007/0098743, 20050260601, 20050220818 and EP Pat. Nos. 1385466, 1606411 and 1520175; herpes simplex virus, see, e.g., U.S. Pat. Nos. 7,897,146, 7,731,952, 7,550,296, 7,537,924, 6,723,316, 6,428,968 and U.S. Pat. Pub. Nos. 2011/0177032, 2011/0158948, 2010/0092515, 2009/0274728, 2009/0285860, 2009/0215147, 2009/0010889, 2007/0110720, 2006/0039894 and 20040009604; retroviruses, see, e.g., U.S. Pat. Nos. 6,689,871, 6,635,472, 5,851,529, 5,716,826, 5,716,613 and U.S. Pat. Pub. No. 20110212530; and adeno-associated viruses, see, e.g., U.S. Pat. Nos. 8,007, 780, 7,968,340, 7,943,374, 7,906,111, 7,927,585, 7,811,814, 7,662,627, 7,241,447, 7,238,526, 7,172,893, 7,033,826, 7,001,765, 6,897,045, and 6,632,670.

Oncolytic viruses also include viruses that have been genetically altered to attenuate their virulence, to improve their safety profile, enhance their tumor specificity, and they have also been equipped with additional genes, for example cytotoxins, cytokines, prodrug converting enzymes to improve the overall efficacy of the viruses (see, e.g., Kirn et al., (2009) *Nat Rev Cancer* 9:64-71; Garcia-Aragoncillo et al., (2010) *Curr Opin Mol Ther* 12:403-411; see U.S. Pat. Nos. 7,588,767, 7,588,771, 7,662,398 and 7,754,221 and U.S. Pat. Publ. Nos. 2007/0202572, 2007/0212727, 2010/0062016, 2009/0098529, 2009/0053244, 2009/0155287, 2009/0117034, 2010/0233078, 2009/0162288, 2010/0196325, 2009/0136917 and 2011/0064650.

For example, other activities can be introduced and/or anti-tumor activity can be enhanced by including nucleic acid encoding a heterologous gene product that is a therapeutic and/or diagnostic agent or agents. In some examples, the oncolytic viruses provide oncolytic therapy of a tumor cell without the expression of a therapeutic gene. In other examples, the oncolytic viruses can express one or more genes whose products are useful for tumor therapy. For example, a virus can express proteins that cause cell death or whose products cause an anti-tumor immune response. Such genes can be considered therapeutic genes. A variety of therapeutic gene products, such as toxic or apoptotic proteins, or siRNA, are known in the art, and can be used with the oncolytic viruses in the combinations, compositions and methods provided herein. The therapeutic genes can act by directly killing the host cell, for example, as a channel-forming or other lytic protein, or by triggering apoptosis, or by inhibiting essential cellular processes, or by triggering an immune response against the cell, or by interacting with a compound that has a similar effect, for example, by converting a less active compound to a cytotoxic compound. Exemplary thereof are gene products selected from among an anticancer agent, an anti-metastatic agent, an antiangiogenic agent, an immunomodulatory molecule, an antigen, a cell matrix degradative gene, genes for tissue regeneration and reprogramming human somatic cells to pluripotency, and other genes described herein or known to one of skill in the art. In these examples, the tumor-specific replication process is capable of directly killing the infected tumor cells (oncolytic viruses) and/or strongly amplifying the copy number of the therapeutic gene carried by the viral vector.

Exemplary therapeutic genes that can be inserted into any oncolytic virus are described herein in below and exemplified with respect to vaccinia virus. It is understood that an oncolytic virus can be modified to include nucleic acid sequences encoding any of the therapeutic genes described below or any known to one of skill in the art. The sequence of nucleotides encoding a gene is typically inserted into or in place of a non-essential gene or region in the genome of the virus. Thus, oncolytic viruses herein also include viruses that contain nucleic acid encoding a heterologous gene product that is a therapeutic and/or diagnostic agent or agents. Exemplary of such oncolytic viruses are viruses derived from the Lister strain, such as LIVP, including any containing nucleic acid encoding a heterologous gene product (e.g. GLV-1h68 and derivatives thereof). Such viruses are further described in detail below. Among other therapeutic vaccinia viruses are the virus designated JX-594, which is a vaccinia virus that expresses GM-CSF described, for example, in U.S. Pat. No. 6,093,700, and the Wyeth strain vaccinia virus designated JX-594, which is a TK-deleted vaccinia virus that expresses GM-CSF (see, International PCT Publication No. WO 2004/014314, U.S. Pat. No. 5,364,773; Mastrangelo et al. (1998) *Cancer Gene Therapy* 6:409-422; Kim et al. (2006) *Molecular Therapeutics* 14:361-370). Other oncolytic viruses include, but are not limited to, JX-954 (Parato et al. (2012) Mol. Ther., 20:749-58); ColoAd1 (Kuhn et al. (2008) PLoS One, 3:e2409; MV-CEA and MV-NIS (Msaouel et al. (2009) Curr. Opin. Mol. Ther., 11:43-53); Synco-B18R (Fu et al. (2012) Mol. Ther., 20:1871-81); OncoVEX GM-CSF (Kaufman et al. (2010) Future Oncol. 6:941-9), Reo-001 (Reolysin®, Galanis et al. (2012) Mol. Ther., 20:1998-2003); NTX-010 (Morton et al. (2010) Pediatr Blood Cancer, 55:295-303); and Coxsackieviruses A13, A15, A18, A20 and A21(e.g. CAVATAK™, which is coxsackievirus A21.)

In addition, adenoviruses, such as the ONYX viruses and others, have been modified, such as be deletion of EA1 genes, so that they selectively replicate in cancerous cells, and, thus, are oncolytic. Adenoviruses also have been engineered to have modified tropism for tumor therapy and also as gene therapy vectors. Exemplary of such is ONYX-015, H101 and Ad5ΔCR (Hallden and Portella (2012) Expert Opin Ther Targets, 16:945-58) and TNFerade (McLoughlin et al. (2005) Ann. Surg. Oncol., 12:825-30). A conditionally replicative adenovirus is Oncorine®, which is approved in China.

Any oncolytic virus, such as any described above or herein or others known in the art, can benefit from the adjunct therapies provided herein. Exemplary oncolytic viruses for use in the adjunct therapies provided herein are further described below. In particular examples, the oncolytic virus is a vaccinia virus, such as an LIVP, Western Reserve or Copenhagen strain of virus, or a recombinant or modified virus thereof that encodes a heterologous gene product.

1. Vaccinia Viruses

Vaccinia viruses are oncolytic viruses that possess a variety of features that make them particularly suitable for use in treatment of hyperproliferative diseases and disorders, such as wound and cancer gene therapy. For example, vaccinia is a cytoplasmic virus, thus, it does not insert its genome into the host genome during its life cycle. Unlike many other viruses that require the host's transcription machinery, vaccinia virus can support its own gene expression in the host cell cytoplasm using enzymes encoded in the viral genome. Vaccinia viruses also have a broad host and cell type range. In particular vaccinia viruses can accumulate in immunoprivileged cells or immunoprivileged tissues, including tumors and/or metastases, and also including wounded tissues and cells. Yet, unlike other oncolytic viruses, vaccinia virus can typically be cleared from the subject to whom the viruses are administered by activity of the subject's immune system, and hence are less toxic than other viruses such as adenoviruses. Thus, while the viruses can typically be cleared from the subject to whom the viruses are administered by activity of the subject's immune system, viruses can nevertheless accumulate, survive and proliferate in immunoprivileged cells and tissues such as tumors because such immunoprivileged areas are isolated from the host's immune system.

Vaccinia viruses also can be easily modified by insertion of heterologous genes. This can result in the attenuation of the virus and/or permit delivery of therapeutic proteins. For example, vaccinia virus genome has a large carrying capacity for foreign genes, where up to 25 kb of exogenous DNA fragments (approximately 12% of the vaccinia genome size) can be inserted. The genomes of several of the vaccinia strains have been completely sequenced, and many essential and nonessential genes identified. Due to high sequence homology among different strains, genomic information from one vaccinia strain can be used for designing and generating modified viruses in other strains. Finally, the techniques for production of modified vaccinia strains by genetic engineering are well established (Moss, Curr. Opin. Genet. Dev. 3 (1993), 86 -90; Broder and Earl, Mol. Biotechnol. 13 (1999), 223-245; Timiryasova et al., Biotechniques 31 (2001), 534-540).

Various vaccinia viruses have been demonstrated to exhibit antitumor activities. In one study, for example, nude mice bearing nonmetastatic colon adenocarcinoma cells were systemically injected with a WR strain of vaccinia virus modified by having a vaccinia growth factor deletion and an enhanced green fluorescence protein inserted into the thymidine kinase locus. The virus was observed to have antitumor effect, including one complete response, despite a lack of exogenous therapeutic genes in the modified virus (McCart et al. (2001) *Cancer Res* 1:8751-8757). In another study, vaccinia melanoma oncolysate (VMO) was injected into sites near melanoma positive lymph nodes in a Phase III clinical trial of melanoma patients. As a control, New York City Board of Health strain vaccinia virus (VV) was administered to melanoma patients. The melanoma patients treated with VMO had a survival rate better than that for untreated patients, but similar to patients treated with the VV control (Kim et al. (2001) *Surgical Oncol* 10:53-59).

LIVP strains of vaccinia virus also have been used for the diagnosis and therapy of tumors, and for the treatment of wounded and inflamed tissues and cells (see e.g. Lin et al. (2007) Surgery, 142:976-983; Lin et al. (2008) J. Clin. Endocrinol., Metab., 93:4403-7; Kelly et al. (2008) Hum gene There., 19:774-782; Yu et al. (2009) Mol Cancer Ther., 8:141-151; Yu et al. (2009) Mol Cancer, 8:45; U.S. Pat. Nos. 7,588,767; 8,052,968; and U.S. Patent Publication No. US20040234455). For example, when administered (e.g. intravenously administered or directly administered to a tissue), LIVP strains have been demonstrated to accumulate in internal tumors at various loci in vivo, and have been demonstrated to effectively treat human tumors of various tissue origin, including, but not limited to, breast tumors, thyroid tumors, pancreatic tumors, metastatic tumors of pleural mesothelioma, squamous cell carcinoma, lung carcinoma and ovarian tumors. LIVP strains of vaccinia, including attenuated forms thereof, exhibit less toxicity than WR strains of vaccinia virus, and results in increased and longer survival of treated tumor-bearing animal models (see e.g. U.S. Patent Publication No. US20110293527).

Vaccinia is a cytoplasmic virus, thus, it does not insert its genome into the host genome during its life cycle. Vaccinia virus has a linear, double-stranded DNA genome of approximately 180,000 base pairs in length that is made up of a single continuous polynucleotide chain (Baroudy et al. (1982) *Cell,* 28:315-324). The structure is due to the presence of 10,000 base pair inverted terminal repeats (ITRs). The ITRs are involved in genome replication. Genome replication is believed to involve self-priming, leading to the formation of high molecular weight concatemers (isolated from infected cells) which are subsequently cleaved and repaired to make virus genomes. See, e.g., Traktman, P., Chapter 27, Poxvirus DNA Replication, pp. 775-798, in DNA Replication in Eukaryotic Cells, Cold Spring Harbor Laboratory Press (1996). The genome encodes for approximately 250 genes. In general, the nonsegmented, noninfectious genome is arranged such that centrally located genes are essential for virus replication (and are thus conserved), while genes near the two termini effect more peripheral functions such as host range and virulence. Vaccinia viruses practice differential gene expression by utilizing open reading frames (ORFs) arranged in sets that, as a general principle, do not overlap.

Vaccinia virus possesses a variety of features for use in cancer gene therapy and vaccination including broad host and cell type range, and low toxicity. For example, while most oncolytic viruses are natural pathogens, vaccinia virus has a unique history in its widespread application as a smallpox vaccine that has resulted in an established track record of safety in humans. Toxicities related to vaccinia administration occur in less than 0.1% of cases, and can be effectively addressed with immunoglobulin administration. In addition, vaccinia virus is an attractive therapeutic virus because it possesses a large carrying capacity for foreign genes (up to 25 kb of exogenous DNA fragments, which is approximately 12% of the vaccinia genome size can be inserted into the vaccinia genome), has high sequence homology among different strains for designing and generating modified viruses in other strains, and the techniques for production of modified vaccinia strains by genetic engineering are well established (Moss (1993) *Curr. Opin. Genet. Dev.* 3: 86-90; Broder and Earl (1999) *Mol. Biotechnol.* 13: 223-245; Timiryasova et al. (2001) *Biotechniques* 31: 534-540). Vaccinia virus strains have been shown to specifically colonize solid tumors, while not infecting other organs (see, e.g., Zhang et al. (2007) *Cancer Res* 67:10038-10046; Yu et al., (2004) *Nat Biotech* 22:313-320; Heo et al., (2011) *Mol Ther* 19:1170-1179; Liu et al. (2008) *Mol Ther* 16:1637-1642; Park et al., (2008) *Lancet Oncol,* 9:533-542).

A variety of vaccinia virus strains can be used in the combinations, compositions and methods herein, including, but not limited to, Western Reserve (WR) (SEQ ID NO: 12), Copenhagen (SEQ ID NO: 13), Tashkent, Tian Tan, Lister, Wyeth, IHD-J, and IHD-W, Brighton, Ankara, MVA, Dairen I, LIPV, LC16M8, LC16MO, LIVP, WR 65-16, Connaught, New York City Board of Health, or modified forms thereof encoding a heterologous gene product. Exemplary of known viruses are set forth in Table 3. For example, among vaccinia viruses for use in the combinations, compositions or methods provided herein include, but are not limited to, Lister strain or LIVP strain of vaccinia viruses or modified forms thereof. For example, a recombinant derivative of LIVP, designated GLV-1h68 (set forth in SEQ ID NO: 3; GenBank Acc. No. EU410304) and GLV-1h64 (set forth in SEQ ID NO: 14) exhibit tumor targeting properties and an improved safety profile compared to its parental LIVP strain (set forth in SEQ ID NO: 2) and the WR strain (Zhang et al. (2009) *Mol. Genet. Genomics,* 282:417-435).

TABLE 3

| Name | Abbreviations | Reference (e.g. GenBank Accession No.) |
|---|---|---|
| Vaccinia virus strain Western Reserve | WR | AY243312 |
| Vaccinia virus strain Copenhagen | COP | M35027 |
| Vaccinia Lister major strain | LIST | AY678276 |
| Vaccinia Lister isolate LC16MO | LC | AY678277 |
| Vaccinia Lister clone VACV107 | VACV107 | DQ121394 |
| Vaccinia virus strain ACAM2000 | ACAM | AY313847 |
| Vaccinia virus strain DUKE | DUKE | DQ439815; Li et al. (2006) Virology J, 3: 88 |

TABLE 3-continued

| Name | Abbreviations | Reference (e.g. GenBank Accession No.) |
|---|---|---|
| Vaccinia virus strain Ankara | MVA | U94848 |
| Vaccinia virus Clone3 | CLONE3 | AY138848 |

Lister and LIVP Strains

Exemplary vaccinia viruses are Lister or LIVP vaccinia viruses. Lister (also referred to as Elstree) vaccinia virus is available from any of a variety of sources. For example, the Elstree vaccinia virus is available at the ATCC under Accession Number VR-1549. The Lister vaccinia strain has high transduction efficiency in tumor cells with high levels of gene expression.

The vaccinia virus provided in the combinations, compositions and methods herein can be based on modifications to the Lister strain of vaccinia virus. LIVP is a vaccinia strain derived from Lister (ATCC Catalog No. VR-1549). As described elsewhere herein, the LIVP strain can be obtained from the Lister Institute of Viral Preparations, Moscow, Russia; the Microorganism Collection of FSRI SRC VB Vector; or can be obtained from the Moscow Ivanovsky Institute of Virology (C0355 K0602). The LIVP strain was used for vaccination throughout the world, particularly in India and Russia, and is widely available. LIVP and its production are described, for example, in U.S. Pat. Nos. 7,588,767, 7,588,771, 7,662,398 and 7,754,221 and U.S. Patent Publication Nos. 2007/0202572, 2007/0212727, 2010/0062016, 2009/0098529, 2009/0053244, 2009/0155287, 2009/0117034, 2010/0233078, 2009/0162288, 2010/0196325, 2009/0136917, 2011/0064650; Zhang et al. (2009) *Mol. Genet. Genomics,* 282:417-435). A sequence of an LIVP strain is set forth in SEQ ID NO: 1 or 2.

LIVP strains in the compositions provided herein also include clonal strains that are derived from LIVP and that can be present in a virus preparation propagated from LIVP. The LIVP clonal strains have a genome that differs from the parental sequence set forth in SEQ ID NO: 1 or 2. The clonal strains provided herein exhibit greater anti-tumorigenicity and/or reduced toxicity compared to the recombinant or modified virus strain designated GLV-1h68 (having a genome set forth in SEQ ID NO: 3; see e.g. U.S. Patent Publication No. US2012/0308484).

The LIVP and clonal strains have a sequence of nucleotides that have at least 70%, such as at least 75%, 80%, 85% or 90% sequence identity to SEQ ID NO: 1 or 2. For example, the clonal strains have a sequence of nucleotides that has at least 91%, 92%, 93%, 94%, 95%, 95%, 97%, 98%, 99%, 99.1%, 99.2%, 99.3%, 99.4%, 99.5%, 99.6%, 99.7%, 99.8%, 99.9% or 100% sequence identity to SEQ ID NO: 1 or 2. Such LIVP clonal viruses include viruses that differ in one or more open reading frames (ORF) compared to the parental LIVP strain that has a sequence of amino acids set forth in SEQ ID NO: 1 or 2. The LIVP clonal virus strains provided herein can contain a nucleotide deletion or mutation in any one or more nucleotides in any ORF compared to SEQ ID NO: 1 or 2, or can contain an addition or insertion of viral DNA compared to SEQ ID NO: 1 or 2.

LIVP strains in the combinations, compositions or methods provided herein include those that have a nucleotide sequence corresponding to nucleotides 2,256-181,114 of SEQ ID NO: 5, nucleotides 11,243-182,721 of SEQ ID NO: 6, nucleotides 6,264-181,390 of SEQ ID NO: 7, nucleotides 7,044-181,820 of SEQ ID NO: 8, nucleotides 6,674-181,409 of SEQ ID NO: 9, nucleotides 6,716-181,367 of SEQ ID NO: 10 or nucleotides 6,899-181,870 of SEQ ID NO: 11, or to a complement thereof. In some examples, the LIVP strain for use in the combinations, compositions and methods is a clonal strain of LIVP or a modified form thereof containing a sequence of nucleotides that has at least 85%, 86%, 87%, 88%, 89%, 90%, 91%, 92%, 93%, 94%, 95%, 96%, 97%, 98%, 99% or more sequence identity to a sequence of nucleotides 2,256-181,114 of SEQ ID NO: 5, nucleotides 11,243-182,721 of SEQ ID NO: 6, nucleotides 6,264-181,390 of SEQ ID NO: 7, nucleotides 7,044-181,820 of SEQ ID NO: 8, nucleotides 6,674-181,409 of SEQ ID NO: 9, nucleotides 6,716-181,367 of SEQ ID NO: 10 or nucleotides 6,899-181,870 of SEQ ID NO: 11. LIVP clonal strains provided herein generally also include terminal nucleotides corresponding to a left and/or right inverted terminal repeat (ITR).

Exemplary LIVP strains include, but are not limited to, virus strains designated LIVP 1.1.1 having a genome containing a sequence of nucleotides set forth in SEQ ID NO: 5 or a sequence of nucleotides that exhibits at least 85% sequence identity to SEQ ID NO: 5; a virus strain designated LIVP 2.1.1 having a genome containing a sequence of nucleotides set forth in SEQ ID NO: 6 or a sequence of nucleotides that exhibits at least 85% sequence identity to SEQ ID NO: 6; a virus strain designated LIVP 4.1.1 having a genome containing a sequence of nucleotides set forth in SEQ ID NO: 7 or a sequence of nucleotides that exhibits at least 85% sequence identity to SEQ ID NO: 7; a virus strain designated LIVP 5.1.1 having a genome containing a sequence of nucleotides set forth in SEQ ID NO: 8 or a sequence of nucleotides that exhibits at least 85% sequence identity to SEQ ID NO: 8; a virus strain designated LIVP 6.1.1 having a sequence of nucleotides set forth in SEQ ID NO: 9 or a sequence of nucleotide that exhibits at least 85% sequence identity to SEQ ID NO: 9; a virus strain designated LIVP 7.1.1 having a genome containing a sequence of nucleotides set forth in SEQ ID NO: 10 or a sequence of nucleotides that exhibits at least 85% sequence identity to SEQ ID NO: 10; or a virus strain designated LIVP 8.1.1 having a genome containing a sequence of nucleotides set forth in SEQ ID NO: 11 or a sequence of nucleotides that exhibits at least 85 sequence identity to SEQ ID NO: 11. For example, LIVP clonal strains include any having a genome containing a sequence of nucleotides that exhibits at least 86%, 87%, 88%, 89%, 90%, 91%, 92%, 93%, 94%, 95%, 96%, 97%, 98%, 99% or more sequence identity to any of SEQ ID NOS:5-11.

2. Heterologous Nucleic Acid and Modified Viruses

Oncolytic viruses, such as a vaccinia virus (e.g. an LIVP virus) can be modified to express a heterologous gene product. The large genome size of poxviruses, such as the vaccinia viruses in the combinations, compositions and methods provided herein, allows large inserts of heterologous DNA and/or multiple inserts of heterologous DNA to be incorporated into the genome (Smith and Moss (1983) *Gene* 25(1):21-28). Oncolytic viruses, such as vaccinia viruses, e.g. an LIVP virus strain or clonal strain as set forth in any of SEQ ID NOS: 1, 2 or 5-11, can be modified by insertion of 1, 2, 3, 4, 5, 6, 7, 8, 9, 10 or more heterologous DNA molecules. Generally, the one or more heterologous DNA molecules are inserted into a non-essential region of the virus genome. For example, the one or more heterologous DNA molecules are inserted into a locus of the virus genome that is non-essential for replication in proliferating cells, such as tumor cells. Exemplary insertion sites are provided herein below and are known in the art.

In some examples, the virus can be modified to express an exogenous or heterologous gene. Exemplary exogenous gene products include proteins and RNA molecules. The modified viruses can express a therapeutic gene product, a detectable gene product (e.g. a diagnostic or reporter gene product), a gene product for manufacturing or harvesting, an antigenic gene product for antibody harvesting, or a viral gene product. Viruses also can be modified to alter attenuation of the virus, which includes any method of increasing or decreasing the transcriptional or translational load.

Exemplary therapeutic proteins that can be expressed by the viruses provided herein and used in the methods provided herein include, but are not limited to, erythropoietin (e.g., SEQ ID NO: 20), an anti-VEGF single chain antibody (e.g., SEQ ID NO: 21), a plasminogen K5 domain (e.g., SEQ ID NO: 22), a human tissue factor-αvβ3-integrin RGD fusion protein (e.g., SEQ ID NO: 23), interleukin-24 (e.g., SEQ ID NO: 24), or immune stimulators, such as SIL-6-SIL-6 receptor fusion protein (e.g., SEQ ID NO: 25).

In some examples, the viruses can be modified to express two or more gene products, such as 2, 3, 4, 5, 6, 7, 8, 9, 10 or more gene products, where any combination of the two or more gene products can be one or more detectable gene products, therapeutic gene products, gene products for manufacturing or harvesting or antigenic gene products for antibody harvesting or a viral gene product. In one example, a virus can be modified to express an anticancer gene product. In another example, a virus can be modified to express two or more gene products for detection or two or more therapeutic gene products. In some examples, one or more proteins involved in biosynthesis of a luciferase substrate can be expressed along with luciferase. When two or more exogenous genes are introduced, the genes can be regulated under the same or different regulatory sequences, and the genes can be inserted in the same or different regions of the viral genome, in a single or a plurality of genetic manipulation steps. In some examples, one gene, such as a gene encoding a detectable gene product, can be under the control of a constitutive promoter, while a second gene, such as a gene encoding a therapeutic gene product, can be under the control of an inducible promoter. Methods for inserting two or more genes into a virus are known in the art and can be readily performed for a wide variety of viruses using a wide variety of exogenous genes, regulatory sequences, and/or other nucleic acid sequences.

The heterologous DNA can be any gene of interest, including any from the list of human genes and genetic disorders authored and edited by Dr. Victor A. McKusick and his colleagues at Johns Hopkins University and elsewhere, and developed for the World Wide Web by NCBI, the National Center for Biotechnology Information; online, Mendelian Inheritance in Man, OMIM™ Center for Medical Genetics, Johns Hopkins University (Baltimore, Md.), and National Center for Biotechnology Information, National Library of Medicine (Bethesda, Md.), 1999; and those available in public databases, such as PubMed and GenBank (see, e.g., (ncbi.nlm.nih.gov/entrez/query.fcgi?db=OMIM).

In particular, viruses provided herein can be modified to express an anti-tumor antibody, an anti-metastatic gene or metastasis suppressor genes; cell matrix degradative genes; hormones; growth factors; immune modulatory molecules, including a cytokine, such as interleukins or interferons, a chemokine, including CXC chemokines, costimulatory molecules; ribozymes; transporter protein; antibody or fragment thereof; antisense RNA; siRNA; microRNAs; protein ligands; a mitosis inhibitor protein; an antimiotic oligopeptide; an anti-cancer polypeptide; anti-cancer antibiotics; angiogenesis inhibitors; anti-angiogenic factors; tissue factors; a prodrug converting enzyme; genes for tissue regeneration and reprogramming human somatic cells to pluripotency; enzymes that modify a substrate to produce a detectable product or signal or are detectable by antibodies; a viral attenuation factors; a superantigen; proteins that can bind a contrasting agent, chromophore, or a compound of ligand that can be detected; tumor suppressors; cytotoxic protein; cytostatic protein; genes for optical imaging or detection including luciferase, a fluorescent protein such as a green fluorescent protein (GFP) or GFP-like protein, a red fluorescent protein (RFP), a far-red fluorescent protein, a near-infrared fluorescent protein, a yellow fluorescent protein (YFP), an orange fluorescent protein (OFP), a cerulean fluorescent protein (CFP), or a blue fluorescent protein (BFP), and phycobiliproteins from certain cyanobacteria and eukaryotic algae, including phycoerythrins (red) and the phycocyanins (blue); genes for PET imaging; genes for MRI imaging; or genes to alter attenuation of the viruses.

a. Exemplary Modifications

Exemplary modified viruses, including heterologous genes for modification of viruses herein, are known in the art (see e.g. U.S. Pub. Nos. US2003-0059400, US2003-0228261, US 2005-0031643 now U.S. Pat. Nos. 7,588,767, 7,588,771 and 7,662,398, US 2008-0193373, US2009-0117034, US2009-0098529, US2009-0053244, US 2009-0155287, US2009-0081639, US 2009-0117034 and US2009-0136917; U.S. Pat. Nos. 7,588,767 and 7,763,420; and International Pub. No. WO 2005/047458, WO 2008/100292 and WO 2008/150496, WO 2009/139921). A non-limiting description of exemplary genes encoding heterologous proteins for modification of virus strains is set forth in Table 4. The sequence of the gene and encoded proteins are known to one of skill in the art from the literature.

TABLE 4

Exemplary Genes and Gene Products

Detectable gene products
  Optical Imaging
    Luciferase
      bacterial luciferase
      luciferase (from *Vibrio harveyi* or *Vibrio fischerii*)
        luxA
        luxB
        luxC
        luxD
        luxE
        luxAB
        luxCD
        luxABCDE
      firefly luciferase TABLE 4-continued

| Exemplary Genes and Gene Products |
|---|

*Renilla* luciferase from *Renilla reniformis*
*Gaussia* luciferase
luciferases found among marine arthropods
luciferases that catalyze the oxidation of *Cypridina* (*Vargula*) luciferin
luciferases that catalyze the oxidation of *Coleoptera* luciferin
luciferase photoproteins
    aequorin photoprotein to which luciferin is non-covalently bound
click beetle luciferase
    CBG99
    CBG99-mRFP1
Fusion Proteins
    Ruc-GFP
Fluorescent Proteins
GFP
    aequorin from *Aequorea victoria*
    GFP from *Aequorea victoria*
    GFP from *Aequorea coerulescens*
    GFP from the anthozoan coelenterates *Renilla reniformis* and *Renilla kollikeri* (sea pansies)
    Emerald (Invitrogen, Carlsbad, CA)
    EGFP (Clontech, Palo Alto, CA)
    Azami-Green (MBL International, Woburn, MA)
    Kaede (MBL International, Woburn, MA)
    ZsGreen1 (Clontech, Palo Alto, CA)
    CopGFP (Evrogen/Axxora, LLC, San Diego, CA)
    Anthozoa reef coral
    *Anemonia* sea anemone
    *Renilla* sea pansy
    *Galaxea* coral
    *Acropora* brown coral
    *Trachyphyllia* stony coral
    Pectiniidae stony coral
    GFP-like proteins
RFP
    RFP from the corallimorph *Discosoma* (DsRed) (Matz et al. (1999) Nature Biotechnology 17: 969-973)
    *Heteractis* reef coral, *Actinia* or *Entacmaea* sea anemone
    RFPs from *Discosoma* variants
        mRFP1 (Wang et al. (2004) *Proc. Natl. Acad. Sci. U.S.A.* 101: 16745-9)
        mCherry (Wang et al. (2004) *PNAS USA.* 101(48): 16745-9)
        tdTomato (Wang et al. (2004) *PNAS USA.* 101(48): 16745-9)
        mStrawberry (Wang et al. (2004) *PNAS USA.* 101(48): 16745-9)
        mTangerine (Wang et al. (2004) *PNAS USA.* 101(48): 16745-9)
        DsRed2 (Clontech, Palo Alto, CA)
        DsRed-T1 (Bevis and Glick (2002) Nat. Biotechnol. 20: 83-87)
        Anthomedusa J-Red (Evrogen)
        *Anemonia* AsRed2 (Clontech, Palo Alto, CA)
far-red fluorescent protein
    TurboFP635
    mNeptune monomeric far-red fluorescent protein
    *Actinia* AQ143 (Shkrob et al. (2005) *Biochem J.* 392(Pt 3): 649-54)
    *Entacmaea* eqFP611 (Wiedenmann et al. (2002) *PNAS USA.* 99(18): 11646-51)
    *Discosoma* variants
        mPlum (Wang et al.. (2004) *PNAS USA.* 101(48): 16745-9)
        mRasberry (Wang et al. (2004) *PNAS USA.* 101(48): 16745-9)
        *Heteractis* HcRed1 and t-HcRed (Clontech, Palo Alto, CA)
IFP (infrared fluorescent protein)
near-infrared fluorescent protein
YFP
    EYFP (Clontech, Palo Alto, CA)
    YPet (Nguyen and Daugherty (2005) *Nat Biotechnol.* 23(3): 355-60)
    Venus (Nagai et al. (2002) *Nat. Biotechnol.* 20(1): 87-90)
    ZsYellow (Clontech, Palo Alto, CA)
    mCitrine (Wang et al. (2004) *PNAS USA.* 101(48): 16745-9)
OFP
    cOFP (Strategene, La Jolla, CA)
    mKO (MBL International, Woburn, MA)
    mOrange (Wang et al. (2004) *PNAS USA.* 101(48): 16745-9)
CFP
    Cerulean (Rizzo (2004) *Nat Biotechnol.* 22(4): 445-9)
    mCFP (Wang et al. (2004) *PNAS USA.* 101(48): 16745-9)
    AmCyan1 (Clontech, Palo Alto, CA)
    MiCy (MBL International, Woburn, MA)
    CyPet (Nguyen and Daugherty (2005) *Nat Biotechnol.* 23(3): 355-60)
BFP
    EBFP (Clontech, Palo Alto, CA);
    phycobiliproteins from certain cyanobacteria and eukaryotic algae, phycoerythrins (red) and the phycocyanins (blue)

TABLE 4-continued

Exemplary Genes and Gene Products

R-Phycoerythrin (R-PE)
B-Phycoerythrin (B-PE)
Y-Phycoerythrin (Y-PE
C-Phycocyanin (P-PC)
R-Phycocyanin (R-PC)
Phycoerythrin 566 (PE 566)
Phycoerythrocyanin (PEC)
Allophycocyanin (APC)
frp Flavin Reductase
CBP Coelenterazine-binding protein 1
PET imaging
    Cyp11B1 transcript variant 1
    Cyp11B1 transcript variant 2
    Cyp11B2
    AlstR
    PEPR-1
    LAT-4 (SLC43A2)
    Cyp51 transcript variant 1
    Cyp51 transcript variant 2
Transporter proteins
Solute carrier transporter protein families (SLC)
    SLC1 solute carrier 1 transporter protein family
    SLC1A1, SLC1A2, SLC1A3, SLC1A4, SLC1A5, SLC1A6, SLC1A7
    SLC2 solute carrier 2 transporter protein family
    SLC2A1, SLC2A2, SLC2A3, SLC2A4, SLC2A5, SLC2A6, SLC2A7, SLC2A8,
    SLC2A9, SLC2A10, SLC2A11, SLC2A12, SLC2A13, SLC2A14
    SLC3 solute carrier 3 transporter protein family
    SLC3A1, SLC3A2
    SLC 4 solute carrier 4 transporter protein family
    SLC4A1, SLC4A2, SLC4A3, SLC4A4, SLC4A5, SLC4A6, SLC4A7, SLC4A8,
    SLC4A9, SLC4A10, SLC4A11
    SLC5 solute carrier 5 transporter protein family
    SLC5A1 sodium/glucose cotransporter 1
    SLC5A2 sodium/glucose cotransporter 2
    SLC5A3 sodium/myo-inositol cotransporter
    SLC5A4 low affinity sodium-glucose cotransporter
    SLC5A5 sodium/iodide cotransporter
    SLC5A6 sodium-dependent multivitamin transporter
    SLC5A7 high affinity choline transporter 1
    SLC5A8 sodium-coupled monocarboxylate transporter 1
    SLC5A9 sodium/glucose cotransporter 4
    SLC5A10 sodium/glucose cotransporter 5, isoform 1
    sodium/glucose cotransporter 5, isoform 2
    sodium/glucose cotransporter 5, isoform 3
    sodium/glucose cotransporter 5, isoform 4
    SLC5A11 sodium/myo-inositol cotransporter 2, isoform 1
    sodium/myo-inositol cotransporter 2, isoform 2
    sodium/myo-inositol cotransporter 2, isoform 3
    sodium/myo-inositol cotransporter 2, isoform 4
    SLC5A12 sodium-coupled monocarboxylate transporter 2, isoform 1
    sodium-coupled monocarboxylate transporter 2, isoform 2
        Sodium Iodide Symporter (NIS)
        hNIS (NM_000453)
        hNIS (BC105049)
        hNIS (BC105047)
        hNIS (non-functional hNIS variant containing an additional 11 aa)
    SLC6 solute carrier 6 transporter protein family
    SLC6A1 sodium- and chloride-dependent GABA transporter 1
    SLC6A2 norepinephrine transporter (sodium-dependent noradrenaline transporter)
    SLC6A3 sodium-dependent dopamine transporter
    SLC6A4 sodium-dependent serotonin transporter
    SLC6A5 sodium- and chloride-dependent glycine transporter 1
    SLC6A6 sodium-and chloride-dependent taurine transporter
    SLC6A7 sodium-dependent proline transporter
    SLC6A8 sodium- and chloride-dependent creatine transporter
    SLC6A9 sodium- and chloride-dependent glycine transporter 1, isoform 1
    sodium- and chloride-dependent glycine transporter 1, isoform 2
    sodium- and chloride-dependent glycine transporter 1, isoform 3
    SLC6A10 sodium- and chloride-dependent creatine transporter 2
    SLC6A11 sodium- and chloride-dependent GABA transporter 3
    SLC6A12 sodium- and chloride-dependent betaine transporter
    SLC6A13 sodium- and chloride-dependent GABA transporter 2
    SLC6A14 Sodium- and chloride-dependent neutral and basic amino acid transporter
    B(0+)
    SLC6A15 Orphan sodium- and chloride-dependent neurotransmitter transporter
    NTT73
    SLC6A16 Orphan sodium- and chloride-dependent neurotransmitter transporter
    NTT5

TABLE 4-continued

Exemplary Genes and Gene Products

SLC6A17 Orphan sodium- and chloride-dependent neurotransmitter transporter NTT4
Sodium SLC6A18 Sodium- and chloride-dependent transporter XTRP2
SLC6A19 Sodium-dependent neutral amino acid transporter B(0)
SLC6A20 Sodium- and chloride-dependent transporter XTRP3
Norepinephrine Transporter (NET)
    Human Net (hNET) transcript variant 1 (NM_001172504)
    Human Net (hNET) transcript variant 2 (NM_001172501)
    Human Net (hNET) transcript variant 3 (NM_001043)
    Human Net (hNET) transcript variant 4 (NM_001172502)
    Non-Human Net
SLC7 solute carrier 7 transporter protein family
SLC7A1, SLC7A2, SLC7A3, SLC7A4, SLC7A5, SLC7A6, SLC7A7, SLC7A8, SLC7A9, SLC7A10, SLC7A11, SLC7A13, SLC7A14
SLC8 solute carrier 8 transporter protein family
SLC8A1, SLC8A2, SLC8A3
SLC9 solute carrier 9 transporter protein family
SLC9A1, SLC9A2, SLC9A3, SLC9A4, SLC9A5, SLC9A6, SLC9A7, SLC9A8, SLC9A9, SLC9A10, SLC9A11
SLC10 solute carrier 10 transporter protein family
SLC10A1, SLC10A2, SLC10A3, SLC10A4, SLC10A5, SLC10A6, SLC10A7
SLC11 solute carrier 11 transporter protein family
SLC11A1
SCL11A2 or hDMT
    SLC11A2 transcript variant 4
    SLC11A2 transcript variant 1
    SLC11A2 transcript variant 2
    SLC11A2 transcript variant 3
    SLC11A2 transcript variant 5
    SLC11A2 transcript variant 6
    SLC11A2 transcript variant 7
SLC12 solute carrier 12 transporter protein family
SLC12A1, SLC12A1, SLC12A2, SLC12A3, SLC12A4, SLC12A5, SLC12A6, SLC12A7, SLC12A8, SLC12A9
SLC13 solute carrier 13 transporter protein family
SLC13A1, SLC13A2, SLC13A3, SLC13A4, SLC13A5
SLC14 solute carrier 14 transporter protein family
SLC14A1, SLC14A2
SLC15 solute carrier 15 transporter protein family
SLC15A1, SLC15A2, SLC15A3, SLC15A4
SLC16 solute carrier 16 transporter protein family
SLC16A1, SLC16A2, SLC16A3, SLC16A4, SLC16A5, SLC16A6, SLC16A7, SLC16A8, SLC16A9, SLC16A10, SLC16A11, SLC16A12, SLC16A13, SLC16A14
SLC17 solute carrier 17 transporter protein family
SLC17A1, SLC17A2, SLC17A3, SLC17A4, SLC17A5, SLC17A6, SLC17A7, SLC17A8
SLC18 solute carrier 18 transporter protein family
SLC18A1, SLC18A2, SLC18A3
SLC19 solute carrier 19 transporter protein family
SLC19A1, SLC19A2, SLC19A3
SLC20 solute carrier 20 transporter protein family
SLC20A1, SLC20A2
SLC21 solute carrier 21 transporter protein family
    subfamily 1; SLCO1A2, SLCO1B1, SLCO1B3, SLCO1B4, SLCO1C1
    subfamily 2; SLCO2A1, SLCO2B1
    subfamily 3; SLCO3A1
    subfamily 4; SLCO4A1, SLCO4C1
    subfamily 5; SLCO5A1
SLC22 solute carrier 22 transporter protein family
SLC22A1, SLC22A2, SLC22A3, SLC22A4, SLC22A5, SLC22A6, SLC22A7, SLC22A8, SLC22A9, SLC22A10, SLC22A11, SLC22A12, SLC22A13, SLC22A14, SLC22A15, SLC22A16, SLC22A17, SLC22A18, SLC22A19, SLC22A20
SLC23 solute carrier 23 transporter protein family
SLC23A1, SLC23A2, SLC23A3, SLC23A4
SLC24 solute carrier 24 transporter protein family
SLC24A1, SLC24A2, SLC24A3, SLC24A4, SLC24A5, SLC24A6
SLC25 solute carrier 25 transporter protein family
SLC25A1, SLC25A2, SLC25A3, SLC25A4, SLC25A5, SLC25A6, SLC25A7, SLC25A8, SLC25A9, SLC25A10, SLC25A11, SLC25A12, SLC25A13, SLC25A14, SLC25A15, SLC25A16, SLC25A17, SLC25A18, SLC25A19, SLC25A20, SLC25A21, SLC25A22, SLC25A23, SLC25A24, SLC25A25, SLC25A26, SLC25A27, SLC25A28, SLC25A29, SLC25A30, SLC25A31, SLC25A32, SLC25A33, SLC25A34, SLC25A35, SLC25A36, SLC25A37, SLC25A38, SLC25A39, SLC25A40, SLC25A41, SLC25A42, SLC25A43, SLC25A44, SLC25A45, SLC25A46

TABLE 4-continued

Exemplary Genes and Gene Products

SLC26 solute carrier 26 transporter protein family
    SLC26A1, SLC26A2, SLC26A3, SLC26A4, SLC26A5, SLC26A6, SLC26A7,
    SLC26A8, SLC26A9, SLC26A10, SLC26A11
SLC27 solute carrier 27 transporter protein family
    SLC27A1, SLC27A2, SLC27A3, SLC27A4, SLC27A5, SLC27A6
SLC28 solute carrier 28 transporter protein family
    SLC28A1, SLC28A2, SLC28A3
SLC29 solute carrier 29 transporter protein family
    SLC29A1, SLC29A2, SLC29A3, SLC29A4
SLC30 solute carrier 30 transporter protein family
    SLC30A1, SLC30A2, SLC30A3, SLC30A4, SLC30A5, SLC30A6, SLC30A7,
    SLC30A8, SLC30A9, SLC30A10
SLC31 solute carrier 31 transporter protein family
    SLC31A1
SLC32 solute carrier 32 transporter protein family
    SLC32A1
SLC33 solute carrier 33 transporter protein family
    SLC33A1
SLC34 solute carrier 34 transporter protein family
    SLC34A1, SLC34A2, SLC34A3
SLC35 solute carrier 35 transporter protein family
        subfamily A; SLC35A1, SLC35A2, SLC35A3, SLC35A4, SLC35A5
        subfamily B; SLC35B1, SLC35B2, SLC35B3, SLC35B4
        subfamily C; SLC35C1, SLC35C2
        subfamily D; SLC35D1, SLC35D2, SLC35D3
        subfamily E; SLC35E1, SLC35E2, SLC35E3, SLC35E4
SLC36 solute carrier 36 transporter protein family
    SLC36A1, SLC36A2, SLC36A3, SLC36A4
SLC37 solute carrier 37 transporter protein family
    SLC37A1, SLC37A2, SLC37A3, SLC37A4
SLC38 solute carrier 38 transporter protein family
    SLC38A1, SLC38A2, SLC38A3, SLC38A4, SLC38A5, SLC38A6
SLC39 solute carrier 39 transporter protein family
    SLC39A1, SLC39A2, SLC39A3, SLC39A4, SLC39A5, SLC39A6, SLC39A7,
    SLC39A8, SLC39A9, SLC39A10, SLC39A11, SLC39A12, SLC39A13,
    SLC39A14
SLC40 solute carrier 40 transporter protein family
    SLC40A1
SLC41 solute carrier 41 transporter protein family
    SLC41A1, SLC41A2, SLC41A3
SLC42 solute carrier 42 transporter protein family
    RHAG, RhBG, RhCG
SLC43 solute carrier 43 transporter protein family
    SLC43A1
    SLC43A2
    SLC43A3
SLC44 solute carrier 44 transporter protein family
    SLC44A1, SLC44A2, SLC44A3, SLC44A4, SLC44A5
SLC45 solute carrier 45 transporter protein family
    SLC45A1, SLC45A2, SLC54A3, SLC45A4
SLC46 solute carrier 46 transporter protein family
    SLC46A1, SLC46A2
SLC47 solute carrier 47 transporter protein family
    SLC47A1, SLC47A2
MRI Imaging
    Human transferrin receptor
    Mouse transferrin receptor
    Human ferritin light chain (FTL)
    Human ferritin heavy chain
    FTL 498-199InsTC, a mutated form of the ferritin light chain
    Bacterial ferritin
        *E. coli*
        *E. coli* strain K12
        *S. aureus* strain MRSA252
        *S. aureus* strain NCTC 8325
        *H. pylori* B8
    bacterioferritin
    codon optimized bacterioferritin
    MagA
Enzymes that modify a substrate to produce a detectable product or signal, or are
detectable by antibodies
    alpha-amylase
    alkaline phosphatase
    secreted alkaline phosphatase
    peroxidase
    T4 lysozyme
    oxidoreductase
    pyrophosphatase TABLE 4-continued

| Exemplary Genes and Gene Products |
|---|

Therapeutic genes
therapeutic gene product
antigens
        tumor specific antigens
        tumor-associated antigens
        tissue-specific antigens
        bacterial antigens
        viral antigens
        yeast antigens
        fungal antigens
        protozoan antigens
        parasite antigens
        mitogens
an antibody or fragment thereof
        virus-specific antibodies
antisense RNA
siRNA
    siRNA directed against expression of a tumor-promoting gene
        an oncogene
        growth factor
        angiogenesis promoting gene
        a receptor
    siRNA molecule directed against expression of any gene essential for cell growth, cell replication or cell survival.
    siRNA molecule directed against expression of any gene that stabilizes the cell membrane or otherwise limits the number of tumor cell antigens released from the tumor cell.
protein ligands
an antitumor oligopeptide
an antimitotic peptide
        tubulysin,
        phomopsin
        hemiasterlin
        taltobulin (HTI-286, 3)
        cryptophycin
a mitosis inhibitor protein
an antimitotic oligopeptide
an anti-cancer polypeptide antibiotic
anti-cancer antibiotics
tissue factors
    Tissue Factor (TF)
    $\alpha v\beta 3$-integrin RGD fusion protein
Immune modulatory molecules
    GM-CSF
    MCP-1 or CCL2 (Monocyte Chemoattractant Protein-1) Human
    MCP-1 murine
    IP-10 or Chemokine ligand 10 (CXCL10)
    LIGHT
    P60 or SEQSTM1 (Sequestosome 1 transcript variant 1)
    P60 or SEQSTM1 (Sequestosome 1 transcript variant 3)
    P60 or SEQSTM1 (Sequestosome 1 transcript variant 2)
    OspF
    OspG
    STAT1alpha
    STAT1beta
Interleukins
    IL-18 (Interleukin-18)
    IL-11 (Interleukin-11)
    IL-6 (Interleukin-6)
    sIL-6R-IL-6
    interleukin-12
    interleukin-1
    interleukin-2
    IL-24 (Interleukin-24)
    IL-24 transcript variant 1
    IL-24 transcript variant 4
    IL-24 transcript variant 5
    IL-4
    IL-8
    IL-10
chemokines
    IP-10 (CXCL)
    Thrombopoietin
    members of the C-X-C and C-C chemokine families
    RANTES
    MIP1-alpha
    MIP1-beta
    MIP-2

TABLE 4-continued

Exemplary Genes and Gene Products

CXC chemokines
    GROα
    GROβ (MIP-2)
    GROγ
    ENA-78
    LDGF-PPBP
    GCP-2
    PF4
    Mig
    IP-10
    SDF-1α/β
    BUNZO/STRC33
    I-TAC
    BLC/BCA-1
    MDC
    TECK
    TARC
    HCC-1
    HCC-4
    DC-CK1
    MIP-3α
    MIP-3β
    MCP-2
    MCP-3 (Monocyte Chemoattractant Protein-3, CCL7)
    MCP-4
    MCP-5 (Monocyte Chemoattractant Protein-5; CCL12)
    Eotaxin (CCL11)
    Eotaxin-2/MPIF-2
    I-309
    MIP-5/HCC-2
    MPIF-1
    6Ckine
    CTACK
    MEC
    lymphotactin
    fractalkine
Immunoglobulin superfamily of cytokines
    B7.1
    B7.2
Anti-angiogenic genes/angiogenesis inhibitors
    Human plasminogen k5 domain (hK5)
    PEDF (SERPINF1) (Human)
    PEDF (mouse)
    anti-VEGF single chain antibody (G6)
    anti-DLL4 s.c. antibody GLAF-3
    tTF-RGD (truncated human tissue factor protein fused to an RGD peptide)
viral attenuation factors
    Interferons
        IFN-γ
        IFN-α
        IFN-β
Antibody or scFv
    Therapeutic antibodies (i.e. anticancer antibodies)
        Rituximab (RITUXAN)
        ADEPT
        Trastuzumab (Herceptin)
        Tositumomab (Bexxar)
        Cetuximab (Erbitux)
        Ibritumomab (90Y-Ibritumomab tiuexetan; Zevalin)
        Alemtuzumab (Campath-1H)
        Epratuzumab (Lymphocide)
        Gemtuzumab ozogamicin (Mylotarg)
        Bevacimab (Avastin) and Edrecolomab (Panorex)
        Infliximab
Metastasis suppressor genes
    NM23 or NME1 Isoform a
    NM23 or NME1 Isoform b
Anti-metastatic genes
    E-Cad
    Gelsolin
    LKB1 (STK11)
    RASSF1
    RASSF2
    RASSF3
    RASSF4
    RASSF5
    RASSF6
    RASSF7

TABLE 4-continued

Exemplary Genes and Gene Products

RASSF8
    Syk
    TIMP-1 (Tissue Inhibitor of Metalloproteinase Type-1)
    TIMP-2 (Tissue Inhibitor of Metalloproteinase Type-2)
    TIMP-3 (Tissue Inhibitor of Metalloproteinase Type-3)
    TIMP-4 (Tissue Inhibitor of Metalloproteinase Type-4)
    BRMS-1
    CRMP-1
    CRSP3
    CTGF
    DRG1
    KAI1
    KiSS1 (kisspeptin)
    kisspeptin fragments
        kisspeptin-10
        kisspeptin-13
        kisspeptin-14
        kisspeptin-54
    Mkk4
    Mkk6
    Mkk7
    RKIP
    RHOGDI2
    SSECKS
    TXNIP/VDUP1
Cell matrix-degradative genes
    Relaxin 1
    hMMP9
Hormones
    Human Erythropoietin (EPO)
MicroRNAs
    pre-miRNA 181a (sequence inserted into viral genome)
    miRNA 181a
    mmu-miR-181a MIMAT0000210 mature miRNA 181a
    pre-miRNA 126 (sequence inserted into the vial genome)
    miRNA 126
    hsa-miR-126 MI000471
    hsa-miR-126 MIMAT0000445
    pre-miRNA 335 (sequence inserted into the viral genome)
    miRNA 335
    hsa-miR-335 MI0000816
    hsa-miR-335 MIMAT0000765
Genes for tissue regeneration and reprogramming Human somatic cells to pluripotency
    nAG
    Oct4
    NANOG
    Ngn (Neogenin 1) transcript variant 1
    Ngn (Neogenin 1) transcript variant 2
    Ngn (Neogenin 1) transcript variant 3
    Ngn3
    Pdx1
    Mafa
Additional Genes
    Myc-CTR1
    FCU1
    mMnSOD
    HACE1
    nppa1
    GCP-2 (Granulocyte Chemotactic Protein-2, CXCL6)
    hADH
    Wildtype CDC6
    Mut CDC6
    GLAF-3 anti-DLL4 scFv
    GLAF-4 anti-FAP (Fibroblast Activation Protein) scFv (Brocks et al., (2001) *Mol. Medicine* 7(7): 461-469)
    GLAF-5 anti-FAP scFv
    BMP4
    wildtype F14.5L
Other Proteins
    WT1
    p53
    *pseudomonas* A endotoxin
    diphtheria toxin
    Arf or p16
    Bax
    Herpes simplex virus thymidine kinase
    *E. coli* purine nucleoside phosphorylase
    angiostatin TABLE 4-continued Exemplary Genes and Gene Products endostatin
Rb
BRCA1
cystic fibrosis transmembrane regulator (CFTR)
Factor VIII
low density lipoprotein receptor
alpha-galactosidase
beta-glucocerebrosidase
insulin
parathyroid hormone
alpha-1-antitrypsin
rsCD40L
Fas-ligand
TRAIL
TNF
microcin E492
xanthineguanine phosphoribosyltransferase (XGPRT)
E. coli guanine phosphoribosyltransferase (gpt)
hyperforin
endothelin-1 (ET-1)
connective tissue growth factor (CTGF)
vascular endothelial growth factor (VEGF)
cyclooxygenase
COX-2
cyclooxygenase-2 inhibitor
MPO (Myeloperoxidase)
Apo A1 (Apolipoprotein A1)
CRP (C Reactive Protein)
Fibrinogen
SAP (Serum Amyloid P)
FGF-basic (Fibroblast Growth Factor-basic)
PPAR-agonist
PE37/TGF-alpha fusion protein
Replacement of the A34R gene with another A34R gene from a different strain in order
to increase the EEV form of the virus
    A34R from VACV IHD-J
    A34R with a mutation at codon 151 (Lys 151 to Asp)
    A34R with a mutation at codon 151 (Lys 151 to Glu)
Non-coding Sequence
    Non-proteins
    Non-coding nucleic acid
Ribozymes
    Group I introns
    Group II introns
    RNaseP
    hairpin ribozymes
    hammerhead ribozymes
Prodrug converting enzymes
    varicella zoster thymidine kinase
    cytosine deaminase
    purine nucleoside phosphorylase (e.g., from E. coli)
    beta lactamase
    carboxypeptidase G2
    carboxypeptidase A
    cytochrome P450
        cytochrome P450-2B1
        cytochrome P450-4B1
    horseradish peroxidase
    nitroreductase
    rabbit carboxylesterase
    mushroom tyrosinase
    beta galactosidase (lacZ) (i.e., from E. coli)
    beta glucuronidase (gusA)
    thymidine phosphorylase
    deoxycytidine kinase
    linamerase
Proteins detectable by antibodies
    chloramphenicol acetyl transferase
    hGH
Viral attenuation factors
    virus-specific antibodies
        mucins
        thrombospondin
    tumor necrosis factors (TNFs)
        TNFα

TABLE 4-continued

Exemplary Genes and Gene Products

Superantigens
Toxins
    diphtheria toxin
    *Pseudomonas* exotoxin
    *Escherichia coli* Shiga toxin
    *Shigella* toxin
    *Escherichia coli* Verotoxin 1
    Toxic Shock Syndrome Toxin 1
    Exfoliating Toxins (EXft)
    Streptococcal Pyrogenic Exotoxin (SPE) A, B and C
    Clostridial *Perfringens* Enterotoxin (CPET)
    staphylococcal enterotoxins
        SEA, SEB, SEC1, SEC2, SED, SEE and SEH
    Mouse Mammary Tumor Virus proteins (MMTV)
    Streptococcal M proteins
    *Listeria monocytogenes* antigen p60
    *mycoplasma* arthritis superantigens
Proteins that can bind a contrasting agent, chromophore, or a compound or ligand that can be detected
    siderophores
        enterobactin
        salmochelin
        yersiniabactin
        aerobactin
Growth Factors
    platelet-derived growth factor (PDG-F)
    keratinocyte growth factor (KGF)
    insulin-like growth factor-1 (IGF-1)
    insulin-like growth factor-binding proteins (IGFBPs)
    transforming growth factor (TGF-alpha)
    Growth factors for blood cells
        Granulocyte Colony Stimulating Factor (G-CSF)
    growth factors that can boost platelets
Other Groups
    BAC (Bacterial Artificial Chromosome) encoding several or all proteins of a specific pathway, e.g. woundhealing-pathway
    MAC (Mammalian Artificial Chromosome) encoding several or all proteins of a specific pathway, e.g. woundhealing-pathway
    tumor antigen
    RNAi
    ligand binding proteins
    proteins that can induce a signal detectable by MRI
    angiogenins
    photosensitizing agents
    anti-metabolites
    signaling modulators
    chemotherapeutic compounds
    lipases
    proteases
    pro-apoptotic factors
    anti-cancer vaccine
        antigen vaccines
        whole cell vaccines (i.e., dendritic cell vaccines)
        DNA vaccines
        anti-idiotype vaccines
    tumor suppressors
    cytotoxic protein
    cytostatic proteins
    costimulatory molecules
        cytokines and chemokines
    cancer growth inhibitors
    gene therapy
    BCG vaccine for bladder cancer
Proteins that interact with host cell proteins b. Control of Heterologous Gene Expression In some examples, the heterologous nucleic acid also can contain one or more regulatory sequences to regulate expression of an open reading frame encoding the heterologous RNA and/or protein. Suitable regulatory sequences which, for example, are functional in a mammalian host cell are well known in the art. Expression can also be influenced by one or more proteins or RNA molecules expressed by the virus. Gene regulatory elements, such as promoters and enhancers, possess cell type specific activities and can be activated by certain induction factors (e.g., hormones, growth factors, cytokines, cytostatic agents, irradiation, heat shock) via responsive elements. A controlled and restricted expression of these genes can be achieved using such regulatory elements as internal promoters to drive the expression of therapeutic genes in viral vector constructs.

For example, the one or more heterologous nucleic acid molecules can be operably linked to a promoter for expression of the heterologous RNA and/or protein. For example, a heterologous nucleic acid that is operably linked to a promoter is also called an expression cassette. Hence, viruses provided herein can have the ability to express one or more heterologous genes. Gene expression can include expression of a protein encoded by a gene and/or expression of an RNA molecule encoded by a gene. In some embodiments, the viruses provided herein can express exogenous genes at levels high enough that permit harvesting products of the exogenous genes from the tumor. Expression of heterologous genes can be controlled by a constitutive promoter, or by an inducible promoter. In other examples, organ or tissue-specific expression can be controlled by regulatory sequences. In order to achieve expression only in the target organ, for example, a tumor to be treated, the foreign nucleotide sequence can be linked to a tissue specific promoter and used for gene therapy. Such promoters are well known to those skilled in the art (see, e.g., Zimmermann et al., *Neuron* 12: 11-24 (1994); Vidal et al., *EMBO J.* 9: 833-840 (1990); Mayford et al., *Cell* 81: 891-904 (1995); and Pinkert et al., *Genes & Dev.* 1: 268-76 (1987)).

Exemplary promoters for the expression of heterologous genes are known in the art. The heterologous nucleic acid can be operatively linked to a native promoter or a heterologous promoter that is not native to the virus. Any suitable promoters, including synthetic and naturally-occurring and modified promoters, can be used. Exemplary promoters include synthetic promoters, including synthetic viral and animal promoters. Native promoter or heterologous promoters include, but are not limited to, viral promoters, such as vaccinia virus and adenovirus promoters.

In one example, the promoter is a poxvirus promoter, such as, for example, a vaccinia virus promoter. Vaccinia viral promoters for the expression of one or more heterologous genes can be synthetic or natural promoters, and include vaccinia early, intermediate, early/late and late promoters. Exemplary vaccinia viral promoters for controlling heterologous gene expression include, but are not limited to, $P_{7.5k}$, $P_{11k}$, $P_{SE}$, $P_{SEL}$, $P_{SL}$, HSR, TK, P28, C11R, G8R, F17R, I3L, I8R, A1L, A2L, A3L, H1L, H3L, H5L, H6R, H8R, D1R, D4R, D5R, D9R, D11L, D12L, D13L, M1L, N2L, P4b or K1 promoters. Other viral promoters include, but are not limited to, adenovirus late promoter, Cowpox ATI promoter, or T7 promoter. Strong late promoters can be used to achieve high levels of expression of the heterologous genes. Early and intermediate-stage promoters also can be used. In one example, the promoters contain early and late promoter elements, for example, the vaccinia virus early/late promoter $P_{7.5k}$, vaccinia late promoter $P_{11k}$, a synthetic early/late vaccinia $P_{SEL}$ promoter (Patel et al., (1988) *Proc. Natl. Acad. Sci. USA* 85: 9431-9435; Davison and Moss, (1989) *J Mol Biol* 210: 749-769; Davison et al. (1990) *Nucleic Acids Res.* 18: 4285-4286; Chakrabarti et al. (1997), *BioTechniques* 23: 1094-1097). The viruses provided herein can exhibit differences in characteristics, such as attenuation, as a result of using a stronger promoter versus a weaker promoter. For example, in vaccinia, synthetic early/late and late promoters are relatively strong promoters, whereas vaccinia synthetic early, $P_{7.5k}$ early/late, $P_{7.5k}$ early, and $P_{28}$ late promoters are relatively weaker promoters (see e.g., Chakrabarti et al. (1997) *BioTechniques* 23(6) 1094-1097). Combinations of different promoters can be used to express different gene products in the same virus or two different viruses.

As is known in the art, regulatory sequences can permit constitutive expression of the exogenous gene or can permit inducible expression of the exogenous gene. Further, the regulatory sequence can permit control of the level of expression of the exogenous gene. In some examples, such as gene product manufacture and harvesting, the regulatory sequence can result in constitutive, high levels of gene expression. In some examples, such as anti-(gene product) antibody harvesting, the regulatory sequence can result in constitutive, lower levels of gene expression. In tumor therapy examples, a therapeutic protein can be under the control of an internally inducible promoter or an externally inducible promoter.

Hence, expression of heterologous genes can be controlled by a constitutive promoter or by an inducible promoter. Inducible promoters can be used to provide tissue specific expression of the heterologous gene or can be inducible by the addition of a regulatory molecule to provide temporal specific induction of the promoter. In some examples, inducible expression can be under the control of cellular or other factors present in a tumor cell or present in a virus-infected tumor cell. In further examples, inducible expression can be under the control of an administrable substance, including IPTG, RU486 or other known induction compounds. Additional regulatory sequences can be used to control the expression of the one or more heterologous genes inserted the virus. Any of a variety of regulatory sequences are available to one skilled in the art according to known factors and design preferences.

c. Exemplary Modified or Recombinant Viruses

Exemplary modified or recombinant vaccinia viruses for use in the combinations, compositions or methods herein are those derived from the Lister strain, and in particular the attenuated Lister strain LIVP. Recombinant LIVP viruses containing heterologous nucleic acid have been generated and are known in the art. The modified LIVP viruses can be modified by insertion, deletion or amino acid replacement of heterologous nucleic acid compared to an LIVP strain having a genome set forth in any one of SEQ ID NOS: 1, 2 or 5-11, or having a genome that exhibits at least 85% or more sequence identity to any of SEQ ID NOS: 1, 2 or 5-11. Table 5 sets forth exemplary viruses, the reference or parental LIVP (e.g. LIVP set forth in SEQ ID NO: 2 or GLV-1h68 set forth in SEQ ID NO: 3) and the resulting genotype. The exemplary modifications of the Lister strain can be adapted to other vaccinia viruses (e.g., Western Reserve (WR), Copenhagen, Tashkent, Tian Tan, Lister, Wyeth, IHD-J, and IHD-W, Brighton, Ankara, MVA, Dairen I, LIPV, LC16M8, LC16MO, LIVP, WR 65-16, Connaught, New York City Board of Health).

TABLE 5

Recombinant Viruses

| Virus Name | Parent Virus | Genotype | | | | |
|---|---|---|---|---|---|---|
| | | F14.5L | J2R | A56R | A34R | A35R |
| GLV-1h68 | LIVP | (PSE/L)Ruc-GFP | (PSE/L)rTrfR-(P7.5)lacZ | (P11)gusA | wt | wt |
| GLV- | GLV-1h68 | (PSE/L)Ruc- | (PSE/L)rTrfR- | (P11)gusA | A34R | wt |

TABLE 5-continued

Recombinant Viruses

| Virus Name | Parent Virus | F14.5L | J2R | A56R | A34R | A35R |
|---|---|---|---|---|---|---|
| 1i69 | | GFP | (P7.5)lacZ | | from IHD-J | |
| GLV-1h70 | GLV-1h68 | (PSE/L)Ruc-GFP | (PSE/L)rTrfR-(P7.5)lacZ | ko | wt | wt |
| GLV-1h71 | GLV-1h68 | ko | (PSE/L)rTrfR-(P7.5)lacZ | (P11)gusA | wt | wt |
| GLV-1h72 | GLV-1h68 | (PSE/L)Ruc-GFP | ko | (P11)gusA | wt | wt |
| GLV-1h73 | GLV-1h70 | ko | (PSE/L)rTrfR-(P7.5)lacZ | ko | wt | wt |
| GLV-1h74 | GLV-1h73 | ko | ko | ko | wt | wt |
| GLV-1h76 | GLV-1h68 | (PSE/L)Ruc-GFP | (PSE)GM-CSF | (P11)gusA | wt | wt |
| GLV-1h77 | GLV-1h68 | (PSE/L)Ruc-GFP | (PSE/L)GM-CSF | (P11)gusA | wt | wt |
| GLV-1h78 | GLV-1h68 | (PSE/L)Ruc-GFP | (PSL)GM-CSF | (P11)gusA | wt | wt |
| GLV-1h79 | GLV-1h68 | (PSE/L)Ruc-GFP | (PSE/L)mMCP-1 | (P11)gusA | wt | wt |
| GLV-1h80 | GLV-1h68 | (PSE/L)Ruc-GFP | (PSL)mMCP-1 | (P11)gusA | wt | wt |
| GLV-1h81 | GLV-1h68 | (PSE/L)Ruc-GFP | (PSE/L)rTrfR-(P7.5)lacZ | (PSE/L)hk5 | wt | wt |
| GLV-1h82 | GLV-1h22 | (PSE/L)Ruc-GFP | (PSE/L)TrfR-(P7.5)lacZ | (PSE/L)ftn | wt | wt |
| GLV-1h83 | GLV-1h68 | (PSE/L)Ruc-GFP | (PSE/L)rTrfR-(P7.5)lacZ | (PSE/L)ftn | wt | wt |
| GLV-1h84 | GLV-1h68 | ko | (PSE/L)CBG99-mRFP1 | ko | wt | wt |
| GLV-1h85 | GLV-1h72 | ko | ko | (P11)gusA | wt | wt |
| GLV-1h86 | GLV-1h72 | (PSE/L)Ruc-GFP | ko | ko | wt | wt |
| GLV-1j87 | GLV-1h68 | (PSE/L)Ruc-GFP | (PSE/L)rTrfR-(P7.5)lacZ | (P11)gusA | wt | ko |
| GLV-1j88 | GLV-1h73 | ko | (PSE/L)rTrfR-(P7.5)lacZ | ko | wt | ko |
| GLV-1j89 | GLV-1h74 | ko | ko | ko | wt | ko |
| GLV-1h90 | GLV-1h68 | (PSE/L)Ruc-GFP | (PSE/L)rTrfR-(P7.5)lacZ | (PSE)sIL-6R/IL-6 | wt | wt |
| GLV-1h91 | GLV-1h68 | (PSE/L)Ruc-GFP | (PSE/L)rTrfR-(P7.5)lacZ | (PSE/L)sIL-6R/IL-6 | wt | wt |
| GLV-1h92 | GLV-1h68 | (PSE/L)Ruc-GFP | (PSE/L)rTrfR-(P7.5)lacZ | (PSL)sIL-6R/IL-6 | wt | wt |
| GLV-1h93 | GLV-1h68 | (PSE/L)Ruc-GFP | (PSE/L)rTrfR-(P7.5)lacZ | (PSE)FCU1 | wt | wt |
| GLV-1h94 | GLV-1h68 | (PSE/L)Ruc-GFP | (PSE/L)rTrfR-(P7.5)lacZ | (PSEL)FCU1 | wt | wt |
| GLV-1h95 | GLV-1h68 | (PSE/L)Ruc-GFP | (PSE/L)rTrfR-(P7.5)lacZ | (PSL)FCU1 | wt | wt |
| GLV-1h96 | GLV-1h68 | (PSE)IL-24 | (PSE/L)rTrfR-(P7.5)lacZ | (P11)gusA | wt | wt |
| GLV-1h97 | GLV-1h68 | (PSEL)IL-24 | (PSE/L)rTrfR-(P7.5)lacZ | (P11)gusA | wt | wt |
| GLV-1h98 | GLV-1h68 | (PSL)IL-24 | (PSE/L)rTrfR-(P7.5)lacZ | (P11)gusA | wt | wt |
| GLV-1h99 | GLV-1h68 | (PSE)hNET | (PSE/L)rTrfR-(P7.5)lacZ | (P11)gusA | wt | wt |
| GLV-1h100 | GLV-1h68 | (PSE/L)Ruc-GFP | (PSE)hNET | (P11)gusA | wt | wt |
| GLV-1h101 | GLV-1h68 | (PSE/L)Ruc-GFP | (PSL)hNET | (P11)gusA | wt | wt |
| GLV-1h102 | GLV-1h68 | (PSE/L)Ruc-GFP | (PSE/L)rTrfR-(P7.5)lacZ | (PSE)hDMT | wt | wt |
| GLV-1h103 | GLV-1h68 | (PSE/L)Ruc-GFP | (PSL)hMCP1 | (P11)gusA | wt | wt |
| GLV-1h104 | GLV-1h68 | (PSE/L)Ruc-GFP | (PSE)tTF-RGD | (P11)gusA | wt | wt |
| GLV-1h105 | GLV-1h68 | (PSE/L)Ruc-GFP | (PSE/L)tTF-RGD | (P11)gusA | wt | wt |
| GLV-1h106 | GLV-1h68 | (PSE/L)Ruc-GFP | (PSL)tTF-RGD | (P11)gusA | wt | wt |

TABLE 5-continued

Recombinant Viruses

| Virus Name | Parent Virus | Genotype | | | | |
|---|---|---|---|---|---|---|
| | | F14.5L | J2R | A56R | A34R | A35R |
| GLV-1h107 | GLV-1h68 | (PSE/L)Ruc-GFP | (PSE)G6-FLAG | (P11)gusA | wt | wt |
| GLV-1h108 | GLV-1h68 | (PSE/L)Ruc-GFP | (PSE/L)G6-FLAG | (P11)gusA | wt | wt |
| GLV-1h109 | GLV-1h68 | (PSE/L)Ruc-GFP | (PSL)G6-FLAG | (P11)gusA | wt | wt |
| GLV-1h110 | GLV-1h68 | (PSE/L)Ruc-GFP | (PSE/L)rTrfR-(P7.5)lacZ | (PSE)bfr | wt | wt |
| GLV-1h111 | GLV-1h68 | (PSE/L)Ruc-GFP | (PSE/L)rTrfR-(P7.5)lacZ | (PSE/L)bfr | wt | wt |
| GLV-1h112 | GLV-1h68 | (PSE/L)Ruc-GFP | (PSE/L)rTrfR-(P7.5)lacZ | (PSL)bfr | wt | wt |
| GLV-1h113 | GLV-1h68 | (PSE/L)Ruc-GFP | (PSE/L)rTrfR-(P7.5)lacZ | (PSE/L)bfr$_{opt}$ | wt | wt |
| GLV-1h114 | GLV-1h68 | (PSE/L)Ruc-GFP | (PSE/L)rTrfR-(P7.5)lacZ | (PSE)mtr | wt | wt |
| GLV-1h115 | GLV-1h68 | (PSE/L)Ruc-GFP | (PSE/L)rTrfR-(P7.5)lacZ | (PSE/L)mtr | wt | wt |
| GLV-1h116 | GLV-1h68 | (PSE/L)Ruc-GFP | (PSE)mMnSOD | (P11)gusA | wt | wt |
| GLV-1h117 | GLV-1h68 | (PSE/L)Ruc-GFP | (PSE/L)mMnSOD | (P11)gusA | wt | wt |
| GLV-1h118 | GLV-1h68 | (PSE/L)Ruc-GFP | (PSL)mMnSOD | (P11)gusA | wt | wt |
| GLV-1h119 | GLV-1h68 | (PSE/L)Ruc-GFP | (PSE)mIP-10 | (P11)gusA | wt | wt |
| GLV-1h120 | GLV-1h68 | (PSE/L)Ruc-GFP | (PSE/L)mIP-10 | (P11)gusA | wt | wt |
| GLV-1h121 | GLV-1h68 | (PSE/L)Ruc-GFP | (PSL)mIP-10 | (P11)gusA | wt | wt |
| GLV-1h122 | GLV-1h68 | (PSE/L)Ruc-GFP | (PSE)mLIGHT | (P11)gusA | wt | wt |
| GLV-1h123 | GLV-1h68 | (PSE/L)Ruc-GFP | (PSE/L)mLIGHT | (P11)gusA | wt | wt |
| GLV-1h124 | GLV-1h68 | (PSE/L)Ruc-GFP | (PSL)mLIGHT | (P11)gusA | wt | wt |
| GLV-1h125 | GLV-1h68 | (PSE/L)Ruc-GFP | (PSE)CBP | (P11)gusA | wt | wt |
| GLV-1h126 | GLV-1h68 | (PSE/L)Ruc-GFP | (PSE/L)CBP | (P11)gusA | wt | wt |
| GLV-1h127 | GLV-1h68 | (PSE/L)Ruc-GFP | (PSL)CBP | (P11)gusA | wt | wt |
| GLV-1h128 | GLV-1h68 | (PSE/L)Ruc-GFP | (PSE)P60 | (P11)gusA | wt | wt |
| GLV-1h129 | GLV-1h68 | (PSE/L)Ruc-GFP | (PSE/L)P60 | (P11)gusA | wt | wt |
| GLV-1h130 | GLV-1h68 | (PSE/L)Ruc-GFP | (PSL)P60 | (P11)gusA | wt | wt |
| GLV-1h131 | GLV-1h68 | (PSE/L)Ruc-GFP | (PSE)hFLH | (P11)gusA | wt | wt |
| GLV-1h132 | GLV-1h68 | (PSE/L)Ruc-GFP | (PSE/L)hFLH | (P11)gusA | wt | wt |
| GLV-1h133 | GLV-1h68 | (PSE/L)Ruc-GFP | (PSL)hFLH | (P11)gusA | wt | wt |
| GLV-1h134 | GLV-1h68 | (PSE/L)CBG99-mRFP1 | (PSE/L)rTrfR-(P7.5)lacZ | (P11)gusA | wt | wt |
| GLV-1e135 | GLV-1h68 | wt | (PSE/L)rTrfR-(P7.5)lacZ | | wt | wt |
| GLV-1h136 | GLV-1h68 | (PSE/L)Ruc-GFP | (PSE)PEDF | (P11)gusA | wt | wt |
| GLV-1h137 | GLV-1h68 | (PSE/L)Ruc-GFP | (PSE/L)PEDF | (P11)gusA | wt | wt |
| GLV-1h138 | GLV-1h68 | (PSE/L)Ruc-GFP | (PSL)PEDF | (P11)gusA | wt | wt |
| GLV-1h139 | GLV-1h68 | (PSE/L)Ruc-GFP | (PSE/L)rTrfR-(P7.5)lacZ | (PSE)hNET | wt | wt |
| GLV-1h140 | GLV-1h68 | (PSE/L)Ruc-GFP | (PSE)CYP11B1 | (P11)gusA | wt | wt |
| GLV-1h141 | GLV-1h68 | (PSE/L)Ruc-GFP | (PSE/L)CYP11B1 | (P11)gusA | wt | wt |
| GLV-1h142 | GLV-1h68 | (PSE/L)Ruc-GFP | (PSL)CYP11B1 | (P11)gusA | wt | wt |
| GLV-1h143 | GLV-1h68 | (PSE/L)Ruc-GFP | (PSE)CYP11B2 | (P11)gusA | wt | wt |

TABLE 5-continued

Recombinant Viruses

| Virus Name | Parent Virus | F14.5L | J2R | A56R | A34R | A35R |
|---|---|---|---|---|---|---|
| GLV-1h144 | GLV-1h68 | (PSE/L)Ruc-GFP | (PSE/L)CYP11B2 | (P11)gusA | wt | wt |
| GLV-1h145 | GLV-1h68 | (PSE/L)Ruc-GFP | (PSL)CYP11B2 | (P11)gusA | wt | wt |
| GLV-1h146 | GLV-1h100 | (PSE/L)Ruc-GFP | (PSE)hNET | (PSE)IL-24 | wt | wt |
| GLV-1h147 | GLV-1h68 | (PSE/L)Ruc-GFP | (PSE)HACE1 | (P11)gusA | wt | wt |
| GLV-1h148 | GLV-1h68 | (PSE/L)Ruc-GFP | (PSE/L)HACE1 | (P11)gusA | wt | wt |
| GLV-1h149 | GLV-1h68 | (PSE/L)Ruc-GFP | (PSL)HACE1 | (P11)gusA | wt | wt |
| GLV-1h150 | GLV-1h101 | (PSE/L)Ruc-GFP | (PSL)hNET | (PSE)IL-24 | wt | wt |
| GLV-1h151 | GLV-1h68 | (PSE/L) Ruc-GFP | (PSE/L)TfR-(P7.5)lacZ | (PSE)hNIS | wt | wt |
| GLV-1h153 | GLV-1h68 | (PSE/L) Ruc-GFP | (PSE/L)TfR-(P7.5)lacZ | (PSE)hNISa | wt | wt |
| GLV-1h154 | GLV-1h22 | ($P_{SE/L}$) Ruc-GFP | ($P_{SE/L}$)TfR-($P_{7.5}$)lacZ | ($P_{SE/L}$)bfr$_{opt}$ | wt | wt |
| GLV-1h155 | GLV-1h22 | (PSE/L) Ruc-GFP | (PSE/L)TfR-(P7.5)lacZ | (PSE/L)hFH | wt | wt |
| GLV-1h156 | GLV-1h113 | (PSE/L) Ruc-GFP | (PSE/L)mtr | (PSE/L)bfr$_{opt}$ | wt | wt |
| GLV-1h157 | GLV-1h68 | (PSE/L) Ruc-GFP | (PSE/L)mtr | (PSE/L)hFH | wt | wt |
| GLV-1h158 | GLV-1h68 | (PSE/L) Ruc-GFP | (PSE/L)TfR-(P7.5)lacZ | (PSE/L)G6-scAb | wt | wt |
| GLV-1h159 | GLV-1h68 | (PSE/L) Ruc-GFP | (PSE/L)TfR-(P7.5)lacZ | (PSL)G6-scAb | wt | wt |
| GLV-1h160 | GLV-1h68 | (PSE/L)Ruc-GFP | (PSEL)luxAB | (P11)gusA | wt | wt |
| GLV-1h161 | GLV-1h68 | (PSE/L)Ruc-GFP | (PSE/L)TfR-(P7.5)lacZ | (PSEL)luxCD | wt | wt |
| GLV-1h162 | GLV-1h68 | (PSEL)luxE | (PSE/L)rTrfR-(P7.5)lacZ | (P11)gusA | wt | wt |
| GLV-1h163 | GLV-1h100 | (PSE/L)Ruc-GFP | (PSE)hNET | (PSE/L)G6-scAb | wt | wt |
| GLV-1h164 | GLV-1h100 | (PSE/L)Ruc-GFP | (PSE)hNET | (PSL)G6-scAb | wt | wt |
| GLV-1h165 | GLV-1h68 | (PSE/L)Ruc-GFP | (PSE)nAG | (P11)gusA | wt | wt |
| GLV-1h166 | GLV-1h68 | (PSE/L)Ruc-GFP | (PSEL)NAG | (P11)gusA | wt | wt |
| GLV-1h167 | GLV-1h68 | (PSE/L)Ruc-GFP | (PSL)nAG | (P11)gusA | wt | wt |
| GLV-1h168 | GLV-1h68 | (PSE/L)Ruc-GFP | (PSE)RLN | (P11)gusA | wt | wt |
| GLV-1h169 | GLV-1h68 | (PSE/L)Ruc-GFP | (PSEL)RLN | (P11)gusA | wt | wt |
| GLV-1h170 | GLV-1h68 | (PSE/L)Ruc-GFP | (PSL)RLN | (P11)gusA | wt | wt |
| GLV-1h171 | GLV-1h68 | (PSE/L)Ruc-GFP | (PSE)NM23A | (P11)gusA | wt | wt |
| GLV-1h172 | GLV-1h68 | (PSE/L)Ruc-GFP | (PSEL)NM23A | (P11)gusA | wt | wt |
| GLV-1h173 | GLV-1h68 | (PSE/L)Ruc-GFP | (PSL)NM23 | (P11)gusA | wt | wt |
| GLV-1h174 | GLV-1h68 | (PSE/L)Ruc-GFP | (PSE)NPPA1 | (P11)gusA | wt | wt |
| GLV-1h175 | GLV-1h68 | (PSE/L)Ruc-GFP | (PSEL)NPPA1 | (P11)gusA | wt | wt |
| GLV-1h176 | GLV-1h68 | (PSE/L)Ruc-GFP | (PSL)NPPA1 | (P11)gusA | wt | wt |
| GLV-1h177 | GLV-1h68 | (PSE/L)Ruc-GFP | (PSE)STAT1α | (P11)gusA | wt | wt |
| GLV-1h178 | GLV-1h68 | (PSE/L)Ruc-GFP | (PSEL)STAT1α | (P11)gusA | wt | wt |
| GLV-1h179 | GLV-1h68 | (PSE/L)Ruc-GFP | (PSL)STAT1α | (P11)gusA | wt | wt |
| GLV-1h180 | GLV-1h68 | (PSE/L)Ruc-GFP | (PSE)CPG2 | (P11)gusA | wt | wt |
| GLV-1h181 | GLV-1h68 | (PSE/L)Ruc-GFP | (PSEL)CPG2 | (P11)gusA | wt | wt |

TABLE 5-continued

Recombinant Viruses

| Virus Name | Parent Virus | Genotype F14.5L | J2R | A56R | A34R | A35R |
|---|---|---|---|---|---|---|
| GLV-1h182 | GLV-1h68 | (PSE/L)Ruc-GFP | (PSL)CPG2 | (P11)gusA | wt | wt |
| GLV-1h183 | GLV-1h68 | (PSE/L)Ruc-GFP | (PSE)Ecad | (P11)gusA | wt | wt |
| GLV-1h184 | GLV-1h68 | (PSE/L) Ruc-GFP | (PSE/L)TfR-(P7.5)lacZ | (PSE)magA | wt | wt |
| GLV-1h185 | GLV-1h68 | (PSE/L)Ruc-GFP | (PSL)Ecad | (P11)gusA | wt | wt |
| GLV-1h186 | GLV-1h68 | (PSE/L) Ruc-GFP | (PSE/L)TfR-(P7.5)lacZ | (PSEL)FTL 498-499InsTC | wt | wt |
| GLV-1h187 | GLV-1h68 | (PSE/L) Ruc-GFP | (PSE/L)TfR-(P7.5)lacZ | (PSEL)FTL | wt | wt |
| GLV-1h188 | GLV-1h68 | (PSE/L) Ruc-GFP | (PSE/L)TfR-(P7.5)lacZ | (PSE)FUKW | wt | wt |
| GLV-1h189 | GLV-1h68 | (PSE/L) Ruc-GFP | (PSE/L)TfR-(P7.5)lacZ | (PSEL)FUKW | wt | wt |
| GLV-1h190 | GLV-1h68 | (PSE/L) Ruc-GFP | (PSE/L)TfR-(P7.5)lacZ | (PSL)FUKW | wt | wt |
| GLV-1h191 | GLV-1h68 | (PSE/L)Ruc-GFP | (PSE)STAT1β | (P11)gusA | wt | wt |
| GLV-1h192 | GLV-1h68 | (PSE/L)Ruc-GFP | (PSEL)STAT1β | (P11)gusA | wt | wt |
| GLV-1h193 | GLV-1h68 | (PSE/L)Ruc-GFP | (PSL) STAT1β | (P11)gusA | wt | wt |
| GLV-1h194 | GLV-1h161 | (PSE)luxE | (PSE/L)TfR-(P7.5)lacZ | (PSEL)luxCD | wt | wt |
| GLV-1h195 | GLV-1h161 | (PSE/L)Ruc-GFP | (PSE)luxAB | (PSEL)luxCD | wt | wt |
| GLV-1h196 | GLV-1h68 | (PSE/L)Ruc-GFP | (PSE)181a | (P11)gusA | wt | wt |
| GLV-1h197 | GLV-1h68 | | | | | |
| GLV-1h198 | GLV-1h68 | (PSE/L)Ruc-GFP | (PSL)181a | (P11)gusA | wt | wt |
| GLV-1h199 | GLV-1h68 | (PSE/L)Ruc-GFP | (PSE)335 | (P11)gusA | wt | wt |
| GLV-1h201 | GLV-1h68 | (PSE/L)Ruc-GFP | (PSL)335 | (P11)gusA | wt | wt |
| GLV-1h202 | GLV-1h68 | | | | | |
| GLV-1h203 | GLV-1h68 | (PSE/L)Ruc-GFP | (PSEL)126 | (P11)gusA | wt | wt |
| GLV-1h204 | GLV-1h68 | | | | | |
| GLV-1h205 | GLV-1h68 | (PSE/L) Ruc-GFP | (PSE/L)TfR-(P7.5)lacZ | (PSE)NANOG | wt | wt |
| GLV-1h208 | GLV-1h68 | (PSE/L) Ruc-GFP | (PSE/L)TfR-(P7.5)lacZ | (PSE)Oct4 | wt | wt |
| GLV-1h210 | GLV-1h68 | (PSE/L)Ruc-GFP | (P7.5E)hEPO | (P11)gusA | wt | wt |
| GLV-1h211 | GLV-1h68 | (PSE/L)Ruc-GFP | (PSE)hEPO | (P11)gusA | wt | wt |
| GLV-1h212 | GLV-1h68 | (PSE/L)Ruc-GFP | (PSEL)hEPO | (P11)gusA | wt | wt |
| GLV-1h213 | GLV-1h68 | (PSE/L)Ruc-GFP | (PSL)hEPO | (P11)gusA | wt | wt |
| GLV-1h214 | GLV-1h68 | (PSE/L)Ruc-GFP | (PSE)OspF | (P11)gusA | wt | wt |
| GLV-1h215 | GLV-1h68 | (PSE/L)Ruc-GFP | (PSE)OspG | (P11)gusA | wt | wt |
| GLV-1h216 | GLV-1h68 | (PSE/L)Ruc-GFP | (PSEL)OspG | (P11)gusA | wt | wt |
| GLV-1h217 | GLV-1h68 | (PSE/L)Ruc-GFP | (PSL)OspG | (P11)gusA | wt | wt |
| GLV-1h218 | GLV-1h84 | ko | (PSE/L)CBG99-mRFP1 | (PSE)RLN | wt | wt |
| GLV-1h219 | GLV-1h84 | ko | (PSE/L)CBG99-mRFP1 | (PSEL)RLN | wt | wt |
| GLV-1h220 | GLV-1h84 | ko | (PSE/L)CBG99-mRFP1 | (PSL)RLN | wt | wt |
| GLV-1h221 | GLV-1h160 | (PSE)luxE | (PSEL)luxAB | (P11)gusA | wt | wt |
| GLV-1h222 | GLV-1h68 | (PSE/L)Ruc-GFP | (PSE)Ngn3 | (P11)gusA | wt | wt |

TABLE 5-continued

Recombinant Viruses

| Virus Name | Parent Virus | Genotype F14.5L | J2R | A56R | A34R | A35R |
|---|---|---|---|---|---|---|
| GLV-1h223 | GLV-1h68 | (PSE/L)Ruc-GFP | (PSEL)Ngn3 | (P11)gusA | wt | wt |
| GLV-1h224 | GLV-1h68 | (PSE/L)Ruc-GFP | (PSL)Ngn3 | (P11)gusA | wt | wt |
| GLV-1h225 | GLV-1h68 | (PSE/L)Ruc-GFP | (PSE)hADH | (P11)gusA | wt | wt |
| GLV-1h226 | GLV-1h68 | (PSE/L)Ruc-GFP | (PSEL)hADH | (P11)gusA | wt | wt |
| GLV-1h227 | GLV-1h68 | (PSE/L)Ruc-GFP | (PSL)hADH | (P11)gusA | wt | wt |
| GLV-1h228 | GLV-1h194 | (PSE)luxE | (PSE)luxAB | (PSEL)luxCD | wt | wt |
| GLV-1h229 | GLV-1h195 | (PSEL)luxE | (PSE)luxAB | (PSEL)luxCD | wt | wt |
| GLV-1h230 | GLV-1h68 | (PSE/L)Ruc-GFP | (PSE)Myc-CTR1 | (P11)gusA | wt | wt |
| GLV-1h231 | GLV-1h68 | (PSE/L)Ruc-GFP | (PSL)Myc-CTR1 | (P11)gusA | wt | wt |
| GLV-1h232 | GLV-1h68 | (PSE/L)Ruc-GFP | (PSE)CTR1 | (P11)gusA | wt | wt |
| GLV-1h233 | GLV-1h68 | (PSE/L)Ruc-GFP | (PSE)mPEDF | (P11)gusA | wt | wt |
| GLV-1h234 | GLV-1h68 | (PSE/L)Ruc-GFP | (PSEL)mPEDF | (P11)gusA | wt | wt |
| GLV-1h235 | GLV-1h68 | (PSE/L)Ruc-GFP | (PSL)mPEDF | (P11)gusA | wt | wt |
| GLV-1h236 | GLV-1h73 | (PSE/L)Ruc-GFP | rtfr(PE/L) (P7.5)lacZ | (PSE)WTCDC6 | wt | wt |
| GLV-1h237 | GLV-1h73 | (PSE/L)Ruc-GFP | rtfr(PE/L) (P7.5)lacZ | (PSE)MutCDC6 | wt | wt |
| GLV-1h238 | GLV-1h68 | (PSE/L) Ruc-GFP | (PSE/L)TfR-(P7.5)lacZ | (PSL)CBG99-mRFP1 | wt | wt |
| GLV-1h239 | GLV-1h68 | (PSE/L)Ruc-GFP | (PSE)GLAF-3 | (P11)gusA | wt | wt |
| GLV-1h240 | GLV-1h68 | (PSE/L)Ruc-GFP | (PSEL)GLAF-3 | (P11)gusA | wt | wt |
| GLV-1h241 | GLV-1h68 | (PSE/L)Ruc-GFP | (PSL)GLAF-3 | (P11)gusA | wt | wt |
| GLV-1h242 | GLV-1h68 | (PSE/L)Ruc-GFP | (PE))luxABCDE | (P11)gusA | wt | wt |
| GLV-1h243 | GLV-1h242 | (PSE/L)Ruc-GFP | (PE))luxABCDE | (PSE)frp | wt | wt |
| GLV-1h244 | GLV-1h189 | (PSE/L) Ruc-GFP | (PSE)hNISa | (PSEL)FUKW | wt | wt |
| GLV-1h245 | GLV-1h189 | (PSE/L) Ruc-GFP | (PSEL)hNISa | (PSEL)FUKW | wt | wt |
| GLV-1h246 | GLV-1h189 | (PSE/L) Ruc-GFP | (PSL)hNISa | (PSEL)FUKW | wt | wt |
| GLV-1h247 | GLV-1h68 | (PSE/L) Ruc-GFP | (PSE/L)TfR-(P7.5)lacZ | (PSE)IFP | wt | wt |
| GLV-1h248 | GLV-1h68 | (PSE/L) Ruc-GFP | (PSE/L)TfR-(P7.5)lacZ | (PSEL)IFP | wt | wt |
| GLV-1h249 | GLV-1h68 | (PSE/L) Ruc-GFP | (PSE/L)TfR-(P7.5)lacZ | (PSL)IFP | wt | wt |
| GLV-1h250 | GLV-1h190 | (PSE/L) Ruc-GFP | (PSE/L)TfR-(P7.5)lacZ | (PSL)FUKW | wt | wt |
| GLV-1h251 | GLV-1h68 | (PSE)hNISa | (PSE/L)rTrfR-(P7.5)lacZ | (P11)gusA | wt | wt |
| GLV-1h252 | GLV-1h68 | (PSE/L)Ruc-GFP | (PSE)hNISa | (P11)gusA | wt | wt |
| GLV-1h253 | GLV-1h71 | ko | (PSE/L)TfR-(P7.5)lacZ | (PSE)FUKW | wt | wt |
| GLV-1h254 | GLV-1h71 | ko | (PSE/L)TfR-(P7.5)lacZ | (PSL)FUKW | wt | wt |
| GLV-1h255 | GLV-1h68 | (PSE/L)Ruc-GFP | (PSE)hMMP9 | (P11)gusA | wt | wt |
| GLV-1h256 | GLV-1h68 | (PSE/L)Ruc-GFP | (PSL)hMMP9 | (P11)gusA | wt | wt |
| GLV-1h257 | GLV-1h68 | (PSE/L) Ruc-GFP | (PSE/L)TfR-(P7.5)lacZ | (PSE)mNeptune | wt | wt |
| GLV-1h258 | GLV-1h68 | (PSE/L) Ruc-GFP | (PSE/L)TfR-(P7.5)lacZ | (PSEL)mNeptune | wt | wt |
| GLV-1h259 | GLV-1h68 | (PSE/L) Ruc-GFP | (PSE/L)TfR-(P7.5)lacZ | (PSL)mNeptune | wt | wt |

TABLE 5-continued

Recombinant Viruses

| Virus Name | Parent Virus | Genotype F14.5L | J2R | A56R | A34R | A35R |
|---|---|---|---|---|---|---|
| GLV-1h260 | GLV-1h68 | (PSE)mNeptune | (PSE/L)rTrfR-(P7.5)lacZ | (P11)gusA | wt | wt |
| GLV-1h261 | GLV-1h68 | (PSEL)mNeptune | (PSE/L)rTrfR-(P7.5)lacZ | (P11)gusA | wt | wt |
| GLV-1h262 | GLV-1h68 | (PSL)mNeptune | (PSE/L)rTrfR-(P7.5)lacZ | (P11)gusA | wt | wt |
| GLV-1h263 | GLV-1h164 | (PSE)mNeptune | (PSE)hNET | (PSL)G6-scAb | wt | wt |
| GLV-1h264 | GLV-1h164 | (PSEL)mNeptune | (PSE)hNET | (PSL)G6-scAb | wt | wt |
| GLV-1h265 | GLV-1h164 | (PSL)mNeptune | (PSE)hNET | (PSL)G6-scAb | wt | wt |
| GLV-1h266 | GLV-1h189 | (PSE/L) Ruc-GFP | (PSE)AlstR | (PSEL)FUKW | wt | wt |
| GLV-1h267 | GLV-1h189 | (PSE/L) Ruc-GFP | (PSEL)AlstR | (PSEL)FUKW | wt | wt |
| GLV-1h268 | GLV-1h189 | (PSE/L) Ruc-GFP | (PSL)AlstR | (PSEL)FUKW | wt | wt |
| GLV-1h269 | GLV-1h189 | (PSE/L) Ruc-GFP | (PSE)PEPR1 | (PSEL)FUKW | wt | wt |
| GLV-1h270 | GLV-1h189 | (PSE/L) Ruc-GFP | (PSEL)PEPR1 | (PSEL)FUKW | wt | wt |
| GLV-1h271 | GLV-1h189 | (PSE/L) Ruc-GFP | (PSL)PEPR1 | (PSEL)FUKW | wt | wt |
| GLV-1h272 | GLV-1h189 | (PSE/L) Ruc-GFP | (PSE)LAT4 | (PSEL)FUKW | wt | wt |
| GLV-1h273 | GLV-1h189 | (PSE/L) Ruc-GFP | (PSEL)LAT4 | (PSEL)FUKW | wt | wt |
| GLV-1h274 | GLV-1h189 | (PSE/L) Ruc-GFP | (PSL)LAT4 | (PSEL)FUKW | wt | wt |
| GLV-1h275 | GLV-1h189 | (PSE/L) Ruc-GFP | (PSE)Cyp51 | (PSEL)FUKW | wt | wt |
| GLV-1h276 | GLV-1h189 | (PSE/L) Ruc-GFP | (PSEL)Cyp51 | (PSEL)FUKW | wt | wt |
| GLV-1h277 | GLV-1h189 | (PSE/L) Ruc-GFP | (PSL)Cyp51 | (PSEL)FUKW | wt | wt |
| GLV-1h284 | GLV-1h189 | (PSE/L)Ruc-GFP | (PSE)BMP4 | (PSEL)FUKW | wt | wt |
| GLV-1h285 | GLV-1h189 | (PSE/L)Ruc-GFP | (PSEL)BMP4 | (PSEL)FUKW | wt | wt |
| GLV-1h286 | GLV-1h189 | (PSE/L)Ruc-GFP | (PSL)BMP4 | (PSEL)FUKW | wt | wt |

For example, GLV-1h68 (also named RVGL21, SEQ ID NO: 3; described in U.S. Pat. Pub. No. 2005-0031643, now U.S. Pat. Nos. 7,588,767, 7,588,771, 7,662,398) is an attenuated virus of the LIVP parental strain containing a genome set forth in SEQ ID NO: 2. GLV-1h68 contains DNA insertions in gene loci F14.5L (also designated in LIVP as F3) gene locus, thymidine kinase (TK) gene locus, and hemagglutinin (HA) gene locus with expression cassettes encoding detectable marker proteins. Specifically, GLV-1h68 contains an expression cassette containing a Ruc-GFP cDNA molecule (a fusion of DNA encoding *Renilla luciferase* and DNA encoding GFP) under the control of a vaccinia synthetic early/late promoter $P_{SEL}$ (($P_{SEL}$)Ruc-GFP) inserted into the F14.5L gene locus; an expression cassette containing a DNA molecule encoding beta-galactosidase under the control of the vaccinia early/late promoter $P_{7.5k}$ (($P_{7.5k}$)LacZ) and DNA encoding a rat transferrin receptor positioned in the reverse orientation for transcription relative to the vaccinia synthetic early/late promoter $P_{SEL}$ (($P_{SEL}$)rTrfR) inserted into the TK gene locus (the resulting virus does not express transferrin receptor protein since the DNA molecule encoding the protein is positioned in the reverse orientation for transcription relative to the promoter in the cassette); and an expression cassette containing a DNA molecule encoding β-glucuronidase under the control of the vaccinia late promoter $P_{11k}$ (($P_{11k}$)gusA) inserted into the HA gene locus.

Other recombinant LIVP viruses are derived from GLV-1h68 and contain heterologous DNA that encodes a gene product or products (see e.g. see e.g. U.S. Pub. Nos. US2003-0059400, US2003-0228261, US2007-0202572, US2007-0212727, US2009-0117034, US2009-0098529, US2009-0053244, US2009-0155287, US2009-0081639, US2009-0136917, US2009-0162288, US2010-0062016, US2010-0233078 and US2010-0196325; U.S. Pat. Nos. 7,588,767, 7,588,771, 7,662,398 and 7,754,221 and 7,763,420; and International Pub. No. WO 2009/139921).

Exemplary of such recombinant viruses include those set forth in Table 5 above, including but not limited to, GLV-1h64 (set forth in SEQ ID NO: 14); viruses that encode the far-red fluorescent protein TurboFP635 (scientific name "Katushka") from the sea anemone *Entacmaea quadricolor* include GLV-1h188 (SEQ ID NO: 15), GLV-1h189 (SEQ ID NO: 16), GLV-1h190 (SEQ ID NO: 17) and GLV-1h253 (SEQ ID NO: 18).

Modified vaccinia viruses also include viruses that are modified by introduction of heterologous nucleic acid into an LIVP strain containing a genome set forth in any of SEQ ID NO: 5-11, or a genome that exhibits at least 85%, 90%, 92%, 95%, 96%, 97%, 98%, 99% or more sequence identity to any of SEQ ID NOS:5-11. For example, exemplary of a modified vaccinia virus is a virus that is modified by insertion, deletion or replacement of heterologous nucleic acid compared to an LIVP strain having a genome set forth in SEQ ID NO: 5. Exemplary of such as strain is GLV-2b372, which contains TurboFP635 (Far-red fluorescent protein "katushka") under the control of the vaccinia synthetic early/late promoter at the TK locus. The genome of GLV-1b372 has the sequence of nucleotides set forth in SEQ ID NO: 19.

d. Methods of Generating Modified Viruses

Oncolytic viruses, such as vaccinia viruses (e.g. LIVP), for use in the combinations, compositions or methods herein can be modified by insertion, deletion, replacement or mutation as described herein, for example insertion or replacement of heterologous nucleic acid, using standard methodologies well known in the art for modifying viruses. Methods for modification include, for example, in vitro recombination techniques, synthetic methods, direct cloning, and in vivo recombination methods as described, for example, in Sambrook et al., Molecular Cloning: A Laboratory Manual, 2nd edition, Cold Spring Harbor Laboratory Press, cold Spring Harbor NY (1989).

For example, generation of recombinant viruses, including recombinant vaccinia virus, is well known in the art, and typically involves the generation of gene cassettes or transfer vectors using standard techniques in molecular biology (see, e.g., U.S. Pat. No. 7,588,767 and US2009-0053244-A1, which describe exemplary methods of generating recombinant LIVP vaccinia viruses). Such techniques include various nucleic acid manipulation techniques, nucleic acid transfer protocols, nucleic acid amplification protocols, and other molecular biology techniques known in the art. For example, point mutations or small insertions or deletions can be introduced into a gene of interest through the use of oligonucleotide mediated site-directed mutagenesis. In another example, homologous recombination can be used to introduce a mutation in the nucleic acid sequence or insertion or deletion of a nucleic acid molecule into a target sequence of interest. In some examples, mutations, insertions or deletions of nucleic acid in a particular gene can be selected for using a positive or negative selection pressure. See, e.g., Current Techniques in Molecular Biology, (Ed. Ausubel, et al.).

Nucleic acid amplification protocols include, but are not limited to, the polymerase chain reaction (PCR), or amplification via viruses or organisms, such as, but not limited to, bacteria, yeast, insect or mammalian cells. Use of nucleic acid tools such as plasmids, vectors, promoters and other regulating sequences, are well known in the art for a large variety of viruses and cellular organisms.

Nucleic acid transfer protocols include calcium chloride transformation/transfection, electroporation, liposome mediated nucleic acid transfer, N-[1-(2,3-dioloyloxy)propyl]-N,N,N-trimethylammonium methylsulfate meditated transformation, and others. Further a large variety of nucleic acid tools are available from many different sources, including various commercial sources. One skilled in the art will be readily able to select the appropriate tools and methods for genetic modifications of any particular virus according to the knowledge in the art and design choice.

Hence, any of a variety of modifications can be readily accomplished using standard molecular biological methods known in the art. The modifications will typically be one or more truncations, deletions, mutations or insertions of the viral genome. In one example, the modification can be specifically directed to a particular sequence in the viral genome. The modifications can be directed to any of a variety of regions of the viral genome, including, but not limited to, a regulatory sequence, a gene-encoding sequence, an intergenic sequence, a sequence without a known role, or a non-essential region of the viral genome. Any of a variety of regions of viral genomes that are available for modification are readily known in the art for many viruses, including LIVP.

Heterologous nucleic acid molecules are typically inserted into the viral genome in an intergenic region or in a locus that encodes a nonessential viral gene product. Insertion of heterologous nucleic acid at such sites generally does not significantly affect viral infection or replication in the target tissue. Exemplary insertion sites are known in the art and include, but are not limited to, J2R (thymidine kinase (TK)), A56R (hemagglutinin (HA)), F14.5L, vaccinia growth factor (VGF), A35R, NIL, E2L/E3L, K1L/K2L, superoxide dismutase locus, 7.5K, C7-K1L (host range gene region), B13R+B14R (hemorrhagic region), A26L (A type inclusion body region (ATI)) or I4L (large subunit, ribonucleotide reductase) gene loci. Insertion sites for the viruses also include sites that correspond to intragenic regions described in other poxviruses such as Modified Vaccinia Ankara (MVA) virus (exemplary sites set forth in U.S. Pat. No. 7,550,147), NYVAC (exemplary sites set forth in U.S. Pat. No. 5,762,938).

Methods for the generation of recombinant viruses using recombinant DNA techniques are well known in the art (e.g., see U.S. Pat. Nos. 4,769,330; 4,603,112; 4,722,848; 4,215,051; 5,110,587; 5,174,993; 5,922,576; 6,319,703; 5,719,054; 6,429,001; 6,589,531; 6,573,090; 6,800,288; 7,045,313; He et al. (1998) *PNAS* 95(5): 2509-2514; Racaniello et al., (1981) *Science* 214: 916-919; and Hruby et al., (1990) *Clin Micro Rev.* 3:153-170). Methods for the generation of recombinant vaccinia viruses are well known in the art (e.g., see Hruby et al., (1990) *Clin Micro Rev.* 3:153-170, U.S. Pat. Pub. No. 2005-0031643, now U.S. Pat. Nos. 7,588,767, 7,588,771, 7,662,398 and 7,045,313).

For example, generating a recombinant vaccinia virus that expresses a heterologous gene product typically includes the use of a recombination plasmid which contains the heterologous nucleic acid, optionally operably linked to a promoter, with vaccinia virus DNA sequences flanking the heterologous nucleic acid to facilitate homologous recombination and insertion of the gene into the viral genome. Generally, the viral DNA flanking the heterologous gene is complementary to a non-essential segment of vaccinia virus DNA, such that the gene is inserted into a nonessential location. The recombination plasmid can be grown in and purified from *Escherichia coli* and introduced into suitable host cells, such as, for example, but not limited to, CV-1, BSC-40, BSC-1 and TK-143 cells. The transfected cells are then superinfected with vaccinia virus which initiates a replication cycle. The heterologous DNA can be incorporated into the vaccinia viral genome through homologous recombination, and packaged into infection progeny. The recombinant viruses can be identified by methods known in the art, such as by detection of the expression of the heterologous gene product, or by using positive or negative selection methods (U.S. Pat. No. 7,045,313).

In another example, the recombinant vaccinia virus that expresses a heterologous gene product can be generated by direct cloning (see, e.g. U.S. Pat. No. 6,265,183 and Scheiflinger et al. (1992) *Proc. Natl. Acad. Sci. USA* 89: 9977-9981). In such methods, the heterologous nucleic acid, optionally operably linked to a promoter, is flanked by restriction endonuclease cleavage sites for insertion into a unique restriction endonuclease site in the target virus. The virus DNA is purified using standard techniques and is cleaved with the sequence-specific restriction endonuclease, where the sequence is a unique site in the virus genome. Any unique site in the virus genome can be employed provided that modification at the site does not interfere with viral replication. For example, in vaccinia virus strain LIVP, the NotI restriction site is located in the ORF encoding the F14.5L gene with unknown function (Mikryukov et al., *Biotekhnologiya* 4: 442-449 (1988)). Table 6 provides a summary of unique restriction sites contained in exemplary LIVP strains and designates the nucleotide position of each. Such LIVP strains can be modified herein by direct cloning and insertion of heterologous DNA into the site or sites. Generally, insertion is in a site that is located in a non-essential region of the virus genome. For example, exemplary modifications herein include insertion of a foreign DNA sequence into the NotI digested virus DNA.

In some examples, the methods involve homologous recombination and/or use of unique restriction sites in the virus. For example, a recombinant LIVP vaccinia virus with an insertion, for example, in the F14.5L gene (e.g., in the Not I restriction site of an LIVP isolate) can be prepared by the following steps: (a) generating (i) a vaccinia shuttle/transfer plasmid containing the modification (e.g. a gene expression cassette or a modified F14.5L gene) inserted at a restriction site, X (e.g. Not I), where the restriction site in the vector is flanked by parental virus sequences of the target insertion site and (ii) an LIVP virus DNA digested at restriction site X (e.g. Not I) and optionally dephosphorylated; (b) infecting cells with PUV-inactivated helper vaccinia virus and transfecting the infected host cells with a mixture of the constructs of (i) and (ii) of step a; and (c) isolating the recombinant vaccinia viruses from the transfectants. One skilled in the art knows how to perform such methods (see, e.g., Timiryasova et al. (*Biotechniques* 31: 534-540 (2001)). Typically, the restriction site X is a unique restriction site in the virus as described above.

TABLE 6

Unique restriction endonuclease cleavage sites in LIVP clonal isolates

| Restriction Enzyme/Site | | 1.1.1 | 2.1.1 | 4.1.1 | 5.1.1 | 6.1.1 | 7.1.1 | 8.1.1 | LIVP Parental |
|---|---|---|---|---|---|---|---|---|---|
| Name/ sequence | SEQ ID NO | (SEQ ID NO: 5) | (SEQ ID NO: 6) | (SEQ ID NO: 7) | (SEQ ID NO: 8) | (SEQ ID NO: 9) | (SEQ ID NO: 10) | (SEQ ID NO: 11) | (SEQ ID NO: 2) |
| SbfI CCTGCAGG | 26 | 40033/ 40029 | 40756/ 40752 | 39977/ 39973 | 40576/ 40572 | 40177/ 40173 | 40213/ 40209 | 40493/ 40489 | 38630/ 38626 |
| NotI GCGGCCGC | 27 | 42989/ 42998 | 43712/ 43716 | 42933/ 42937 | 43532/ 43536 | 43133/ 43137 | 43169/ 43173 | 43449/ 43453 | 41586/ 41590 |
| SgrAI CRCCGGYG | 28 | 114365/ 114369 | 115107/ 115111 | 114308/ 114312 | 114924/ 114928 | 114489/ 114493 | 114548/ 114552 | 114845/ 114849 | 112975/ 112979 |
| SmaI CCCGGG | 29 | 159260 | NA | NA | NA | NA | NA | NA | NA |
| TspMI CCCGGG | 30 | 159258/ 159262 | NA | NA | NA | NA | NA | NA | NA |
| XmaI CCCGGG | 31 | 159258/ 159262 | NA | NA | NA | NA | NA | NA | NA |
| ApaI CCCGGG | 32 | 180516/ 180512 | NA | 180377/ 180373 | 181027/ 181023 | 180638/ 180634 | 180596/ 180592 | 180972/ 180968 | NA |
| PspOMI CCCGGG | 33 | 180512/ 180516 | NA | 180373/ 180377 | 181023/ 181027 | 180634/ 180638 | 180592/ 180596 | 180968/ 180972 | NA |

In some examples, the virus genomic DNA is first modified by homologous recombination to introduce one or more unique restriction sites in the virus (see, e.g. Mackett et al. (1984) *J. Virol.* 857-864). Following cleavage with the restriction endonuclease, the cleaved DNA is optionally treated with a phosphatase to remove a phosphate moiety from an end of the DNA segment that is produced by cleavage with the endonuclease. Typically, a plasmid vector is generated that contains the heterologous DNA for insertion flanked by the restriction sites. Prior to insertion into the virus, the heterologous DNA is excised from the plasmid by cleavage with the sequence specific restriction endonuclease. The heterologous DNA is then ligated to the cleaved viral DNA and is packaged in a permissive cell line by infection of the cells with a helper virus, such as, but not limited to a fowlpox virus or a puv-inactivated helper vaccinia virus, and transfection of the ligated DNA into the infected cells.

3. Methods of Producing Viruses

Viruses in the combinations, compositions and methods provided herein can be produced by methods known to one of skill in the art. Typically, the virus is propagated in host cells, quantified and prepared for storage before finally being prepared in the compositions described herein. The virus can be propagated in suitable host cells to enlarge the stock, the concentration of which is then determined. In some examples, the infectious titer is determined, such as by plaque assay. The total number of viral particles also can be determined. The viruses are stored in conditions that promote stability and integrity of the virus, such that loss of infectivity over time is minimized. In some examples, a large amount of virus is produced and stored in small aliquots of known concentration that can be used for multiple procedures over an extended period of time. Conditions that are most suitable for various viruses will differ, and are known in the art, but typically include freezing or drying, such as by lyophilization. The viruses can be stored at a concentration of $10^5$-$10^{10}$ pfu/mL, for example, $10^7$-$10^9$ pfu/mL, such as at least or about or $10^6$ pfu/mL, $10^7$ pfu/mL, $10^8$ pfu/mL or $10^9$ pfu/mL. Immediately prior to preparing compositions provided herein, the stored viruses can be reconstituted (if dried for storage) and diluted in an appropriate medium or solution.

The following sections provide exemplary methods that can be used for the production and preparation of viruses for use in preparing viruses.

a. Host Cells for Propagation

Virus strains can be propagated in an appropriate host cell. Such cells can be a group of a single type of cells or a mixture of different types of cells. Host cells can include cultured cell lines, primary cells, and proliferative cells. These host cells can include any of a variety of animal cells, such as mammalian, avian and insect cells and tissues that are susceptible to the virus, such as vaccinia virus, infection, including chicken embryo, rabbit, hamster, and monkey kidney cells. Suitable host cells include, but are not limited to, hematopoietic cells (totipotent, stem cells, leukocytes, lymphocytes, monocytes, macrophages, APC, dendritic cells, non-human cells and the like), pulmonary cells, tracheal cells, hepatic cells, epithelial cells, endothelial cells, muscle cells (e.g., skeletal muscle, cardiac muscle or smooth muscle), fibroblasts, and cell lines including, for example, chicken embryo fibroblast (CEF), CV-1, BSC40, Vero, and BSC-1, and human HeLa cells. Typically, viruses are propagated in cell lines that that can be grown at monolayers or in suspension. For example, exemplary cell lines for the propagation of vaccinia viruses include, but are not limited to, chicken embryo fibroblast (CEF), CV-1, BSC40, Vero, BGM, BSC-1 and RK-13 cells. Purification of the cultured strain from the system can be effected using standard methods.

b. Concentration Determination

The concentration of virus in a solution, or virus titer, can be determined by a variety of methods known in the art. In some methods, a determination of the number of infectious virus particles is made (typically termed plaque forming units (PFU)), while in other methods, a determination of the total number of viral particles, either infectious or not, is made. Methods that calculate the number of infectious virions include, but are not limited to, the plaque assay, in which titrations of the virus are grown on cell monolayers and the number of plaques is counted after several days to several weeks, and the endpoint dilution method, which determines the titer within a certain range, such as one log. Methods that determine the total number of viral particles, including infectious and non-infectious, include, but are not limited to, immunohistochemical staining methods that utilize antibodies that recognize a viral antigen and which can be visualized by microscopy or FACS analysis; optical absorbance, such as at 260 nm; and measurement of viral nucleic acid, such as by PCR, RT-PCR, or quantitation by labeling with a fluorescent dye.

c. Storage Methods

Once the virus has been purified (or to a desired purity) and the titer has been determined, the virus can be stored in conditions which optimally maintain its infectious integrity. Typically, viruses are stored in the dark, because light serves to inactivate the viruses over time. Viral stability in storage is usually dependent upon temperatures. Although some viruses are thermostable, most viruses are not stable for more than a day at room temperature, exhibiting reduced viability (Newman et al., (2003) *J. Inf. Dis.* 187:1319-1322).

Vaccinia virus is generally stable at refrigerated temperatures, and can be stored in solution at 4° C., frozen at, for example −20° C., −70° C. or −80° C., or lyophilized with little loss of viability (Newman et al., (2003) *J. Inf. Dis.* 187:1319-1322, Hruby et al., (1990) *Clin. Microb. Rev.* 3:153-170). Methods and conditions suitable for the storage of particular viruses are known in the art, and can be used to store the viruses used in the methods presented herein.

For short-term storage of viruses, for example, up to 1 day, 2 days, 4 days or 7 days, temperatures of approximately 4° C. are generally recommended. For long-term storage, most viruses can be kept at −20° C., −70° C. or −80° C. When frozen in a simple solution such as PBS or Tris solution (20 mM Tris pH 8.0, 200 NaCl, 2-3% glycerol or sucrose) at these temperatures, the virus can be stable for 6 months to a year, or even longer. Repeated freeze-thaw cycles are generally avoided, however, since it can cause a decrease in viral titer. The virus also can be frozen in media containing other supplements in the storage solution which can further preserve the integrity of the virus. For example, the addition of serum or bovine serum albumin (BSA) to a viral solution stored at −80° C. can help retain virus viability for longer periods of time and through several freeze-thaw cycles.

In other examples, the virus sample is dried for long-term storage at ambient temperatures. Viruses can be dried using various techniques including, but not limited to, freeze-drying, foam-drying, spray-drying and desiccation. Water is a reactant in nearly all of the destructive pathways that degrade viruses in storage. Further, water acts as a plasticizer, which allows unfolding and aggregation of proteins. Since water is a participant in almost all degradation pathways, reduction of the aqueous solution of viruses to a dry powder provides an alternative composition methodology to enhance the stability of such samples. Lyophilization, or freeze-drying, is a drying technique used for storing viruses (see, e.g., Croyle et al., (1998) *Pharm. Dev. Technol.*, 3(3), 373-383). There are three stages to freeze-drying; freezing, primary drying and secondary drying. During these stages, the material is rapidly frozen and dehydrated under high vacuum. Once lyophilized, the dried virus can be stored for long periods of time at ambient temperatures, and reconstituted with an aqueous solution when needed. Various stabilizers can be included in the solution prior to freeze-drying to enhance the preservation of the virus. For example, it is known that high molecular weight structural additives, such as serum, serum albumin or gelatin, aid in preventing viral aggregation during freezing, and provide structural and nutritional support in the lyophilized or dried state. Amino acids such as arginine and glutamate, sugars, such as trehalose, and alcohols such as mannitol, sorbitol and inositol, can enhance the preservation of viral infectivity during lyophilization and in the lyophilized state. When added to the viral solution prior to lyophilization, urea and ascorbic acid can stabilize the hydration state and maintain osmotic balance during the dehydration period. Typically, a relatively constant pH of about 7.0 is maintained throughout lyophilization.

Other methods for the storage of viruses at ambient, refrigerated or freezing temperatures are known in the art, and include, but are not limited to, those described in U.S. Pat. Nos. 5,149,653; 6,165,779; 6,255,289; 6,664,099; 6,872,357; and 7,091,030; and in U.S. Pat. Pub. Nos. 2003-0153065, 2004-0038410 and 2005-0032044.

D. Adjunct Therapy with Complement Inhibitors

Provided herein are combinations and compositions containing an oncolytic virus (e.g. vaccinia virus), such as a lipid-treated oncolytic virus, and a complement inhibitor. Complement is a system of over 30 serum and membrane-bound proteins that form a cascade of reactions that contribute to the elimination, and hence neutralization, of viruses and other microorganisms. In the combinations and compositions provided herein, a complement inhibitor, which is a biomolecule that targets one or more components of the complement system to thereby reduce activation or propagation of complement cascade, reduces the elimination of virus and thereby increases the infectivity of the oncolytic virus compared to the absence of the inhibitor. Hence, the combinations and compositions of an oncolytic virus (e.g. vaccinia virus), such as a lipid-treated oncolytic virus, and a complement inhibitor can be used in adjunct therapies to improve the therapeutic effect of an oncolytic virus, for example, for treatment of proliferative diseases and disorders, such as tumors or cancers.

The complement inhibitor can be administered prior to, simultaneously with, or intermittently with the oncolytic virus. When administered simultaneously, the complement inhibitor can be administered in the same composition with the oncolytic virus or as a combination of two separate composition. Typically, the complement inhibitor is administered prior to the oncolytic virus. For example, the complement inhibitor is administered at least or up to 2 minutes, 3 minutes, 4 minutes, 5 minutes, 10 minutes, 15 minutes, 20 minutes, 30 minutes, 40 minutes, 50 minutes, 1 hour, 1.5 hours, 2 hours, 3 hours, 4 hours, 5 hours, 6 hours, 7 hours, 8 hours, 9 hours, 10 hours, 11 hours or 12 hours prior to administration of the oncolytic virus. Typically, the mode of administration of the oncolytic virus and complement inhibitor is the same so that both agents are exposed to the same bodily fluid. Typically, administration is systemic, such as by subcutaneous or intravenous administration.

In the adjunct therapies provided herein, the presence of a complement inhibitor in a combination or composition with an oncolytic virus increases the infectivity of the virus in a complement-containing bodily fluid (e.g. serum) by at least 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold, 10-fold or more compared to the infectivity of the virus in the bodily fluid (e.g. serum) in the absence of the complement inhibitor. In some examples, an oncolytic virus in combination or composition with a complement inhibitor exhibits increased virus titer after exposure to bodily fluid for a predetermined time (e.g. virus titer AUC or total virus recovery) by at least 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold or more compared to virus titer of the same oncolytic virus in the absence of the complement inhibitor. The predetermined time can be 1 minute to 12 hours, and generally is 1 minute to 2 hours, 1 minute to 1 hour, 1 minute to 30 minutes, for example, at least 2 minutes, 5 minutes, 10 minutes, 15 minutes, 20 minutes, 30 minutes, 40 minutes, 50 minutes, 60 minutes, 70 minutes, 80 minutes, 90 minutes, 100 minutes, 110 minutes, 120 minutes or more. In other examples, an oncolytic virus in combination or composition with a complement inhibitor exhibits increased half-life in a bodily fluid (e.g. serum) by at least 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold or more compared to half-life of the same oncolytic virus in the same bodily fluid (e.g. serum) in absence of the complement inhibitor.

In examples of the adjunct therapies provided herein, the presence of a complement inhibitor in a combination or composition with an oncolytic virus increases binding of the virus to blood cells by at least 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold, 10-fold or more compared to the binding of the virus to blood cells in the absence of the complement inhibitor.

1. The Complement System and Virus Neutralization

The complement system is part of the immune system and plays a role in the elimination of invading foreign organisms and initiates inflammatory responses. There are over 30 soluble and cell-membrane proteins that are part of the complement system. The complement system constitutes an irreversible cascade of proteolytic events, resulting in the formation of multiple effector molecules that stimulate inflammation, facilitate antigen phagocytosis, and lyse some cells directly. The numbering of the complement components is based on the order of their discovery rather than the order of the sequence of reactions within the complement cascade. As a result, the sequence of reactions of the complement cascades is C1, C4, C2, C3, C5, C6, C7, C8, and C9. Several complement proteins are pro-enzyme proteases (termed zymogens) that are themselves activated by proteolytic cleavage to become effector proteases that cut peptide bonds in other complement proteins to activate them in turn. Following activation, the products of the cleavage reactions are designated by adding lower case letters, the larger fragment generally being designated "b" and the smaller fragment as "a" (e.g. C4 is cleaved to generate C4b and C4a).

There are three distinct pathways through which complement can be activated on the pathogen surface: the classical pathway, the alternative pathway, and the lectin pathway. These pathways are distinct in that the components required for their initiation are different, but the pathways are similar in that they converge to generate the same set of effector molecules. The convergence point of the pathways is the cleavage of C3 by C3 convertase (a C3 activating enzyme). Different enzyme complexes have C3 convertase activity. For example, in the classical pathway C4b2b acts as a C3 convertase, whereas in the alternative pathway, C3bBb is a C3 convertase. Cleavage of C3 generates C3b, which acts as an opsonin and as the main effector molecule of the complement system for subsequent complement reactions, and C3a, which is a peptide mediator of inflammation. The addition of C3b to each C3 convertase forms a C5 convertase that cleaves C5 to generate C5a and C5b. C5a, like C3a, is a peptide mediator of inflammation. C5b mediates the "late" events of complement activation initiating the sequence of reactions culminating in the generation of the membrane attack complex (MAC). Although the three pathways produce different C3 and C5 convertases, all of the pathways produce the split products of C3 and C5 and form MAC.

a. Complement Pathways

Virus infection can activate all three complement pathways. The classical pathway is activated by binding of C1q to antibody-antigen complexes formed on the surface of the virus or by C1q directly binding to cell surface components on viruses or other pathogens in the absence of specific antibodies. The lectin pathway is activated upon the interaction of mannan-binding lectin (MBL) with viral surface carbohydrates. The alternative pathway is activated by binding of C3b to the pathogen surface.

i. Classical Pathway

C1q is the first component of the classical pathway of complement. C1q is a calcium-dependent binding protein associated with the collectin family of proteins due to an overall shared structural homology (Malhotra R et al., *Clin Exp Immunol.* 1994, 97(2):4-9; Holmskov et al. *Immunol*

*Today.* 1994, 15(2):67-74). C1q initiates the classical pathway of complement in two different ways. First, the classical pathway is activated by the interaction of C1q with immune complexes (i.e. antigen-antibody complexes of aggregated IgG or IgM antibody). IgA, IgE and IgD do not bind C1q and cannot activate complement. Second, C1q also is able to activate complement in the absence of antibody by the interaction of C1q with non-immune molecules such as polyanions (bacterial lipopolysaccharides, DNA, and RNA), certain small polysaccharides, viral membranes, C reactive protein (CRP), serum amyloid P component (SAP), and bacterial, fungal and virus membrane components.

C1q is part of the C1 complex which contains a single C1q molecule bound to two molecules each of the zymogens C1r and C1s. Binding of more than one of the C1q globular domains to a target surface (such as aggregated antibody or a pathogen), causes a conformational change in the (C1r: C1s)$_2$ complex, which results in the activation of the C1r protease to cleave C1s to generate an active serine protease. Active C1s cleaves subsequent complement components C4 and C2 to generate C4b and C2b, which together form the C3 convertase of the classical pathway. The C3 convertase cleaves C3 into C3b, which covalently attaches to the pathogen surface and acts as an opsonin, and C3a, which stimulates inflammation. Some C3b molecules associate with C4b2b complexes yielding C4b2b3b which is the classical cascade C5 convertase.

ii. Alternative Pathway

The alternative pathway is initiated by foreign pathogens in the absence of antibody. Instead, the initiation of complement by the alternative pathway occurs through the spontaneous hydrolysis of C3 into C3b. A small amount of C3b is always present in body fluids, due to serum and tissue protease activity. C3b is an opsonin that recognizes and binds to pathogen surfaces. C3b on pathogen surfaces is recognized by the protease zymogen Factor B. Factor B, which is the only activating protease of the complement system that circulates as an active enzyme rather than as a zymogen, is cleaved by Factor D. Cleavage of Factor B by Factor D yields the active product Bb which can associate with C3b to form C3bBb, the C3 convertase of the alternative pathway. Similar to the classical pathway, the C3 convertase produces more C3b and C3a from C3. C3b covalently attaches to the pathogen surface and acts as an opsonin, while C3a stimulates inflammation. Some C3b joins the complex to form C3bBb3b, the alternative pathway C5 convertase. C3bBb3b is stabilized by the plasma protein properdin or Factor P which binds to microbial surfaces and stabilizes the convertase.

iii. Lectin Pathway

The lectin pathway (also referred to as the MBL pathway) is initiated following recognition and binding of carbohydrate moieties (e.g. N-acetyl glucosamine and mannose structures) on the surface of pathogens by lectin proteins, such as mannose binding lectin (MBL) and ficolins (i.e. L-ficolin, M-ficolin, and H-ficolin). The lectin molecule interacts with two protease zymogens, MASP-1 and MASP-2. When the lectin protein (e.g. MBL) binds to the pathogen surface, MASP-1 and MASP-2 become activated to form an MBL complex with the lectin protein, resulting in cleavage of C4 and C2 and the generation of the MBL cascade C3 convertase (C4bC2b). When C3 is cleaved by the convertase, C3b then joins the complex to form the MBL cascade C5 convertase.

b. Complement Effector Mechanisms

Regardless of which initiation pathway is used, the end result is the formation of activated fragments of complement proteins (e.g. C3a, C4a, and C5a anaphylatoxins and C5b-9 membrane attack complexes) that ultimately result in the neutralization and elimination of virus. In particular, these fragments mediate several functions including leukocyte chemotaxis, activation of macrophages, vascular permeability and cellular lysis (Frank, M. and Fries, L. Complement. In Paul, W. (ed.) Fundamental Immunology, Raven Press, 1989).

i. Opsonization

An important action of complement is to facilitate the uptake and destruction of pathogens by phagocytic cells. This occurs by a process termed opsonization, whereby complement components bound to target pathogen (e.g. virus), interact with complement receptors on the surface of phagocytic cells such as neutrophils or macrophages. In this instance, the complement effector molecules are termed opsonins. Opsonization of pathogens is a major function of C3b and C4b. iC3b also functions as an opsonin. C3a and C5a increase the expression of C3b receptors on phagocytes and increase their metabolic activity.

ii. Virolysis by the Membrane Attack Complex (MAC)

The final step of the complement cascade by all three pathways is the formation of the membrane attack complex (MAC) bound to the surface of the pathogen. At the point of convergence of the pathways, each pathway generates a C3 convertase on the surface of pathogens. For example, in the classical and lectin pathways, the C3 convertase is formed when C4b and C2b combine on the surface of the pathogens. The C3 convertase cleaves C3 to generate C5 convertase fixed on a pathogen surface.

Once fixed on the pathogen surface, the C5 convertase cleaves serum C5 into C5a and C5b. The C5a acts as a proinflammatory anaphylatoxin, while C5b remains bound to the C5 convertase on the surface. The complex is stabilized by binding of C6. The MAC is complete after further binding of C7, C8 and C9. C7 exposes hydrophobic regions that facilitate penetration into the pathogen membrane, C8 stabilizes the complex in the membrane to initiate pore formation, and the addition of at least four molecules of C9 effects the formation of a tunnel that permits water and solutes to pass, resulting in osmotic lysis and cell death. The formation of the MAC can be disrupted by proteins that bind to the complex before membrane insertion such as Streptococcal inhibitor of complement (SIC), clusterin and anti-C5 antibody (e.g. eculizumab).

iii. Proinflammatory Mediator Anaphylatoxin

Complement activation also can result in other effector functions. For example, complement activation results in the formation of several proinflammatory mediators such as C3a, C4a, and C5a, and stable desArg derivatives thereof. C3a, C4a and C5a, and to a lesser extent their desArg derivatives, are potent bioactive polypeptides or anaphylatoxins that bind to receptors on various cell types to stimulate smooth muscle contraction, increase vascular permeability, and activate mast cells to release inflammatory mediators. C5a also acts as a chemotactic factor for leukocytes and neutrophils, thereby inducing the movement of the cells to the site of infection. For example, phagocytes can move towards increasing concentrations of C5a and subsequently attach, via their CR1 receptors, to C3b molecules attached to the pathogen surface, resulting phagocytosis and elimination of the pathogen by the cell. Finally, complement also can induce humoral immunity against viruses by increasing viral antigen presentation, which is enhanced when antigen-presenting cells, such as dendritic cells, recognize opsonized virus (e.g. C3b-bound virus) via specific complement receptors (e.g. CR1 or CR3).

2. Exemplary Complement Inhibitors

The complement inhibitor used in the combinations, compositions, methods and uses herein can be any biomolecule that inhibits one or more components of at least one of the complement pathways to prevent or reduce activity of the component, and thereby reduce complement activation and/or propagation of the complement cascade. In particular, reducing or inhibiting a complement component can result in a reduction or decrease in one or more of a complement-mediated effector function from among opsonization, anaphylatoxin activity or cell membrane attack complex lysing.

The inhibitor can inhibit activation of at least one native complement component, at least one activated complement component, or at least one complement receptor. For example, the complement inhibitor inhibits activity of one or more of a native or non-activated complement component from among C1, C2, C3, C4, C5, C6, C7, C8, C9, Factor B, Factor D or properdin. In other examples, the complement inhibitor inhibits activity of one or more of an activated complement component from among C1r, C1s, C2a, C3a, C3b, C4a, C4b, C5a, C5b, Bb, C3 convertase, C5 convertase or MAC. In further examples, the complement inhibitor inhibits activity of a complement receptor from among complement receptor 1 (CR1), CR2, CR3 or CR4. In particular, the inhibitor can be one or more of a C1 inhibitor, a C3 inhibitor, a C5 inhibitor, a C5a inhibitor, a C5aR inhibitor, a C3aR inhibitor, a factor P inhibitor, a factor B inhibitor.

Complement inhibitors include peptides, polypeptides, antibodies, small molecules, and nucleic acids (e.g., aptamers, RNAi agents such as short interfering RNAs). The peptide or protein can be natural or purified, or can be synthetic. In particular examples herein, the inhibitor is an antibody or fragment thereof that binds to or inhibits activity of a complement component. For example, the inhibitor is an anti-C2, anti-C3, anti-C4, anti-C5, anti-Factor B or anti-C1q antibody or fragment thereof that specifically binds to C2, C3, C4, C5, Factor B or C1q, respectively. Complement inhibitors are well known to a skilled artisan (see e.g. International Publication No. WO2012/174055; U.S. Pat. Nos. 5,624,837; 5,627,264; 5,847,082; 6,355,245; 6,956,107; 6,998,468; Morgan and Harris (2003) Mol. Immunol, 40:159-70; Ricklin and Lambris (2007) *Nat. Biotechnol.,* 25:1265-1275; Qu et al. (2009) Molecular Immunology, 47:185-195). Exemplary inhibitors are set forth in Table 7.

For example, the complement inhibitor is one that inhibits Factor B. For example, cobra venom factor (CVF) binds to Factor B and thereby consumes available C3 without activation of C3. A Factor B inhibitor also includes, for example, an anti-factor B antibody designated TA 106 (Taligen Therapeutics).

The complement inhibitor can inhibit C1. For example, the complement inhibitor is a polyanionic glycosaminoglycan, such as heparin, which binds and inactivates C1, thereby blocking C3 convertase formation and MAC formation (e.g. Baker, P. J. et al. (1975) J. Immunol, 114:554-558).

The complement inhibitor can inhibit activation of C2 or C4. Such inhibitors include inhibitors that indirectly inhibit activation of C2 or C4. For example, C1-inhibitor (C1-INH) is a protease inhibitor that irreversibly binds to and inactivates C1r and C1s in the C1 complex in the classical pathway or MASP-1 and MASP-2 proteases in the MBL complex of the lectin pathway. Hence, C1-INH prevents the proteolytic cleavage of later complement components C4 and C2 by C1 and MBL. Indirect inhibitors of C2 and C4 also include, for example, antibodies against C1s (Carroll S and Georgiou G (2013) Immunobiology, 218:1041-8). Inhibitors also can include anti-C2/C2a antibodies (see e.g. U.S. Pat. No. 6,998,468).

The complement inhibitor can inhibit C3. For example, the inhibitor is a compstatin, which is a peptide inhibitor that binds to C3 and prevents cleavage thereof (Sahu et al. (1996) J. Immunol., 157:884-891). Compstatin is a small molecular weight disulfide bonded cyclic peptide having the sequence Ile-Cys-Val-Val-Gln-Asp-Trp-Gly-His-His-Arg-Cys-Thr (SEQ ID NO:34). Other C3 inhibitors include a compstatin analog, a compstatin peptidomimetic or a compstatin derivative. Examples of compstatin analogs, derivatives and peptidomimetics are described in the art (see e.g. U.S. Pat. No. 6,319,897, WO/1999/013899 and WO/2004/026328). The structure and function of compstatin and variants thereof are summarized in Ricklin and Lambris (2008) Adv. Exp. Med. Biol., 632:273-292). Since C3 is a central component of all three pathways of complement activation, compstatin and analogs, peptidomimetics or derivatives thereof are able to inhibit activation of the converging protein of all three pathways.

C3 and C5 convertases also can be inhibited by inhibiting C3b or C4b. For example, the complement inhibitor can be a soluble CR1, which is a soluble form of the complement receptor that acts as the C3b/C4b receptor. Thus, soluble CR1 can act as an antagonist of C3b or C4b, and thereby prevent the formation of the convertases (see e.g. published International PCT Pub. No. WO1994/026786).

The complement inhibitor can inhibit C5. For example, the complement inhibitor is a small molecule, such as K76COOH, which is from *Stachybotrys complementi* (e.g. Hong et al. (1981) J. Immunol, 127:104-108). The complement inhibitor also can be an anti-C5 antibody (see subsection below). For example, eculizumab (Alexion Pharmaceuticals, Cheshire, Conn.) is an anti-C5 antibody that binds to C5 and prevents its cleavage into C5a and C5b, and Pexelizumab is an scFv fragment of eculizumab that exhibits similar activity (U.S. Pat. No. 6,355,245). The anti-C5 antibody designated TSA12/22 also is an scFv against C5, and is the framework for the anti-C5 antibody minibody (Mubodina®, Adienee; U.S. Pat. No. 7,999,081). ARC 1905 (Archemix), an anti-C5 aptamer, binds to and inhibits cleavage of C5, inhibiting the generation of C5b and C5a. The C5 inhibitory protein *Ornithodoros moubata* Complement Inhibitor (OmCI, Nunn, M. A. et al J Immunol 2005, 174:2084-2091) from soft tic *Ornithodoros moubata* has been hypothesized to bind to the distal end of the CUB-C5d-MG8 superdomain, which is close to the convertase cleavage site (Fredslund et al. Nat Immunol 2008, 9 (7): 753-760).

The complement inhibitor can inhibit C5a or C5aR. C5a can be inhibited directly using an inhibitor that binds to C5a. For example, TNX-558 (Tanox) is an antibody that neutralizes C5a by binding to C5a. Anti-C5a spiegelmers, which are nucleotide L-RNA oligonucleotides that acts like an aptamer to specifically bind and inhibit C5a and C5a-desArg also are known (e.g. NOX-D19; U.S. Pat. No. 8,507,456 and International PCT Pub. No. WO2013104540). C5a also can be inhibited indirectly by preventing or significantly reducing the binding of C5a to its receptor, C5aR. A number of C5aR inhibitors are known in the art. For example, PMX-53 (Peptech) is a small cyclic hexapeptide that is a C5aR antagonist. Analogs of PMX-53 (e.g. PMX-201 and PMX-205) that also function as C5aR antagonists are also available (see for instance Proctor et al., 2006, Adv Exp Med Biol. 586:329-45 and U.S. Pat. Pub. No. 20060217530). Neutrazumab (G2 Therapies) binds to extracellular loops of C5aR, thereby inhibiting binding of C5a to C5aR. C5a also can be inhibited by reducing or preventing the formation of C5a, using inhibitors that target C5 to prevent cleavage of C5 into C5a and C5b (see above for C5 inhibitors).

Exemplary complement inhibitors, including those that have been approved for clinical use or are currently in clinical trials, are set forth in Table 7. Any of the above complement inhibitors, including any set forth in Table 7, can be used in a combination or composition with an oncolytic vaccinia virus for use to increase the infectivity of the oncolytic virus compared to the absence of the inhibitor. For example, provided herein are combinations or compositions containing an oncolytic virus or lipid-emulsion oncolytic virus and complement inhibitor, such as any complement inhibitor that inhibits C1, C2, C3, C4, C5, C5a, C5aR, C3aR, Factor B, Factor P, C1q or MBP. For example, the inhibitor can be cobra venom factor (CVF), heparin, TA 106, TNX-234, anti-properdin, C1-INH, a compstatin or derivative or analog thereof, soluble CR1, K76COOH, eculizumab, pexelizumab, TSA12/22, MSA12/22, ARC 1005, TNX-558, NOX-D19, PMX-53, PMX-201, PMX-205, neutrazumab, or variants, analogs or derivatives thereof. In particular examples, the complement inhibitor is an anti-C5 antibody eculizumab, pexelizumab, TSA12/22 or MB12/122, or a variant thereof, such as eculizumab.

TABLE 7

Exemplary Complement Inhibitors

| Target | Inhibitor | Reference | Example of Commercial Therapeutic |
|---|---|---|---|
| C1r/C1s | C1-INH | 5,030,578 | Berinert ® (CSL Behring); Cinryze ® (ViroPharma); Cetor-n ® (Sanquin); Rhucin ® (Pharming) |
| C3b/C4b | soluble complement receptor type 1 (sCR1) | WO 1994/026786; WO 1998/002454; 5,856,300; 5,856,297 | TP10 (Celldex Therapeutics, Inc.; also called CDX-1135); TP20 (Celldex Therapeutics, also called sCR1sLEx); Mirococept (Inflazyme Pharmaceuticals, also called APT070) |
| Factor B | anti-Factor B antibody | 7,964,705; 7,999,082 | TA106 (Taligen Therapeutics) |
| Factor D | anti-Factor D antibody | 6,956,107; 7,112,327 | TNX-234 (Tanox) |
| properdin (Factor P) | anti-properdin antibody | 8,435,512 | anti-properdin (Novelmed Therapeutics) |
| C3 | Compstatin and analogs | 6,319,897; WO/1999/013899 and WO/2004/026328 | APL-1 (Apellis Pharmaceuticals; also called POT-4) |
| C5 | anti-C5 antibody | 6,355,245 7,999,081 | eculizumab (Soliris ®, Alexion Pharmaceuticals, also designated 5G1.1); pexelizumab (Alexion Pharmaceuticals); TS-A12/22 (Adienne) |

TABLE 7-continued

Exemplary Complement Inhibitors

| Target | Inhibitor | Reference | Example of Commercial Therapeutic |
|---|---|---|---|
| | anti-C5 minibody | 7,999,081; Marzari et al. (2002) Eur. J. Immunol., 32: 2773-82 | Mubodina ® (Adienne; also called MB 12/22) |
| | Aptamer-based C5 inhibitor | 7,538,211 | ARC 1905 (Archemix) |
| | C5 binding polypeptide | International PCT. Pub. No. WO2013126006 | |
| C5a | anti-C5a antibody | US2003/0129187 | TNX-558 (Tanox) |
| | Anti-C5a spiegelmers | 8,507,466 | NOX-D19 (Noxxon PharmaAg) |
| C5aR | C5aR peptidomimetic | Finch et al. (1999) J. Med. Chem., 42: 1965-1974; Kohl (2006) Curr. Opin. Mol. Ther., 8: 529-38 | PMX-53 (Peptech) |
| | anti-C5aR antibody | 8,071,096 | Neutrazumab (G2 Therapies) |

Anti-C5 Antibody

In particular, provided herein are combinations and compositions containing an oncolytic virus or a lipid-emulsion oncolytic virus and an anti-C5 antibody or antigen-binding fragment thereof. An anti-C5 antibody or antigen-binding fragment thereof binds to complement component C5 or active fragments thereof, and thereby blocks the generation and/or activity of complement components C5a and/or C5b. Through this blocking effect, the antibodies inhibit the proinflammatory (anaphylatoxic) effects of C5a and/or the generation of the C5b-9 membrane attack complex (MAC).

Anti-C5 antibodies include antibodies that specifically bind to C5 with an association constant ($K_a$) that is higher than $10^6$ M$^{-1}$, such as greater than $10^7$ M$^{-1}$, $10^8$ M$^{-1}$, $10^9$ M$^{-1}$, $10^{10}$ M$^{-1}$ or greater. In some embodiments, an anti-C5 antibody has a dissociation constant ($K_d$) of less than $10^{-6}$, $10^{-7}$, $10^{-8}$, $10^{-9}$, $10^{-10}$, $10^{-11}$, or $10^{-12}$M.

Anti-C5 antibodies include antibodies that specifically bind to the beta chain or alpha chain of C5. C5 is synthesized as a single chain precursor protein of 1659 amino acids along with an 18 amino acid leader sequence (SEQ ID NO:35). After removal of the 18 amino acid signal peptide, the pro-C5 precursor is cleaved to remove the four amino acid residue propeptide corresponding to amino acid residues 674 to 677 of SEQ ID NO:35 to yield a mature two-chain protein containing a beta chain (corresponding to amino residues 19-673 of SEQ ID NO:35) and an alpha chain (amino acid residues 678-1676 of SEQ ID NO:35) that are disulfide linked. The C5 convertase activates C5 by cleaving the alpha chain, thereby releasing C5a and generating C5b, which is the remaining portion of the alpha chain linked to the beta chain by the disulfide bond (beta chain+ alpha' chain).

For example, antibodies that are immunoreactive against the C5 beta chain include N19-8 and N20-9 antibody and related antibodies (Moongkarndi et al. Immunobiol. 1982, 162:397; Moongkarndi et al. (1983) Immunobiol. 165:323; Mollnes et al. (1988) Scand. J. Immunol. 28:307-312).

Antibodies that are immunoreactive against the C5 alpha chain are described in U.S. Pat. No. 6,355,245 or U.S. Pat. No. 7,999,081. In particular examples, an antibody that inhibits C5 through binding to the alpha chain are able to both block complement hemolytic activity and the generation of C5a.

Antibodies that are immunoreactive against the C5 alpha chain also are described in U.S. Pat. No. 6,355,245. In particular, among anti-C5 antibodies or antigen-binding fragments in the combinations and compositions provided herein for use in adjunct therapy with an oncolytic virus include antibodies that bind at a C5 epitope designated KSSKC epitope (Val Ile Asp His Gln Gly Thr Lys Ser Ser Lys Cys Val Arg Gln Lys Val Glu Gly Ser Ser; SEQ ID NO:48). For example, the anti-C5 antibody or antigen-binding fragment thereof contains a heavy chain variable region and a light chain variable region, wherein the heavy chain variable region contains CDRs set forth in SEQ ID NO:36-38 and the light chain variable region contains CDRs set forth in SEQ ID NO:39-41. Such antibodies include, but are not limited to, eculizumab or pexelizumab, or variants or derivatives thereof.

The antibody can be a human or humanized antibody. In particular examples, the anti-C5 antibody or antigen-binding fragment thereof is a humanized antibody containing the mouse CDRs set forth in SEQ ID NOS: 36-41 and having a sequence of amino acids containing a heavy chain variable region set forth in SEQ ID NO:42 and a light chain variable region set forth in SEQ ID NO:43.

The anti-C5 antibody herein can be a full-length IgG1, IgG2, IgG3 and/or IgG4 antibody. For example, the anti-C5 antibody can be the anti-C5 antibody designated eculizumab, which is marketed under the name Soliris®. Eculizumab is a humanized IgG2/4 kappa antibody, made up of two 448 amino acid heavy chains and two 214 amino acid light chains. The heavy chains are composed of human IgG2 sequences in constant region 1, the hinge and the adjacent portion of constant region 2, and human IgG4 sequences in the remaining part of constant region 2 and 3. The light chain is composed of human kappa sequences. The sequence of amino acids of the heavy chain of eculizumab is set forth in SEQ ID NO:44 and the sequence of amino acids of the light chain is set forth in SEQ ID NO:45.

The anti-C5 antibody also can be an antigen-binding fragments of a full-length anti-C5 antibody, such as a full-length eculizumab. Antibody fragments, which are derivatives of full-length antibodies that contain less than the full sequence of the full-length antibodies but retain at least a portion of the specific binding abilities of the full-length antibody, for example the variable portions of the heavy and light chain. The antibody fragments also can include antigen-binding portions of an antibody that can be inserted into an antibody framework (e.g., chimeric antibodies) in order to retain the binding affinity of the parent antibody. Examples of antibody fragments include, but are not limited to, Fab, Fab', F(ab')$_2$, single-chain Fv (scFv), Fv, dsFv, diabody, Fd and Fd' fragments, and other fragments, including modified fragments (see, for example, Methods in Molecular Biology, Vol. 207: Recombinant Antibodies for Cancer Therapy Methods and Protocols (2003); Chapter 1; p 3-25, Kipriyanov). Antibody fragments can include multiple chains linked together, such as by disulfide bridges and can be produced recombinantly Antibody fragments also can contain synthetic linkers, such as peptide linkers, to link two or more domains. Methods for generating antigen-binding fragments are well-known known in the art and can be used to modify any antibody provided herein. Fragments of antibody molecules can be generated, such as for example, by enzymatic cleavage. For example, upon protease cleavage by papain, a dimer of the heavy chain constant regions, the Fc domain, is cleaved from the two Fab regions (i.e. the portions containing the variable regions).

Single chain antibodies can be recombinantly engineered by joining a heavy chain variable region ($V_H$) and light chain variable region ($V_L$) of a specific antibody. The particular nucleic acid sequences for the variable regions can be cloned by standard molecular biology methods, such as, for example, by polymerase chain reaction (PCR) and other recombination nucleic acid technologies. Methods for producing scFvs are described, for example, by Whitlow and Filpula (1991) *Methods,* 2: 97-105; Bird et al. (1988) *Science* 242:423-426; Pack et al. (1993) Bio/Technology 11:1271-77; and U.S. Pat. Nos. 4,946,778, 5,840,300, 5,667, 988, 5,658,727, 5,258,498).

For example, the anti-C5 antibody is pexelizumab or a variant thereof. Pexelizumab is a 25 kDa recombinant, humanized single-chain (scFv) antibody that binds to human C5 (Fitch et al. (1999) *Circulation,* 100:2499-506; U.S. Pat. No. 6,355,245). Pexelizumab has the sequence of amino acids set forth in SEQ ID NO:46, and contains: an antibody light chain variable region (amino acids 1-107 of SEQ ID NO:46); two amino acids of an immunoglobulin light chain constant region (amino acids 108 and 109); a flexible peptide linker (amino acids 110-124 of SEQ ID NO:46); and an antibody heavy chain variable region (amino acids 125-247 of SEQ ID NO:46). A variant of pexelizumab is also known, set forth in SEQ ID NO:47, that differs from the amino acid sequence of pexelizumab by two amino acids, and that exhibits a change in its isoelectric point (pI) and an increase in solubility (see US2013/0273052). For example, the variant single chain antibody does not contain an amino terminal alanine that is present in pexelizumab. The variant antibody also contains a substitution of the arginine (R) at position 38 of pexelizumab for glutamine (Q).

Other C5 binding molecules are known in the art, and include single-chain variable fragments (scFV), minibodies and aptamers targeting C5. These C5 inhibitors can bind to different sites (epitopes) on the C5 molecule and may have different modes of action. For example, whereas Eculizumab interacts with C5 at some distance of the convertase cleavage site, the minibody MB12/22 (Mubodina®) interacts with the cleavage site of C5. In contrast to the proteins that inhibit cleavage of C5, the monoclonal antibody TNX-558 binds to a C5a epitope present both on intact C5 and released C5a without inhibiting the cleavage of C5. (Fung et al. (2003) Clin Exp Immunol 133 (2): 160-169).

For example, among other antibodies that are immunoreactive against C5 alpha chain include antibodies described in U.S. Pat. No. 7,999,081. In particular, among anti-C5 antibodies or antigen-binding fragments in the combinations and compositions provided herein for use in adjunct therapy with an oncolytic virus include antibodies that bind at a C5 epitope KDMQLGRLHM KTLLPVSK (SEQ ID NO:49), which corresponds to the epitope on the alpha chain of the C5 component that contains the cleavage region of C5 convertase. Such antibodies include, but are not limited to, TS-A12/22 or MB12/22. The antibodies can include a variable light chain set forth in SEQ ID NO:50 and a variable heavy chain set forth in SEQ ID NO:51. The antibody can be a full-length antibody or a fragment thereof, such as any described above. For example, the antibody is a scFv containing the heavy chain and light chain covalently linked by a linker (e.g. TSA12-22 set forth in SEQ ID NO:52). MB12/22 is the TSAl2-22 antibody that is dimerized by means of rat CH2 CH3 domains.

E. Adjunct Therapy with Lipids and Lipid Emulsions

Provided herein are compositions and combinations that contain an oncolytic virus, such as a vaccinia virus, and a lipid component. Generally, the lipid is a biocompatible lipid. The lipid is typically a hydrophobic lipid, such as a fatty acid or fatty acid derivative. The lipid can be a natural or synthetic lipid. In particular, the lipid component contains a triglyceride, diglyceride, monoglyceride, phospholipid or mixtures thereof. Typically, the lipid component contains triglycerides (or triacylglycerols or triacylglycerides), which are glycerides in which the glycerol backbone is esterified with three fatty acids. Fatty acids are long-chain monocarboxylic acids that can either be saturated (i.e., without double bonds) or mono- or poly-unsaturated. Saturated fatty acids have the general structure of $CH_3(CH_2)_nCOOH$, where n (i.e., the length of the carbon chain) generally ranges from 12 to 24 carbons, with an even number of carbons. The presence of double bonds in the carbon chain, i.e., an unsaturated fatty acid, functions to reduce the melting point of the fatty acid, and thus the triglyceride.

Triglycerides can be characterized by their fatty acid content, based upon the chain length of the fatty acids. Triglycerides are generally classified as short-chain triglycerides (less than 6 carbon atoms), medium-chain triglycerides (6-10 carbon atoms), or long-chain triglycerides (greater than 14 carbon atoms). For example, the lipid component contains a fatty acid that is a long-chain triglyceride, including but not limited to, linoleate, oleate, palmitate, linolenate, or stearate. In other examples, the lipid component contains a fatty acid that is a medium-chain triglyceride (MCT), such as caprylic acid or capric acid. Long-chain triglycerides can also include omega-3 and omega-6 fatty acids, whereas medium-chain triglycerides have saturated fatty acids and thus do not contain omega-3 or omega-6 fatty acids.

Generally, a lipid component that is biocompatible is employed. For example, the lipid component is from a plant oil, vegetable oil, animal oil, fish oil, mineral oil, other chemically synthesized oil that is biocompatible, or mixtures thereof. Exemplary lipid components are described further below or are known in the art. For example, the lipid component is from soybean oil, cottonseed oil, safflower oil, corn oil, coconut oil, sesame oil, peanut oil, olive oil, castor oil or mixtures thereof.

Typically, the lipid component is provided as a lipid emulsion. Lipid emulsions are a heterogeneous system where the lipid phase (or oil phase) is dispersed as droplets in an aqueous phase (e.g., water) and is stabilized by an emulsifying agent. Hence, lipid emulsions generally contain a lipid, an emulsifier, and an aqueous phase. Emulsifiers, such as a phospholipid, stabilize emulsions by reducing the interfacial tension of the system and by providing enough surface charge for droplet-droplet repulsion. Lipid emulsions also can optionally contain other components.

Lipid (i.e., fat) emulsions include those that are injectables commonly formulated for intravenous use as a component of parenteral nutrition therapy, also called injectable or intravenous lipid emulsions (ILE). ILEs generally include a tonicity modifier (e.g., glycerol, also called glycerine or glycerin), for example, to adjust the emulsion so that it is isotonic with blood. The lipid emulsions provide the main source of fuel calories and essential fatty acids to patients who require parenteral nutrition. Soybean oil, a LCT, is frequently used in lipid emulsions for intravenous therapeutic uses as an important source of the essential free fatty acids linolenate and linoleate (Driscoll (2006) Nutr. Clin. Pract. 21:381-386). More recently, ILEs have been used as a vehicle for delivery of highly lipid-soluble drugs such as propofol, paclitaxel, etomidate, and diazepam. ILEs have also been used to treat local anesthetic system toxicity and show promise as an effective antidote for other lipophilic drug poisonings (Rothschild et al. (2010) Scan. J. Trauma Resus. Emerg. Med. 18:51).

Exemplary of ILEs are emulsions of soybean, sesame or safflower oil (e.g., 10-30%) emulsified with egg lecithin containing 60-70% phosphatidylcholine and containing glycerol (i.e., glycerin). For example, Intralipid® lipid emulsion (10%, 20%, 30% fat emulsion) contains 10%-30% soybean oil, respectively, and also contains 1.2% egg yolk phospholipids, 2.25% glycerin and water for injection, and adjusted to a pH of 6 to 8.9 using sodium hydroxide. For example, among the fatty acids in the soybean oil fat emulsion are linoleic (44-62%), oleic (19-30%), palmitic (7-14%), linolenic (4-11%) and stearic (1.4-5.5%). Other lipid emulsions are known in the art, and also are described below.

The lipid emulsion generally is formulated with the oncolytic virus resulting in a lipid-treated oncolytic virus, including lipid-treated oncolytic virus compositions that are emulsions. In other cases, the oncolytic virus can be provided in combination with a lipid emulsion for co-administration of the lipid emulsion prior to, simultaneously with, intermittently with or subsequently to from the oncolytic virus. Generally, when the lipid emulsion is provided in combination with an oncolytic virus, and separately formulated from an oncolytic virus, the concentration of lipid emulsion required to increase virus infectivity is about or at least 3-fold, 4-fold, 5-fold, 6-fold, 7-fold, 8-fold, 9-fold, 10-fold, 50-fold, 100-fold or higher than when the lipid is present with the pretreated virus.

The lipid emulsions provided herein can be used in combinations and compositions with an oncolytic virus, such as a vaccinia virus. The lipid emulsion can be used, for example, in adjunct therapy with an oncolytic virus, e.g., a vaccinia virus, alone, or can be used in conjunction with a complement inhibitor, such as an anti-C5 antibody, e.g., eculizumab.

The combinations and compositions provided herein, i.e., combinations and compositions containing a therapeutic virus, e.g., a vaccinia virus, a lipid emulsion, and, optionally, an anti-C5 antibody, e.g., eculizumab, maintain the infectivity and bioactivity of the therapeutic virus after exposure to blood, for example, after administration into the body. For example, administration of the compositions and combinations provided herein, i.e., compositions and combinations containing a therapeutic virus, such as a vaccinia virus, a lipid emulsion, such as a lipid emulsion that contains long-chain triglycerides, medium-chain triglycerides, oils of marine origin, i.e., fish oils, synthetic lipids, or mixtures thereof, and, optionally, an anti-C5 antibody, can result in a reduction or elimination of complement-mediated inactivation of the therapeutic virus.

Combinations and compositions of an oncolytic virus and a lipid emulsion exhibit increased virus infectivity compared to an oncolytic virus in the absence of a lipid component or lipid emulsion, for example, upon administration or exposure to a bodily fluid (e.g., serum). For example, combinations and compositions containing an oncolytic virus and lipid component, such as a lipid emulsion, exhibits at least 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold, 10-fold or more increased infectivity compared to the infectivity of the virus that is not formulated with lipids as an emulsion. In some examples, a lipid-emulsion oncolytic virus exhibits increased virus titer after exposure of the virus to bodily fluid for a predetermined time (e.g., virus titer AUC or total virus recovery) by at least 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold or more compared to the virus titer of the same oncolytic virus that is not formulated with lipids as an emulsion. The predetermined time can be 1 minute to 12 hours, and generally is 1 minute to 2 hours, 1 minute to 1 hour, 1 minute to 30 minutes, for example, at least 2 minutes, 5 minutes, 10 minutes, 15 minutes, 20 minutes, 30 minutes, 40 minutes, 50 minutes, 60 minutes, 70 minutes, 80 minutes, 90 minutes, 100 minutes, 110 minutes, 120 minutes or more. In other examples, a lipid-emulsion oncolytic virus exhibits increased half-life in a bodily fluid (e.g., serum) by at least 1.2-fold, 1.3-fold, 1.4-fold, 1.5-fold, 1.6-fold, 1.7-fold, 1.8-fold, 1.9-fold, 2.0-fold, 2.5-fold, 3-fold, 4-fold, 5-fold or more compared to the half-life of the same oncolytic virus in the same bodily fluid (e.g., serum) that is not formulated with lipids as an emulsion.

The combinations and compositions (e.g. lipid-treated virus) provided herein containing an oncolytic virus and a lipid component, such as a lipid emulsion, also can be employed in an adjunct therapy or combination therapy with another agent. The other agent can be a therapeutic agent for treating a hyperproliferative disease or disorder or can be an agent that increases the infectivity of the virus. Exemplary of such other agents for use in adjunct therapy or combination therapy are described herein. In particular examples, a lipid-treated virus is co-administered in an adjunct therapy with a complement inhibitor (e.g., anti-C5 antibody, such as eculizumab) that itself also increases virus infectivity.

1. Components of Lipid Emulsions

Lipid emulsions are heterogeneous systems in which the lipid phase (e.g., fat) is dispersed as droplets in an aqueous phase and stabilized by an emulsifying agent. Hence, prepared lipid emulsions typically contain a lipid component, an emulsifier and an aqueous phase. Injectable lipid emulsions (ILEs) are known that generally also contain a tonicity modifier. Lipid emulsions can be prepared by any method known to those of skill in the art, for example, gentle shaking, agitation, or sonication. The components of the emulsion can be mixed or pre-mixed in any order prior to the preparation process, e.g., gentle shaking, agitation, or sonication. The size of the particles of the prepared emulsion can be in the range of from at or about 0.25 microns to at or about 0.75 microns in diameter, for example, the size of the particles can be at or about 0.25, 0.3, 0.35, 0.4, 0.45, 0.5, 0.55, 0.6, 0.65, 0.7, or 0.75 microns in diameter. In one example, the size of the particles of the prepared emulsion is at or about 0.5 microns in diameter.

The components of lipid emulsions (e.g., ILE) are described below. Any virus described in Section C above can be provided in combination or as a composition (e.g. lipid-treated virus or virus emulsion). Typically, the virus is a vaccinia virus, such as a Copenhagen, WR or Lister (e.g., LIVP) virus strain or recombinant or modified form thereof.

a. Lipid Component

Lipid emulsions (e.g., ILE) contain a lipid component that is any lipid that is soluble in hydrocarbons and insoluble in water, i.e., any hydrophobic lipid. Suitable lipids include fatty acids and their derivatives, including, but not limited to, triglycerides, diglycerides, monoglycerides, and phospholipids. Generally, the lipid component in the lipid emulsions provided herein is a biocompatible lipid, such as a naturally occurring plant or vegetable oil, including, but not limited to, soybean oil, cottonseed oil, safflower oil, corn oil, coconut oil, sesame oil, peanut oil, olive oil, castor oil, and mixtures thereof. The lipid component can also be an animal oil; fish oil; for example, cod liver oil; mineral oil; chemically synthesized oil, for example, 2-linoleoyl-1,3-dioctanoyl glycerol; or a semi-synthetic mono-, di- or triglyceride, for example, rac-glyceryl-1-monopalmitic, acyl glyceryl-1-monoolein, 1,2-dipalmitic, 1,3-dipalmitic, trimyristin, tripalmitin, tristearin, triolein, trilaiden and the like. Exemplary lipid components used in the emulsions provided herein are soybean oils. For example, an exemplary soybean oil-containing lipid emulsion is Intralipid®, a soybean oil-in-water emulsion containing egg yolk phospholipids and glycerin that contains 10%, 20%, or 30% soybean oil.

In lipid emulsions, such as ILE, the lipid component is typically present in an amount as a percentage (%) by weight, of the lipid emulsion (wt %), for example, from at or about 2% to at or about 40%, such as 2% to 5%, 2% to 10%, 2% to 15%, 2% to 20%, 2% to 25%, 2% to 30%, 2% to 35%, 2% to 40%, 5% to 10%, 5% to 15%, 5% to 20%, 5% to 25%, 5% to 30%, 5% to 35%, 5% to 40%, 10% to 15%, 10% to 20%, 10% to 25%, 10% to 30%, 10% to 35%, 10% to 40%, 15% to 20%, 15% to 25%, 15% to 30%, 15% to 35%, 15% to 40%, 20% to 25%, 20% to 30%, 20% to 35%, 20% to 40%, 25% to 30%, 25% to 35%, 25% to 40%, 30% to 35%, 30% to 40%, and 35% to 40%, by weight, of the lipid emulsion. Exemplary concentrations of the lipid component in the lipid emulsion are at or about 2%, 5%, 10%, 15%, 20%, 25%, 30%, 35%, and 40% (wt %) of the lipid emulsion. In one example, the lipid component is soybean oil and is present in an amount of at or about 20% by weight, of the lipid emulsion. In another example, the lipid component is soybean oil and is present in an amount of at or about 10% by weight, of the lipid emulsion. In yet another example, the lipid component is soybean oil and is present in an amount of at or about 30% by weight, of the lipid emulsion.

b. Emulsifiers

Lipid emulsions (e.g., ILE) include one or more emulsifiers that stabilize the emulsion by reducing the interfacial tension of the system and by providing enough surface charge for droplet-droplet repulsion. Typically, the emulsifier is a biocompatible emulsifier, such as a naturally-occurring emulsifier, for example, a naturally-occurring phospholipid, such as those derived from egg or soy sources. Suitable emulsifiers include, but are not limited to, egg yolk phospholipids, hydrogenated egg yolk phospholipids, soybean phospholipids, hydrogenated soybean phospholipids, and mixtures thereof. The choice of emulsifier can depend upon the desired application.

In particular, the emulsifier is natural lecithin obtained from egg yolk. Lecithin is biocompatible, nontoxic and is metabolized like natural fat. The emulsifier can also be a synthetic lecithin, such as dihexanoyl-L-α-lecithin. Other emulsifiers can include polyethylene glycol (PEG) lipids, such as polyethylene glycol-modified phosphatidylethanolamine (PEG-PE), non-ionic surfactants, such as Pluronic® F68, and other glycerophospholipids, such as phosphatidylcholine lipids, e.g., cholesterol, stearylamine, phosphatidylserine, and phosphatidylglycerol, and any hydrogenated derivatives. Exemplary emulsifiers used in the lipid emulsions provided herein are egg yolk phospholipids, which contains egg lecithin.

In lipid emulsions, such as ILE, the emulsifier is typically present in an amount as a percentage (%) by weight, of the lipid emulsion (wt %), for example, from at or about 0.2% to at or about 5%, such as 0.2% to 0.5%, 0.2% to 1%, 0.2% to 1.5%, 0.2% to 2%, 0.2% to 2.5%, 0.2% to 3%, 0.2% to 3.5%, 0.2% to 4%, 0.2% to 4.5%, 0.2% to 5%, 0.5% to 1%, 0.5% to 1.5%, 0.5% to 2%, 0.5% to 2.5%, 0.5% to 3%, 0.5% to 3.5%, 0.5% to 4%, 0.5% to 4.5%, 0.5% to 5%, 1% to 1.5%, 1% to 2%, 1% to 2.5%, 1% to 3%, 1% to 3.5%, 1% to 4%, 1% to 4.5%, 1% to 5%, 1.5% to 2%, 1.5% to 2.5%, 1.5% to 3%, 1.5% to 3.5%, 1.5% to 4%, 1.5% to 4.5%, 1.5% to 5%, 2% to 2.5%, 2% to 3%, 2% to 3.5%, 2% to 4%, 2% to 4.5%, 2% to 5%, 2.5% to 3%, 2.5% to 3.5%, 2.5% to 4%, 2.5% to 4.5%, 2.5% to 5%, 3% to 3.5%, 3% to 4%, 3% to 4.5%, 3% to 5%, 3.5% to 4%, 3.5% to 4.5%, 3.5% to 5%, 4% to 4.5%, 4% to 5%, and 4.5% to 5%, by weight, of the lipid emulsion. Exemplary concentrations of the emulsifier in the lipid emulsion are at or about 0.2%, 0.5%, 1%, 1.2%, 1.5%, 2%, 2.5%, 3%, 3.5%, 4%, 4.5% and 5% (wt %) of the lipid emulsion. In one example, the emulsifier is an egg yolk phospholipid and is present in an amount of at or about 1.2% by weight, of the lipid emulsion.

c. Aqueous Phase

Lipid emulsions (e.g., ILE) include an aqueous phase that typically is water. Typically, the amount of aqueous phase, e.g., water, is determined by the amount of water needed to achieve the final desired lipid concentration.

In lipid emulsions, such as ILE, the amount of aqueous phase, e.g., water, in the emulsions provided herein is typically present in an amount as a percentage (%) by weight, of the lipid emulsion (wt %), for example, from at or about 50% to at or about 98%, such as 50% to 55%, 50% to 60%, 50% to 65%, 50% to 70%, 50% to 75%, 50% to 80%, 50% to 85%, 50% to 90%, 50% to 95%, 50% to 98%, 55% to 60%, 55% to 65%, 55% to 70%, 55% to 75%, 55% to 80%, 55% to 85%, 55% to 90%, 55% to 95%, 55% to 98%, 60% to 65%, 60% to 70%, 60% to 75%, 60% to 80%, 60% to 85%, 60% to 90%, 60% to 95%, 60% to 99%, 65% to 70%, 65% to 75%, 65% to 80%, 65% to 85%, 65% to 90%, 65% to 95%, 65% to 98%, 70% to 75%, 70% to 80%, 70% to 85%, 70% to 90%, 70% to 95%, 70% to 99%, 75% to 80%, 75% to 85%, 75% to 90%, 75% to 95%, 75% to 98%, 80% to 85%, 80% to 90%, 80% to 95%, 80% to 98%, 85% to 90%, 85% to 95%, 85% to 98%, 90% to 95%, 90% to 98%, and 95% to 98%, by weight, of the lipid emulsion. Exemplary concentrations of the aqueous phase, e.g., water, in the lipid emulsion are at or about 50%, 55%, 60%, 65%, 70%, 75%, 80%, 85%, 90%, 95% and 98% (wt %) of the lipid emulsion. In one example, the aqueous phase is water and is present in an amount of at or about 80% by weight, of the lipid emulsion.

d. Additional Ingredients

Lipid emulsions (e.g., ILE) can also include one or more additional ingredients, for example, additives that can aid in the formulation of the emulsion or in the preservation of the emulsion during storage.

For example, the emulsions can contain a tonicity modifier. In particular, ILEs are lipid emulsions that are formulated for intravenous administration and contain a tonicity modifier so that the emulsion is isotonic with the blood and can be administered systemically. The tonicity modifier can include, but is not limited to, glycerin (i.e., glycerol or glycerine), sodium chloride, potassium chloride, mannitol, sucrose, lactose, fructose, maltose, dextrose, dextrose anhydrous, xylitol, sorbitol, propylene glycol, polyoxyethylated hydrocarbons, and $C_6$-$C_{20}$ saturated or unsaturated aliphatic acids. An exemplary tonicity modifier used in the lipid emulsions is glycerin.

In lipid emulsions, such as ILE, the tonicity modifier is typically present in an amount as a percentage (%) by weight, of the lipid emulsion (wt %), for example, from at or about 0.2% to at or about 5%, such as 0.2% to 0.5%, 0.2% to 1%, 0.2% to 1.5%, 0.2% to 2%, 0.2% to 2.5%, 0.2% to 3%, 0.2% to 3.5%, 0.2% to 4%, 0.2% to 4.5%, 0.2% to 5%, 0.5% to 1%, 0.5% to 1.5%, 0.5% to 2%, 0.5% to 2.5%, 0.5% to 3%, 0.5% to 3.5%, 0.5% to 4%, 0.5% to 4.5%, 0.5% to 5%, 1% to 1.5%, 1% to 2%, 1% to 2.5%, 1% to 3%, 1% to 3.5%, 1% to 4%, 1% to 4.5%, 1% to 5%, 1.5% to 2%, 1.5% to 2.5%, 1.5% to 3%, 1.5% to 3.5%, 1.5% to 4%, 1.5% to 4.5%, 1.5% to 5%, 2% to 2.5%, 2% to 3%, 2% to 3.5%, 2% to 4%, 2% to 4.5%, 2% to 5%, 2.5% to 3%, 2.5% to 3.5%, 2.5% to 4%, 2.5% to 4.5%, 2.5% to 5%, 3% to 3.5%, 3% to 4%, 3% to 4.5%, 3% to 5%, 3.5% to 4%, 3.5% to 4.5%, 3.5% to 5%, 4% to 4.5%, 4% to 5%, and 4.5% to 5%, by weight, of the lipid emulsion. Exemplary concentrations of the tonicity modifier in the lipid emulsion are at or about 0.2%, 0.5%, 1%, 1.5%, 2%, 2.25%, 2.5%, 3%, 3.5%, 4%, 4.5% and 5% (wt %) of the lipid emulsion. In one example, the tonicity modifier is glycerin and is present in an amount of at or about 2.25% by weight, of the lipid emulsion.

pH adjusters, for example, sodium hydroxide, can be used to adjust the pH of the system to around 8.0 before sterilization. For lipid emulsions, such as ILE, a slightly alkaline pH is preferred because the pH will decrease during sterilization and storage due to the production of free fatty acids. Other additional ingredients can include, for example, stabilizing agents, e.g., carbohydrates, amino acids, and polysorbates, such as 5% dextrose; solubilizing agents, e.g., cetrimide, sodium docusate, glyceryl monooleate, polyvinylpyrrolidone (PVP), and polyethylene glycol (PEG); buffers, e.g., acetates, citrates, phosphate, tartrates, lactates, succinates, and amino acids; preservatives, e.g., butylated hydroxyanisole (BHA), butylated hydroxytoluene (BHT), gentisic acids, vitamin E, ascorbic acid, sodium ascorbate, and sulfur-containing agents such as sulfites, bisulfites, metabisulfites, thioglycerols, and thioglycolates; antioxidants, e.g., α-tocopherol, ascorbic acid, and deferoxamine mesylate; suspending or viscosity agents; chelating agents; surfactants; co-solvents; bacteriostats or antimicrobial agents, e.g., EDTA, sodium benzoate and benzyl alcohol; active ingredients; adsorbents; and mixtures thereof.

2. Exemplary Injectable Lipid Emulsions (ILE)

Injectable (also called intravenous) lipid emulsions (ILE) are well known in the art (see e.g., Hippalgaonkar et al. (2010) AAPS PharmSciTech, 11:1526), and any can be used to prepare combinations or compositions with an oncolytic virus as provided herein. ILEs contain a lipid component, an emulsifier, a tonicity modifier and an aqueous phase. The tonicity modifier typically is glycerin, but can also include sorbitol, xylitol, mannitol, dextrose, glucose, polyethylene glycol, propylene glycol, sucrose, or lactose or other tonicity modifier. The ILE can be classified by the type of lipid in the emulsion. ILEs include those that contain a long-chain triglyceride (LCT) emulsion that contains only LCTs as the lipid component, a medium-chain triglyceride emulsion that contains only MCTs as the lipid component, a fish oil emulsion that contains only fish oil as the lipid component, or a lipid emulsion that contains a mixture of one or more of LCTs, MCTs and fish oils. In some examples, ILEs can be classified as a synthetic lipid emulsion. Exemplary lipid emulsions that fall into these categories are described below.

a. Long-Chain Triglyceride (LCT) Emulsions

ILEs can contain long-chain triglycerides (LCTs), i.e., triglycerides with fatty acid chains of more than 14 carbons. Typical formulations contain LCT concentrations ranging from 10-30%. The LCTs contain free fatty acids such as linoleate, oleate, palmitate, linolenate, and stearate. LCT lipid emulsions are most commonly made from soybean oil, but other oils containing LCTs include, but are not limited to, almond oil, canola oil, corn oil, cottonseed oil, flaxseed oil, grape seed oil, olive oil, palm oil, peanut oil, safflower oil, sesame oil, sunflower oil, and walnut oil.

Typically, LCT lipid emulsions contain soybean oil, which is a good source of the essential free fatty acids linolenate and linoleate. For example, approximately 60% of the total fatty acids in soybean oil are polyunsaturated fatty acids (PUFAs), with a ratio of linoleic acid (n-6) to α-linolenic acid (n-3) of approximately 8:1. An exemplary soybean oil emulsion is Intralipid®, a soybean oil-in-water emulsion containing egg yolk phospholipids (1.2%) and glycerin (2.25%) that is approved for human use. Intralipid® is available in 10%, 20% and 30% (soybean oil) concentrations. The final pH of Intralipid® is adjusted to 8.0 with sodium hydroxide. The role that soybean oil emulsions, e.g., Intralipid®, play in inflammation is unknown, though Intralipid® has been shown to inhibit the in vitro synthesis and secretion of the second (C2) and fourth (C4) components of complement by guinea pig peritoneal macrophages (Strunk et al. (1979) Pediatr. Res. 13:188-193).

Other ILEs containing LCTs from soybean oil include commercially available lipid emulsions, including, but not limited to, Elolipid® 20% (Fresenius Kabi, Bad Homburg, Germany), Mixid® (Otsuka Pharmaceutical Factory, Inc., Tokushima, Japan), Liposyn III® (Hospira, Inc., Lake Forest, Ill.), Ivelip® 10% (Baxter Healthcare Ltd., Auckland, Australia), Ivelip® 20% (Baxter Healthcare Ltd., Auckland, Australia), Endolipid® 10% (B. Braun AG, Melsungen, Germany), and Endolipid® 20% (B. Braun AG, Melsungen, Germany), and any other commercially available soybean oil-containing lipid emulsion.

Emulsions that contain safflower oil are also known. These emulsions have more linoleic acids and less saturated fatty acids as compared to soybean oil. An exemplary safflower oil emulsion approved for human use is Liposyn®, a safflower oil-in-water emulsion that contains egg phosphatides and glycerin. Liposyn® and Intralipid® differ in their fatty acid composition, the major difference being in the α-linolenic acid content, a precursor to n-3 fatty acids, with Liposyn® containing 8% whereas Intralipid® contains 0.5%.

ILEs also include lipid emulsions containing a mixture of LCTs. For example, the lipid emulsion can contain a mixture of soybean oil and safflower oil. An exemplary lipid emulsion that contains a mixture of soybean oil and safflower oil is Liposyn II® (Hospira, Inc., Lake Forest, Ill.), available in both a 10% and 20% concentration, where the amounts of soybean oil and safflower oil are equal in each composition. In another example, the lipid emulsion can contain a mixture of olive oil and soybean oil. These emulsions have a high content of monounsaturated oleic acid and vitamin E (α-tocopherol), with a ratio of approximately 9:1 linoleic acid (n-6) to α-linoleic acid (n-3). An exemplary lipid emulsion that contains a mixture of olive oil and soybean oil is ClinOleic® 20% (Baxter, Maurepas, France). ClinOleic® 20% contains approximate 80% olive oil and approximately 20% soybean oil, along with egg lecithin, glycerol and sodium oleate.

In one example, the lipid emulsion contains either 10%, 20% or 30% of a long-chain triglyceride, for example, soybean oil, 1.2% egg phospholipids, and 2.25%-2.5% glycerol. In another example, the lipid emulsion contains 10% or 20% of a long-chain triglyceride, for example, safflower oil, 1.2% egg phospholipids, and 2.25%-2.5% glycerol. In yet another example, the lipid emulsion contains a mixture of LCTs, for example, 5% soybean oil and 5% safflower oil, 10% soybean oil and 10% safflower oil, or 16% olive oil and 4% soybean oil, and 1.2% egg phospholipids, and 2.25%-2.5% glycerol.

Table 8 below provides a list of commercially available LCT lipid emulsions and the corresponding lipid component(s). The lipid emulsions listed in Table 8 and any other known lipid emulsions that contain LCTs can be used in the compositions and combinations provided herein.

TABLE 8

| Long-chain triglyceride (LCT) lipid emulsions | | | |
|---|---|---|---|
| Lipid emulsion | Lipid component | Emulsifier | Tonicity modifier |
| Intralipid ® 10% | Soybean oil (10%) | Egg phospholipid (1.2%) | Glycerol (2.25%) |
| Intralipid ® 20% | Soybean oil (20%) | Egg phospholipid (1.2%) | Glycerol (2.25%) |
| Intralipid ® 30% | Soybean oil (30%) | Egg phospholipid (1.2%) | Glycerol (2.25%) |
| Elolipid ® | Soybean oil (20%) | Egg phospholipid (1.2%) | Glycerol (2.5%) |
| Liposyn III ® 10% | Soybean oil (10%) | Egg phospholipid (1.2%) | Glycerol (2.5%) |
| Liposyn III ® 20% | Soybean oil (20%) | Egg phospholipid (1.2%) | Glycerol (2.5%) |
| Ivelip ® 10% | Soybean oil (10%) | Egg phospholipid (1.2%) | Glycerol (2.5%) |
| Ivelip ® 20% | Soybean oil (20%) | Egg phospholipid (1.2%) | Glycerol (2.5%) |
| Endolipid ® 10% | Soybean oil (10%) | Egg phospholipid (1.2%) | Glycerol (2.5%) |
| Endolipid ® 20% | Soybean oil (20%) | Egg phospholipid (1.2%) | Glycerol (2.5%) |
| Liposyn ® 10% | Safflower oil (10%) | Egg phospholipid (1.2%) | Glycerol (2.5%) |
| Liposyn ® 20% | Safflower oil (20%) | Egg phospholipid (1.2%) | Glycerol (2.5%) |
| Liposyn II ® 10% | Soybean oil (5%), safflower oil (5%) | Egg phospholipid (1.2%) | Glycerol (2.5%) |
| Liposyn II ® 20% | Soybean oil (10%), safflower oil (10%) | Egg phospholipid (1.2%) | Glycerol (2.5%) |
| ClinOleic ® 20% | Olive oil (16%), soybean oil (4%) | Egg phospholipid (1.2%) | Glycerol (2.25%) | b. Medium-Chain Triglyceride (MCT) Emulsions

ILEs also include medium-chain triglyceride (MCT) emulsions that contain triglycerides with fatty acid chains of between 6 and 10 carbons. The MCTs found in the lipid emulsions are generally caprylic acid (C8) and capric acid (C10). These fatty acids are saturated and typically are found in coconut oil, for example, fractionated coconut oil, and also palm kernel oils. MCTs are typically used in combination with LCTs because MCTs are not a source of essential fatty acids. MCT lipid emulsions include those that are composed of a mixture of caprylic and capric triglycerides. For example, commercially available MCT lipid emulsions that contain a mixture of caprylic and capric triglycerides include, but are not limited to Miglyol® 810 (Sasol Olefins & Surfactants GmbH, Hamburg, Germany), Miglyol® 812 (Sasol Olefins & Surfactants GmbH, Hamburg, Germany), Miglyol® 818 (Sasol Olefins & Surfactants GmbH, Hamburg, Germany), Neobee® M5 (Stepan Specialty Products, LLC, Maywood, N.J.), Captex® 300 (Abitec Corp., Columbus, Ohio), and any other commercially available MCT-containing lipid emulsion.

Table 9 below provides a list of commercially available MCT lipid emulsions and the corresponding lipid component. The lipid emulsions listed in Table 9 and any other known lipid emulsions that contain MCTs can be used in the compositions and combinations provided herein.

TABLE 9

Medium-chain triglyceride (MCT) lipid emulsions

| Lipid emulsion | Lipid component | Emulsifier | Tonicity modifier |
| --- | --- | --- | --- |
| Miglyol ® 810 | Caprylic acid (65-80%), capric acid (20-35%), caproic acid (<2%), lauric acid (<2%), myristic acid (<1%) | Egg phospholipid (1.2%) | Glycerol (2.25%) |
| Miglyol ® 812 | Caprylic acid (50-65%), capric acid (30-45%), caproic acid (<2%), lauric acid (<2%), myristic acid (<1%) | Egg phospholipid (1.2%) | Glycerol (2.25%) |
| Miglyol ® 818 | Caprylic acid (45-65%), capric acid (30-45%), caproic acid (<2%), lauric acid (<3%), myristic acid (<1%), linoleic acid (2-5%) | Egg phospholipid (1.2%) | Glycerol (2.25%) | c. Fish Oil Emulsions

ILEs based on fish oil are also available. Triglycerides typical of fish oils are those triglycerides that have a high concentration of omega-3 fatty acids, for example, higher than 30%. Omega-3 fatty acids are hydrolyzed much more slowly than LCTs, which are in turn hydrolyzed much more slowly than MCTs. The high unsaturated fatty acid content of fish oil emulsions can reduce the generation of pro-inflammatory lipid mediators, such as TNF-α, IL1, IL6 and IL8 from monocytes (Mayer et al. (2003) J. Immunol 171(9):4837-4843). These emulsions are designed to provide essential omega-3 PUFAs and also function to prevent elevated omega-6 to omega-3 PUFA ratios in cell membranes, which can occur after administration of LCT lipid emulsions, e.g., soybean oil emulsions, that are high in potentially inflammatory omega-6 PUFAs (Waitzberg et al. (2006) J. Parenter. Enteral. Nutr. 30:351-367). The potential anti-inflammatory effects of fish oil emulsions are shown to be influenced by the ratio of omega-3 to omega-6 PUFAs (Hagi et al. (2010) J. Parenter. Enteral. Nutr. 34:263-270).

Fish oil emulsions can include fish oils from, for example, any cold-water fish, including, but not limited to, salmon, sardine, mackerel, herring, anchovy, smelt and swordfish. Fish oil lipid emulsions can be composed of fish oil alone, but are typically formulated as a mixture of fish oil and other oils, such as LCTs, e.g., soybean oil, olive oil, of safflower oil, or emulsions rich in MCTs, e.g., coconut oil. An exemplary fish oil emulsion with fish oil as the only lipid component is Omegaven® (Fresenius Kabi GmbH, Bad Homburg, Germany), which contains highly refined fish oil, along with glycerol and egg lecithin.

Table 10 below provides a list of commercially available fish oil lipid emulsions and the corresponding lipid component. The lipid emulsion listed in Table 10 and any other known fish oil lipid emulsions can be used in the compositions and combinations provided herein.

TABLE 10

Fish oil lipid emulsions

| Lipid emulsion | Lipid component | Emulsifier | Tonicity modifier |
| --- | --- | --- | --- |
| Omegaven ® | Fish oil (10%) | Egg phospholipid (1.2%) | Glycerol (2.5%) | d. Mixtures of LCTs, MCTs and Fish Oils

Lipid emulsions have been developed that contain mixtures of LCTs, MCTs and/or fish oils. These emulsions can provide both rapid and slowly metabolized fuels as well as essential fatty acids. For example, a lipid emulsion can contain a mixture of LCTs and MCTs, such as a 50:50 mixture of LCTs and MCTs. Suitable lipid emulsions can also contain mixtures of one or more LCTs, MCTs, and fish oil, for example, an emulsion that contains soybean oil, olive oil, MCTs and fish oil, or an emulsion that contains soybean oil, MCTs and fish oil. ILEs include lipid emulsions that include mixtures of MCTs and fish oil.

Suitable lipid emulsions that contain a mixture of lipids include emulsions with a mixture of LCTs and MCTs. For example, mixtures of a LCT, e.g., soybean oil, and a MCT, e.g., coconut oil, are known. These emulsions can be composed of an equal mixture of soybean oil and a MCT such as coconut oil and supply half of the PUFA as compared to the emulsions containing 100% soybean oil, with a similar ratio of approximately 8:1 of linoleic acid (n-6) to α-linoleic acid (n-3). Exemplary emulsions that contain equal parts LCT and MCT are Lipofundin® MCT/LCT 10% and Lipofundin® MCT/LCT 20% (B. Braun, Inc., Melsungen, Germany).

ILEs also include lipid emulsions that contain a mixture of LCTs, MCTs and fish oil. For example, a suitable lipid emulsion can contain a mixture of LCTs such as soybean oil and/or olive oil, MCTs, and fish oil. An exemplary lipid emulsion is SMOFlipid® 20% (Fresenius-Kabi, Bad Homburg, Germany), an emulsion that contains the LCTs soybean oil (30%) and olive oil (25%), medium-chain triglycerides (30%), and fish oil (15%). Another exemplary lipid emulsion that contains a mixture of LCTs, MCTs and fish oil is Lipoplus® 20% (B. Braun, Inc., Melsungen, Germany). Lipoplus® 20% is an emulsion that contains soybean oil (LCT), MCTs and fish oil.

Table 11 below provides a list of commercially available lipid emulsions that contain a mixture of LCTs, MCTs and/or fish oils and the corresponding lipid component(s). The lipid emulsions listed in Table 11 and any other known lipid emulsions that contain a mixture of LCTs, MCTs and/or fish oils can be used in the compositions and combinations provided herein.

TABLE 1

LCT, MCT and/or fish oil lipid emulsions

| Lipid emulsion | Lipid component | Emulsifier | Tonicity modifier |
| --- | --- | --- | --- |
| Lipofundin ® MCT/LCT 10% | Soybean oil (5%), coconut oil (5%) | Egg phospholipid (1.2%) | Glycerol (2.5%) |

TABLE 1-continued

LCT, MCT and/or fish oil lipid emulsions

| Lipid emulsion | Lipid component | Emulsifier | Tonicity modifier |
|---|---|---|---|
| Lipofundin ® MCT/LCT 20% | Soybean oil (10%), coconut oil (10%) | Egg phospholipid (1.2%) | Glycerol (2.5%) |
| SMOFlipid ® 20% | Soybean oil (6%), coconut oil (6%), olive oil (5%), fish oil (3%) | Egg phospholipid (1.2%) | Glycerol (2.5%) |
| Lipoplus ® 20% | Coconut oil (10%), soybean oil (8%), fish oil (2%) | Egg phospholipid (1.2%) | Glycerol (2.5%) | e. Synthetic Lipid Emulsions

ILEs have been developed that possess physicochemical properties that closely resemble those that contain naturally-occurring lipids. These synthetic lipid emulsions were originally developed to overcome metabolic and immunologic concerns that arose from the use of lipid emulsions containing LCTs, such as soybean oil, and MCTs. Exemplary synthetic lipids include, for example, Structolipid® 20% (Fresenius-Kabi, Bad Homburg, Germany), made by the hydrolysis of soybean oil and MCTs with subsequent random re-esterification of long- and medium-chain fatty acids in the 1, 2, or 3 positions of glycerol, and the synthetic lipid emulsions described in Hultin et al. (1994) J. Lipid Res. 35:1859-1860.

TABLE 12

Synthetic lipid emulsions

| Lipid emulsion | Lipid component | Emulsifier | Tonicity modifier |
|---|---|---|---|
| Structolipid ® | Soybean oil (12.8%), coconut oil (7.2%) | Egg phospholipid (1.2%) | Glycerol (2.25%) |

F. Pharmaceutical Compositions, Formulations and Articles of Manufacture

Provided herein are compositions containing an oncolytic virus, such as any described herein or known to those of skill in the art including vaccinia viruses, such as LIVP viruses and recombinant form thereof, are formulated for co-administration with or are co-formulated with a complement inhibitor, including, but not limited to, an anti-complement antibody, such as an anti-C5 antibody, and/or with lipid or a lipid emulsion (e.g. formulated with 20% soybean oil intravenous fat emulsion). Such compositions and combinations, when co-formulated for administration together or co-administered separately, provide an adjunct therapy to increase the infectivity of the oncolytic virus compared to administration or delivery of the oncolytic virus without such adjunct.

For example, provided herein are combinations or compositions containing an oncolytic virus (e.g. a vaccinia virus, such as an LIVP virus or modified form thereof), and a complement inhibitor (e.g. anti-complement antibody, such as an anti-C5 antibody). The oncolytic virus and complement inhibitor can be formulated as separate compositions or all agents can be formulated together. Typically, the compositions are provided separately. For example, provided herein are combinations of separate compositions that are administered separately that include a first composition containing an oncolytic virus (e.g. a vaccinia virus, such as an LIVP virus or modified form thereof) and a second composition containing a complement inhibitor (e.g. anti-complement antibody, such as an anti-C5 antibody). In such examples, the complement inhibitor can be co-administered (prior to, subsequently with or intermittently with) in combination with a composition containing an oncolytic virus. In other examples, the complement inhibitor and oncolytic virus can be provided in the same composition and can be administered together.

Also, provided herein are compositions of a lipid-emulsion oncolytic virus that contains an oncolytic virus (e.g. a vaccinia virus, such as an LIVP virus or modified form thereof) that is formulated with a lipid emulsion (e.g. 20% soybean oil intravenous fat emulsion). The lipid-emulsion oncolytic virus also can be provided in combination with another agent, such as a therapeutic agent or another agent that increases virus infectivity (e.g. complement inhibitor). The agents can be formulated as separate compositions or all agents can be formulated together. In particular, the lipid-emulsion oncolytic virus can be co-formulated as a composition with another agent (e.g. complement inhibitor) or provided in combination with another agent (e.g. complement inhibitor). When another agent (e.g. complement inhibitor) is provided separately from a lipid-emulsion oncolytic virus, the agent (e.g. complement inhibitor) can be co-administered (prior to, subsequently or intermittently) in combination with a lipid-emulsion oncolytic virus composition. For example, the combination can be provided as a first composition containing an oncolytic virus (e.g. a vaccinia virus, such as an LIVP virus or modified form thereof) that is formulated with a lipid emulsion (e.g. 20% soybean oil intravenous fat emulsion) and a second composition containing a complement inhibitor (e.g. anti-complement antibody, such as an anti-C5 antibody). In other cases, all agents can be formulated together as a single composition.

The particular formulation of the agents is within the level of one of skill in the art to determine, and is dependent on the subject being treated, the route of administration, the disease or condition being treated and other factors that can be considered by the skilled artisan.

The compositions can be formulated for single dosage administration or for multiple dosage administration. The agents can be formulated for direct administration. The compositions can be provided as a liquid or lyophilized formulation. The agents can be formulated into suitable pharmaceutical preparations such as solutions, suspensions, tablets, dispersible tablets, pills, capsules, powders, sustained release formulations or elixirs, for oral administrate, as well as transdermal patch preparation and dry powder inhalers. Typically, the compounds are formulated into pharmaceutical compositions using techniques and procedures well known in the art (see e.g., Ansel Introduction to Pharmaceutical Dosage Forms, Fourth Edition, 1985, 126). Generally, the mode of formulation is a function of the route of administration. The compositions can be co-formulated or provided as separate compositions.

Typically, compositions, including liquid preparations, can be prepared by conventional means with pharmaceutically acceptable additives or excipients. Where the compositions are provided in lyophilized form they can be reconstituted just prior to use by an appropriate buffer, for example, a sterile saline solution. Pharmaceutically acceptable compositions are prepared in view of approvals for a regulatory agency or other agency prepared in accordance with generally recognized pharmacopeia for use in animals and in humans. The compositions can be formulated for single dosage administration or for multiple dosage administration. The compositions can be formulated for direct administration.

The pharmaceutical compositions can contain a suitable pharmaceutical carrier. A pharmaceutically acceptable carrier includes a solid, semi-solid or liquid material that acts as a vehicle carrier or medium for the virus or other agent. Pharmaceutical compositions provided herein can be formulated in various forms, for example in solid, semi-solid, aqueous, liquid, powder or lyophilized form. Exemplary pharmaceutical compositions include, but are not limited to, sterile injectable solutions, sterile packaged powders, eye drops, tablets, pills, powders, lozenges, sachets, cachets, elixirs, suspensions, emulsions, solutions, syrups, aerosols (as a solid or in a liquid medium), ointments, soft and hard gelatin capsules, and suppositories.

Examples of suitable pharmaceutical carriers are known in the art and include, but are not limited to, water, buffers, saline solutions, phosphate buffered saline solutions, various types of wetting agents, sterile solutions, alcohols, gum arabic, vegetable oils, benzyl alcohols, gelatin, glycerin, carbohydrates, such as lactose, sucrose, dextrose, amylose or starch, sorbitol, mannitol, magnesium stearate, talc, silicic acid, viscous paraffin, perfume oil, fatty acid monoglycerides and diglycerides, pentaerythritol fatty acid esters, hydroxy methylcellulose, powders, among others. Pharmaceutical compositions provided herein can contain other additives including, for example, antioxidants, preserving agents, analgesic agents, binders, disintegrants, coloring, diluents, excipients, extenders, glidants, solubilizers, stabilizers, tonicity agents, vehicles, viscosity agents, flavoring agents, sweetening agents, emulsions, such as oil/water emulsions, emulsifying and suspending agents, such as acacia, agar, alginic acid, sodium alginate, bentonite, carbomer, carrageenan, carboxymethylcellulose, cellulose, cholesterol, gelatin, hydroxyethyl cellulose, hydroxypropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, and miscellaneous ingredients, such as, but not limited to, crystalline cellulose, microcrystalline cellulose, citric acid, dextrin, liquid glucose, lactic acid, lactose, magnesium chloride, potassium metaphosphate, starch, among others. Such carriers and/or additives can be formulated by conventional methods and can be administered to the subject at a suitable dose. Stabilizing agents such as lipids, nuclease inhibitors, polymers, and chelating agents can preserve the compositions from degradation within the body. Other suitable formulations for use in a pharmaceutical composition can be found, for example, in *Remington: The Science and Practice of Pharmacy* (2005, Twenty-first edition, Gennaro & Gennaro, eds., Lippencott Williams and Wilkins).

The combinations and compositions provided herein can be used in various methods known to one of skill in the art, and in particular for the therapy of tumors or treatment of wounded and inflamed tissues and cells. The compositions for use alone or together in combination with another composition described herein can be administered by any method known to one of skill in the art, such as systemic (e.g. intravenous), oral, intraperitoneal and intratumoral applications. Typically, the compositions are administered systemically, such as intravenously. When provided as separate compositions, the compositions typically are administered by the same route of administration.

Compositions can be formulated for administration by any route known to those of skill in the art including intramuscular, intravenous, intradermal, intralesional, intraperitoneal injection, subcutaneous, intratumoral, epidural, nasal, oral, vaginal, rectal, topical, local, otic, inhalational, buccal (e.g., sublingual), and transdermal administration or any route. Other modes of administration also are contemplated. Administration can be local, topical or systemic depending upon the locus of treatment. Local administration to an area in need of treatment can be achieved by, for example, but not limited to, local infusion during surgery, topical application, e.g., in conjunction with a wound dressing after surgery, by injection, by means of a catheter, by means of a suppository, or by means of an implant. The most suitable route in any given case depends on a variety of factors, such as the nature of the disease, the progress of the disease, the severity of the disease and the particular composition which is used. Pharmaceutical compositions can be formulated in dosage forms appropriate for each route of administration.

Systemic or parenteral administration, generally characterized by injection or infusion, either subcutaneously, intramuscularly, intravenous, intraperitoneal or intradermally is contemplated herein. The compositions are formulated in a manner that is suitable for the mode of administration. In particular examples, the compositions are formulated for intravenous administration. Preparations for parenteral administration include sterile solutions ready for injection, sterile dry soluble products, such as lyophilized powders, ready to be combined with a solvent just prior to use, sterile suspensions ready for injection, sterile dry insoluble products ready to be combined with a vehicle just prior to use and sterile emulsions.

Injectables can be prepared in conventional forms, either as liquid solutions or suspensions, solid forms suitable for solution or suspension in liquid prior to injection, or as emulsions. The compositions provided herein can be formulated in an aqueous solutions, such as in a physiologically compatible buffer. Exemplary parenteral vehicles or buffers include, but are not limited to, Hanks' solution, Ringer's solution, or physiological saline buffer, phosphate buffered saline (PBS), a sodium chloride solution, Ringer's dextrose, dextrose and sodium chloride, lactated Ringer's or fixed oils. For example, suitable carriers include solutions containing thickening and solubilizing agents, such as glucose, polyethylene glycol, and polypropylene glycol and mixtures thereof. The concentration of the pharmaceutically active compound is adjusted so that an injection or infusion provides an effective amount to produce the desired pharmacological effect.

Compositions also can be administered with other biologically active agents, either sequentially, intermittently or in the same composition. Administration also can include controlled release systems including controlled release formulations and device controlled release, such as by means of a pump.

1. Formulation and Dosage Forms

The compositions can be prepared so that the concentration of the pharmaceutically active compound or agent is adjusted so that administration or delivery (e.g. by injection) provides an effective amount to produce the desired pharmacological effect. The exact dose depends on the age, weight and condition of the patient or animal as is known in the art. The unit-dose parenteral preparations are packaged in an ampoule, a vial or a syringe with a needle. The volume of liquid solution or reconstituted powder preparation, containing the pharmaceutically active compound, is a function of the disease to be treated and the particular article of manufacture chosen for package. All preparations for parenteral administration must be sterile, as is known and practiced in the art.

a. Oncolytic Virus In any examples of the compositions provided herein containing an oncolytic virus, including in combinations with a complement inhibitor (e.g. anti-C5) and/or lipid emulsion, the virus can be prepared at an appropriate concentration in suitable media or pharmaceutical solution depending on the particular application of the composition. Once prepared, the virus can be maintained or stored at a cool temperature (e.g. refrigerated or stored at temperatures greater than −20° C.). For example, immediately prior to use the virus can be maintained on ice until use. If the virus was lyophilized or otherwise dried for storage, then it can be reconstituted in an appropriate aqueous solution. The aqueous solution in which the virus is prepared is typically the medium used in the assay (e.g., DMEM or RPMI) or one that is compatible, such as a buffered saline solution or other isotonic solution. For example, but aqueous solution can be Ringer's solution, Ringer's lactate solution, phosphate-buffered saline (PBS), TRIS-buffered saline (TBS), Hank's balanced salt solution (HBSS), Earle's balanced salt solution (EBSS), standard saline citrate (SSC), HEPES-buffered saline (HBS), Grey's balanced salt solution (GBSS), and normal saline (NaCl).

For pharmaceutical applications, the virus can be immediately prepared or reconstituted in a pharmaceutical solution. Numerous pharmaceutically acceptable solutions for use are well known in the art (see e.g. Remington's Pharmaceutical Sciences (18$^{th}$ edition) ed. A. Gennaro, 1990, Mack Publishing Co., Easton, Pa.). In one example, the viruses can be diluted in a physiologically acceptable solution, such as sterile saline or sterile buffered saline, with or without an adjuvant or carrier. In other examples, the pharmaceutical solution can contain a component that provides viscosity (e.g. glycerol) and/or component that has bactericidal properties (e.g. phenol). The virus can be reconstituted or diluted to provide the desired concentration or amount. The particular concentration can be empirically determined by one of skill in the art depending on the particular application.

Pharmaceutical compositions containing an oncolytic virus, such as a vaccinia virus (e.g. LIVP), can be generated to contain a therapeutically effective amount of virus. For example, the compositions can have a virus concentration of from or from about $10^5$-$10^{10}$ pfu/mL, for example, $5\times10^6$ to $5\times10^9$ or $10^7$-$10^9$ pfu/mL, such as at least or about or $10^6$ pfu/mL, $10^7$ pfu/mL, $10^8$ pfu/mL or $10^9$ pfu/mL. The pharmaceutical compositions can be provided as liquid compositions having a volume of from or from about 0.01 mL to 100 mL, such as from or from about 0.1 mL to 100 mL, 1 mL to 100 mL, 10 mL to 100 mL, 0.01 mL to 10 mL, 0.1 mL to 10 mL, 1 mL to 10 mL, 0.02 mL to 20 mL, 0.05 mL to 5 mL, 0.5 mL to 50 mL, 0.5 mL to 5 mL, for example, at least or about at least or 0.05 mL, 0.5 mL or 1 mL. For example, the compositions can contain an amount of virus that is or is about $1\times10^5$ to $1\times10^{12}$ pfu, such as $1\times10^6$ to $1\times10^{10}$ pfu or $1\times10^7$ to $1\times10^{10}$ pfu, for example at least or about at least or $1\times10^6$, $1\times10^7$, $1\times10^8$, $1\times10^9$, $2\times10^9$, $3\times10^9$, $4\times10^9$, or $5\times10^9$ pfu.

b. Lipid Emulsion (e.g. Lipid-Treated Virus)

Any of the lipid emulsion compositions described above in Section E can be provided as a composition for use in adjunct therapy with an oncolytic virus. The lipid emulsion can be formulated together or separately from the adjunct therapy. For example, the lipid emulsion can be formulated separately and administered independently from the oncolytic virus, such as prior to, simultaneously with, intermittently with or subsequently. Suitable emulsions include any described in Section E above, and typically contain up to 40% oil, for example, between 5 and 40%, such as generally up to or about 10%, 20% or 30% of oil. Exemplary of such emulsions are any of the commercially available fat emulsions, such as Intralipid™, Liposyn™, Infonutrol™, Lipofundin™ and Lipiphysan™. Typically, the emulsion will has fat droplets between 0.1 and 1.0 μm, particularly 0.1 and 0.5 μm, and a pH in the range of 5.5 to 8.0.

Lipid-treated oncolytic virus compositions include emulsions that include an oncolytic virus, a lipid component, an emulsifier, and an aqueous phase. The emulsions can also include one or more additional ingredients, for example, a tonicity modifier, surfactants, co-solvents, bacteriostats, preservatives, active ingredients, and/or adsorbents. The oncolytic virus can be either dissolved in a pre-mixed emulsion composition or alternatively it can be dissolved in an oil (e.g., soybean oil, safflower oil, cottonseed oil, sesame oil, corn oil or almond oil) and an emulsion formed upon mixing with a phospholipid (e.g., eggs phospholipids, soybean phospholipids or soybean lecithin) and water. Thus, the lipid emulsion containing an oncolytic virus can be prepared de novo or extemperaneously. It will be appreciated that other ingredients can be added, for example glycerol or glucose, to adjust the tonicity of the emulsion.

For example, a de novo emulsion can be generated by preparing the virus composition in an aqueous phase with emulsifier by mixing or combining virus with an emulsifier in a suitable aqueous phase. The oily phase containing the lipid component can then be added to the aqueous phase under conditions in which an emulsion is formed. Alternatively, a de novo emulsion can be generated by preparing an oil phase containing the virus, lipid component and emulsifier, which is then added to the aqueous phase under conditions in which an emulsion is formed. The lipid component and virus composition can be emulsified by means of an emulsifier. Emulsification can be achieved by procedures known in the art that achieve mixing of the components. It is understood that the procedures employed to prepare the virus emulsion do not result in inactivation of the virus, for example, due to heat-killing or lysis.

Typically, the lipid-treated oncolytic virus is prepared extemporaneously as an emulsion by addition of the oncolytic virus to a prepared lipid emulsion composition or vice versa. In such examples, the virus composition and lipid emulsion are combined and mixed. Section E describes exemplary lipid emulsions. For example, the lipid emulsion composition can be an ILE, such as any of the commercially available ILEs that are well known to a skilled artisan. Exemplary ILEs are 10%, 20% or 30% soybean oil intravenous fat emulsions, including those marketed under the name Intralipid®. In some examples, the lipid-treated oncolytic virus composition can be prepared by diluting an oncolytic virus composition by addition of a lipid emulsion. For example, an equal volume of virus and a prepared lipid emulsion preparation (e.g. an ILE, 10%, 20% or 30% soybean oil intravenous fat emulsions, for example, Intralipid®) can be combined and mixed. In other examples, a lyophilized oncolytic virus composition can be reconstituted with a lipid emulsion.

Generally, the lipid-treated oncolytic virus is prepared by contacting the virus with a biocompatible lipid component a predetermined time before use or administration. For example, the lipid-treated oncolytic virus composition can be prepared extemperaneously prior to use by addition of the lipid emulsion with virus, followed by incubation for a predetermined period of time before use or administration. This can achieve pre-treatment of the virus with components of the lipid emulsion, such as the lipid components, which can alter the properties of the virus or virus composition. Typically, the incubation time and period is such that the virus is not inactivated or its titer is not otherwise reduced. Such time period and incubation conditions can be determined empirically by a person skilled in the art, and are will within the capabilities of a skilled artisan. For example, methods of assessing virus activity or titer are well known to a skilled artisan, and include any assay as described herein in Section G.

For example, the oncolytic virus, e.g., the vaccinia virus, can be contacted (i.e. pre-treated) with the lipid emulsion (e.g. 10%, 20% or 30% soybean oil intravenous lipid emulsion) for 1 minute to 24 hours, such as 5 minutes to 12 hours, and generally 30 minutes to 6 hours, such as 30 minutes to 3 hours or 30 minutes to 2 hours, for example at least 1 minute, 5 minutes, 10 minutes, 15 minutes, 20 minutes, 25 minutes, 30 minutes, 45 minutes, 1 hour, 1.25 hours, 1.5 hours, 1.75 hours, 2 hours, 2.25 hours, 2.5 hours, 2.75 hours, 3 hours, 3.25 hours, 3.5 hours, 3.75 hours, 4 hours, 4.25 hours, 4.5 hours, 4.75 hours, 5 hours, or more prior to use or administration. The virus and lipid emulsion can be incubated at temperatures at or about 2° C. to 42° C., such as 2° C. to 8° C., 18° C. to 27° C. or 30° C. to 42° C., for example, at least 4° C., 6° C., 8° C., 10° C., 15° C., 20° C., 21° C., 22° C., 23° C. 24° C. 25° C., 26° C., 27° C., 28° C., 29° C. 30° C., 31° C., 32° C., 33° C., 34° C., 35° C., 36° C., 37° C., 38° C., 39° C., 40° C. or more. For example, the virus and lipid emulsions can be incubated at temperatures at or about or up to 37° C. for at least 30 minutes, 1 hour, 2 hours, 3 hours, 4 hours, 5 hours, 6 hours or more.

In any of the examples of lipid-emulsion oncolytic virus compositions, the lipid-emulsion oncolytic virus is prepared to contain an oncolytic virus at concentration in the resulting composition of $10^5$-$10^{12}$ pfu/mL (e.g. at least or about or $10^6$ pfu/mL, $10^7$ pfu/mL, $10^8$ pfu/mL, $10^9$ pfu/mL, $10^{10}$ pfu/mL, $10^{11}$ pfu/mL or $10^{10}$ pfu/mL); a lipid component, such as any described in Section E, present as a percentage (%) by weight of the composition (wt %), for example, from at or about 2% to at or about 40% (e.g. at least 2%, 5%, 10%, 15%, 20%, 25%, 30%, 35%, and 40% (wt %) of the composition); an emulsifier, such as any described in Section E, present in an amount as a percentage (%) by weight of the composition (wt %), for example, from at or about 0.2% to at or about 5% (e.g. at or about or at least 0.2%, 0.5%, 1%, 1.2%, 1.5%, 2%, 2.5%, 3%, 3.5%, 4%, 4.5% and 5% (wt %) of the composition); and an aqueous solution provided in an amount for injection to achieve the appropriate concentration of components. The emulsion also can contain other agents. For example, the lipid-treated oncolytic virus also contains a tonicity modifier as described in Section E in an amount that is at or about 0.2% to at or about 5% (e.g. at or about or at least 0.2%, 0.5%, 1%, 1.5%, 2%, 2.25%, 2.5%, 3%, 3.5%, 4%, 4.5% and 5% (wt %) of the composition).

For example, exemplary of a lipid-treated oncolytic virus provided herein is an emulsion containing $10^5$-$10^{12}$ pfu/mL (e.g. at least or about or $10^6$ pfu/mL, $10^7$ pfu/mL, $10^8$ pfu/mL, $10^9$ pfu/mL, $10^{10}$ pfu/mL, $10^{11}$ pfu/mL or $10^{10}$ pfu/mL) of a vaccinia virus, such as an LIVP, WR or Copenhagen virus strain, a clonal strain thereof or a modified or recombinant form encoding a heterologous gene product; a biocompatible lipid component that is a soybean oil, almond oil, canola oil, corn oil, cottonseed oil, flaxseed oil, grape seed oil, olive oil, palm oil, peanut oil, safflower oil, sesame oil, sunflower oil, and walnut oil present, or mixture thereof, as a percentage (%) by weight of the composition (wt %), for example, from at or about 2% to at or about 40% (e.g. at least 2%, 5%, 10%, 15%, 20%, 25%, 30%, 35%, and 40% (wt %) of the composition); a biocompatible emulsifier that is an egg yolk phospholipid, hydrogenated egg yolk phospholipid, soybean phospholipid, hydrogenated soybean phospholipid, or mixtures thereof present in an amount as a percentage (%) by weight of the composition (wt %), for example, from at or about 0.2% to at or about 5% (e.g. at or about or at least 0.2%, 0.5%, 1%, 1.2%, 1.5%, 2%, 2.5%, 3%, 3.5%, 4%, 4.5% and 5% (wt %) of the composition); and an aqueous solution provided in an amount for injection to achieve the appropriate concentration of components. In some examples, the lipid-treated oncolytic virus can contain a tonicity modifier, such as glycerol, present in an amount that is at or about 0.2% to at or about 5% (e.g. at or about or at least 0.2%, 0.5%, 1%, 1.5%, 2%, 2.25%, 2.5%, 3%, 3.5%, 4%, 4.5% and 5% (wt %) of the composition).

In particular examples, the lipid-treated oncolytic virus provided herein is an emulsion containing a vaccinia virus (e.g. an LIVP, WR or Copenhagen virus strain, a clonal strain thereof or a modified or recombinant form encoding a heterologous gene product) in a 10%, 20% or 30% (wt %) soybean oil intravenous fat emulsion (such as the marketed ILE formulation Intralipid®). For example, such a lipid-emulsion oncolytic virus contains $10^5$-$10^{12}$ pfu/mL (e.g. at least or about or $10^6$ pfu/mL, $10^7$ pfu/mL, $10^8$ pfu/mL, $10^9$ pfu/mL, $10^{10}$ pfu/mL, $10^{11}$ pfu/mL or $10^{10}$ pfu/mL); 10%, 20% or 30% (wt %) soybean oil; at or about 1.2% (wt %) egg yolk phospholipids; at or about 2.25% (wt %) glycerin; and an aqueous solution provided in an amount for injection to achieve the appropriate concentration of components.

If necessary to adjust the dosage of virus for administration, any of the generated lipid-treated oncolytic virus compositions can be further diluted prior to use. Generally, the composition is diluted to a virus concentration of $1\times10^7$ pfu/mL to $1\times10^9$ pfu/mL, such as generally at least $5\times10^7$, $6\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$ pfu/mL. In particular, the dilution of the lipid-treated oncolytic virus is generally in an aqueous solution that is a buffered saline solution or other isotonic solution. For example, the aqueous solution can be Ringer's solution, Ringer's lactate solution, phosphate-buffered saline (PBS), TRIS-buffered saline (TBS), Hank's balanced salt solution (HBSS), Earle's balanced salt solution (EBSS), standard saline citrate (SSC), HEPES-buffered saline (HBS), Grey's balanced salt solution (GBSS), and normal saline (NaCl).

It is understood that dilution of a lipid-treated oncolytic composition will reduce the effective concentration of all components therein. Since the lipid is affecting the virus, and is not itself acting as the active agent per se (in contrast to embodiments herein involving co-administration with a lipid emulsion), a lower concentration of lipid in the resulting administered lipid-treated composition is sufficient to effect an increased virus infectivity of the lipid-treated virus. For example, the effective concentration of the lipid component in a lipid-treated virus can be less than 3-fold or more less than, such as up to 5-fold, 10-fold or 100-fold more less, than the effective concentration of the lipid component when administered as a lipid emulsion composition separately.

Hence, the resulting lipid-treated composition for administration can contain an oncolytic virus at concentration in the resulting composition of $10^5$-$10^{10}$ pfu/mL, such as $1\times10^7$ pfu/mL to $1\times10^9$ pfu/mL; a lipid component, such as any described in Section E, present as a percentage (%) by weight of the composition (wt %), for example, from at or about 0.001% to at or about 20%, such as generally less than 10% (e.g. at least 0.001%, 0.01%, 0.1%, 1.0%, 2.0%, 3.0%, 4.0%, 5.0%, 6.0%, 7.0%, 8.0, 9.0% (wt %) of the composition); an emulsifier, such as any described in Section E, present in an amount as a percentage (%) by weight of the composition (wt %), for example, from at or about 0.0002% to at or about 5%, such as generally less than 2% (e.g. at or about or at least 0.0002%, 0.002%, 0.02%, 0.2% or 1% (wt %) of the composition); and an aqueous solution provided in an amount for injection to achieve the appropriate concentration of components (e.g. 50% and 99% (wt %)); and optionally a tonicity modifier as described in Section E in an amount that is at or about 0.0002% to at or about 5%, such as generally less than 2% (e.g. at or about or at least 0.0002%, 0.002%, 0.02%, 0.2% or 1% (wt %) of the composition).

In the lipid-treated oncolytic virus compositions provided herein, generally, the volume of the compositions is 0.01 mL to 100 mL, such as from or from about 0.1 mL to 100 mL, 1 mL to 100 mL, 10 mL to 100 mL, 0.01 mL to 10 mL, 0.1 mL to 10 mL, 1 mL to 10 mL, 0.02 mL to 20 mL, 0.05 mL to 5 mL, 0.5 mL to 50 mL, 0.5 mL to 5 mL, for example, at least or about at least or 0.05 mL, 0.5 mL or 1 mL. Hence, the resulting composition can contain an oncolytic virus (e.g. a vaccinia virus) in an amount that is from or from about $1\times10^5$ to $1\times10^{12}$ pfu, such as $1\times10^6$ to $1\times10^{10}$ pfu or $1\times10^7$ to $1\times10^{10}$ pfu, for example at least or about at least or $1\times10^6$, $1\times10^7$, $1\times10^8$, $1\times10^9$, $2\times10^9$, $3\times10^9$, $4\times10^9$, or $5\times10^9$ pfu.

c. Complement Inhibitor Compositions

Compositions containing a complement inhibitor, either separate or formulated together with an oncolytic virus or lipid-treated oncolytic virus, contain a therapeutically amount of inhibitor for single dosage or multiple dosage administration. The particular formulation and concentration of inhibitor is dependent on the particular inhibitor employed. Since such inhibitors are known to a skilled artisan, including those approved for clinical use, such concentrations are known or can be empirically determined.

In the compositions or combinations of compositions provided herein, the complement inhibitor, such as an anti-C5 antibody (e.g. eculizumab), is formulated in an amount for direct administration in a range between or between about 1 mg to 5000 mg, such as 10 mg to 5000 mg, 100 mg to 5000 mg, 100 mg to 2500 mg, 100 mg to 1000 mg, 100 mg to 500 mg, 500 mg to 5000 mg, 500 mg to 2500 mg, 500 mg to 1000 mg, 1000 mg to 2500 mg, 2000 mg to 5000 mg or 1500 mg to 2500 mg, generally at least or about at least or about 100 mg, 200 mg, 300 mg, 400 mg, 500 mg, 600 mg, 700 mg, 800 mg, 900 mg or 1000 mg. The composition can be provided as a lyophilized form for later reconstitution or as a liquid formulation.

For example, in the compositions or combinations of compositions provided herein, the complement inhibitor, such as an anti-C5 antibody (e.g. eculizumab), is formulated in an amount at a concentration of between about 0.1 mg/mL to 100 mg/mL; between about 0.5 mg/mL to 50 mg/mL; between or about 1 mg/mL to 100 mg/mL; between or about 1 mg/mL to 50 mg/mL; between or about 5 mg/mL to 50 mg/mL; between about 9 mg/mL and 90 mg/mL; between about 9 mg/mL and 50 mg/mL; between about 10 mg/mL and 50 mg/mL; between about 15 mg/mL and 50 mg/mL; between about 15 mg/mL and 100 mg/mL; between about 15 mg/mL and 100 mg/mL; between about 20 mg/mL and 100 mg/mL; between about 20 mg/mL and 80 mg/mL; between about 25 mg/mL and 100 mg/mL; between about 25 mg/mL and 85 mg/mL; between about 20 mg/mL and 50 mg/mL; between about 25 mg/mL and 50 mg/mL; between about 30 mg/mL and 100 mg/mL; between about 30 mg/mL and 50 mg/mL; between about 40 mg/mL and 100 mg/mL; between about 50 mg/mL and 100 mg/mL; or between about 20 mg/mL and 50 mg/mL.

The volume of the composition can be formulated in a volume that is 0.01 mL to 100 mL, such as from or from about 0.1 mL to 100 mL, 1 mL to 100 mL, 1 mL to 50 mL, 5 mL to 100 mL, 5 mL to 50 mL, 10 mL to 100 mL, 10 mL to 50 mL, 20 mL to 100 mL, 20 mL to 50 mL, 30 mL to 100 mL or 30 mL to 50 mL, for example, at least or about at least or 0.05 mL, 0.5 mL, 1 mL, 2 mL, 3 mL, 4 mL, 5 mL, 6 mL, 7 mL, 8 mL, 9 mL, 10 mL, 20 mL, 30 mL, 40 mL, 50 mL or more. The entire vial contents can be withdrawn for administration, or can be divided up into a plurality of dosages for multiple administration. It is understood that formulations of a complement inhibitor can contain other components, including carriers, polymers, lipids and other excipients.

For example, eculizumab, is formulated as a preservative-free formulation as a 10 mg/mL solution supplied in a 30 mL volume. Each 30 mL vial contains 300 mg of eculizumab, 13.8 mg sodium phosphate monobasic, 53.4 mg sodium phosphate dibasic, 263.1 mg sodium chloride, 6.6 mg polysorbate 80 and water for injection.

2. Combinations

Any of the combinations and compositions provided herein can be provided in further combination with an additional agent. In one example, lipid-emulsion oncolytic viruses provided herein can be provided in combination with other further agents. In some cases, the further agent can be a complement inhibitor as described elsewhere herein. In other cases, the further agent can be a different agent that is not a complement inhibitor. In still further cases, an oncolytic virus or lipid-emulsion oncolytic virus provided in combination with a complement inhibitor can also be provided in further combination with another additional agent. The choice of additional agent can depend on the particular virus being employed, the particular treatment or diagnosis to be achieved, the disease being treated, the severity or extent of the disease or condition, the health of the subject being treated and other factors within the level of a skilled artisan.

In examples of combinations herein, an additional agent can be a second virus or lipid-emulsion oncolytic virus, other agent to increase infectivity of the virus or other therapeutic or diagnostic agent. For example, the additional agent can be a therapeutic compound, a therapeutic or diagnostic virus, an antiviral or chemotherapeutic agent or an agent or compound for modulation of gene expression of endogenous or heterologous genes encoded by the virus.

For example, combinations provided herein can contain an additional agent that is a therapeutic compound. Therapeutic compounds for the combinations provided herein can be, for example, an anti-cancer or chemotherapeutic compound. Exemplary therapeutic compounds include, for example, cytokines, growth factors, photosensitizing agents, radionuclides, toxins, siRNA molecules, enzyme/prodrug pairs, anti-metabolites, signaling modulators, anti-cancer antibiotics, anti-cancer antibodies, angiogenesis inhibitors, chemotherapeutic compounds, antimetastatic compounds or a combination of any thereof. Viruses provided herein can be combined with an anti-cancer compound, such as a platinum coordination complex. Exemplary platinum coordination complexes include, for example, cisplatin, carboplatin, oxaliplatin, DWA2114R, NK121, IS 3 295, and 254-S. Exemplary chemotherapeutic agents also include, but are not limited to, methotrexate, vincristine, adriamycin, non-sugar containing chloroethylnitrosoureas, 5-fluorouracil, mitomycin C, bleomycin, doxorubicin, dacarbazine, taxol, fragyline, Meglamine GLA, valrubicin, carmustine, polifeprosan, MM1270, BAY 12-9566, RAS farnesyl transferase inhibitor, farnesyl transferase inhibitor, MMP, MTA/LY231514, lometrexol/LY264618, Glamolec, CI-994, TNP-470, Hycamtin/topotecan, PKC412, Valspodar/PSC833, Novantrone/mitoxantrone, Metaret/suramin, BB-94/batimastat, E7070, BCH-4556, CS-682, 9-AC, AG3340, AG3433, Incel/VX-710, VX-853, ZD0101, IS1641, ODN 698, TA 2516/marimastat, BB2516/marimastat, CDP 845, D2163, PD183805, DX8951f, Lemonal DP 2202, FK 317, picibanil/OK-432, valrubicin/AD 32, strontium-89/Metastron, Temodal/temozolomide, Yewtaxan/paclitaxel, Taxol/paclitaxel, Paxex/paclitaxel, Cyclopax/oral paclitaxel, Xeloda/capecitabine, Furtulon/doxifluridine, oral taxoids, SPU-077/cisplatin, HMR 1275/flavopiridol, CP-358 (774)/EGFR, CP-609 (754)/RAS oncogene inhibitor, BMS-182751/oral platinum, UFT(Tegafur/Uracil), Ergamisol/levamisole, Campto/levamisole, Eniluracil/776C85/5FU enhancer, Camptosar/irinotecan, Tomudex/raltitrexed, Leustatin/cladribine, Caelyx/liposomal doxorubicin, Myocet/liposomal doxorubicin, Doxil/liposomal doxorubicin, Evacet/liposomal doxorubicin, Fludara/fludarabine, Pharmorubicin/epirubicin, DepoCyt, ZD1839, LU 79553/Bis-Naphthalimide, LU 103793/Dolastain, Gemzar/gemcitabine, ZD 0473/Anormed, YM 116, Iodine seeds, CDK4 and CDK2 inhibitors, PARP inhibitors, D4809/dexifosfamide, Ifex/Mesnex/ifosfamide, Vumon/teniposide, Paraplatin/carboplatin, Platinol/cisplatin, VePesid/Eposin/Etopophos/etoposide, ZD 9331, Taxotere/docetaxel, prodrugs of guanine arabinoside, taxane analogs, nitrosoureas, alkylating agents such as melphalan and cyclophosphamide, aminoglutethimide, asparaginase, busulfan, carboplatin, chlorambucil, cytarabine HCl, dactinomycin, daunorubicin HCl, estramustine phosphate sodium, etoposide (VP16-213), floxuridine, fluorouracil (5-FU), flutamide, hydroxyurea (hydroxycarbamide), ifosfamide, interferon alfa-2a, interferon alfa-2b, leuprolide acetate (LHRH-releasing factor analogue), lomustine (CCNU), mechlorethamine HCl (nitrogen mustard), mercaptopurine, mesna, mitotane (o,p'-DDD), mitoxantrone HCl, octreotide, plicamycin, procarbazine HCl, streptozocin, tamoxifen citrate, thioguanine, thiotepa, vinblastine sulfate, amsacrine (m-AMSA), azacitidine, erythropoietin, hexamethylmelamine (HMM), interleukin 2, mitoguazone (methyl-GAG; methyl glyoxal bis-guanylhydrazone; MGBG), pentostatin (2'deoxycoformycin), semustine (methyl-CCNU), teniposide (VM-26) and vindesine sulfate. Additional exemplary therapeutic compounds for the use in pharmaceutical compositions and combinations provided herein include cytokines, growth factors, photosensitizing agents, radionuclides, toxins, siRNA molecules, enzyme/pro-drug pairs, anti-metabolites, signaling modulators, anti-cancer antibiotics, anti-cancer antibodies, angiogenesis inhibitors, and chemotherapeutic compounds.

Other exemplary therapeutic compounds include, for example, compounds that are substrates for enzymes encoded and expressed by the virus, or other therapeutic compounds provided herein or known in the art to act in concert with a virus. For example, the virus can express an enzyme that converts a prodrug into an active chemotherapy drug for killing the cancer cell. Hence, combinations provided herein can contain a therapeutic compound, such as a prodrug. An exemplary virus/therapeutic compound combination can include a virus encoding Herpes simplex virus thymidine kinase with the prodrug ganciclovir. Additional exemplary enzyme/pro-drug pairs, for the use in combinations provided include, but are not limited to, varicella zoster thymidine kinase/ganciclovir, cytosine deaminase/5-fluorouracil, purine nucleoside phosphorylase/6-methylpurine deoxyriboside, beta lactamase/cephalosporin-doxorubicin, carboxypeptidase G2/4-[(2-chloroethyl)(2-mesyloxyethyl)amino]benzoyl-L-glutamic acid, cytochrome P450/acetominophen, horseradish peroxidase/indole-3-acetic acid, nitroreductase/CB1954, rabbit carboxylesterase/7-ethyl-10-[4-(1-piperidino)-1-piperidino]carbonyloxycamptothecin (CPT-11), mushroom tyrosinase/bis-(2-chloroethyl)amino-4-hydroxyphenylaminomethanone 28, beta galactosidase/1-chloromethyl-5-hydroxy-1,2-dihydro-3H-benz[e]indole, beta glucuronidase/epirubicin-glucuronide, thymidine phosphorylase/5'-deoxy-5-fluorouridine, deoxycytidine kinase/cytosine arabinoside, beta-lactamase and linamerase/linamarin. Any of a variety of known combinations provided herein or otherwise known in the art can be included in the combinations provided herein.

In some examples, the combination can include compounds that can kill or inhibit viral growth or toxicity. Such compounds can be used to alleviate one or more adverse side effects that can result from viral infection (see, e.g. U.S. Patent Pub. No. US 2009-0162288-A1). Combinations provided herein can contain antibiotic, antifungal, anti-parasitic or antiviral compounds for treatment of infections. In some examples, the antiviral compound is a chemotherapeutic agent that inhibits viral growth or toxicity. Exemplary antibiotics which can be included in a combination with a virus provided herein include, but are not limited to, ceftazidime, cefepime, imipenem, aminoglycoside, vancomycin and antipseudomonal β-lactam. Exemplary antifungal agents which can be included in a combination with a virus provided herein include, but are not limited to, amphotericin B, dapsone, fluconazole, flucytosine, griseofulvin, itraconazole, ketoconazole, miconazole, clotrimazole, nystatin, and combinations thereof. Exemplary antiviral agents can be included in a combination with a virus provided herein include, but are not limited to, cidofovir, alkoxyalkyl esters of cidofovir (CDV), cyclic CDV, and (S)-9-(3-hydroxy-2 phosphonylmethoxypropyl)adenine, 5-(dimethoxymethyl)-2'-deoxyuridine, isatin-beta-thiosemicarbazone, N-methanocarbathymidine, brivudine, 7-deazaneplanocin A, ST-246, Gleevec, 2'-beta-fluoro-2',3'-dideoxyadenosine, indinavir, nelfinavir, ritonavir, nevirapine, AZT, ddI, ddC, and combinations thereof. Typically, combinations with an antiviral agent contain an antiviral agent known to be effective against the virus of the combination. Exemplary antiviral compounds include, for example, cidofovir, alkoxyalkyl esters of cidofovir, ganciclovir, acyclovir, ST-246, Gleevec, and derivatives thereof.

In some examples, the combination can include a detectable compound. A detectable compound can include, for example, a ligand, substrate or other compound that can interact with and/or bind specifically to a protein or RNA encoded and expressed by the virus, and can provide a detectable signal, such as a signal detectable by tomographic, spectroscopic, magnetic resonance, or other known techniques. In some examples, the protein or RNA is an exogenous protein or RNA. In some examples, the protein or RNA expressed by the virus modifies the detectable compound where the modified compound emits a detectable signal. Exemplary detectable compounds can be, or can contain, an imaging agent such as a magnetic resonance, ultrasound or tomographic imaging agent, including a radionuclide. The detectable compound can include any of a variety of compounds as provided elsewhere herein or are otherwise known in the art. Exemplary proteins that can be expressed by the virus and a detectable compound combinations employed for detection include, but are not limited to luciferase and luciferin, β-galactosidase and (4,7,10-tri (acetic acid)-1-(2-β-galactopyranosylethoxy)-1,4,7,10-tetraazacyclododecane) gadolinium (Egad), and other combinations known in the art.

In some examples, the combination can include a gene expression modulating compound that regulates expression of one or more genes encoded by the virus. Compounds that modulate gene expression are known in the art, and include, but are not limited to, transcriptional activators, inducers, transcriptional suppressors, RNA polymerase inhibitors and RNA binding compounds such as siRNA or ribozymes. Any of a variety of gene expression modulating compounds known in the art can be included in the combinations provided herein. Typically, the gene expression modulating compound included with a virus in the combinations provided herein will be a compound that can bind, inhibit or react with one or more compounds, active in gene expression such as a transcription factor or RNA of the virus of the combination. An exemplary virus/expression modulator combinations can be a virus encoding a chimeric transcription factor complex having a mutant human progesterone receptor fused to a yeast GAL4 DNA-binding domain an activation domain of the herpes simplex virus protein VP16 and also containing a synthetic promoter containing a series of GAL4 recognition sequences upstream of the adenovirus major late E1B TATA box, where the compound can be RU486 (see, e.g., Yu et al., (2002) *Mol Genet Genomics* 268:169-178). A variety of other virus/expression modulator combinations known in the art also can be included in the combinations provided herein.

In some examples, the combination can contain one or more additional therapeutic and/or diagnostic viruses or other therapeutic and/or diagnostic microorganism (e.g. therapeutic and/or diagnostic bacteria) for diagnosis or treatment. Exemplary therapeutic and/or diagnostic viruses are known in the art and include, but are not limited to, therapeutic and/or diagnostic poxviruses, herpesviruses, adenoviruses, adeno-associated viruses, and reoviruses.

3. Packaging and Articles of Manufacture

For purposes herein, the compositions typically are provided separately (e.g. lipid-emulsion oncolytic virus or oncolytic virus; complement inhibitor; and, optionally an additional agent). The lipid-emulsion oncolytic virus or oncolytic virus; complement inhibitor; and, optionally an additional agent can be packaged as separate compositions for administration together, sequentially or intermittently. In some examples, an oncolytic virus and a prepared lipid emulsion (e.g. ILE composition) are packaged in a kit separately for extemperaneous preparation of a lipid-emulsion oncolytic virus. The combinations can be packaged as a kit.

Hence, selected combinations and compositions also can be provided as kits. Kits can include a pharmaceutical composition or combination described herein and optionally, include instructions for application including dosages, dosing regimens and instructions for modes of administration. Kits also can include a pharmaceutical composition described herein and an item for diagnosis. The kits also can include pharmaceutical compositions or combinations described herein, and an item for administration provided as an article of manufacture.

Also provided are articles of manufacture containing packaging materials, any pharmaceutical composition or combination provided herein, and a label that indicates that the compositions and combinations are to be used for treatment of proliferative disorders, for example cancers. Exemplary of articles of manufacture are containers including single chamber and dual chamber containers. The containers include, but are not limited to, tubes, bottles and syringes. The containers can further include a needle for intravenous or subcutaneous administration. The agents can be provided together or separately, for packaging as articles of manufacture.

The articles of manufacture provided herein contain packaging materials. Packaging materials for use in packaging pharmaceutical products are well known to those of skill in the art. See, for example, U.S. Pat. Nos. 5,323,907, 5,052,558 and 5,033,252, each of which is incorporated herein in its entirety. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The choice of package depends on the agents, and whether such compositions will be packaged together or separately. In general, the packaging is non-reactive with the compositions contained therein. In other examples, some of the components can be packaged as a mixture. In other examples, all components are packaged separately. Thus, for example, the components can be packaged as separate compositions that, upon mixing just prior to administration, can be directly administered together. For example, an oncolytic virus and a lipid emulsion preparation can be packaged as separate compositions that can be mixed together to pre-treat the virus prior to use. Alternatively, the components can be packaged as separate compositions for administration separately.

The components can be packaged in a container. The components can be separately packaged in the same container. Generally, examples of such containers include those that have an enclosed, defined space that contains the polymer-conjugated hyaluronan-degrading enzyme, and a separate enclosed, defined space containing the other components or component such that the subsequent areas are separated by a readily removable membrane which, upon removal, permits the components to mix, or which permits the components to be separately administered. Any container or other article of manufacture is contemplated, so long as the agents are separated from the other components prior to administration. For suitable embodiments see e.g., containers described in U.S. Pat. Nos. 3,539,794 and 5,171,081.

G. Methods of Assessing Infectivity and Virus Activity

The combinations and compositions provided herein can be tested to determine the infectivity of the oncolytic virus (e.g. vaccinia virus) contained therein, including its anti-tumorigenicity for infection of tumor cells. Assays also can be performed to assess the toxicity or safety. Such assays are well known in the art, and exemplary of such assays are described below. For example, compositions and combinations provided herein, including compositions containing a lipid-treated virus (e.g. lipid-treated virus emulsion) is tested in one or more in vitro and/or in vivo assays that assess infectivity, such as viral titer, viral nucleic acid replication, virus production, viral gene expression from tumor cells, effects on the host cell, cytotoxicity of tumor cells, tumor cell selectivity, tumor cell type selectivity, specific and nonspecific immune response, and therapeutic efficacy. The activity of the virus when administered as an adjunct therapy with another agent, e.g. as a combination or composition with a complement inhibitor (e.g. anti-C5 antibody) or lipid emulsion (e.g. lipid-treated virus) can be compared to the activity of the virus in the absence of the adjunct therapy.

1. Viral Infectivity and Anti-Tumorigenicity

Assays or methods to assess viral infectivity or anti-tumorigenicity are well-known in the art (see e.g. U.S. Patent Pub. No. US-2009-0136917 and US-2012-0308484). Typically, any assay assesses the property or ability of the oncolytic virus to infect target cells, such as tumor cells, when provided as a combination or composition as described herein. Such properties or activities include, but are not limited to, virus titer, virus clearance, receptor binding to a target cell (e.g. tumor cell), target cell (e.g. tumor cell) uptake, or virus replication and gene expression. The assays generally are performed in the presence of or following exposure or incubation of virus or other adjunct therapy with components that typically inactivate the virus. For example, assays are performed in the presence of a bodily fluid, such as blood or serum or other bodily fluid. The bodily fluid is typically a fluid that contains immunomodulatory proteins. In particular, the bodily fluid contains components of the complement system. The bodily fluid also can contain cells, such as immune cells. The assays can be performed in vitro or in vivo.

The assay can be performed in vitro. For example, an oncolytic virus composition can be exposed or incubated with a bodily fluid (e.g. serum, such as human serum) for a predetermined time in the presence or absence of an adjunct therapy. The predetermined time generally is a time period that results in inactivation, clearance or reduced infectivity of the virus in the absence of the adjunct therapy. Such time period can be determined empirically by a skilled artisan, and is dependent on the particular type of bodily fluid. For example, as shown in the Examples herein, exposure of virus to serum for up to 30 minutes results in inactivation of virus as evidenced by an over 2-fold decreased recovery of virus. Generally, the predetermined time is 5 minutes to 6 hours, and generally at least 10 minutes, 20 minutes, 30 minutes, 45 minutes, 1 hour, 2 hours or more.

For example, in examples where the adjunct therapy is provided as a composition (e.g. lipid-treated virus), the bodily fluid is treated with the oncolytic virus composition for a predetermined time, such as a time between or between about 20 minutes to 2 hours, such as at least or about 30 minutes. In other examples where the virus is provided separately from the additional agent in the adjunct therapy (e.g. complement inhibitor or lipid emulsion), the bodily fluid can be treated with the agent and virus simultaneously, where each are provided separately. Alternatively, the bodily fluid is first pretreated with the agent prior to treatment with the virus. The time period for pretreatment of the bodily fluid can be empirically determined by a skilled artisan. For example, a time course experiment can be performed. Generally, the time period is 5 minutes to 6 hours, and generally at least 10 minutes, 20 minutes, 30 minutes, 45 minutes, 1 hour, 2 hours or more. The pretreated bodily fluid is then treated with an oncolytic virus composition for the predetermined time.

In any of such examples, the infectivity of the virus in the bodily fluid can be assessed by monitoring the virus recovery or titer in the bodily fluid. For example, a standard plaque assay can be used. Titration of virus by plaque assay is known to one of skill in the art. Typically, serial dilutions of the bodily fluid treated with virus is made, and diluted virus is added to a monolayer of cells, for example, monolayers of permissive cell line, such as, for example, CV-1, Vero, BHK, RK13 or HEK-293 cell line, and incubated with virus. In some examples, the plaque assay can be performed directly on a cell monolayer of a tumor cells provided that the tumor cells can form a monolayer. Following incubation, an agarose overlay is added to the monolayer of cells without dislodging the cells, and the plate is further incubated until plaques become visible. A dye or color stain solution that is taken up by healthy cells but not dead cells, such as neutral red, is added to each of the wells or the plate. After incubation, the dye or stain is removed such that the plaques are observed to be clear, while non-lysed cells remain stained. Titer (pfu/mL) is calculated by counting the number of plaques in the well and dividing by the dilution factor (d) and the volume (V) of diluted virus added to the well (# plaques/d×V). The virus yield can be converted to pfu/cell by dividing the total amount of virus present in the sample by the number of cells originally infected in the sample.

Alternatively, the bodily fluid containing virus can be assessed for the ability of the virus to infect target cells (e.g. tumor cells). For example, assays to assess infectivity of tumor cells include, but are not limited to viral titer (as assessed by the number of plaques produced in a plaque assay) or the changes in viral gene expression or host gene expression (see, e.g. U.S. Patent Pub. No. 2009-0136917). Assays to assess infectivity can be assessed on cell lysates of cells infected in vitro with any of the compositions provided herein containing an oncolytic virus (e.g. vaccinia virus), for example, various tumor cell lines, primary tissues or cells as well as tumor cells such as from a biopsy. For example, a tissue or cell sample can be obtained (e.g., biopsy) from a subject (e.g., human or non-human animal subject), and the sample can be infected with one or more types of viruses. In other examples, tumor cell lines can be used. Tumor cell lines are known and available to one of skill in the art, for example, from the American Type Culture Collection (ATTC; Manassas, Va.) or from the European Collection of Cell Cultures (ECACC). Tumor cell lines also are available from the Division of Cancer Treatment and Diagnosis (DCTD) Tumor Repository (National Cancer Institute/National Institute of Health; dtp.nih.gov/index.html.) Exemplary of tumor cell lines include human and other animal cell lines and include, but are not limited to, DU145 human prostate carcinoma cells, LNCaP human prostate cancer cells, MCF-7 human breast cancer cells, MRC-5 human lung fibroblast cells, MDA-MB-438 human breast cancer cells, MDA-MB-231 human breast carcinoma cells, PC3 human prostate cancer cells, T47D human breast cancer cells, THP-1 human acute myeloid leukemia cells, U87 human glioblastoma cells, SH-SY5Y human neuroblastoma cells, Saos-2 human cells, A549 human lung carcinoma cells, A2780 human ovarian carcinoma cells, HCT 116 human colon cells, HT-29 human colon cells, SW260 human colon cells, HT-180 human fibrosarcoma, MIA PaCa-2 human pancreatic carcinoma cells, PANC-1 human pancreatic cells, CMT 64 C57BL/6 mouse cell, JC mouse mammary cells, TIB-75 mouse hepatic cells, CT26 WT mouse colon carcinoma cells, MC-38 mouse adenocarcinoma cells, B16-F10 mouse melanoma cells, 4T1 murine mammary carcinoma cells and hamster pancreatic tumor HP-1 cells.

In particular examples, infectivity is assessed in vivo. For example, combinations or compositions provided herein containing an oncolytic virus can be administered to a subject (e.g. human or non-human animal subject) and properties or activities indicative of infectivity can be monitored and compared to administration of the virus alone in absence of the adjunct therapy. For example, following administration of an adjunct therapy herein (e.g. as a composition or combination with an oncolytic virus), a bodily fluid (e.g. blood or serum) can be collected and virus titer directly determined. Alternatively, target cells (e.g. tumor cells) can be harvested, and plaque assays performed on supernatants or cells lysates of tumors or cells infected with the virus using a standard plaque assay as described above.

Pharmacokinetics (PK) and pharmacodynamics (PD) assays of oncolytic virus (e.g. vaccinia virus) in the adjunct therapies provided herein can be performed using methods described herein or known in the art (see, e.g., Klutchko, et al., (1998) *J. Med. Chem.* 41:3276-3292). Examples of parameters of measurement generally include the maximum (peak) plasma concentration ($C_{max}$), the peak time (i.e. when maximum plasma concentration occurs; $T_{max}$), the minimum plasma concentration (i.e. the minimum plasma concentration between doses; $C_{min}$), the elimination half-life ($T_{1/2}$) and area under the curve (i.e. the area under the curve generated by plotting time versus plasma concentration; AUC), following administration. The concentration of virus in the plasma following administration can be measured using any method known in the art suitable for assessing concentrations of virus in samples of blood, and typically includes any assay that measures viral titer or is indicative of viral titer, such as a standard plaque assay. PK and PD assays can be performed in any animal model described herein or known in the art, including healthy animal models, diseased animal models (e.g. tumor models) and humans.

In vivo parameters associated with infection of target cells (e.g. tumor cells) can be assessed. Such properties or activities include, but are not limited to, a desirable therapeutic index in an animal model of cancer, release of tumor antigens and preferential accumulation of the virus in tumor tissues following administration. Other indicators of infectivity of target cells also can be assessed. For example, expression of viral genes, tumor proteins and/or housekeeping genes that are correlated with viral replication and/or infectivity in tumor cells can be assessed (see e.g. U.S. Patent Pub. No. 2009-0136917).

Other indirect effects resulting from virus infection of cells can be assessed. A virus can destroy tumor cells by replicating such that continual amplification of the virus results in infection of adjacent cells and their subsequent destruction. Oncolytic viruses also exhibit anti-tumorigenicity by expression of proteins that are cytotoxic to cancer cells. In further examples, viruses can exhibit anti-tumorigenicity by initiating specific and nonspecific anti-tumor immune responses, for example, the initiation of cytokine expression from infected cells (e.g. TNF) or through a specific response (e.g. CTL response). Hence, any of the above parameters can be assessed as indicative of anti-tumorigenicity, and hence infectivity, of a virus.

Virus compositions, provided as a combination or composition in the adjunct therapies provided herein, can be tested to determine if they are cytotoxic or kill tumor cells. For example, viruses can eliminate tumor cells via induction of cell death and/or lysis of the tumor cell (i.e. oncolysis). The cell killing activity of the virus can be assessed by a variety of techniques known in the art including, but not limited to, cytotoxicity/cell viability assays that can be employed to measure cell necrosis and/or apoptosis following virus infection, such as MTT (3-(4,5-dimethylthiazol-2-yl)-2,5-diphenyltetrazolium bromide) assays and other related tetrazolium salt based assays (e.g. XTT, MTS or WST), ATP assays, apoptosis assays, such as TUNEL staining of infected cells, DNA fragmentation assays, DNA laddering assays, and cytochrome C release assays. Such assays are well known to one of skill in the art.

Virus compositions, provided as a combination or composition in the adjunct therapies provided herein, can be tested to determine if the virus causes shrinkage of tumor size and/or delays tumor progression. Tumor size can be assessed in vivo in tumor-bearing human or animal models treated with virus. Tumor shrinkage or tumor size can be assessed by various assays known in art, such as, by weight, volume or physical measurement. For example, tumor-bearing animal models can be generated using methods well-known in the art, including xenograft models or syngeneic models are used. Tumor size and volume can be monitored based on techniques known to one of skill in the art. For example, tumor size and volume can be monitored by radiography, ultrasound imaging, necropsy, by use of calipers, by microCT or by $^{18}$F-FDG-PET. Tumor size also can be assessed visually. In particular examples, tumor size (diameter) is measured directly using calipers. In other examples, tumor volume can be measured using an average of measurements of tumor diameter (D) obtained by caliper or ultrasound assessments. The volume can be determined from the formula $V=D^3 \times \pi/6$ (for diameter measured using calipers) or $V=D^2 \times d \times \pi/6$ (for diameter measured using ultrasound where d is the depth or thickness). In additional examples, tumors can be harvested from the animals and weighed. In further examples, the harvested tumors can be lysed. For example, lysis of tumors can be by freeze thaw of the harvested tumor several times (e.g. at least 2 times, 3 times or 4 times) shortly after removal of the tumor from the animal. For example, the tumor is lysed by 3 freeze thaw cycles within 2 hours of removal. The virus in the tumor lysates can be titered as described above and the amount of virus in each tumor sample determined. In some examples, the virus titer can be expressed as tissue culture infectious dose normalized to the tissue weight ($TCID_{50}$/mg tissue). In particular examples, the effect of the virus on other organs or tissues in the animal can be assessed. For example, other organs can be harvested from the animals, weighed and/or lysed for viral titer determination.

2. Toxicity/Safety

The adjunct therapies provided herein with an oncolytic virus can be tested for parameters indicative of its toxicity/safety property. Viruses can be toxic to their hosts by manufacturing one or more compounds that worsen the health condition of the host. Toxicity to the host can be manifested in any of a variety of manners, including septic shock, neurological effects, or muscular effects. Typically, vaccinia virus exhibits minimal to no toxicity to a host, such that the host does not die or become severely ill from the toxic effects of the virus. For example, the viruses are not toxic or exhibit minimal toxicity if a host typically has no significant long-term effect from the presence of the viruses in the host, beyond any effect on tumorous, metastatic or necrotic organs or tissues. For example, minimal toxicity can be a minor fever or minor infection, which lasts for less than about a month, and following the fever or infection, the host experiences no adverse effects resultant from the fever or infection. In another example, the minimal toxicity can be measured as an unintentional decline in body weight of about 5% or less for the host after administration of the virus. In other examples, the virus has no toxicity to the host.

Parameters indicative of toxicity or safety of a virus can be tested in vitro or in vivo. Typically, assessment is in vivo. Exemplary methods include administration of the virus to a subject (e.g. animal model) and assessment of one or more properties associated with toxicity including, but not limited to, survival of the subject, decrease in body weight, existence of side effects such as fever, rash or other allergy, fatigue or abdominal pain, induction of an immune response in the subject, tissue distribution of the virus, amount of tumor antigens that are released and decreased rate of pock formation. Hence, any of the above parameters can be assessed as indicative of toxicity/safety of a virus.

H. Adjunct Therapy for Increasing Viral Infectivity

Oncolytic virus adjunct therapies provided herein, such as combinations or compositions of an oncolytic virus and a complement inhibitor (e.g. anti-C5 antibody) or a lipid emulsion (e.g. lipid-treated virus), can be used in therapeutic methods and uses in which an oncolytic virus is employed. In particular, the combinations and compositions provided herein are particularly suitable for treatment of hyperproliferative diseases or conditions, such as in the treatment of tumors or cancers. If the virus encodes a detectable protein, the adjunct therapy also can be used in methods of diagnosis of a hyperproliferative disease or disorder or monitoring of treatments with a hyperproliferative disease or disorder.

For example, compositions and combinations provided herein that include an oncolytic virus (e.g. vaccinia virus) and biocompatible lipid (e.g. an LCT, such as in soybean oil), for example co-formulation of an oncolytic virus with a lipid or lipid emulsion (e.g. lipid-treated virus) or co-administration of an oncolytic virus and a lipid emulsion, can be used in therapeutic or diagnostic methods in which an oncolytic virus (e.g. vaccinia virus) is employed or can be employed. In other examples, the compositions and combinations provided herein that include an oncolytic virus (e.g., a vaccinia virus) and a complement inhibitor (e.g. anti-C5 antibody, such as eculizumab), can be used in therapeutic or diagnostic methods in which an oncolytic virus (e.g. vaccinia virus) is employed or can be employed. In such examples, the compositions and combinations for use in the methods and uses provided herein can contain an oncolytic virus (e.g., a vaccinia virus), a complement inhibitor (e.g. anti-C5 antibody) and also optionally a biocompatible lipid components (e.g. lipid emulsion containing a biocompatible lipid) that is formulated together or separately from the oncolytic virus. For example, the compositions and combinations for use in the methods and uses provided herein can include an oncolytic virus that is a lipid-treated virus and a complement inhibitor (e.g. anti-C5 antibody).

Because the active agent in the adjunct therapy (i.e. the complement inhibitor or lipid emulsion) increases virus infectivity, there is more effective virus available after initial immune clearance. This means that the same anti-tumor effect can be achieved with a lower dose of virus in the adjunct therapy as achieved by a higher dose of virus when the oncolytic virus is not administered in combination with an additional agent as provided herein. Likewise, the adjunct therapy herein also permits the use of a significantly higher dose of input virus (i.e. a dose of virus without dose limiting toxicity), which could translate into higher titer of virus surviving immune clearance and greater therapeutic efficacy because more virus can reach the tumor.

The combinations and compositions provided herein can be used or modified for use in any known methods (or uses) in which oncolytic viruses have been employed or can be employed (see e.g. U.S. Pub. Nos. US2003-0059400, US2003-0228261, US2009-0117034, US2009-0098529, US2009-0053244, US2009-0081639 and US2009-0136917; U.S. Pat. Nos. 7,588,767 and 7,763,420; and International Pub. No. WO 2009/139921). Any oncolytic virus, and in particular any vaccinia virus, such as any LIVP virus (e.g. the GLV-1h68 virus and derivatives thereof) can be used in the combination or compositions herein for use in therapeutic and diagnostic methods described below and discussed throughout the disclosure herein.

The diagnostic and therapeutic methods provided herein include, but are not limited to, delivering a combinations or compositions provided herein to a subject containing a tumor and/or metastases or wound. In one example, in examples of treatments or methods provided herein, delivery of the composition can be effected by systemic administration, for example intravenous administration of the composition to the subject. The subject can be any subject, such as an animal subject, including mammal or avian species. For example, the animal subject can be a human or non-human animal including, but not limited to, a goat, sheep, horse, cat, or dog. In particular examples, the animal subject is a human subject.

The composition and combinations provided herein also can be used in further combination with other treatments. For example, treatment also can be accomplished by perfusion, direct injection or local application of the area with an additional anti-cancer therapy. Such treatment can be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

1. Hyperproliferative Disease or Disorder

The combination and compositions provided herein can be used for the treatment of disease or conditions associated with immunoprivileged cells or tissues, including proliferative disorders or conditions, including the treatment (such as inhibition) of cancerous cells, neoplasms, tumors, metastases, cancer stem cells, and other immunoprivileged cells or tissues, such as wounds and wounded or inflamed tissues.

In particular, provided herein are methods of treating cancerous cells, neoplasms, tumors, metastases and cancer stem cells. The viruses in the combinations and compositions provided herein preferentially accumulate in tumors or metastases. In some examples, the administration of a virus provided herein results in a slowing of tumor growth, and in some cases an inhibition in tumor growth. In other examples, the administration of a virus provided herein results in a decrease in tumor volume, including elimination or eradication of the tumor.

Methods of reducing or inhibiting tumor growth, inhibiting metastasis growth and/or formation, decreasing the size of a tumor or metastasis, eliminating a tumor or metastasis and/or cancer stem cell or other tumor therapeutic methods provided herein include causing or enhancing an anti-tumor immune response in the host. The immune response of the host, being anti-tumor in nature, can be mounted against tumors and/or metastases in which viruses have accumulated, and can also be mounted against tumors and/or metastases in which viruses have not accumulated, including tumors and/or metastases that form after administration of the virus to the subject. Hence, the virus compositions provided for administration in the combinations and compositions herein can be used in methods to inhibit or prevent recurrence of a neoplastic disease or new tumor growth, where the methods include administering to a subject an adjunct therapy provided herein containing a composition containing an oncolytic virus, whereby the virus can accumulate in a tumor and/or metastasis, and can cause or enhance an anti-tumor immune response, and the anti-tumor immune response can inhibit or prevent recurrence of a neoplastic disease or inhibit or prevent new tumor growth.

For example, viruses in the combinations or compositions provided herein, when administered or delivered to a subject, can be used to stimulate humoral and/or cellular immune response, induce strong cytotoxic T lymphocytes responses in subjects who can benefit from such responses. For example, the virus can provide prophylactic and therapeutic effects against a tumor infected by the virus or other infectious diseases, by rejection of cells from tumors or lesions using viruses that express immunoreactive antigens (Earl et al., *Science* 234: 728-831 (1986); Lathe et al., *Nature* (London) 32: 878-880 (1987)), cellular tumor-associated antigens (Bernards et al., *Proc. Natl. Acad. Sci. USA* 84: 6854-6858 (1987); Estin et al., *Proc. Natl. Acad. Sci. USA* 85: 1052-1056 (1988); Kantor et al., *J. Natl. Cancer Inst.* 84: 1084-1091 (1992); Roth et al., *Proc. Natl. Acad. Sci. USA* 93: 4781-4786 (1996)) and/or cytokines (e.g., IL-2, IL-12), costimulatory molecules (B7-1, B7-2) (Rao et al., *J. Immunol.* 156: 3357-3365 (1996); Chamberlain et al., *Cancer Res.* 56: 2832-2836 (1996); Oertli et al., *J. Gen. Virol.* 77: 3121-3125 (1996); Qin and Chatterjee, *Human Gene Ther.* 7: 1853-1860 (1996); McAneny et al., *Ann. Surg. Oncol.* 3: 495-500 (1996)), or other therapeutic proteins.

Methods of adjunct therapy provided herein that includes administering a composition containing a virus also can cause tumor cell lysis or tumor cell death. For example viruses, such as the viruses in combinations and compositions provided herein, can cause cell lysis or tumor cell death as a result of expression of an endogenous gene or as a result of an exogenous gene. Endogenous or exogenous genes can cause tumor cell lysis or inhibit cell growth as a result of direct or indirect actions, as is known in the art, including lytic channel formation or activation of an apoptotic pathway. Gene products, such as exogenous gene products can function to activate a prodrug to an active, cytotoxic form, resulting in cell death where such genes are expressed.

As shown previously, solid tumors can be treated with viruses, such as vaccinia viruses, resulting in an enormous tumor-specific virus replication, which can lead to tumor protein antigen and viral protein production in the tumors (U.S. Patent Publication No. 2005-0031643, now U.S. Pat. Nos. 7,588,767, 7,588,771, 7,662,398), which provide and exemplify the GLV-1h68 virus and derivatives thereof. Vaccinia virus administration to mice resulted in lysis of the infected tumor cells and a resultant release of tumor-cell-specific antigens. Continuous leakage of these antigens into the body led to a very high level of antibody titer (in approximately 7-14 days) against tumor proteins, viral proteins, and the virus encoded engineered proteins in the mice. The newly synthesized anti-tumor antibodies and the enhanced macrophage, neutrophils count were continuously delivered via the vasculature to the tumor and thereby provided for the recruitment of an activated immune system against the tumor. The activated immune system then eliminated the foreign compounds of the tumor including the viral particles. This interconnected release of foreign antigens boosted antibody production and continuous response of the antibodies against the tumor proteins to function like an autoimmunizing vaccination system initiated by vaccinia viral infection and replication, followed by cell lysis, protein leakage and enhanced antibody production.

In one example, the tumor treated is a cancer or neoplastic disease, such as carcinoma, sarcoma, lymphoma or leukemia. For example, the cancer is a pancreatic cancer, non-small cell lung cancer, multiple myeloma or leukemia, although the cancer is not limited in this respect, and other metastatic diseases can be treated by the combinations provided herein. For example, the tumor can be a tumor of the lung and bronchus, breast, colon and rectum, kidney, stomach, esophagus, liver and intrahepatic bile duct, urinary bladder, brain and other nervous system, head and neck, oral cavity and pharynx, cervix, uterine corpus, thyroid, ovary, testes, prostate, malignant melanoma, cholangiocarcinoma, thymoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS. Exemplary tumors include, for example, pancreatic tumors, ovarian tumors, lung tumors, colon tumors, prostate tumors, cervical tumors and breast tumors. In one example, the tumor is a carcinoma such as, for example, an ovarian tumor or a pancreatic tumor.

In particular, the methods can be used for treating solid tumors that include, but are not limited to, sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The methods also can be used for treatment of cancers that metastasize. It is understood by those in the art that metastasis is the spread of cells from a primary tumor to a noncontiguous site, usually via the bloodstream or lymphatics, which results in the establishment of a secondary tumor growth. Examples of cancers contemplated for treatment include, but are not limited to melanoma, bladder, non-small cell lung, small cell lung, lung, hepatocarcinoma, retinoblastoma, astrocytoma, glioblastoma, neuroblastoma, head, neck, breast, pancreatic, gum, tongue, prostate, renal, bone, testicular, ovarian, mesothelioma, cervical, gastrointestinal lymphoma, brain, or colon cancer and any other tumors or neoplasms that are metastasized or at risk of metastasis.

2. Dosage and Administration

Any mode of administration of a virus and other agents in the adjunct therapy, e.g. co-administered or co-formulated with the virus, to a subject can be used, provided the mode of administration permits the virus to enter a tumor or metastasis. Modes of administration can include, but are not limited to, systemic, parenteral, intravenous, intraperitoneal, subcutaneous, intramuscular, transdermal, intradermal, intra-arterial (e.g., hepatic artery infusion), intravesicular perfusion, intrapleural, intraarticular, topical, intratumoral, intralesional, endoscopic, multipuncture (e.g., as used with smallpox vaccines), inhalation, percutaneous, subcutaneous, intranasal, intratracheal, oral, intracavity (e.g., administering to the bladder via a catheter, administering to the gut by suppository or enema), vaginal, rectal, intracranial, intraprostatic, intravitreal, aural, ocular or topical administration. In some examples, a diagnostic or other therapeutic agent as described elsewhere herein also can be similarly administered.

One skilled in the art can select any mode of administration compatible with the subject and the virus, and that also is likely to result in the virus reaching tumors and/or metastases. The route of administration can be selected by one skilled in the art according to any of a variety of factors, including the nature of the disease, the kind of tumor, and the particular virus contained in the pharmaceutical composition.

The compositions in the adjunct therapies provided herein can be administered by a single injection, by multiple injections, or continuously. For example, the composition(s) can be administered by slow infusion including using an intravenous pump, syringe pump, intravenous drip or slow injection. For example, continuous administration of the compositions can occur over the course of minutes to hours, such as between or between about 1 minutes to 1 hours, such as between 20 and 60 minutes. The components of the composition(s) can be administered separately or together.

For example, in methods provided herein employing separate administration of a composition containing an oncolytic virus (e.g. vaccinia virus) and a composition containing a complement inhibitor (e.g. anti-C5 antibody), the separate compositions can be administered simultaneously or at different times. For example, the composition containing a complement inhibitor can be administered prior to, subsequently or intermittently from the composition containing the oncolytic virus. Typically, the composition containing the complement inhibitor is administered prior to the composition containing the oncolytic virus, for example, 5 minutes to 12 hours, such as at least 10 minutes, 20 minutes, 30 minutes, 40 minutes, 50 minutes, 1 hour, 2 hours or more prior to administration of the oncolytic virus.

In examples of methods provided herein employing separate administration of a composition containing an oncolytic virus (e.g. vaccinia virus) and a composition containing a lipid emulsion, such as, for example, Intralipid® lipid emulsion, the separate compositions can be administered simultaneously or at different times. For example, the composition containing a lipid emulsion can be administered prior to, subsequently or intermittently from the composition containing the oncolytic virus. Typically, the composition containing the lipid emulsion is administered prior to the composition containing the oncolytic virus, for example, 5 minutes to 12 hours, such as at least 10 minutes, 20 minutes, 30 minutes, 40 minutes, 50 minutes, 1 hour, 2 hours or more prior to administration of the oncolytic virus.

The dosage regimen can be any of a variety of methods and amounts, and can be determined by one skilled in the art according to known clinical factors. As is known in the medical arts, dosages for any one patient can depend on many factors, including the subject's species, size, body surface area, age, sex, immunocompetence, and general health, the particular virus to be administered, duration and route of administration, the kind and stage of the disease, for example, tumor size, and other treatments or compounds, such as chemotherapeutic drugs, being administered concurrently. In addition to the above factors, such levels can be affected by the infectivity of the virus, and the nature of the virus, as can be determined by one skilled in the art.

For example, vaccinia virus, in particular Lister strain, such as LIVP viruses, generally exhibits little to no host toxicity, and hence higher dosages can be tolerated than for other oncolytic viruses. Although administration of a bolus of virus directly into the blood stream can result in rapid dissemination of the virus throughout the organism, the vaccinia virus compositions herein are efficiently delivered and infect immunoprivileged cells and tissues, for example, tumors. Systemic administration, such as intravenous administration, of the virus compositions is possible because the virus is able to accumulate in immunoprivileged cells and tissues (e.g. tumors), yet is efficiently cleared from the subject and does not significantly accumulate in non-tumor tissues. This can result in decreased toxicity. For example, a dose limiting toxicity (DLT) of vaccinia virus (e.g. GL-ONC1) has not been achieved with doses up to $5 \times 10^9$ pfu, such that the maximum tolerated dose (MTD) is greater than $5 \times 10^9$ pfu. In contrast, other oncolytic viruses (e.g. JX-594) can be more toxic so that the maximum tolerated dose (MTD) is only up to $1 \times 10^9$ pfu. While the adjunct therapy herein increases virus infectivity so that there is more effective virus available after initial immune clearance, the low toxicity of vaccinia virus (e.g. LIVP virus) means that a sufficiently high dosage still can be achieved without causing a DLT. Thus, dosages far higher than $5 \times 10^9$ pfu can be realized.

In the present adjunct therapy methods, appropriate minimum dosage levels and dosage regimes of viruses in the compositions herein can be levels sufficient for the virus to survive, grow and replicate in a tumor, metastasis or other wound or lesion. Generally, the virus is administered in an amount that is at least or about or $1 \times 10^5$ pfu. For example, the dose level can range from $1 \times 10^6$ to $1 \times 10^{12}$ pfu, such as $1 \times 10^6$ to $1 \times 10^{10}$, $1 \times 10^6$ to $1 \times 10^8$ or $1 \times 10^8$ to $1 \times 10^{10}$, each inclusive. Exemplary doses for administering a virus to a 65 kg human can include at least about $1 \times 10^5$ plaque forming units (pfu), at least about $5 \times 10^5$ pfu, at least about $1 \times 10^6$ pfu, at least about $5 \times 10^6$ pfu, at least about $1 \times 10^7$ pfu, at least about $1 \times 10^8$ pfu, at least about $1 \times 10^9$ pfu, at least about $2 \times 10^9$ pfu, at least about $3 \times 10^9$ pfu, at least about $4 \times 10^9$ pfu, at least about $5 \times 10^9$ pfu, at least about $6 \times 10^9$ pfu, at least about $7 \times 10^9$ pfu, at least about $8 \times 10^9$ pfu, at least about $9 \times 10^9$ pfu, at least about $1 \times 10^{10}$ pfu, at least about $1 \times 10^{11}$ pfu, at least about $1 \times 10^{12}$ pfu, at least about $1 \times 10^{13}$ pfu, or at least about $1 \times 10^{14}$ pfu at least one time over a cycle of administration.

Generally, appropriate maximum dosage levels or dosage regimes of viruses are levels that are not toxic to the host, levels that do not cause splenomegaly of 3 times or more, levels that do not result in colonies or plaques in normal tissues or organs after about 1 day or after about 3 days or after about 7 days.

It is understood that the particular dosage that is administered using the adjunct therapy provided herein typically is a dosage that achieves a higher efficacy of treatment than a monotherapy with the oncolytic virus administered at the same dosage. Alternatively, the particular dosage administered can be a dosage that is higher or greater than employed in a monotherapy with the oncolytic virus, while maintaining the same or similar therapeutic efficacy.

The particular dosage employed is a function of the route of administration. For example, generally higher dosage amounts are administered for intravenous, intrapleural or intraperitoneal administration than for other more localized routes of administration. For example, lower dosage amounts can be employed for intracranial or intrathecal injections. The particular dosage can be empirically determined by a skilled artisan depending on the particular virus and adjunct therapy employed. For example, for a vaccinia virus (e.g. LIVP), a dose level ranging from $1 \times 10^9$ to $1 \times 10^{10}$ pfu can be employed for intravenous, intrapleural or intraperitoneal routes of administration. In contrast, for a vaccinia virus (e.g. LIVP), a dose that is one or two logs lower can be employed for intracranial or intrathecal injection, such as a dose level ranging from $1 \times 10^7$ to $1 \times 10^9$.

In the dosage regime, the amount of virus can be delivered as a single administration or multiple times over a cycle of administration. Hence, in examples herein employing an adjunct therapy as a co-formulation of the virus and another agent that increases virus infectivity (e.g. complement inhibitor and/or biocompatible lipid, such as lipid-treated virus), the other agent also can be administered as a single administration or multiple times over a cycle of administration in accord with the viral dosage regime. In contrast, in examples herein employing an adjunct therapy that includes separate administration of another agent that increases virus infectivity (e.g. complement inhibitor and/or biocompatible lipid, such as lipid emulsion), the other agent can be administered in a cycle of administration that is similar to that employed for the virus or a different cycle of administration can be employed. For example, the other agent can be administered only one time in the cycle of administration, for example, prior to the first administration with virus in a cycle of administration. The particular regime employed can be determined empirically by a skilled artisan, and is dependent on factors that include the particular virus employed, the particular adjunct therapy, the particular subject being treated, the particular disease or condition, the severity of the disease or condition and other factors routinely considered by a skilled medical practitioner.

In some examples, a single administration of virus is sufficient to establish a virus in a tumor, where the virus can proliferate and can cause or enhance an anti-tumor response in the subject; such methods do not require additional administrations of a virus in order to cause or enhance an anti-tumor response in a subject, which can result, for example in inhibition of tumor growth, inhibition of metastasis growth or formation, reduction in tumor or size, elimination of a tumor or metastasis, inhibition or prevention of recurrence of a neoplastic disease or new tumor formation, or other cancer therapeutic effects.

In other examples, the virus can be administered on different occasions, separated in time typically by at least one day. For example, the compositions can be administered two times, three time, four times, five times, or six times or more, with one day or more, two days or more, one week or more, or one month or more time between administrations. Separate administrations can increase the likelihood of delivering a virus to a tumor or metastasis, where a previous administration has been ineffective in delivering a virus to a tumor or metastasis. Separate administrations can increase the locations on a tumor or metastasis where virus proliferation can occur or can otherwise increase the titer of virus accumulated in the tumor, which can increase the scale of release of antigens or other compounds from the tumor in eliciting or enhancing a host's anti-tumor immune response, and also can, optionally, increase the level of virus-based tumor lysis or tumor cell death. Separate administrations of a virus can further extend a subject's immune response against viral antigens, which can extend the host's immune response to tumors or metastases in which viruses have accumulated, and can increase the likelihood of a host mounting an anti-tumor immune response.

When separate administrations are performed, each administration can be a dosage amount that is the same or different relative to other administration dosage amounts. In one example, all administration dosage amounts are the same. In other examples, a first dosage amount can be a larger dosage amount than one or more subsequent dosage amounts, for example, at least 10× larger, at least 100× larger, or at least 1000× larger than subsequent dosage amounts. In one example of a method of separate administrations in which the first dosage amount is greater than one or more subsequent dosage amounts, all subsequent dosage amounts can be the same, smaller amount relative to the first administration.

Separate administrations can include any number of two or more administrations, including two, three, four, five or six administrations. One skilled in the art can readily determine the number of administrations to perform or the desirability of performing one or more additional administrations according to methods known in the art for monitoring therapeutic methods and other monitoring methods provided herein. Accordingly, the methods provided herein include methods of providing to the subject one or more administrations of a virus, where the number of administrations can be determined by monitoring the subject, and, based on the results of the monitoring, determining whether or not to provide one or more additional administrations. Deciding on whether or not to provide one or more additional administrations can be based on a variety of monitoring results, including, but not limited to, indication of tumor growth or inhibition of tumor growth, appearance of new metastases or inhibition of metastasis, the subject's anti-virus antibody titer, the subject's anti-tumor antibody titer, the overall health of the subject, the weight of the subject, the presence of virus solely in tumor and/or metastases, the presence of virus in normal tissues or organs.

The time period between administrations can be any of a variety of time periods. The time period between administrations can be a function of any of a variety of factors, including monitoring steps, as described in relation to the number of administrations, the time period for a subject to mount an immune response, the time period for a subject to clear the virus from normal tissue, or the time period for virus proliferation in the tumor or metastasis. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear the virus from normal tissue; for example, the time period can be more than the time period for a subject to clear the virus from normal tissue, such as more than about a day, more than about two days, more than about three days, more than about five days, or more than about a week. In another example, the time period can be a function of the time period for virus proliferation in the tumor or metastasis; for example, the time period can be more than the amount of time for a detectable signal to arise in a tumor or metastasis after administration of a virus expressing a detectable marker, such as about 3 days, about 5 days, about a week, about ten days, about two weeks, or about a month.

For example, an amount of virus is administered two times, three times, four times, five times, six times or seven times over a cycle of administration. The amount of virus can be administered on the first day of the cycle, the first and second day of the cycle, each of the first three consecutive days of the cycle, each of the first four consecutive days of the cycle, each of the first five consecutive days of the cycle, each of the first six consecutive days of the cycle, or each of the first seven consecutive days of the cycle. Generally, the cycle of administration is 7 days, 14 days, 21 days or 28 days. Depending on the responsiveness or prognosis of the patient the cycle of administration is repeated over the course of several months or years.

In the examples of adjunct therapies herein employing a composition containing a virus and a biocompatible lipid component (e.g. lipid emulsion), such as any of the lipid-treated compositions described in Section F, the effective amount of biocompatible lipid component (e.g. lipid emulsion) that is administered is not pertinent. This is because the lipid is being employed to pretreat the virus, which results in altered properties of the virus; the lipid component is not itself necessarily acting as an active agent in the administration methods.

In contrast, in examples where the biocompatible lipid (e.g. lipid emulsion) is administered as a combination separately from the virus composition, the biocompatible lipid (e.g. lipid emulsion) is being employed as an active agent. In such examples, the lipid emulsion is typically administered at a sufficiently high concentration or amount that the lipid emulsion itself exhibits direct immunomodulatory effects on immune cells, for example NK cells. For example, the lipid emulsion is administered as a composition containing at least 0.1%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0% or more of a biocompatible lipid component (e.g. soybean oil, such as Intralipid® lipid emulsion). For example, the lipid emulsion is administered in an amount to deliver 1 gram (g) to 50 g, 1 g to 40 g, 1 g to 30 g, 1 g to 20 g, 1 g to 10 g, 1 g to 5 g, 5 g to 50 g, 5 g to 40 g, 5 g to 30 g, 5 g to 20 g, 5 g to 10 g, 10 g to 50 g, 10 g to 40 g, 10 g to 30 g, 10 g to 20 g, 20 g to 50 g, 20 g to 40 g, or 20 g to 30 g of the biocompatible lipid component. The composition containing the lipid component (e.g. lipid emulsion) can be administered in a total volume that is 1 mL to 500 mL, 1 mL to 200 mL, 1 mL to 100 mL, 1 mL to 50 mL, 50 mL to 500 mL, 50 mL to 200 mL, 50 mL to 100 mL, 100 mL to 500 mL, 100 mL to 200 mL, or 200 mL to 500 mL. The composition, such as any described in Sections E or F, can be administered directly, or can be diluted prior to administration. For example, a composition containing a lipid component (e.g. a lipid emulsion, such as an ILE, i.e. Intralipid® lipid emulsion) can be diluted with saline or other aqueous solution or isotonic buffer prior to administration.

In any of the examples herein of an adjunct therapy containing a complement inhibitor (e.g. an anti-C5 antibody, such as eculizumab), such as combinations and compositions herein with an oncolytic virus, the complement inhibitor is administered in a dosage amount sufficient to effect inhibition of the target complement protein, such as a sufficient amount to inhibit or reduce an effector function associated with the particular target protein. Such dosages or amounts are known to a skilled artisan for known complement inhibitors, or can be empirically determined by a skilled artisan.

For example, the complement inhibitor (e.g. an anti-C5 antibody, such as eculizumab) is administered to deliver a dose of between 1 ng/kg and 100 mg/kg body weight as a single bolus, or in a repeated regimen, or a combination thereof as readily determined by the skilled artisan. In certain embodiments, the dosage is at least 0.1 mg/kg, or at least 0.2 mg/kg, or at least 0.3 mg kg, or at least 0.4 mg/kg, or at least 0.5 mg/kg, or at least 0.6 mg/kg, or at least 0.7 mg/kg, or at least 0.8 mg/kg, or at least 0.9 mg/kg, or at least 1 mg/kg, or at least 2 mg/kg, or at least 3 mg/kg, or at least 4 mg/kg, or at least 5 mg/kg, or at least 6 mg/kg, or at least 7 mg/kg, or at least 8 mg/kg, or at least 9 mg/kg, or at least 10 mg/kg, or at least 15 mg/kg, or at least 20 mg/kg, or at least 25 mg/kg, or at least 30 mg/kg, or at least 35 mg/kg, or at least 40 mg/kg, or at least 45 mg/kg, or at least 50 mg/kg, or at least 55 mg/kg, or at least 60 mg/kg, or at least 65 mg kg, or at least 70 mg/kg, or at least 75 mg/kg, or at least 80 mg/kg, or at least 85 mg/kg, or at least 90 mg/kg, or at least 95 mg/kg, or at least 100 mg/kg, as a single administration in a cycle of administration or on another suitable periodic regimen. In a particular embodiment, the dosage is between about 0.5 mg/kg and about 20 mg/kg, or between about 1 mg/kg and about 10 mg/kg, or between about 2 mg/kg and about 6 mg/kg.

For example, wherein the complement inhibitor (e.g. an anti-C5 antibody, such as eculizumab) is administered in an amount to deliver 100 mg to 5000 mg, 200 mg to 2000 mg, 500 mg to 1000 mg, 200 mg to 5000 mg, 200 mg to 1000 mg, 500 mg to 5000 mg, 1000 mg to 2000 mg, 1000 mg to 5000 mg or 2000 mg to 5000 mg, for example at least 800 mg, 900 mg, 1000 mg, 1200 mg to 1500 mg. The composition containing can be administered in a total volume that is 1 mL to 500 mL, 1 mL to 200 mL, 1 mL to 100 mL, 1 mL to 50 mL, 50 mL to 500 mL, 50 mL to 200 mL, 50 mL to 100 mL, 100 mL to 500 mL, 100 mL to 200 mL, or 200 mL to 500 mL.

3. Combination Therapy

The subject also can be undergoing secondary treatment for a tumor, cancer, wound or hyperproliferative surface lesion. For example, the methods herein include further combination therapy with a secondary anti-cancer therapy. Examples of such therapy include, but are not limited to, surgical therapy, chemotherapy, radiation therapy, immunotherapy, treatment with another therapeutic substance or agent and/or administration with another therapeutic virus. These can be administered simultaneously, sequentially or intermittently with the adjunct therapies provided herein.

a. Oncolytic or Therapeutic Virus

Methods are provided for administering to a subject in combination with an adjunct therapy provided herein another oncolytic or therapeutic virus. The virus can be any virus that is capable of effecting treatment of diseases or conditions associated with immunoprivileged cells or tissues, including proliferative disorders or conditions, including the treatment (such as inhibition) of cancerous cells, neoplasms, tumors, metastases, cancer stem cells, and other immunoprivileged cells or tissues, such as wounds and wounded or inflamed tissues. For example, the virus is an oncolytic virus. The virus can contain a heterologous gene product that encodes a therapeutic protein or that is detectable or capable of being detected. For example, the virus can be a vaccinia virus (e.g. Lister strain or LIVP), an adenovirus, an adeno-associated virus, a retrovirus, a herpes simplex virus, a reovirus, a mumps virus, a foamy virus, an influenza virus, a myxoma virus, a vesicular stomatitis virus, or any other virus described herein or known in the art, or derivatives or modified forms thereof.

The virus can be provided as combinations of compositions and/or as kits that include the virus and compositions provided herein packaged for administration and optionally including instructions therefore. The additional virus compositions can contain the viruses formulated for single dosage administration (i.e., for direct administration) and can require dilution or other additions.

Administration can be effected simultaneously, sequentially or intermittently. The time period between administrations can be any time period that achieves the desired effects, as can be determined by one skilled in the art. Selection of a time period between administrations of different viruses can be determined according to parameters similar to those for selecting the time period between administrations of the same virus, including results from monitoring steps, the time period for a subject to mount an immune response, the time period for a subject to clear virus from normal tissue, or the time period for virus proliferation in the tumor or metastasis. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear the virus from normal tissue; for example, the time period can be more than the time period for a subject to clear the virus from normal tissue, such as more than about a day, more than about two days, more than about three days, more than about five days, or more than about a week. In another example, the time period can be a function of the time period for virus proliferation in the tumor or metastasis; for example, the time period can be more than the amount of time for a detectable signal to arise in a tumor or metastasis after administration of a virus expressing a detectable marker, such as about 3 days, about 5 days, about a week, about ten days, about two weeks, or about a month.

b. Therapeutic Compounds

Any therapeutic or anti-cancer agent can be used as the second, therapeutic or anti-cancer agent in the combined cancer treatment methods provided herein. The methods can include administering one or more therapeutic compounds to the subject in addition to the adjunct therapy provided herein to a subject. Therapeutic compounds can act independently, or in conjunction with the virus, for tumor therapeutic effects. Therapeutic compounds or agents also include those that are immunotherapeutic compounds. Therapeutic compounds to be administered can be any of those provided herein or in the art.

Therapeutic compounds that can act independently include any of a variety of known chemotherapeutic compounds that can inhibit tumor growth, inhibit metastasis growth and/or formation, decrease the size of a tumor or metastasis, eliminate a tumor or metastasis, without reducing the ability of a virus to accumulate in a tumor, replicate in the tumor, and cause or enhance an anti-tumor immune response in the subject.

Therapeutic compounds that act in conjunction with the viruses include, for example, compounds that alter the expression of the viruses or compounds that can interact with a virally-expressed gene, or compounds that can inhibit virus proliferation, including compounds toxic to the virus. Therapeutic compounds that can act in conjunction with the virus include, for example, therapeutic compounds that increase the proliferation, toxicity, tumor cell killing or immune response eliciting properties of a virus, and also can include, for example, therapeutic compounds that decrease the proliferation, toxicity or cell killing properties of a virus. Optionally, the therapeutic agent can exhibit or manifest additional properties, such as, properties that permit its use as an imaging agent, as described elsewhere herein.

For example, tumors, cancers and metastasis can be a monotherapy-resistant tumor such as, for example, one that does not respond to therapy with virus alone or other therapeutic agent (e.g. anti-cancer agent alone), but that does respond to therapy with a combination of virus and other therapeutic agent (e.g. anti-cancer agent). Typically, a therapeutically effective amount of a virus composition provided herein is administered to the subject and the virus localizes and accumulates in the tumor. Subsequent to administering the virus, the subject is administered a therapeutically effective amount of another therapeutic agent, for example an anti-cancer agent, such as a chemotherapeutic agent (e.g. cisplatin). In one example, the other therapeutic agent is administered once-daily for five consecutive days. One of skill in the art could determine when to administer the therapeutic agent subsequent to the virus using, for example, in vivo animal models. Using the methods provided herein, administration of a virus composition provided herein and other therapeutic agent can cause a reduction in tumor volume, can cause tumor growth to stop or be delayed or can cause the tumor to be eliminated from the subject. The status of tumors, cancers and metastasis following treatment can be monitored using any of the methods provided herein and known in the art.

Therapeutic compounds or agents include, but are not limited to, chemotherapeutic agents, nanoparticles, radiation therapy, siRNA molecules, enzyme/pro-drug pairs, photosensitizing agents, toxins, microwaves, a radionuclide, an angiogenesis inhibitor, a mitosis inhibitor protein (e.g., cdc6), an antitumor oligopeptide (e.g., antimitotic oligopeptides, high affinity tumor-selective binding peptides), a signaling modulator, anti-cancer antibiotics, or a combination thereof.

Exemplary photosensitizing agents include, but are not limited to, for example, indocyanine green, toluidine blue, aminolevulinic acid, texaphyrins, benzoporphyrins, phenothiazines, phthalocyanines, porphyrins such as sodium porfimer, chlorins such as tetra(m-hydroxyphenyl)chlorin or tin(IV) chlorin e6, purpurins such as tin ethyl etiopurpurin, purpurinimides, bacteriochlorins, pheophorbides, pyropheophorbides or cationic dyes. In one example, a vaccinia virus, such as a vaccinia virus provided herein, is administered to a subject having a tumor, cancer or metastasis in combination with a photosensitizing agent.

Radionuclides, which depending up the radionuclide, amount and application can be used for diagnosis and/or for treatment. They include, but are not limited to, for example, a compound or molecule containing $^{32}$Phosphorus, $^{60}$Cobalt, $^{90}$Yttrium, $^{99}$Technitium, $^{103}$Palladium, $^{106}$Ruthenium, $^{111}$Indium, $^{117}$Lutetium, $^{125}$Iodine, $^{131}$Iodine, $^{137}$Cesium, $^{153}$Samarium, $^{186}$Rhenium, $^{188}$Rhenium, $^{192}$Iridium, $^{198}$Gold, $^{211}$Astatine, $^{212}$Bismuth or $^{213}$Bismuth. In one example, a vaccinia virus, such as a vaccinia virus provided herein, is administered to a subject having a tumor, cancer or metastasis in combination with a radionuclide.

Toxins include, but are not limited to, chemotherapeutic compounds such as, but not limited to, 5-fluorouridine, calicheamicin and maytansine. Signaling modulators include, but are not limited to, for example, inhibitors of macrophage inhibitory factor, toll-like receptor agonists and stat3 inhibitors. In one example, a vaccinia virus, such as a vaccinia virus provided herein, is administered to a subject having a tumor, cancer or metastasis in combination with a toxin or a signaling modulator.

Chemotherapeutic compounds include, but are not limited to, alkylating agents such as thiotepa and cyclophosphamide; alkyl sulfonates such as busulfan, improsulfan and piposulfan; aziridines such as benzodepa, carboquone, meturedepa and uredepa; ethylenimine and methylmelamines, including altretamine, triethylenemelamine, triethylenephosphoramide, triethylenethiophosphoramide and trimethylmelamine nitrogen mustards such as chlorambucil, chlornaphazine, chlorophosphamide, estramustine, ifosfamide, mechlorethamine, mechlorethamine oxide hydrochloride, melphalan, novobiocin, phenesterine, prednimustine, trofosfamide, uracil mustard; nitrosoureas such as carmustine, chlorozotocin, fotemustine, lomustine, nimustine, ranimustine; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defosfamide; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; cyclophosphamide; thiotepa; taxoids, e.g., paclitaxel and docetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; Navelbine; Novantrone; teniposide; daunomycin; aminopterin; Xeloda; ibandronate; CPT11; topoisomerase inhibitor RFS 2000; difluoromethylornithine (DMFO); retinoic acid; esperamycins; capecitabine; and pharmaceutically acceptable salts, acids or derivatives of any of the above. Also included are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); and anti-androgens such as flutamide, nilutamide, bicalutamide, leuprolide and goserelin; and pharmaceutically acceptable salts, acids or derivatives of any of the above. Such chemotherapeutic compounds that can be used herein include compounds whose toxicities preclude use of the compound in general systemic chemotherapeutic methods. Chemotherapeutic agents also include new classes of targeted chemotherapeutic agents such as, for example, imatinib (sold by Novartis under the trade name Gleevec in the United States), gefitinib (developed by AstraZeneca under the trade name Iressa) and erlotinib. Particular chemotherapeutic agents include, but are not limited to, cisplatin, carboplatin, oxaliplatin, DWA2114R, NK121, IS 3 295, 254-S, vincristine, prednisone, doxorubicin and L-asparaginase; mechlorethamine, vincristine, procarbazine and prednisone (MOPP), cyclophosphamide, vincristine, procarbazine and prednisone (C-MOPP), bleomycin, vinblastine, gemcitabine and 5-flurouracil. Exemplary chemotherapeutic agents are, for example, cisplatin, carboplatin, oxaliplatin, DWA2114R, NK121, IS 3 295, and 254-S.

Exemplary anti-cancer antibiotics include, but are not limited to, anthracyclines such as doxorubicin hydrochloride (adriamycin), idarubicin hydrochloride, daunorubicin hydrochloride, aclarubicin hydrochloride, epirubicin hydrochloride and pirarubicin hydrochloride, phleomycins such as phleomycin and peplomycin sulfate, mitomycins such as mitomycin C, actinomycins such as actinomycin D, zinostatinstimalamer and polypeptides such as neocarzinostatin.

Anti-cancer antibodies include, but are not limited to, Rituximab, ADEPT, Trastuzumab (Herceptin), Tositumomab (Bexxar), Cetuximab (Erbitux), Ibritumomab (Zevalin), Alemtuzumab (Campath-1H), Epratuzumab (Lymphocide), Gemtuzumab ozogamicin (Mylotarg), Bevacimab (Avastin), Tarceva (Erlotinib), SUTENT (sunitinib malate), Panorex (Edrecolomab), RITUXAN (Rituximab), Zevalin (90Y-ibritumomab tiuexetan), Mylotarg (Gemtuzumab Ozogamicin) and Campath (Alemtuzumab).

Cancer growth inhibitors use cell-signaling molecules which control the growth and multiplication of cells, such as cancer cells. Drugs that block these signaling molecules can stop cancers from growing and dividing. Cancer growth inhibitors include drugs that block tyrosine kinases (i.e. tyrosine kinase inhibitors; TKIs) or that inhibit the proteasome inhibitors. Examples of TKIs include, but are not limited to, Erlotinib (Tarceva, OSI-774), Iressa (Gefitinib, ZD 1839), Imatinib (Glivec, STI 571) and Bortezomib (Velcade).

In one example, nanoparticles can be designed such that they carry one or more therapeutic agents provided herein. Additionally, nanoparticles can be designed to carry a molecule that targets the nanoparticle to the tumor cells. In one non-limiting example, nanoparticles can be coated with a radionuclide and, optionally, an antibody immunoreactive with a tumor-associated antigen. In one example, a vaccinia virus in protein polymer composition, such as any provided herein, is administered to a subject having a tumor, cancer or metastasis in combination with a nanoparticle carrying any of the therapeutic agents provided herein.

Radiation therapy has become a foremost choice of treatment for a majority of cancer patients. The wide use of radiation treatment stems from the ability of gamma-irradiation to induce irreversible damage in targeted cells with the preservation of normal tissue function. Ionizing radiation triggers apoptosis, the intrinsic cellular death machinery in cancer cells, and the activation of apoptosis seems to be the principal mode by which cancer cells die following exposure to ionizing radiation. In one example, a vaccinia virus in protein polymer composition, such as any provided herein, is administered to a subject having a tumor, cancer or metastasis in combination with radiation therapy.

Therapeutic compounds also include those that can act in conjunction with the virus to increase the proliferation, toxicity, tumor cell killing or immune response eliciting properties of a virus are compounds that can alter gene expression, where the altered gene expression can result in an increased killing of tumor cells or an increased anti-tumor immune response in the subject. A gene expression-altering compound can, for example, cause an increase or decrease in expression of one or more viral genes, including endogenous viral genes and/or exogenous viral genes. For example, a gene expression-altering compound can induce or increase transcription of a gene in a virus such as an exogenous gene that can cause cell lysis or cell death, that can provoke an immune response, that can catalyze conversion of a prodrug-like compound, or that can inhibit expression of a tumor cell gene. Any of a wide variety of compounds that can alter gene expression are known in the art, including IPTG and RU486. Exemplary genes whose expression can be up-regulated include proteins and RNA molecules, including toxins, enzymes that can convert a prodrug to an anti-tumor drug, cytokines, transcription regulating proteins, siRNA and ribozymes. In another example, a gene expression-altering compound can inhibit or decrease transcription of a gene in a virus such as a heterologous gene that can reduce viral toxicity or reduces viral proliferation. Any of a variety of compounds that can reduce or inhibit gene expression can be used in the methods provided herein, including siRNA compounds, transcriptional inhibitors or inhibitors of transcriptional activators. Exemplary genes whose expression can be down-regulated include proteins and RNA molecules, including viral proteins or RNA that suppress lysis, nucleotide synthesis or proliferation, and cellular proteins or RNA molecules that suppress cell death, immunoreactivity, lysis, or viral replication.

In another example, therapeutic compounds that can act in conjunction with the virus to increase the proliferation, toxicity, tumor cell killing, or immune response eliciting properties of a virus are compounds that can interact with a virally expressed gene product, and such interaction can result in an increased killing of tumor cells or an increased anti-tumor immune response in the subject. A therapeutic compound that can interact with a virally-expressed gene product can include, for example a prodrug or other compound that has little or no toxicity or other biological activity in its subject-administered form, but after interaction with a virally expressed gene product, the compound can develop a property that results in tumor cell death, including but not limited to, cytotoxicity, ability to induce apoptosis, or ability to trigger an immune response. In one non-limiting example, the virus carries an enzyme into the cancer cells. Once the enzyme is introduced into the cancer cells, an inactive form of a chemotherapy drug (i.e., a prodrug) is administered. When the inactive prodrug reaches the cancer cells, the enzyme converts the prodrug into the active chemotherapy drug, so that it can kill the cancer cell. Thus, the treatment is targeted only to cancer cells and does not affect normal cells. The prodrug can be administered concurrently with, or sequentially to, the virus. A variety of prodrug-like substances are known in the art and an exemplary set of such compounds are disclosed elsewhere herein, where such compounds can include gancyclovir, 5-fluorouracil, 6-methylpurine deoxyriboside, cephalosporin-doxorubicin, 4-[(2-chloroethyl)(2-mesyloxyethyl)amino]benzoyl-L-glutamic acid, acetaminophen, indole-3-acetic acid, CB1954, 7-ethyl-10-[4-(1-piperidino)-1-piperidino]carbonyloxycamptothecin, bis-(2-chloroethyl)amino-4-hydroxyphenyl-aminomethanone 28, 1-chloromethyl-5-hydroxy-1,2-dihydro-3H-benz[e]indole, epirubicin-glucuronide, 5'-deoxy-5-fluorouridine, cytosine arabinoside, linamarin, and a nucleoside analogue (e.g., fluorouridine, fluorodeoxyuridine, fluorouridine arabinoside, cytosine arabinoside, adenine arabinoside, guanine arabinoside, hypoxanthine arabinoside, 6-mercaptopurineriboside, theoguanosine riboside, nebularine, 5-iodouridine, 5-iododeoxyuridine, 5-bromodeoxyuridine, 5-vinyldeoxyuridine, 9-[(2-hydroxy)ethoxy]methylguanine (acyclovir), 9-[(2-hydroxy-1-hydroxymethyl)-ethoxy]methylguanine (DHPG), azauridien, azacytidine, azidothymidine, dideoxyadenosine, dideoxycytidine, dideoxyinosine, dideoxyguanosine, dideoxythymidine, 3'-deoxyadenosine, 3'-deoxycytidine, 3'-deoxyinosine, 3'-deoxyguanosine, 3'-deoxythymidine).

In another example, therapeutic compounds that can act in conjunction with the virus to decrease the proliferation, toxicity or cell killing properties of a virus are compounds that can inhibit viral replication, inhibit viral toxins or cause viral death. A therapeutic compound that can inhibit viral replication, inhibit viral toxins, or cause viral death can generally include a compound that can block one or more steps in the viral life cycle, including, but not limited to, compounds that can inhibit viral DNA replication, viral RNA transcription, viral coat protein assembly, outer membrane or polysaccharide assembly. Any of a variety of compounds that can block one or more steps in a viral life cycle are known in the art, including any known antiviral compound (e.g., cidofovir), viral DNA polymerase inhibitors, viral RNA polymerase inhibitors, inhibitors of proteins that regulate viral DNA replication or RNA transcription. In another example, a virus can contain a gene encoding a viral life cycle protein, such as DNA polymerase or RNA polymerase that can be inhibited by a compound that is, optionally, non-toxic to the host organism.

Therapeutic compounds also include, but are not limited to, compounds that exert an immunotherapeutic effect, stimulate or suppress the immune system, carry a therapeutic compound, or a combination thereof. Such therapeutic compounds include, but are not limited to, anti-cancer antibodies, radiation therapy, siRNA molecules and compounds that suppress the immune system (i.e. immunosuppressors, immunosuppressive agents). In some cases, it is desirable to administer an immunosuppressive agent to a subject to suppress the immune system prior to the administration of the virus in order to minimize any adverse reactions to the virus. Exemplary immunosuppressive agents include, but are not limited to, glucocorticoids, alkylating agents, antimetabolites, cytokines and growth factors (e.g. interferons) and immunosuppressive antibodies (e.g., anti-CD3 and anti-IL2 receptor antibodies). For example, immunosuppressive agents include biological response modifiers, such as monoclonal antibodies (mAbs), cancer vaccines, growth factors for blood cells, cancer growth inhibitors, anti-angiogenic factors, interferon alpha, interleukin-2 (IL-2), gene therapy and BCG vaccine for bladder cancer Cytokines and growth factors include, but are not limited to, interleukins, such as, for example, interleukins (e.g. interleukin-1, interleukin-2, interleukin-6 and interleukin-12), tumor necrosis factors, such as tumor necrosis factor alpha (TNF-α), interferons such as interferon gamma (IFN-γ) or interferon alpha (IFN-α), Granulocyte Colony Stimulating Factor (G-CSF; also called filgrastim (Neupogen) or lenograstim (Granocyte)), Granulocyte and Macrophage Colony Stimulating Factor (GM-CSF; also called molgramostim), angiogenins, erythropoietin (EPO) and tissue factors.

Cancer vaccines include, for example, antigen vaccines, whole cell vaccines, dendritic cell vaccines, DNA vaccines and anti-idiotype vaccines. Antigen vaccines are vaccines made from tumor-associated antigens in, or produced by, cancer cells. Antigen vaccines stimulate a subject's immune system to attack the cancer. Whole cell vaccines are vaccines that use the whole cancer cell, not just a specific antigen from it, to make the vaccine. The vaccine is made from a subject's own cancer cells, another subject's cancer cells or cancer cells grown in a laboratory. The cells are treated in the laboratory, usually with radiation, so that they can't grow, and are administered to the subject via injection or through an intravenous drip into the bloodstream so they can stimulate the immune system to attack the cancer. One type of whole cell vaccine is a dendritic cell vaccine, which help the immune system to recognize and attack abnormal cells, such as cancer cells. Dendritic cell vaccines are made by growing dendritic cells alongside the cancer cells in the lab. The vaccine is administered to stimulate the immune system to attack the cancer. Anti-idiotype vaccines are vaccines that stimulate the body to make antibodies against cancer cells. Cancer cells make some tumor-associated antigens that the immune system recognizes as foreign. But because cancer cells are similar to non-cancer cells, the immune system can respond weakly. DNA vaccines boost the immune response. DNA vaccines are made from DNA from cancer cells that carry the genes for the tumor-associated antigens. When a DNA vaccine is injected, it enables the cells of the immune system to recognize the tumor-associated antigens, and activates the cells in the immune system (i.e., breaking tolerance).

The dose scheme of the combination therapy administered is such that the combination of the two or more therapeutic modalities is therapeutically effective. Dosages will vary in accordance with such factors as the age, health, sex, size and weight of the patient, the route of administration, the toxicity of the drugs, frequency of treatment and the relative susceptibilities of the cancer to each of the therapeutic modalities. For combination therapies with additional therapeutic agents provided herein (e.g. chemotherapeutic compounds), dosages for the administration of such compounds are known in the art or can be determined by one skilled in the art according to known clinical factors (e.g., subject's species, size, body surface area, age, sex, immunocompetence, and general health, duration and route of administration, the kind and stage of the disease, for example, tumor size, and other viruses, treatments, or compounds, such as other chemotherapeutic drugs, being administered concurrently). As will be understood by one of skill in the art, the optimal treatment regimen will vary and it is within the scope of the treatment methods to evaluate the status of the disease under treatment and the general health of the patient prior to, and following one or more cycles of combination therapy in order to determine the optimal therapeutic combination.

I. EXAMPLES

The following examples are included for illustrative purposes only and are not intended to limit the scope of the invention.

Example 1

Generation of Modified LIVP Viruses

A recombinant, replication-competent vaccinia virus derived from the vaccinia virus LIVP strain (Lister strain from the Institute of Viral Preparations, Moscow, Russia) was generated containing an expression cassette containing a Ruc-GFP cDNA molecule (a fusion of DNA encoding *Renilla luciferase* and DNA encoding GFP) under the control of a vaccinia synthetic early/late promoter $P_{SEL}$ (($P_{SEL}$) Ruc-GFP) inserted into the F14.5L gene locus; an expression cassette containing a DNA molecule encoding beta-galactosidase under the control of the vaccinia early/late promoter $P_{7.5k}$ (($P_{7.5k}$)LacZ), DNA encoding a rat transferrin receptor positioned in the reverse orientation for transcription relative to the vaccinia synthetic early/late promoter $P_{SEL}$ (($P_{SEL}$)rTrfR) inserted into the TK gene locus (the resulting virus does not express transferrin receptor protein since the DNA molecule encoding the protein is positioned in the reverse orientation for transcription relative to the promoter in the cassette); and an expression cassette containing a DNA molecule encoding β-glucuronidase under the control of the vaccinia late promoter $P_{11k}$ (($P_{11k}$)gusA) inserted into the HA gene locus. The genome of the resulting recombinant virus has the sequence of nucleotides set forth in SEQ ID NO:3.

The virus was produced in CV-1 cells and purified to generate the virus strain designated GLV-1h68. The virus was produced in chicken embryo fibroblast (CEF) cells and purified to generate the virus strain designated GL-ONC1. The virus was produced in CV-1 cells and purified to generate the virus strain designated GL-ONC1A. The virus strains have the same genomic sequence, but differ in the manufacturing procedures used for propagation and purification of virus.

Example 2

Effect of Eculizumab on Human Serum Inactivation of GLV-1h68

The effect of the anti-C5 mAb eculizumab (SEQ ID NO:44, heavy chain and SEQ ID NO:45, light chain; Soliris®, Lot 10007A; Alexion Pharmaceuticals, Chesire, Conn.) on the infectivity of vaccinia virus strain GLV-1h68 in human serum was evaluated. GLV-1h68 virus described in Example 1 ($2.5 \times 10^5$ pfu/mL) was exposed to either human serum, human serum that had been heated to 58° C. for 30 minutes to inactivate complement in the serum, or human serum that had been pretreated with either 0.001 mg/mL, 0.01 mg/mL, 0.1 mg/mL or 1 mg/mL eculizumab.

After exposure of the virus to the serum for 30 minutes at room temperature, the infectivity of the virus compositions was assessed by viral plaque assay on CV-1 cells. A viral titer assay was performed in a standard plaque assay using African green monkey kidney fibroblast CV-1 cells (ATCC No. CCL-70; American Type Culture Collection, Manassas, Va.). CV-1 cells were plated in a 24-well plate at $2.5 \times 10^5$ cells per well and grown until near confluency. Wells containing a cell monolayer were infected with serial dilutions of the virus compositions. The cells in each well were overlaid with virus overlay medium (DMEM+5% FBS+1% Antibiotic-Antimycotic Solution+1.5% carboxymethylcellulose), and the cells were further incubated until plaques were visible. After addition of color dye to visualize the plaques, viral titer (pfu/mL) was calculated by counting the number of plaques in the well and dividing by the dilution factor (d) and volume (V) of diluted virus added to the well.

Results are provided in Table 13 below. The results show that exposure of the GLV-1h68 virus to human serum alone resulted in a 58% loss in virus titer (42% recovered titer), while exposure of GLV-1h68 to the heat-inactivated control serum had no effect on the infectivity of the virus (100% recovered titer). The amount of recovered titer varied with the concentration of eculizumab in the sample and ranged from 38% to 81% recovered titer. At concentrations of eculizumab of 0.1 mg/mL and 1 mg/mL there was an increase in recovered titer of virus compared to absence of treatment with the antibody, and thus a decrease in loss of virus titer upon exposure to serum. Infectivity was preserved approximately 2-fold when the virus was exposed to serum pretreated with eculizumab as compared to untreated serum. The results indicate that inactivation of complement by treating human serum with 0.1 mg/mL or 1 mg/mL of the anti-C5 mAb eculizumab reduced the loss of infectivity of GLV-1h68 as compared to human serum that had not been treated with eculizumab.

TABLE 13

% Recovered titer of GLV-1h68 in human serum with varying concentrations of eculizumab

| Serum exposure | Eculizumab concentration (mg/mL) | Recovered titer (%) |
|---|---|---|
| Heat-inactivated human serum | 0 | 100 |
| Human serum | 0 | 42 |
| Human serum | 0.001 | 40 |
| Human serum | 0.01 | 38 |
| Human serum | 0.1 | 72 |
| Human serum | 1 | 81 |

Example 3

Adsorption of GLV-1h68 to Human Blood Cells in the Presence of Serum

The adsorption of vaccinia virus strain GLV-1h68 described in Example 1 to human whole blood cells was evaluated. Whole human blood cells were prepared from a normal human donor by collecting blood in EDTA and isolating cells by centrifugation. The cells were washed with phosphate buffered saline (PBS) to remove any plasma/EDTA and were resuspended in PBS to the original blood volume. GLV-1h68 virus ($2.0 \times 10^7$ pfu/mL) was exposed to whole human blood cells (33% of blood concentration) in either phosphate buffered saline (PBS), human serum, heat-inactivated human serum that had been heated to 58° C. for 30 minutes to inactivate complement in the serum, or human serum that had been pretreated with 1 mg/mL eculizumab (Soliris®, Lot 10007A; Alexion Pharmaceuticals, Chesire, Conn.).

After exposure for 60 minutes at 37° C., the virus fraction bound to blood cells was separated from the unbound fraction by centrifugation and washed with PBS to remove loosely bound virus. The infectivity of the virus was assessed by the viral plaque assay on CV-1 cells described in Example 2. The recovered titer of cell-bound and unbound virus was determined.

The Results are set forth in Table 14. The results show that 21% of the GLV-1h68 virus in PBS was cell-bound, while 79% remained unbound, for a total recovery of 100%. This value was used as a comparative standard relative to the values obtained in the human serum compositions, and the percent recovered titer of cell-bound virus and unbound virus compared to PBS control was determined.

In human serum, the total amount of virus recovered (bound and unbound) relative to PBS was reduced to only 67%, indicating that the virus was inactivated by the serum. When virus was exposed to heat-inactivated serum, which inactivates complement, there was an increase in total recovery of virus (bound and unbound) of 78% compared to the human serum treated samples. This result demonstrates that inhibiting complement can reduce virus inactivation by serum. Exposure of virus to human serum in the presence of the anti-C5 mAb eculizumab resulted in an even greater total recovery of virus (bound and unbound) of 150% compared to the PBS reference control. The recovery of 150% compared to the PBS control likely indicates that a fraction of the total virus in the PBS sample was lost during the centrifugation and washing of the cell-bound virus.

In addition to effects on total virus recovery, treatment with human serum resulted in 49% of the virus being cell-bound and 18% remaining unbound. In the heat-treated serum with inactivated complement, 5% of the virus was cell-bound and 73% unbound. Thus, the results show that heat-treating the serum inactivated complement and reduced the binding of the virus to blood cells, in addition to also reducing the inactivation of the unbound virus. In contrast, the amount of cell-bound virus in the human serum sample pretreated with 1 mg/mL eculizumab was 118% and the amount of unbound virus 32%, relative to the PBS control. This result demonstrates that inactivation of complement by treating human serum with 1 mg/mL of the anti-C5 mAb eculizumab increased the binding of GLV-1h68 to human blood cells. Thus, the results show that treatment with the anti-C5 mAb both reduces inactivation of the virus by serum and increases the propensity of binding of the virus to blood cells.

TABLE 14

Cell-bound and unbound GLV-1h68 in human serum and PBS

| Treatment | Cell-bound virus (%) | Unbound virus (%) | Total virus (%) |
|---|---|---|---|
| PBS | 21 | 79 | 100 |
| Heat-inactivated human serum | 5 | 73 | 78 |
| Human serum | 49 | 18 | 67 |
| Human serum + 1 mg/mL eculizumab | 118 | 32 | 150 |

Example 4

Effect of Eculizumab on the Adsorption of GLV-1h68, GL-ONC1 and GL-ONC1A to Human Blood Cells in Serum The effect of eculizumab (Soliris®, Lot 10007A; Alexion Pharmaceuticals, Chesire, Conn.) on the adsorption of vaccinia virus strains GLV-1h68, GL-ONC1 and GL-ONC1A to human whole blood cells in human serum was evaluated. GLV-1h68, GL-ONC1 and GL-ONC1A viruses ($2.0 \times 10^7$ pfu/mL), described in Example 1, were exposed to whole human blood cells purified as described in Example 3 in either human serum or human serum that had been pretreated with 1 mg/mL eculizumab. After exposure for 30 minutes at room temperature, the virus fraction bound to blood cells was separated from the unbound fraction by centrifugation and washed with PBS to remove loosely bound virus. The infectivity of the virus was assessed by the viral plaque assay on CV-1 cells as described in Example 2. The recovered titer of cell-bound and unbound virus was determined, and the percent recovered titer of cell-bound virus and unbound virus compared to PBS control was calculated.

The results are shown in Table 15 below. The results show that similar to GLV-1h68, exposure of the other virus strains GL-ONC1 and GL-ONC1A to human serum pretreated with anti-C5 mAb eculizumab also increased total recovery of the virus (bound and unbound) and therefore reduced inactivation of the virus by serum. The results also show that the fraction of cell-bound virus increased in all three vaccinia viruses that had been exposed to human serum pretreated with 1 mg/mL eculizumab as compared to human serum that had not been pretreated with eculizumab (relative to PBS control). The most substantial increase occurred with GLV-1h68, but all three viruses exhibited increased binding to blood cells after exposure to eculizumab.

The results show that virus infectivity was substantially preserved when virus was exposed to serum treated with anti-C5 mAb eculizumab. Thus, the results show that treatment with anti-C5 mAb increased the retention of infectivity of GLV-1h68 and two related virus strains by the inactivation of C5 complement activity in serum. Infectivity was increased approximately 2-fold when virus was exposed to serum treated with anti-C5 mAb eculizumab compared to untreated serum. In addition, exposure to serum treated with anti-C5 mAb eculizumab also increased the amount of GLV-1h68, and two related viruses manufactured by alternative processes, that bound to human blood cells, thereby also preserving infectivity compared to unbound virus.

TABLE 15

Cell-bound and unbound GLV-1h68, GL-ONC1 and GL-ONC1A in human serum and human serum pre-treated with eculizumab

| Virus | Treatment | Cell-bound virus (%) | Unbound virus (%) | Total virus (%) |
|---|---|---|---|---|
| GLV-1h68 | Human serum | 38 | 13 | 51 |
| GLV-1h68 | Human serum + 1 mg/mL eculizumab | 94 | 18 | 112 |
| GL-ONC1 | Human serum | 25 | 27 | 52 |
| GL-ONC1 | Human serum + 1 mg/mL eculizumab | 43 | 37 | 80 |
| GL-ONC1A | Human serum | 52 | 36 | 88 |
| GL-ONC1A | Human serum + 1 mg/mL eculizumab | 106 | 34 | 140 |

Example 5

Effect of Intralipid® Lipid Emulsion on Human Serum Inactivation of GLV-1h68

The effect of the soybean oil emulsion Intralipid® (20% lipid suspension, Lot 5LBD3129V; Sigma-Aldrich Corp., St. Louis, Mo.) on the infectivity of vaccinia virus strain in human serum was evaluated.

1. GLV-1h68

GLV-1h68 as described in Example 1 was either untreated or was pretreated with Intralipid® for 1 hour at 37° C. Briefly, a virus stock suspension (ranging from $1-10 \times 10^9$ pfu/mL in 1 mM Tris-HCl, pH 9.0) were mixed with an equal volume of Intralipid® lipid emulsion (20% lipid emulsion) and incubated for 1 hour at 37° C. with occasional mixing. The virus was then diluted to the appropriate concentration in phosphate buffered saline (PBS) for use in the experiment. Untreated GLV-1h68 virus or GLV-1h68 virus pretreated with Intralipid® lipid emulsion were exposed to either human serum or control medium DMEM (2% FBS) at three different concentrations ($5 \times 10^7$ pfu/mL, $5 \times 10^5$ pfu/mL and $5 \times 10^4$ pfu/mL). After exposure for 30 minutes at room temperature, the infectivity of the viruses was assessed by the viral plaque assay on CV-1 cells described in Example 2.

The results are shown in Table 16. Exposure of untreated or treated GLV-1h68 to the control medium (DMEM+2% FBS) did not result in any substantial differences in virus infectivity at all concentrations tested, since the recovered titer was substantially the same for the tested groups. In contrast, the results show that exposure of GLV-1h68 to human serum did reduce the recovered titer, consistent with serum inactivation of virus. The results indicate that treating GLV-1h68 at varying concentrations with Intralipid® lipid emulsion reduced the virus sensitivity to serum inactivation by approximately 2-fold.

Further experiments were performed by adding Intralipid® to serum at concentrations similar to that present with virus pretreated with Intralipid® lipid emulsion, and prior to addition of virus. The results show that preadministration of Intralipid® to serum at these concentrations did not reduce the amount of serum inactivation of the virus in the same manner as when the virus was pretreated with Intralipid® lipid emulsion. Intralipid® addition to serum did reduce the amount of serum inactivation of virus, but only at concentrations about 5 fold higher than would have been present with the pretreated virus.

TABLE 16

% Recovered titer of GLV-1h68 in human serum and DMEM after treatment with Intralipid ® lipid emulsion

| Virus: Treatment | Virus concentration | Medium | Recovered titer (%) |
|---|---|---|---|
| GLV-1h68 | $5 \times 10^7$ pfu/mL | DMEM | 100 |
| GLV-1h68: Intralipid ® | $5 \times 10^7$ pfu/mL | DMEM | 102 |
| GLV-1h68 | $5 \times 10^7$ pfu/mL | Human serum | 50 |
| GLV-1h68: Intralipid ® | $5 \times 10^7$ pfu/mL | Human serum | 85 |
| GLV-1h68 | $5 \times 10^5$ pfu/mL | DMEM | 100 |
| GLV-1h68: Intralipid ® | $5 \times 10^5$ pfu/mL | DMEM | 106 |
| GLV-1h68 | $5 \times 10^5$ pfu/mL | Human serum | 32 |
| GLV-1h68: Intralipid ® | $5 \times 10^5$ pfu/mL | Human serum | 61 |
| GLV-1h68 | $5 \times 10^4$ pfu/mL | DMEM | 100 |
| GLV-1h68: Intralipid ® | $5 \times 10^4$ pfu/mL | DMEM | 76 |
| GLV-1h68 | $5 \times 10^4$ pfu/mL | Human serum | 28 |
| GLV-1h68: Intralipid ® | $5 \times 10^4$ pfu/mL | Human serum | 59 |

2. Other Vaccinia Virus Strains

The effect of Intralipid® on human serum inactivation of another exemplary vaccinia virus strain was assessed. Untreated virus or virus pretreated with Intralipid® lipid emulsion for 4 hours at 37° C. were exposed to either human serum or the control medium DMEM (2% FBS) at two different concentrations ($5 \times 10^7$ pfu/mL and $5 \times 10^5$ pfu/mL). After exposure for 30 minutes at room temperature, the infectivity of the viruses was assessed by the viral plaque assay on CV-1 cells described in Example 2.

The results are shown in Table 17 below. Similar to the results with GLV-1h68, exposure of untreated or treated virus to the control medium (DMEM+2% FBS) did not result in any substantial differences in virus infectivity at all concentrations tested, since the recovered titer was substantially the same for the tested groups. The results show that treatment of virus with Intralipid® lipid emulsion reduced the loss in infectivity of the viruses exposed to human serum by approximately half

TABLE 17

% Recovered titer of Vaccinia Virus in human serum and DMEM after treatment with Intralipid ® lipid emulsion

| Virus Treatment | Virus concentration | Medium | Recovered titer (%) |
|---|---|---|---|
| no pretreatment | $5 \times 10^7$ pfu/mL | DMEM | 100 |
| pretreatment: Intralipid ® | $5 \times 10^7$ pfu/mL | DMEM | 100 |

TABLE 17-continued

% Recovered titer of Vaccinia Virus in human serum and DMEM after treatment with Intralipid ® lipid emulsion

| Virus Treatment | Virus concentration | Medium | Recovered titer (%) |
|---|---|---|---|
| no pretreatment | $5 \times 10^7$ pfu/mL | Human serum | 36 |
| pretreatment: Intralipid ® | $5 \times 10^7$ pfu/mL | Human serum | 66 |
| no pretreatment | $5 \times 10^5$ pfu/mL | DMEM | 100 |
| treatment: Intralipid ® | $5 \times 10^5$ pfu/mL | DMEM | 100 |
| no pretreatment | $5 \times 10^5$ pfu/mL | Human serum | 18 |
| treatment: Intralipid ® | $5 \times 10^5$ pfu/mL | Human serum | 27 |

Example 6

Effect of Intralipid® Lipid Emulsion on the Adsorption of GLV-1h68 to Human Blood Cells in the Presence of Serum The effect of the soybean oil emulsion Intralipid® (20% lipid suspension, Lot 5LBD3129V; Sigma-Aldrich Corp., St. Louis, Mo.) on the adsorption of vaccinia virus strain GLV-1h68 in human serum was evaluated. GLV-1h68 ($3.3\times10^7$ pfu/mL) as described in Example 1 was either untreated or was pretreated with Intralipid® lipid emulsion for 1 hour at 37° C. as described in Example 5. Untreated GLV-1h68 virus or GLV-1h68 virus pretreated with Intralipid® were exposed to human whole blood cells (purified as described in Example 3) in human serum. After exposure for 60 minutes at 37° C., the virus fraction bound to blood cells was separated from the unbound fraction by centrifugation and washed with PBS to remove loosely bound virus.

Table 18 below depicts the results. The results show that treatment of GLV-1h68 with Intralipid® lipid emulsion increased total recovery of virus (bound and unbound), indicating that the pretreatment with Intralipid® reduces virus inactivation caused by serum. The results show that treating the GLV-1h68 with Intralipid® did not affect the amount of virus that bound to blood cells as compared to the untreated GLV-1h68. The amount of unbound virus that was recovered, however, was substantially greater for the Intralipid®-treated virus than for the untreated virus, indicating a lesser sensitivity of the unbound virus to serum inactivation.

TABLE 18

| Cell-bound and unbound untreated or Intralipid ®-treated GLV-1h68 in human serum | | | |
|---|---|---|---|
| Virus: Treatment | Cell-bound virus (%) | Unbound virus (%) | Total virus (%) |
| GLV-1h68 | 50 | 13 | 63 |
| GLV-1h68: Intralipid ® lipid emulsion | 52 | 48 | 100 |

Example 7

Pharmacokinetic Evaluation of Nude and Wild Type Mice to Determine the Effect of Intralipid® Pretreatment of Vaccinia Virus The pharmacokinetic effects of Intralipid® lipid emulsion-pretreated Vaccinia virus in tumor-bearing nude and wild type BALB/C mice (Harlan, female, 20-24 grams body weight) following intravenous injection were evaluated. Mice were injected subcutaneously with mouse 4T1 mammary carcinoma cell (ATCC) to establish tumors. Specifically, $1\times10^5$ 4 T1 cells in 0.1 cc of PBS were injected subcutaneously on the upper right thigh of each animal. At time of virus injection, 11 days after tumor cell implantation, mice were observed to have tumors of approximately 250-500 $mm^3$. Because this study was only intended to evaluate the blood concentration of virus, tumors were not harvested or evaluated in these animals.

A vaccinia virus strain containing a heterologous nucleic acid molecule encoding a detectable marker TurboFP635 was treated with Intralipid® lipid emulsion as described in Example 5. Vaccinia virus strain ($5\times10^6$ pfu/mouse) that was untreated or that was pretreated with the soybean oil emulsion Intralipid® lipid emulsion (20% lipid suspension, Lot 5LBD3129V; Sigma-Aldrich Corp., St. Louis, Mo.) were administered to nude mice (Group A, untreated, n=4; Group B, pretreated n=5) and BALB/c mice (Group C, untreated, n=5; Group D, pretreated n=5) via tail vein. In several mice the intravenous tail vein injection was unsuccessful and the virus was injected into the abdominal aorta. Blood samples were collected from the abdominal aorta at regular intervals post-injection (p.i.) beginning at approximately 1 minute p.i. to 120 minutes p.i. The samples were anticoagulated with EDTA, immediately frozen on dry ice, and assessed by viral plaque assay for infectious virus on CV-1 cells as described in Example 2. PK parameters were calculated in Microsoft Excel using a PK calculation module.

With respect to virus titer (pfu/mL) in the blood, the results show that the highest concentration of virus post-injection occurred at the earliest time point measured (approximately 1 minute p.i.) and declined rapidly with each measurement. In Groups of mice where the virus was pretreated with Intralipid® lipid emulsion, there was a consistently higher detection of virus titer in the blood at the earlier time points than in the corresponding mice administered untreated virus.

| Group | Average Time Post-Injection (Min ± SD) | Average Titer/ mL Blood | SD Titer/ mL Blood |
|---|---|---|---|
| A | Preinjection | Not Detectable | Not Detectable |
| (Nude mice; | 0.9 ± 0.1 | $2.6 \times 10^6$ | $2.0 \times 10^6$ |
| no | 2.1 ± 0.1 | $4.7 \times 10^5$ | $3.8 \times 10^5$ |
| pretreatment) | 5.5 ± 0.6 | $4.5 \times 10^4$ | $1.8 \times 10^4$ |
| | 10.2 ± 0.2 | $2.0 \times 10^4$ | $1.3 \times 10^4$ |
| | 30.5 ± 3.5 | $1.8 \times 10^4$ | $2.1 \times 10^4$ |
| | 61.0 ± 1.4 | $2.1 \times 10^3$ | 0.0 |
| B | Preinjection | Not Detectable | Not Detectable |
| (Nude mice; | 1.4 ± 0.4 | $3.6 \times 10^6$ | $2.5 \times 10^6$ |
| Intralipid ® | 3.2 ± 0.8 | $4.7 \times 10^5$ | $3.3 \times 10^5$ |
| lipid | 5.4 ± 0.2 | $2.9 \times 10^5$ | $2.6 \times 10^5$ |
| emulsion) | 10.7 ± 1.0 | $7.0 \times 10^4$ | $7.9 \times 10^4$ |
| | 33.6 ± 3.3 | $6.7 \times 10^3$ | $5.7 \times 10^3$ |
| | 44.7 ± 0.9 | $6.4 \times 10^3$ | $1.6 \times 10^2$ |
| | 67.9 ± 12.3 | $2.1 \times 10^3$ | $1.5 \times 10^3$ |
| C | Preinjection | Not Detectable | Not Detectable |
| (Balb/C | 1.0 ± 0.1 | $3.8 \times 10^6$ | $3.0 \times 10^6$ |
| mice; no | 2.0 ± 0.4 | $1.1 \times 10^6$ | $9.2 \times 10^5$ |
| pretreatment) | 5.4 ± 0.3 | $8.7 \times 10^4$ | $5.7 \times 10^4$ |
| | 10.8 ± 0.5 | $6.7 \times 10^4$ | $3.4 \times 10^4$ |
| | 33.5 ± 9.9 | $4.4 \times 10^4$ | $5.5 \times 10^4$ |
| D | Preinjection | Not Detectable | Not Detectable |
| (Balb/C | 1.1 ± 0.2 | $7.2 \times 10^6$ | $1.9 \times 10^6$ |
| mice; | 2.2 ± 0.3 | $4.6 \times 10^6$ | $2.7 \times 10^6$ |
| Intralipid ® | 5.3 ± 0.8 | $7.3 \times 10^5$ | $5.5 \times 10^5$ |
| lipid | 10.5 ± 0.5 | $1.8 \times 10^5$ | $1.9 \times 10^5$ |
| emulsion) | 36.1 ± 13.6 | $4.6 \times 10^4$ | $3.0 \times 10^4$ |

Results were analyzed through 10 minutes post-injection for maximum blood titer ($C_{max}$), calculated half-life in blood ($t\frac{1}{2}$), the rate constant for elimination of the virus from blood ($K_{elim}$), and the tissue exposure to the injected virus (AUC) from 1 to 10 minutes ($AUC_{0-10}$) and from 1 to infinity ($AUC_{0-inf}$). The group average results and percent differences between the group average PK values are illustrated in Tables 19 and 20, respectively.

TABLE 19

Group average PK values

|  | Group A (n = 4) | Group B (n = 5) | Group C (n = 5) | Group D (n = 5) |
|---|---|---|---|---|
| Mouse strain | Nude | Nude | BALB/c | BALB/c |
| Virus Treatment | no pretreatment | Intralipid® lipid emulsion | no pretreatment | Intralipid® lipid emulsion |
| $C_{max}$ (pfu/mL) | $2.6 \times 10^6$ | $3.6 \times 10^6$ | $3.8 \times 10^6$ | $7.2 \times 10^6$ |
| $t_{max}$ (min) | 0.9 | 1.4 | 1.0 | 1.1 |
| $t\frac{1}{2}$ (min) | 0.8 | 1.1 | 0.8 | 1.3 |
| $K_{elim}$ | 0.09 | 0.10 | 0.10 | 0.13 |
| $AUC_{0-10}$ (pfu · min/mL) | $2.8 \times 10^6$ | $5.5 \times 10^6$ | $4.8 \times 10^6$ | $1.8 \times 10^7$ |
| $AUC_{0-inf}$ (pfu · min/mL) | $2.9 \times 10^6$ | $5.5 \times 10^6$ | $5.2 \times 10^6$ | $1.8 \times 10^7$ |

TABLE 20

Percent difference in group average PK values

|  | Group comparison | | | |
|---|---|---|---|---|
|  | B vs. A | D vs. C | A vs. C | B vs. D |
| Mouse strain | Nude | BALB/c | Nude vs. BALB/c | Nude vs. BALB/c |
| Virus: Treatment | Intralipid® treated vs. untreated | Intralipid® lipid treated vs. untreated | untreated (nude) vs. untreated (BALB/C) | Intralipid® lipid treated (nude) vs. Intralipid® lipid emulsion treated (BALB/C) |
| $C_{max}$ | 140% | 191% | 68% | 50% |
| $t_{max}$ | n/a | n/a | n/a | n/a |
| $t\frac{1}{2}$ | 139% | 151% | 97% | 89% |
| $K_{elim}$ | 110% | 126% | 86% | 76% |
| $AUC_{0-10}$ | 193% | 367% | 59% | 31% |
| $AUC_{0-inf}$ | 192% | 344% | 55% | 31% |

The group average PK values were compared between the four groups of mice. Comparison of the group average PK values between the Group A (nude) and Group C (BALB/c) mice that received untreated virus revealed that the total tissue exposure ($AUC_{0-inf}$) of the nude mice was less than the BALB/c mice (55%) due to a decrease in the $C_{max}$ of the nude mice compared to the BALB/c mice (68%). However, the $t\frac{1}{2}$ was comparable in both groups (97%).

Comparison of the group average PK values between the mice injected with untreated virus and the mice injected with the Intralipid® lipid emulsion-treated virus resulted in an increase in the total tissue exposure ($AUC_{0-inf}$) in the mice injected with the Intralipid® lipid emulsion-treated virus as compared to the mice injected with untreated virus. There was a 192% increase in $AUC_{0-inf}$ in nude mice and a 344% increase in the BALB/c mice (Group B vs. Group A and Group D vs. Group C, respectively), corresponding to a 140% increase in the $C_{max}$ and a 139% increase in the $t\frac{1}{2}$ in nude mice and a 191% increase in the $C_{max}$ and a 151% increase in the $t\frac{1}{2}$ in the BALB/c mice.

The differences in PK values between the nude mice and the BALB/c mice injected with the Intralipid® lipid emulsion-treated virus were consistent with the differences observed with the untreated virus. The half-lives of the two viruses were substantially comparable in nude and BALB/c mice.

Overall, pretreatment of virus with Intralipid® lipid emulsion increased the maximum exposure of virus in blood ($AUC_{0-inf}$) by 2-3 fold post-injection. The increase was due to a reduction in the rate of elimination of the virus ($K_{elim}$) and an increase in the circulation half-life ($t\frac{1}{2}$).

Example 8

Effect of Eculizumab on Human Serum Inactivation of GLV-1h68 with Serum from Five Human Blood Donors The effect of the anti-C5 mAb eculizumab (SEQ ID NO:44, heavy chain and SEQ ID NO:45, light chain; sold under the trademark Soliris®, Lot 10007A; Alexion Pharmaceuticals, Chesire, Conn.) on the infectivity of vaccinia virus strain GLV-1h68 was evaluated in serum from five additional human blood donors. GLV-1h68 virus described in Example 1 ($2.5 \times 10^5$ pfu/mL) was exposed to either human serum, human serum that had been heated to 58° C. for 30 minutes to inactivate complement in the serum, or human serum that had been pretreated with 1 mg/mL eculizumab.

After exposure of the virus to the serum for 30 minutes at room temperature, the infectivity of the virus compositions was assessed by viral plaque assay on CV-1 cells. A viral titer assay was performed in a standard plaque assay using African green monkey kidney fibroblast CV-1 cells (ATCC No. CCL-70; American Type Culture Collection, Manassas, Va.). CV-1 cells were plated in a 24-well plate at $2.5 \times 10^5$ cells per well and grown until near confluency. Wells containing a cell monolayer were infected with serial dilutions of the virus compositions. The cells in each well were overlaid with virus overlay medium (DMEM+5% FBS+1% Antibiotic-Antimycotic Solution+1.5% carboxymethylcellulose), and the cells were further incubated until plaques were visible. After addition of color dye to visualize the plaques, viral titer (pfu/mL) was calculated by counting the number of plaques in the well and dividing by the dilution factor (d) and volume (V) of diluted virus added to the well. Tests were conducted in triplicate and the average of 6 measures (2 per replicate) are reported.

Results are provided in Table 21 below. The results show that exposure of the GLV-1h68 virus to various human sera alone resulted in recovery of virus titer ranging from 3% to 38%. Addition of eculizumab to the serum for 30 minutes at room temperature prior to exposure of the virus resulted in substantial increase in the recovered virus titers, ranging from 24% to 91%. The fold increase in titer recovery in serum with eculizumab compared to serum alone ranged from 2.4 to 7.4. The results indicate that inhibiting complement by treating human serum with 1 mg/mL of the anti-C5 mAb eculizumab reduced the loss of infectivity of GLV-1h68 as compared to serum that had not been treated with eculizumab.

While the results demonstrated variable amounts of virus inactivation activity in the various sera, increase in infectious virus recovery after treatment with eculizumab was obtained with all sera from the five individual blood donors. Four of the donor sera, #1 to #4, contained very little, if any, anti-vaccinia neutralizing antibody as evident from the recovery of nearly 100% of the virus after exposure to serum that had been heat-treated to inactivate complement activity, but not antibody activity. For Donor #5, only 68% of the virus was recovered after exposure to serum that had been heat-treated, indicating that this serum had substantial anti-vaccinia neutralizing antibody. Yet in all cases, exposure of virus to serum in the presence of eculizumab increased the recovery of infectious virus by 2.4 to 7.4 fold over serum alone.

TABLE 21

% Recovered titer of GLV-1h68 in human serum from five healthy human blood donors without or with eculizumab

| Blood Donor | Serum exposure | Recovered titer (%) | Fold Increase over serum alone |
|---|---|---|---|
| #1 | Serum | 22 | N/A |
| | Serum + Eculizumab (1 mg/mL) | 77 | 3.5 |
| | Heat inactivated serum | 98 | N/A |
| #2 | Serum | 22 | N/A |
| | Serum + Eculizumab (1 mg/mL) | 60 | 2.7 |
| | Heat inactivated serum | 107 | N/A |
| #3 | Serum | 25 | N/A |
| | Serum + Eculizumab (1 mg/mL) | 63 | 2.5 |
| | Heat inactivated serum | 100 | N/A |
| #4 | Serum | 38 | N/A |
| | Serum + Eculizumab (1 mg/mL) | 91 | 2.4 |
| | Heat inactivated serum | 124 | N/A |
| #5 | Serum | 3 | N/A |
| | Serum + Eculizumab (1 mg/mL) | 24 | 7.4 |
| | Heat inactivated serum | 68 | N/A |

Example 9

Adsorption of GLV-1h68 to Human Blood Cells from Five Healthy Human Blood Donors in the Presence of Matched Serum The adsorption of vaccinia virus strain GLV-1h68 described in Example 1 to human whole blood cells was evaluated. Whole human blood cells were prepared from five healthy human blood donors by collecting blood in EDTA and isolating cells by centrifugation. The cells were washed with phosphate buffered saline (PBS) to remove any plasma/EDTA and were resuspended in PBS to the original blood volume. GLV-1h68 virus ($2.0 \times 10^6$ pfu/mL) was exposed to whole human blood cells (33% of blood concentration) in either human serum, heat-inactivated human serum that had been heated to 58° C. for 30 minutes to inactivate complement in the serum, or human serum that had been pretreated with 1 mg/mL eculizumab (Soliris®, Lot 10007A; Alexion Pharmaceuticals, Chesire, Conn.). GLV-1h68 ($2.0 \times 10^6$ pfu/mL) in PBS serve as a control.

After exposure for 60 minutes at 37° C., the virus fraction bound to blood cells was separated from the unbound fraction by centrifugation and washed with PBS to remove loosely bound virus. The infectivity of the virus was assessed by the viral plaque assay on CV-1 cells described in Example 2. The recovered titer of cell-bound virus was determined Tests were conducted in triplicate and the average of 6 measures (2 per replicate) are reported.

The Results are set forth in Table 22. The results show that 21% of the GLV-1h68 virus in PBS was cell-bound, while 79% remained unbound, for a total recovery of 100%. This value was used as a comparative standard relative to the values obtained in the human serum compositions, and the percent recovered titer of cell-bound virus and unbound virus compared to PBS control was determined.

In human serum, the fraction of virus recovered bound to blood cells ranged from 27% to 90% for blood cells and serum from Donors 1 to 4. For Donor 5, who had substantial levels of serum anti-vaccinia neutralizing antibody, the fraction of virus recovered cell-bound in serum was 2%, indicating that the virus was inactivated by the serum. When virus was exposed to heat-inactivated serum, which inactivates complement, there was a substantial decrease in the fraction of virus recovered bound to blood cells was ≤4% for all donors. This result demonstrates that while reducing the amount of virus inactivation by the serum, heat-inactivating complement also reduces the amount of virus bound to blood cells.

Exposure of virus to human serum in the presence of the anti-C5 mAb eculizumab resulted in an increase in the fraction of virus recovered bound to blood cells. For Donors 1 to 4, 89% to 173% of the virus was recovered bound to blood cells (1.9 to 3.4 fold increase over serum alone). For Donor 5, whose serum contained anti-vaccinia neutralizing antibody, 53% of the virus was recovered bound to cells in serum in the presence of anti-C5 mAb eculizumab (27.3 fold increase over serum alone). This indicates that inhibiting complement by treatment of serum with eculizumab increases the fraction of bound virus in blood from individuals even with anti-vaccinia neutralizing antibody. Additionally, for some individuals exposure of virus with serum treated with eculizumab boosts the infectivity of the virus that is bound to blood cells in excess of that obtained with the virus in PBS.

TABLE 22

GLV-1h68 bound to human blood cells in human serum

| Blood Donor | Serum exposure | Cell-bound virus titer (%) | Fold increase over serum alone |
|---|---|---|---|
| #1 | Serum | 27 | N/A |
| | Serum + Eculizumab (1 mg/mL) | 89 | 3.4 |
| | Heat inactivated serum | 4 | N/A |
| #2 | Serum | 36 | N/A |
| | Serum + Eculizumab (1 mg/mL) | 98 | 2.7 |
| | Heat inactivated serum | 3 | N/A |
| #3 | Serum | 55 | N/A |
| | Serum + Eculizumab (1 mg/mL) | 128 | 2.4 |
| | Heat inactivated serum | 3 | N/A |
| #4 | Serum | 90 | N/A |
| | Serum + Eculizumab (1 mg/mL) | 173 | 1.9 |
| | Heat inactivated serum | 4 | N/A |
| #5 | Serum | 2 | N/A |
| | Serum + Eculizumab (1 mg/mL) | 53 | 27.3 |
| | Heat inactivated serum | 1 | N/A |

Example 10

Effect of Intralipid® Lipid Emulsion on NK Cell Activity

Intralipid® lipid emulsion (20% lipid suspension, Lot 5LBD3129V; Sigma-Aldrich Corp., St. Louis, Mo.) was assessed to test the effect of Intralipid® lipid emulsion on the cytotoxicity of human NK cells using the standard human NK cell target K-562 (human erythroleukemia cell line). Intralipid® lipid emulsion at the following concentrations 0.4 microliters (IL), 0.8 µL, 1 µL, 2 µL and 4 µL was added to 1 ml of media containing 800,000 human NK cells. The results showed that even at the lowest concentration, the Intralipid® lipid emulsion suppressed the cytotoxicity of the NK cells with a more pronounced effect at 1 µL/ml.

Since modifications will be apparent to those of skill in the art, it is intended that the inventions are limited only by the scope of the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10238700B2). An electronic copy of the "Sequence Listing" will also be available from the USPTO upon request and payment of the fee set forth in 37 CFR 1.19(b)(3).

The invention claimed is:

1. A method of increasing infectivity of an oncolytic virus, comprising administering the oncolytic virus and an anti-C5 antibody to a subject, wherein:
the oncolytic virus is a vaccinia virus;
the virus and antibody are administered separately, in the same composition, sequentially or intermittently;
the antibody binds to the alpha chain of complement C5, and is selected from among eculizumab, pexelizumab, TSA12/22 and MB12/122, and variants thereof that bind to the C5 alpha chain;
the variants of eculizumab and pexelizumab specifically bind to the alpha chain of human complement component C5, and a) inhibit complement activation in a human body fluid, b) inhibit the binding of purified human complement component C5 to either human complement component C3 or human complement component C4, and c) do not specifically bind to the human complement activation product free C5a;
the variants of TSA12/22 and MB12/122 specifically bind to C5 alpha chain of the C5 component of the complement system and recognize the region corresponding to residues 727-744 of SEQ ID NO: 53 of the C5 component of human complement or a region having at least 80% homology thereto, wherein the antibody inhibits the conversion of the C5 alpha chain to C5a and C5b, a light chain of the antibody is a lambda chain or a kappa chain, and a variable region of a heavy chain is the VH3 region; and
the anti-C5 antibody is administered in an amount effective for inhibiting complement activation in a subject.

2. The method of claim 1, wherein the anti-C5 antibody is eculizumab or pexelizumab.

3. The method of claim 1, wherein the virus and antibody are administered in the same composition.

4. The method of claim 1, wherein the virus and antibody are administered separately.

5. The method of claim 4, wherein the antibody is administered before the virus is administered.

6. A composition, comprising, in a pharmaceutically acceptable carrier:
an oncolytic virus, wherein the oncolytic virus is a vaccinia virus; and
an anti-complement component 5 (C5) antibody that binds to the C5 alpha chain and is selected from among eculizumab, pexelizumab, TSA12/22 and MB12/122, and variants thereof that bind to the C5 alpha chain, wherein:
the variants of eculizumab and pexelizumab specifically bind to the alpha chain of human complement component C5, and a) inhibit complement activation in a human body fluid, b) inhibit the binding of purified human complement component C5 to either human complement component C3 or human complement component C4, and c) do not specifically bind to the human complement activation product free C5a;
the variants of TSA12/22 and MB12/122 specifically bind to C5 alpha chain of the C5 component of the complement system and recognize a region corresponding to residues 727-744 of SEQ ID NO: 53 of the C5 component of human complement or a region having at least 80% homology thereto, wherein the variant antibody inhibits the conversion of the C5alpha chain to C5a and C5b, a light chain of the antibody is a lambda chain or a kappa chain, and a variable region of a heavy chain is the VH3 region; and
the anti-C5 antibody is in an amount effective for inhibiting complement activation in a subject.

7. The composition of claim 6, further comprising a biocompatible lipid component that is comprised of fatty acids and/or fatty acid derivatives.

8. The composition of claim 7, wherein the virus is in a lipid emulsion or treated with a lipid emulsion that comprises:
a biocompatible lipid component in a concentration between 10% and 30%, inclusive, by weight, of the lipid emulsion, wherein the biocompatible lipid component is selected from among soybean oil, safflower oil, olive oil, and mixtures thereof;
an egg yolk phospholipid(s) in a concentration that is at or about 1.2% by weight, of the lipid emulsion;
glycerin in a concentration between 2.25% and 2.5%, inclusive, by weight, of the lipid emulsion; and
water in a concentration that is between 60% and 90%, inclusive, by weight, of the lipid emulsion.

9. The method of claim 1, wherein the vaccinia virus is modified to contain nucleic acid encoding a heterologous gene product.

10. The composition of claim 6, wherein the vaccinia virus is modified to contain nucleic acid encoding a heterologous gene product.

11. The composition of claim 6, wherein the vaccinia virus is selected from among Lister, Western Reserve (WR), Copenhagen (Cop), Bern, Paris, Tashkent, Tian Tan, Wyeth (DRYVAX), IHD-J, IHD-W, Brighton, Ankara, CVA382, Modified Vaccinia Ankara (MVA), Dairen I, LC16m8, LC16M0, LIVP, ACAM2000, WR 65-16,Connaught, New York City Board of Health (NYCBH), EM-63 and NYVAC strain.

12. The method of claim 1, wherein the vaccinia virus is a Lister strain virus.

13. The composition of claim 6, wherein the virus is a vaccinia virus that is an LIVP virus or a clonal strain of an LIVP virus or a modified LIVP virus that comprises heterologous nucleic acid encoding an anti-cancer therapeutic or a reporter gene product.

14. The method of claim 1, wherein the virus is an LIVP virus or a clonal strain of an LIVP virus or a modified LIVP virus that comprises heterologous nucleic acid encoding an anti-cancer therapeutic or a reporter gene product.

15. A combination, comprising:
a first composition comprising an oncolytic virus, wherein the oncolytic virus is a vaccinia virus; and
a second composition comprising an anti-C5 antibody that binds to the C5 alpha chain, and is in an amount effective for inhibiting complement activation in a subject, wherein the anti-C5 antibody is selected from among eculizumab, pexelizumab, TSA12/22 and MB12/122, and variants thereof that bind to the C5 alpha chain, wherein:
the variants of eculizumab and pexelizumab specifically bind to the alpha chain of human complement component C5, and a) inhibit complement activation in a human body fluid, b) inhibit the binding of purified human complement component C5 to either human complement component C3 or human complement component C4, and c) do not specifically bind to the human complement activation product free C5a;
the variants of TSA12/22 and MB12/122 specifically bind to C5 alpha chain of the C5 component of the complement system and recognize the region corresponding to residues 727-744 of SEQ ID NO: 53 of the C5 component of human complement or a region having at least 80% homology thereto, wherein the antibody inhibits the conversion of the C5 alpha chain to C5a and C5b, wherein a light chain of the antibody is a lambda chain or a kappa chain, and a variable region of a heavy chain is the VH3 region.

16. The combination of claim 15, further comprising a third composition comprising a lipid emulsion containing a biocompatible lipid component that is comprised of fatty acids and/or fatty acid derivatives.

17. The combination of claim 15, wherein the vaccinia virus is selected from among Lister, Western Reserve (WR), Copenhagen (Cop), Bern, Paris, Tashkent, Tian Tan, Wyeth (DRYVAX), IHD-J, IHD-W, Brighton, Ankara, CVA382, Modified Vaccinia Ankara (MVA), Dairen I, LC16m8, LC16M0, LIVP, ACAM2000, WR 65-16, Connaught, New York City Board of Health (NYCBH), EM-63 and NYVAC strain.

18. The combination of claim 17, wherein the virus is a Lister strain virus that is an LIVP virus or a clonal strain of an LIVP virus or a derivative thereof that comprises heterologous nucleic acid encoding an anti-cancer therapeutic or a reporter gene product.

19. The method of claim 1, wherein the oncolytic virus is treated with a lipid emulsion containing a biocompatible lipid component that is comprised of fatty acids and/or fatty acid derivatives.

20. The method of claim 1, wherein the oncolytic virus is administered with or is in an composition comprising a biocompatible lipid component that is comprised of fatty acids and/or fatty acid derivatives, wherein the composition is an emulsion.

21. The method of claim 1, wherein the oncolytic virus is GLV-1h68 or a derivative thereof.

22. The combination of claim 15, wherein the oncolytic virus is GLV-1h68 or a derivative thereof.

23. The method of claim 1, wherein the anti-C5 alpha chain antibody is TSA12/22 or MB12/122.

24. The composition of claim 6, wherein the anti-C5 alpha chain antibody is eculizumab or pexelizumab.

25. The composition of claim 6, wherein the anti-C5 antibody is TSA12/22 or MB12/122.

* * * * *

UNITED STATES PATENT AND TRADEMARK OFFICE
CERTIFICATE OF CORRECTION

PATENT NO. : 10,238,700 B2
APPLICATION NO. : 15/109214
DATED : March 26, 2019
INVENTOR(S) : Szalay et al.

It is certified that error appears in the above-identified patent and that said Letters Patent is hereby corrected as shown below:

On the Title Page

In Item (56) References Cited, in OTHER PUBLICATIONS, on page 3, 1st Column, Line 18, please replace "Molecular Biology $2^{nd}$ d edition" with —Molecular Biology $2^{nd}$ edition—.

In the Specification

At Column 10, Line 54, please replace "of complement, Such agents" with —of complement. Such agents—;

At Column 17, Line 30, please replace "5 g to 1 g" with —5 g to 10 g—;

At Column 18, Line 30, please replace "regimen Typical amounts" with —regimen. Typical amounts—;

At Column 34, Line 7, please replace "SEQ ID NO:4" with —SEQ ID NO:46—;

At Column 49, Line 47, please replace "C2and C4" with —C2 and C4—;

At Column 77, Line 37, please replace "HSR" with —H5R—;

At Column 92, Line 19, please replace "NIL" with —N1L—;

At Column 105, Line 63, please replace "produced recombinantly Antibody fragments" with —produced recombinantly. Antibody fragments—;

At Column 116, Line 48, please replace "TABLE 1" with —TABLE 11—;

At Column 158, Line 5, please replace "4 TI cells" with —4TI cells—;

Signed and Sealed this
Eleventh Day of June, 2019

Andrei Iancu
*Director of the United States Patent and Trademark Office*

CERTIFICATE OF CORRECTION (continued)
U.S. Pat. No. 10,238,700 B2

At Column 161, Line 36, please replace "determined Tests were" with —determined. Tests were—;

At Column 163, Line 4, please replace "microliters (IL)" with —microliters (µL)—.

In the Claims

At Column 163, Lines 51-59, to Column 164, Lines 11-30, please replace Claim 6 with the following amended claim:
—6. A composition, comprising, in a pharmaceutically acceptable carrier:
an oncolytic virus, wherein the oncolytic virus is a vaccinia virus; and
an anti-complement component 5 (C5) antibody that binds to the C5 alpha chain and is selected from among eculizumab, pexelizumab, TSA12/22 and MB12/122, and variants thereof
that bind to the C5 alpha chain, wherein:
    the variants of eculizumab and pexelizumab specifically bind to the alpha chain of
human complement component C5, and a) inhibit complement activation in a human body fluid,
b) inhibit the binding of purified human complement component C5 to either human
complement component C3 or human complement component C4, and c) do not specifically
bind to the human complement activation product free C5a;
    the variants of TSA12/22 and MB12/122 specifically bind to the C5 alpha chain of the
C5 component of the complement system and recognize a region corresponding to residues 727-744 of SEQ ID NO: 53 of the C5 component of human complement or a region having at least
80% homology thereto, wherein the variant antibody inhibits the conversion of the C5 alpha
chain to C5a and C5b, a light chain of the antibody is a lambda chain or a kappa chain, and a
variable region of a heavy chain is the VH3 region; and
    the anti-C5 antibody is in an amount effective for inhibiting complement activation in a
subject.—;

At Column 164, Lines 34-47, please replace Claim 8 with the following amended claim:
—8. The composition of claim 7, wherein the virus is in a lipid emulsion or treated
with a lipid emulsion that comprises:
    a biocompatible lipid component in a concentration between 10% and 30%, inclusive, by
weight, of the lipid emulsion, wherein the biocompatible lipid component is selected from
among soybean oil, safflower oil, olive oil, and mixtures thereof;
    an egg yolk phospholipid(s) in a concentration that is at or about 1.2%, by weight, of the
lipid emulsion;
    glycerin in a concentration between 2.25% and 2.5%, inclusive, by weight, of the lipid
emulsion; and
    water in a concentration that is between 60% and 90%, inclusive, by weight, of the lipid
emulsion.—;

At Column 164, Line 54, to Column 165, Line 4, please replace Claim 11 with the following amended claim:
—11. The composition of claim 6, wherein the vaccinia virus is selected from among Lister, Western Reserve (WR), Copenhagen (Cop), Bern, Paris, Tashkent, Tian Tan, Wyeth
(DRYVAX), IHD-J, IHD-W, Brighton, Ankara, CVA382, Modified Vaccinia Ankara (MVA),

CERTIFICATE OF CORRECTION (continued)
U.S. Pat. No. 10,238,700 B2

Dairen I, LC16m8, LC16M0, LIVP, ACAM2000, WR 65-16, Connaught, New York City Board of Health (NYCBH), EM-63 and NYVAC strains.—;

At Column 165, Line 16, to Column 166, Line 3, please replace Claim 15 with the following amended claim:
—15. A combination, comprising:
    a first composition comprising an oncolytic virus, wherein the oncolytic virus is a vaccinia virus; and
    a second composition comprising an anti-C5 antibody that binds to the C5 alpha chain, and is in an amount effective for inhibiting complement activation in a subject, wherein the anti-C5 antibody is selected from among eculizumab, pexelizumab, TSA12/22 and MB12/122, and variants thereof that bind to the C5 alpha chain, wherein:
    the variants of eculizumab and pexelizumab specifically bind to the alpha chain of human complement component C5, and a) inhibit complement activation in a human body fluid, b) inhibit the binding of purified human complement component C5 to either human complement component C3 or human complement component C4, and c) do not specifically bind to the human complement activation product free C5a; and
    the variants of TSA12/22 and MB 12/122 specifically bind to the C5 alpha chain of the C5 component of the complement system and recognize the region corresponding to residues 727-744 of SEQ ID NO: 53 of the C5 component of human complement or a region having at least 80% homology thereto, wherein the antibody inhibits the conversion of the C5 alpha chain to C5a and C5b, wherein a light chain of the antibody is a lambda chain or a kappa chain, and a variable region of a heavy chain is the VH3 region.—;

At Column 166, Lines 8-15, please replace Claim 17 with the following amended claim:
—17. The combination of claim 15, wherein the vaccinia virus is selected from among Lister, Western Reserve (WR), Copenhagen (Cop), Bern, Paris, Tashkent, Tian Tan, Wyeth (DRYVAX), IHD-J, IHD-W, Brighton, Ankara, CVA382, Modified Vaccinia Ankara (MVA), Dairen I, LC16m8, LC16M0, LIVP, ACAM2000, WR 65-16, Connaught, New York City Board of Health (NYCBH), EM-63 and NYVAC strains.—;

At Column 166, Lines 25-29, please replace Claim 20 with the following amended claim:
—20. The method of claim 1, wherein the oncolytic virus is administered with or is in a composition comprising a biocompatible lipid component that is comprised of fatty acids and/or fatty acid derivatives, wherein the composition is an emulsion.—.